US012778954B2

(12) United States Patent
Peloso et al.

(10) Patent No.: US 12,778,954 B2
(45) Date of Patent: Nov. 3, 2026

(54) METHODS OF TREATING GOUT

(71) Applicant: Horizon Therapeutics USA, Inc., Deerfield, IL (US)

(72) Inventors: Paul Michael Peloso, Naples, FL (US); Brian David Lamoreaux, Deerfield, IL (US); Swarnendra K. Verma, Newport Beach, CA (US)

(73) Assignee: Horizon Therapeutics USA, Inc., Deerfield, IL (US)

( * ) Notice: Subject to any disclaimer, the term of this patent is extended or adjusted under 35 U.S.C. 154(b) by 831 days.

(21) Appl. No.: 18/020,761

(22) PCT Filed: Aug. 10, 2021

(86) PCT No.: PCT/US2021/045350

§ 371 (c)(1),
(2) Date: Feb. 10, 2023

(87) PCT Pub. No.: WO2022/035828

PCT Pub. Date: Feb. 17, 2022

(65) Prior Publication Data

US 2023/0301999 A1 Sep. 28, 2023

Related U.S. Application Data

(60) Provisional application No. 63/148,982, filed on Feb. 12, 2021, provisional application No. 63/063,826, filed on Aug. 10, 2020.

(51) Int. Cl.

| | |
|---|---|
| ***A61K 31/519*** | (2006.01) |
| ***A61K 38/44*** | (2006.01) |
| ***A61K 47/34*** | (2017.01) |
| ***A61K 47/60*** | (2017.01) |
| ***A61P 19/06*** | (2006.01) |

(52) U.S. Cl.

CPC ............ *A61K 31/519* (2013.01); *A61K 38/44* (2013.01); *A61K 47/34* (2013.01); *A61K 47/60* (2017.08); *A61P 19/06* (2018.01); *C12Y 107/03003* (2013.01)

(58) Field of Classification Search

CPC ............ A61P 19/06; C12Y 107/03003; A61K 31/519; A61K 38/44; A61K 47/34; A61K 47/60

See application file for complete search history.

(56) References Cited

U.S. PATENT DOCUMENTS

| | | | |
|---|---|---|---|
| 1,141,973 | A | 6/1915 | Nichols |
| 3,451,996 | A | 6/1969 | Sumyk et al. |
| 3,613,231 | A | 10/1971 | Pugh et al. |
| 3,616,231 | A | 10/1971 | Bergmeyer et al. |
| 3,931,399 | A | 1/1976 | Bohn et al. |
| 4,027,676 | A | 6/1977 | Mattei |
| 4,064,010 | A | 12/1977 | Harris et al. |
| 4,141,973 | A | 2/1979 | Balazs |
| 4,169,764 | A | 10/1979 | Takezawa et al. |
| 4,179,337 | A | 12/1979 | Davis et al. |
| 4,251,431 | A | 2/1981 | Carswell et al. |
| 4,297,344 | A | 10/1981 | Schwinn et al. |
| 4,301,153 | A | 11/1981 | Rosenberg |
| 4,312,979 | A | 1/1982 | Takemoto et al. |
| 4,315,852 | A | 2/1982 | Leibowitz et al. |
| 4,317,878 | A | 3/1982 | Nakanishi et al. |
| 4,343,735 | A | 8/1982 | Menge et al. |
| 4,343,736 | A | 8/1982 | Uemura et al. |
| 4,376,110 | A | 3/1983 | David et al. |
| 4,421,650 | A | 12/1983 | Nagasawa et al. |
| 4,425,431 | A | 1/1984 | Takemoto et al. |
| 4,445,745 | A | 5/1984 | Cartesse |
| 4,450,103 | A | 5/1984 | Konrad et al. |
| 4,460,575 | A | 7/1984 | D'Hinterland et al. |
| 4,460,683 | A | 7/1984 | Gloger et al. |
| 4,485,176 | A | 11/1984 | Bollin, Jr. et al. |
| 4,753,796 | A | 6/1988 | Moreno et al. |
| 4,766,106 | A | 8/1988 | Katre et al. |
| 4,797,474 | A | 1/1989 | Patroni et al. |
| 4,816,567 | A | 3/1989 | Cabilly et al. |
| 4,847,079 | A | 7/1989 | Kwan |
| 4,847,325 | A | 7/1989 | Shadle et al. |

(Continued)

FOREIGN PATENT DOCUMENTS

| | | | |
|---|---|---|---|
| AU | 5251599 | A | 2/2000 |
| CA | 2193993 | A1 | 1/1996 |

(Continued)

OTHER PUBLICATIONS

Abeles, A.M., "PEG-ing down (and preventing?) the cause of pegloticase failure," Arthritis Research & Therapy, Jun. 2014, 16:112., 2 pages.

Abstract Review: "Management of Gout After Pegloticase; Observations of US Clinical Practice from Trio Health and the American Rheumatology Network (ARN)," ACR Convergence, 2020, Abstract ID: 903234, 9 pages.

Abstract Review: "Management of Gout with Pegloticase; Real-World Utilization and Outcomes from Trio Health and the American Rheumatology Network (ARN)," ACR Convergence, 2020, Abstract ID: 903292, 11 pages.

Abuchowski, A. et al., "Effect of Covalent Attachment of Polyethylene Glycol on Immunogenicity and Circulating Life of Bovine Liver Catalase," The Journal of Biological Chemistry, American Society for Biochemistry and Molecular Biology, United States, Jun. 10, 1977, vol. 252, No. 11, pp. 3582-3586.

Abuchowski, A. et al., "Reduction of Plasma Urate Levels in the Cockerel With Polyethylene Glycol-Uricase," The Journal of Pharmacology Experimental Therapeutics, Nov. 1981, vol. 219, No. 2, pp. 352-354.

(Continued)

*Primary Examiner* — Erich A Leeser

(74) *Attorney, Agent, or Firm* — David Roadcap

(57) ABSTRACT

The disclosure provides methods of treating gout in patients comprising administering a PEGylated uricase in a shortened infusion period less than 120 minutes and a shortened infusion volume of less than 250 mL. Also provided are methods of treating gout in patients comprising co-administering a PEGylated uricase and methotrexate (MTX). Also provided are methods of reducing immunogenicity of a PEGylated uricase and prolonging the urate lowering effect comprising co-administration of the PEGylated uricase and MTX.

14 Claims, 2 Drawing Sheets

(56) References Cited

U.S. PATENT DOCUMENTS 4,917,888 A 4/1990 Katre et al.
4,945,086 A 7/1990 Benitz et al.
4,946,778 A 8/1990 Ladner et al.
4,966,963 A 10/1990 Patroni
4,987,076 A 1/1991 Takashio et al.
4,992,531 A 2/1991 Patroni et al.
5,008,377 A 4/1991 Patroni et al.
5,010,183 A 4/1991 Macfarlane
5,114,916 A 5/1992 Shirahata et al.
5,122,614 A 6/1992 Zalipsky
5,225,539 A 7/1993 Winter
5,283,317 A 2/1994 Saifer et al.
5,286,637 A 2/1994 Veronese et al.
5,362,641 A 11/1994 Fuks et al.
5,382,518 A 1/1995 Caput et al.
5,428,128 A 6/1995 Mensi-Fattohi et al.
5,458,135 A 10/1995 Patton et al.
5,468,478 A 11/1995 Saifer et al.
5,529,915 A 6/1996 Phillips et al.
5,541,098 A 7/1996 Caput et al.
5,567,422 A 10/1996 Greenwald
5,585,089 A 12/1996 Queen et al.
5,612,460 A 3/1997 Zalipsky
5,624,903 A 4/1997 Muller et al.
5,633,227 A 5/1997 Muller et al.
5,637,749 A 6/1997 Greenwald
5,643,575 A 7/1997 Martinez et al.
5,653,974 A 8/1997 Hung et al.
5,711,944 A 1/1998 Gilbert et al.
5,762,923 A 6/1998 Gross et al.
5,766,897 A 6/1998 Braxton
5,806,115 A 9/1998 Brown
5,811,096 A 9/1998 Aleman et al.
5,816,397 A 10/1998 Pratt
5,824,784 A 10/1998 Kinstler et al.
5,880,255 A 3/1999 Delgado et al.
5,919,455 A 7/1999 Greenwald et al.
5,929,231 A 7/1999 Malkki et al.
5,932,462 A 8/1999 Harris et al.
5,948,668 A 9/1999 Hartman et al.
5,955,336 A 9/1999 Shigyo et al.
6,006,753 A 12/1999 Efendic
6,130,318 A 10/2000 Wild et al.
6,201,110 B1 3/2001 Olsen et al.
6,211,341 B1 4/2001 Zeelon et al.
6,245,901 B1 6/2001 Von Der Osten et al.
6,468,210 B2 10/2002 Iliff
6,475,143 B2 11/2002 Iliff
6,524,241 B2 2/2003 Iliff
6,527,713 B2 3/2003 Iliff
6,569,093 B2 5/2003 Iliff
6,575,235 B2 6/2003 Zupanick et al.
6,576,235 B1 6/2003 Williams et al.
6,608,892 B2 8/2003 Shaffer et al.
6,783,965 B1 8/2004 Sherman et al.
6,897,206 B2 5/2005 Sackeyfio et al.
6,913,915 B2 7/2005 Ensor et al.
7,056,713 B1 6/2006 Hershfield et al.
7,723,089 B2 5/2010 Williams et al.
7,811,800 B2 10/2010 Hartman et al.
7,927,589 B2 4/2011 Williams et al.
7,927,852 B2 4/2011 Sherman et al.
7,964,381 B2 6/2011 Hartman et al.
8,034,594 B2 10/2011 Hartman et al.
8,067,553 B2 11/2011 Williams et al.
8,148,123 B2 4/2012 Hartman et al.
8,178,334 B2 5/2012 Hartman et al.
8,188,224 B2 5/2012 Hartman et al.
8,293,228 B2 10/2012 Hartman et al.
8,465,735 B2 6/2013 Hartman et al.
8,541,205 B2 9/2013 Hartman et al.
8,618,267 B2 12/2013 Williams et al.
8,913,915 B2 12/2014 Makino
8,921,064 B2 12/2014 Sherman et al.
9,017,980 B2 4/2015 Hartman et al.
9,377,454 B2 6/2016 Rosario-Jansen et al.
9,402,827 B2 8/2016 Miner et al.
9,534,013 B2 1/2017 Fischer et al.
9,670,467 B2 6/2017 Hartman et al.
9,885,024 B2 2/2018 Williams et al.
9,926,537 B2 3/2018 Hartman et al.
9,926,538 B2 3/2018 Hartman et al.
10,139,399 B2 11/2018 Rosario-Jansen et al.
10,160,958 B2 12/2018 Hartman et al.
10,731,139 B2 8/2020 Hartman et al.
10,823,727 B2 11/2020 Rosario-Jansen et al.
11,345,899 B2 5/2022 Hartman et al.
11,598,767 B2 3/2023 Rosario-Jansen et al.
11,639,927 B2 5/2023 Rosario-Jansen et al.
11,781,119 B2 10/2023 Hartman et al.
2002/0010319 A1 1/2002 Ansaldi et al.
2002/0151703 A1 10/2002 Yokoyama et al.
2003/0082786 A1 5/2003 Ensor et al.
2003/0166249 A1 9/2003 Williams et al.
2005/0014240 A1 1/2005 Sherman et al.
2005/0084478 A1 4/2005 Liu et al.
2006/0188971 A1 8/2006 Hershfield et al.
2007/0274977 A1 11/2007 Hartman et al.
2008/0031864 A1 2/2008 Williams et al.
2008/0057048 A1 3/2008 Sherman et al.
2008/0145876 A1 6/2008 Armstrong et al.
2008/0159976 A1 7/2008 Hartman et al.
2009/0023715 A1 1/2009 Brown et al.
2009/0169534 A1 7/2009 Hartman et al.
2009/0209021 A1 8/2009 Hartman et al.
2009/0317889 A1 12/2009 Fischer et al.
2010/0152305 A1 6/2010 Cedarbaum
2010/0160351 A1 6/2010 Jenkins et al.
2010/0323422 A1 12/2010 Williams et al.
2010/0323423 A1 12/2010 Williams et al.
2011/0104751 A1 5/2011 Hartman et al.
2011/0217755 A1 9/2011 Hartman et al.
2011/0287466 A1 11/2011 Sherman et al.
2012/0070876 A1 3/2012 Hartman et al.
2012/0149083 A1 6/2012 Williams et al.
2012/0225046 A1 9/2012 Hartman et al.
2012/0301454 A1 11/2012 Rosario-Jansen et al.
2012/0309085 A1 12/2012 Hartman et al.
2013/0052677 A1 2/2013 Williams et al.
2013/0084273 A1 4/2013 Hartman et al.
2013/0330803 A1 12/2013 Hartman et al.
2014/0363414 A1 12/2014 Sherman et al.
2015/0197732 A1 7/2015 Hartman et al.
2016/0035091 A1 2/2016 Kubassova
2016/0158318 A1 6/2016 Cohen et al.
2016/0160188 A1 6/2016 Williams et al.
2016/0377604 A1 12/2016 Rosario-Jansen et al.
2017/0166873 A1 6/2017 Fischer et al.
2017/0258927 A1 9/2017 Johnston
2017/0298326 A1 10/2017 Hartman et al.
2017/0313993 A1 11/2017 Hartman et al.
2017/0313994 A1 11/2017 Hartman et al.
2017/0313995 A1 11/2017 Hartman et al.
2017/0321193 A1 11/2017 Hartman et al.
2018/0008665 A1 1/2018 Qiao et al.
2018/0127432 A1 5/2018 Trzupek et al.
2018/0188242 A1 7/2018 Rosario-Jansen et al.
2018/0223263 A1 8/2018 Sherman et al.
2018/0289776 A1 10/2018 Johnston
2019/0316097 A1 10/2019 Hartman et al.
2019/0317083 A1 10/2019 Rosario-Jansen et al.
2020/0056160 A1 2/2020 Fischer et al.
2020/0237879 A1 7/2020 Kent et al.
2020/0237880 A1 7/2020 Kent et al.
2020/0237881 A1* 7/2020 Kent ...................... A61P 19/06
2020/0353057 A1 11/2020 Kent et al.
2021/0079362 A1 3/2021 Hartman et al.
2021/0181187 A1 6/2021 Rosario-Jansen et al.
2022/0073886 A1 3/2022 Fischer et al.
2022/0323445 A1* 10/2022 Peloso ................. A61K 31/519
2022/0323550 A1 10/2022 Peloso
2022/0409620 A1 12/2022 Kent et al.
2023/0028134 A1 1/2023 Rosario-Jansen et al.
2023/0034252 A1 2/2023 Hartman et al.

(56) References Cited

U.S. PATENT DOCUMENTS

| | | | |
|---|---|---|---|
| 2023/0085022 | A1 | 3/2023 | Kent et al. |
| 2023/0173035 | A1 | 6/2023 | Kent et al. |
| 2023/0251247 | A1 | 8/2023 | Rosario-Jansen et al. |
| 2024/0026312 | A1 | 1/2024 | Fischer et al. |
| 2024/0033331 | A1 | 2/2024 | Kent et al. |

FOREIGN PATENT DOCUMENTS

| | | | |
|---|---|---|---|
| CN | 1322141 | A | 11/2001 |
| CN | 1322243 | A | 11/2001 |
| CN | 101168052 | A | 4/2008 |
| CN | 101198693 | A | 6/2008 |
| CN | 104066324 | A | 9/2014 |
| DE | 837379 | C | 8/1955 |
| DE | 279486 | A1 | 6/1990 |
| DE | 279489 | A1 | 6/1990 |
| EP | 0028033 | A2 | 5/1981 |
| EP | 0034307 | A2 | 8/1981 |
| EP | 0043980 | A2 | 1/1982 |
| EP | 0055188 | A1 | 6/1982 |
| EP | 0204283 | A2 | 12/1986 |
| EP | 0226448 | A2 | 6/1987 |
| EP | 0279486 | A2 | 8/1988 |
| EP | 0321134 | A2 | 6/1989 |
| EP | 0408461 | A1 | 1/1991 |
| EP | 0727437 | A2 | 8/1996 |
| EP | 1100542 | A2 | 5/2001 |
| EP | 1100880 | A2 | 5/2001 |
| EP | 2349280 | A1 | 8/2011 |
| JP | S5599189 | A | 7/1980 |
| JP | S55135590 | A | 10/1980 |
| JP | S57192435 | A | 11/1982 |
| JP | S6255079 | A | 3/1987 |
| JP | S62223192 | A | 10/1987 |
| JP | H01216939 | A | 8/1989 |
| JP | H0354581 | A | 3/1991 |
| JP | H03148298 | A | 6/1991 |
| JP | H06255079 | A | 9/1994 |
| JP | H09154581 | A | 6/1997 |
| JP | H10500565 | A | 1/1998 |
| JP | H10502360 | A | 3/1998 |
| JP | H1175876 | A | 3/1999 |
| JP | 3148208 | B2 | 3/2001 |
| JP | 3148298 | B2 | 3/2001 |
| JP | 2002522399 | A | 7/2002 |
| JP | 2002524053 | A | 8/2002 |
| JP | 2003521937 | A | 7/2003 |
| JP | 2005241424 | A | 9/2005 |
| JP | 2008505656 | A | 2/2008 |
| JP | 2008535499 | A | 9/2008 |
| JP | 2008535500 | A | 9/2008 |
| JP | 2013009960 | A | 1/2013 |
| JP | 5599189 | B2 | 10/2014 |
| KR | 19980069019 | A | 10/1998 |
| KR | 0159107 | B1 | 11/1998 |
| KR | 100318706 | B1 | 12/2001 |
| KR | 100333148 | B1 | 12/2002 |
| KR | 100365606 | B1 | 2/2003 |
| KR | 100369838 | B1 | 9/2003 |
| KR | 100488848 | B1 | 5/2005 |
| RU | 2246318 | C2 | 2/2005 |
| RU | 2281954 | C2 | 8/2006 |
| RU | 2290439 | C2 | 12/2006 |
| WO | WO-8604145 | A1 | 7/1986 |
| WO | WO-8700056 | A1 | 1/1987 |
| WO | WO-9216221 | A1 | 10/1992 |
| WO | WO-9419007 | A1 | 9/1994 |
| WO | WO-9419470 | A1 | 9/1994 |
| WO | WO-9423735 | A1 | 10/1994 |
| WO | WO-9423740 | A1 | 10/1994 |
| WO | WO-9511987 | A1 | 5/1995 |
| WO | WO-9525785 | A1 | 9/1995 |
| WO | WO-9601274 | A1 | 1/1996 |
| WO | WO-9623064 | A1 | 8/1996 |
| WO | WO-9808873 | A1 | 3/1998 |
| WO | WO-9831383 | A1 | 7/1998 |
| WO | WO-0007629 | A2 | 2/2000 |
| WO | WO-0008196 | A2 | 2/2000 |
| WO | WO-0008196 | A3 | 3/2000 |
| WO | WO-0159078 | A2 | 8/2001 |
| WO | WO-02070007 | A1 | 9/2002 |
| WO | WO-03011211 | A2 | 2/2003 |
| WO | WO-03045436 | A1 | 6/2003 |
| WO | WO-2004092393 | A1 | 10/2004 |
| WO | WO-2005110386 | A2 | 11/2005 |
| WO | WO-2006110761 | A2 | 10/2006 |
| WO | WO-2006110819 | A2 | 10/2006 |
| WO | WO-2007100741 | A2 | 9/2007 |
| WO | WO-2008051178 | A2 | 5/2008 |
| WO | WO-2010071865 | A1 | 6/2010 |
| WO | WO-2010151823 | A1 | 12/2010 |
| WO | WO-2010151831 | A1 | 12/2010 |
| WO | WO-2011032175 | A1 | 3/2011 |
| WO | WO-2013066353 | A1 | 5/2013 |
| WO | WO-2017156513 | A1 | 9/2017 |
| WO | WO-2018089808 | A1 | 5/2018 |
| WO | 2018/169811 | A1 | 9/2018 |
| WO | WO-2020160322 | A1 | 8/2020 |
| WO | WO-2020160324 | A1 | 8/2020 |
| WO | WO-2020160325 | A1 | 8/2020 |
| WO | WO-2022035828 | A1 | 2/2022 |

OTHER PUBLICATIONS

Acetaminophen Extra Strength-acetaminophen tablet, Physicians Total Care, Inc., Apr. 29, 2016 (Apr. 29, 2016), pp. 1-4. Retrieved from the Internet: https://bit.ly/36wVn98 on Nov. 7, 2020 (Nov. 7, 2020).

Adams, P., et al., "Current Estimates From the National Health Interview Survey, 1996, " Vital Health Study, Oct. 1999, Series 10, No. 200, 212 Pages.

"Aggregate", Stedman's Medical Dictionary 27th Edition, PDR Electronic Library, Accessed on Jun. 10, 2009, 1 Page, Retrieved from URL: http://www.thomsonhe.com/pdrel/librarian/ND.

Alamillo J.M., et al, "Purification and Molecular Properties of Urate Oxidase From Chlamydomonas Reinhardtii," Biochimica et Biophysica Acta, Elsevier Science Publishers B.V., Netherlands, Jan. 29, 1991, vol. 1076, pp. 203-208.

Albert et al., Increased Efficacy and Tolerability of Pegloticase in Patients With Uncontrolled Gout Co-Treated With Methotrexate: A Retrospective Study. Rheumatol Ther. Jul. 27, 2020, vol. 7, pp. 639-648.

Al-Shawi A., et al., "A Novel Immunoradiometric Assay for Human Liver Ferritin," Journal of Clinical Pathology, Apr. 1983, vol. 36, No. 4, pp. 440-444, Abstract only.

Alvares K., et al., "Rat Urate Oxidase Produced by Recombinant Baculovirus Expression: Formation of Peroxisome Crystalloid Core-like Structures," Cell Biology, Proceedings of the National Academy of Sciences of the USA, Jun. 1992, vol. 89, pp. 4908-4912.

Alvares K., et al., "The Nucleotide Sequence of a Full Length cDNA Clone Encoding Rat Liver Urate Oxidase," Biochemical and Biophysical Research Communications, Academic Press, Inc., United States, Feb. 15, 1989, vol. 158, No. 3, pp. 991-995.

Alvarez-Hernandez et al., "Validation of the health assessment questionnaire disability index in patients with gout," Arthritis & Rheumatism, May 2008, vol. 59, No. 5, pp. 665-669.

Alvarez-Lario et al., "Uric acid and evolution," Rheumatology, Jul. 2010, 49, pp. 2010-2015.

"Amino Acid Sequence of Amino Truncated Chimeric Pig-Baboon Uricase," May 30, 2000, Retrieved from EBI Accession No. GSP: AAY69153, 2 Pages, XP002404207.

Antonopoulos C.A., et al., "The Precipitation of Polyanions by Long-Chain Aliphatic Ammonium Compounds," Biochimica et Biophysica Acta, Dec. 9, 1961, vol. 54, pp. 213-226.

Arellano et al., "Allopurinol hypersensitivity syndrome: a review," Mar. 1993, 27(3), pp. 337-343.

Assadi F., "Managing New Onset Gout in Pediatric Renal Transplant Recipients: when, how, to what extent," Journal of Nephrology, Jul.-Aug. 2013, 26(4), pp. 624-628 2013.

(56) References Cited

OTHER PUBLICATIONS

Augustsson J., et al., "Low-Dose Glucocorticoid Therapy Decreases Risk for Treatment-Limiting Infusion Reaction to Infliximab in Patients with Rheumatoid Arthritis," Extended Report, Annals of the Rheumatic Diseases, Nov. 2007, vol. 66, pp. 1462-1466.
Baraf et al., "Infusion-related reactions with pegloticase, a recombinant uricase for the treatment of chronic gout refractory to conventional therapy," Journal of Clinical Rheumatology, Dec. 2014, 20(8):427-432.
Baraf H.S.B., et al., "Resolution of Tophi With Intravenous Peguricase in Refractory Gout," Arthritis & Rheumatism, 2005, September Supplement, vol. 52, No. 9, p. S105.
Baraf H.S.B., et al., "Resolution of Tophi With Intravenous Peguricase in Refractory Gout," Presented at American College of Rheumatology, Annual Scientific Meeting, San Diego, CA, Poster 194, Nov. 13-17, 2005, 1 Page.
Baraf H.S.B., et al., "Resolution of Tophi With Intravenous Peguricase in Treatment-Failure Gout," Presented at the EULAR—Annual European Congress of Rheumatology, Amsterdam, Netherlands, Poster 465, Annals of the Rheumatic Diseases, Jun. 21-24, 2006, vol. 65, Supplement 2: 256, 1 Page.
Baraf H.S.B., et al., "Tophus Burden Reduction With Pegloticase: Results From Phase 3 Randomized Trials and Open-Label Extension in Patients With Chronic Gout Refractory to Conventional Therapy," Arthritis Research & Therapy, Sep. 26, 2013, vol. 15, No. 5:R137, 11 Pages.
Bayat S., et al., "Development of a Dual-Energy Computed Tomography Scoring System for Measurement of Urate Deposition in Gout," Arthritis Care & Research, Jun. 2016, vol. 68, No. 6, pp. 769-775.
Becker M., et al., "Activation of Hydroxylic Polymers—by Reaction with Carbonate or Chloroformate Ester in Presence of Amine," English Abstract, Derwent World Patents Index, Accession No. 8448552, 2004, 1 Page.
Becker M.A., et al., "Febuxocat Compared with Allopurinol in Patients with Hyperuricemia and Gout," The New England Journal of Medicine, Dec. 8, 2005, vol. 353, No. 23, pp. 2450-2461.
Becker M.A., "Hyperuricemia and Gout," The Metabolic and Molecular Bases of Inherited Disease, Edited by Scriver C.R, Beaudet A.L, Sly W.S, Valle D, 8th Edition, New York, McGraw-Hill, 2001, vol. 11, pp. 2513-2535.
Benbacer L., et al., "Interspecies Aminopeptidase-n Chimeras Reveal Species-specific Receptor Recognition by Canine Coronavirus, Feline Infectious Peritonitis Virus, and Transmissible Gastroenteritis Virus," Journal of Virology, Jan. 1997, vol. 71, No. 1, pp. 734-737, JPN6014045520.
Ben-Bassat A., et al., "Amino-Terminal Processing of Proteins," Nature, Mar. 19, 1987, vol. 326, 1 Page.
Ben-Bassat A., et al., "Processing of the Initiation Methionine From Proteins: Properties of the *Escherichia coli* Methionine Aminopeptidase and Its Gene Structure," Journal of Bacteriology, Feb. 1987, vol. 169, No. 2, pp. 751-757.
Berendsen H.J.C., "A Glimpse of the Holy Grail?," Science, Oct. 23, 1998, vol. 282, pp. 642-643.
Berhanu A., et al., "Pegloticase Failure and a Possible Solution: Immunosuppression to Prevent Intolerance and Inefficacy in Patients With Gout," Seminars in Arthritis and Rheumatism, 2017, vol. 46, No. 6, pp. 754-758.
Bessen et al., "Concomitant immunosuppressant use with pegloticase in patients with tophaceous gout—a case series," International Journal of Clinical Rheumatology 2019;14(6):238-245.
Bessen et al., "Recapture and improved outcome of pegloticase response with methotrexate—A report of two cases and review of the literature," Seminars in Arthritis and Rheumatism, Accepted Manuscript, (2018), 12 pages.
Bessen et al., "Recapture and improved outcome of pegloticase response with methotrexate—A report of two cases and review of the literature," Seminars in Arthritis and Rheumatism, Aug. 2019, vol. 49, No. 1, pp. 56-61.
Bird, R. E., et al., "Single-chain antigen-binding proteins", Science (1988); 242(4877): 423-426.
Bleyer et al., "Pharmacokinetics and pharmacodynamics of pegloticase in patients with end-stage renal failure receiving hemodialysis," May 2015, 83(5), pp. 286-292, https://pubmed.ncbi.nlm.nih.gov/25816806/.
Blumberg B.S., et al., "Further Evidence on the Protein Complexes of Some Hyauronic Acids," Biochemical Journal, Jan. 1958, vol. 68, pp. 183-188.
Bossavy J.P., et al., "Comparison of the Antithrombotic Effect of PEG-Hirudin and Heparin in a Human Ex Vivo Model of Arterial Thrombosis," Arteriosclerosis, Thrombosis and Vascular Biology, Journal of the American Heart Association, United States, May 1999, vol. 19, pp. 1348-1353.
Botson et al., "Pegloticase in combination with methotrexate in patients with uncontrolled gout: A multicenter, open-label study (MIRROR)," The Journal of Rheumatology, May 2021;48:767-774, doi: 10.3899/jrheum.200460.
Botson et al., "Pretreatment and Coadministration with Methotrexate Improved Durability of Pegloticase (Krystexxa) Response: A Prospective, Proof-of-Concept, Case Series," Abstract, Arthritis Rheumatology, 2018; 70 (suppl 10), https://acrabstracts.org/abstract/pretreatment-andcoadministration- with-methotrexate-improved-durability-of-pegloticase-krystexxa-response-aprospective- proof-of-concept-case-series/, Accessed Sep. 11, 2018, 2 pages.
Botson et al., "Pretreatment and co-administration with methotrexate improved durability of pegloticase response: a prospective observational, proof-of-concept, case series [Abstract]," SAT0404 Annals of the Rheumatic Diseases, Jun. 2019, vol. 78, Issue Suppl. 2, A1289-A1290.
Botson et al., "Pretreatment and Co-Administration with Methotrexate Improved Durability of Pegloticase Response: A Prospective, Observational, Proof-of-Concept, Case Series," Poster presented at the 2018 Annual Scientific Meeting of the American College of Rheumatology, Oct. 19-24, 2018, 1 page.
Botson et al., "Pretreatment and co-administration with methotrexate improved durability of pegloticase response," Journal of Clinical Rheumatology, vol. 28, No. 1, Jan. 2022, e129-e134.
Bradley C.M., et al., "Limits of Cooperativity in a Structurally Modular Protein: Response of the Notch Ankyrin Domain to Analogous Alanine Substitutions in Each Repeat," Journal of Molecular Biology, Nov. 22, 2002, vol. 324, pp. 373-386.
Braun A., et al., "Development and Use of Enzyme-Linked Immunosorbent Assays (ELISA) for the Detection of Protein Aggregates in Interferon-Alpha (IFN-.alpha) Formulations," Pharmaceutical Research, Plenum Publishing Corporation, United States, Oct. 1997, vol. 14, No. 10, pp. 1394-1400.
Braun A., et al., "Protein Aggregates Seem to Play a Key Role Among the Parameters Influencing the Antigenicity of Interferon Alpha (IFN-.alpha.) in Normal and Transgenic Mice," Pharmaceutical Research, Plenum Publishing Corporation, United States, Oct. 1997, vol. 14, No. 10, pp. 1472-1478.
Brenda Enzyme Database: "E.C. 1.7.3.3, Urate Oxidase," 42 Pages, [Retrieved on Mar. 27, 2008] Retrieved from URL: www.brenda-enzymes.info.
Bringham, M. D. et al., "Immunosuppressant Use and Gout in the Prevalent Solid Organ Transplantation Population," J of the American Society of Nephrology, Progress in Transplantation, Jun. 2020, 30(2), pp. 103-110.
Broadwell et al., "Community Practice Experiences with a Variety of Immunomodulatory Agents Co-Administered with Pegloticase for the Treatment of Uncontrolled Gout," Rheumatology and Therapy, Dec. 2022, 9(6), pp. 1549-1558.
Buch M.H., et al., "Shortening Infusion Times for Infliximab Administration," Rheumatology, Apr. 2006, vol. 45, pp. 485-486.
Burnham N.L., "Polymers for Delivering Peptides and Proteins," American Journal of Hospital Pharmacy, American Society of Hospital Pharmacists, Inc., United States, Jan. 15, 1994, vol. 51, pp. 210-218.
Calabrese L.H., et al., "Frequency, Distribution and Immunologic Nature of Infusion Reactions in Subjects Receiving Pegloticase for Chronic Refractory Gout," Arthritis Research & Therapy, Dec. 2017, vol. 19, No. 1:19, 1-7 Pages.

(56) References Cited

OTHER PUBLICATIONS

Caliceti P., et al., "Biopharmaceutical Properties of Uricase Conjugated to Neutral and Amphiphilic Polymers," Bioconjugate Chemistry, American Chemical Society, Jun. 2, 1999, vol. 10, No. 4, pp. 638-646.
Carter W.A., "Interferon: Evidence for Subunit Structure," Proceedings of the National Academy of Sciences of the United States of America, Oct. 1970, vol. 67, No. 2, pp. 620-628.
Chen et al., " Contemporary Prevalence of Gout and Hyperuricemia in the United States and Decadal Trends: The National Health and Nutrition Examination Survey 2007-2016," Arthritis Rheumatology, Jun. 2019; 71(6), pp. 991-999.
Chen R.H.-L., et al., "Properties of Two Urate Oxidases Modified by the Covalent Attachment of Poly(Ethylene Glycol)," Biochimica et Biophysica Acta (BBA)—Enzymology, Aug. 13, 1981, vol. 660, pp. 293-298.
Chua C.C., et al., "Use of Polyethylene Glycol-Modified Uricase (PEG-Uricase) to Treat Hyperuricemia in a Patient with Non-Hodgkin Lymphoma," Annals of Internal Medicine, American College of Physicians, United States, Jul. 15, 1988, vol. 109, pp. 114-117.
Cipolleta E., et al., "Association between gout flare and subsequent cardiovascular events among patients with gout," JAMA, Aug. 2022, 328(5), pp. 440-450.
Cipolleta, E., et al., "Risk of venous thromboembolism with gout flares," Arthritis & Rheumatology, Feb. 2023, 30 pages.
Clark R., et al., "Long-acting Growth Hormone Produced by Conjugation with Polyethylene Glycol," Journal of Biological Chemistry, Sep. 6, 1996, vol. 271, No. 36, pp. 21969-21977.
ClinicalTrials.gov Identifier NCT02598596 (Year: 2015), 14 pages.
ClinicalTrials.gov Identifier NCT03303989 (Year: 2017), 30 pages.
Clive, D. M. "Renal Transplant-Associated Hyperuricemia and Gout," Journal of the American Society of Nephrology, May 1, 2000 (May 1, 2000), vol. 11, No. 5, pp. 974-979.
Cole, S. et al. "The EBV-Hybridoma Technique and Its Application to Human Lung Cancer," Monoclonal Antibodies and Cancer Therapy 27, Jan. 1985, pp. 77-96.
Colloc'H N., et al., "Crystal Structure of the Protein Drug Urate Oxidase-Inhibitor Complex at 2.05 ANG. Resolution," Nature Structural Biology, Nature Publishing Group, Nov. 1997, vol. 4, No. 11, pp. 947-952.
Conley T.G., et al., "Thermodynamics and Stoicheiometry of the Binding of Substrate Analogues to Uricase," Biochemical Journal, The Biochemical Society, United Kingdom, Jun. 1, 1980, vol. 187, pp. 727-732.
Cooper J.F., "Resolving LAL Test Interferences," Journal of Parenteral Science and Technology, Jan.-Feb. 1990, vol. 44, No. 1, pp. 13-15.
Cote, R. et al., "Generation of human monoclonal antibodies reactive with cellular antigens," Proceedings of the National Academy of Sciences, Apr. 1983, vol. 80, pp. 2026-2030.
Crivelli E., et al., "A Single Step Method for the Solubilization and Refolding of Recombinant Protein from *E. coli* Inclusion Bodies," Australian Journal of Biotechnology, Apr. 1991, vol. 5, No. 2, pp. 78-80, 86.
Davis F.F., et al., "Enzyme-Polyethylene Glycol Adducts: Modified Enzymes with Unique Properties," In Enzyme Engineering, Edited by Broun G.B., et al., Plenum Press, New York, 1978, vol. 4, pp. 169-173.
Davis S., et al., "Hypouricaemic Effect of Polyethyleneglycol Modified Urate Oxidase," The Lancet, London, GB, Aug. 8, 1981, pp. 281-283, XP000577404.
Declaration of Fischer M., Under 37 C.F.R Section 1.132 for U.S. Appl. No. 11/918,292, mailed Aug. 17, 2011, 3 Pages.
Declaration of Rosario-Jansen T., et al., Under 37 C.F.R. Section 1.132 for U.S. Appl. No. 13/379,704, mailed Jul. 24, 2014, 4 Pages.
Declaration of Sherman M.R., Ph.D. Under 37 C.F.R. Section 1.132 for U.S. Appl. No. 09/501,730, mailed Sep. 20, 2002, 5 Pages.
Declaration of Sherman M.R., Under 37 C.F.R. Section 1,132 for U.S. Appl. No. 09/839,946, mailed Sep. 18, 2007, 19 Pages.
Declaration of Sherman M.R., Under 37 C.F.R. Section 1,132 for U.S. Appl. No. 09/839,946, mailed May 26, 2005, 8 Pages.
Delgado et al., "The uses and properties of PEG-linked proteins". Critical Reviews in Therapeutic Drug Carrier Systems (Jan. 1, 1992); 9(3-4): 249-304.
Derynck R., et al., "Expression of Human Fibroblast Interferon Gene in *Escherichia coli*," Nature, Sep. 18, 1980, vol. 287, pp. 193-197.
Donadio, D., et al., "Anaphylaxis-like Manifestations After Intravenous Injection of Urate Oxidase in an Asthmatic Child With Acute Leukemia," La Nouvelle Presse Medicale, 1981, vol. 10, pp. 711-712. (1 page English Translation).
"EC 1.7.3.3, urate oxidase," BRENDA Enzyme Database, available via internet at www.brenda.uni-koeln.de/ (cited in related U.S. Appl. No. 09/501,730, filed Feb. 10, 2000, in Notice of Allowance dated Jan. 13, 2004), 25 pages.
Embery, G., "Glycosaminoglycans of Human Dental Pulp," Journal de Biologie Buccale, Sep. 1976, vol. 4, pp. 229-236.
Emmerson, B.T., "The Management of Gout," The New England Journal of Medicine, Feb. 15, 1996, vol. 334, No. 7, pp. 445-451.
Estimated Glomerular Filtration Rate (eGFR), Kidney Health Australia, May 31, 2017, (Apr. 31, 2017), pp. 1-3. Retrieved from the Internet: https://kidney.org.au/uploads/resources/egfr-fact-sheet.pdf on Nov. 7, 2020 (Nov. 7, 2020).
European Examination Report for European Application No. 01923265.1, dated Dec. 13, 2007, European Patent Office, Munich, DE, 6 Pages.
European Search Report for European Application No. 05011069.1, mailed Aug. 5, 2005, 6 Pages.
European Search Report for European Application No. 99938996.8, mailed Mar. 4, 2002, 2 Pages.
"ExPasy ProtParam Tool," pp. 1-2, [Retrieved on Dec. 19, 2018], Retrieved from the Internet: URL: https://web.expasy.org/cgi-bin/protparam/protparam.
Extended European Search Report for European Application No. 09175303.8, mailed Jan. 26, 2010, 6 Pages.
Extended European Search Report for European Application No. 10007912.8, mailed Oct. 25, 2010, 06 Pages.
Extended European Search Report for European Application No. 10158016.5, mailed May 11, 2010, 10 Pages.
Extended European Search Report for European Application No. 10180428.4, mailed Feb. 24, 2011, 7 Pages.
Extended European Search Report for European Application No. 10180672.7, mailed Mar. 30, 2011, 6 Pages.
Extended European Search Report for European Application No. 10792756.8, mailed Oct. 18, 2013, 04 Pages.
Extended European Search Report for European Application No. 14192835.8, mailed Jun. 5, 2015, 9 Pages.
Extended European Search Report for European Application No. 15156612.2, mailed Aug. 14, 2015, 7 Pages.
Extended European Search Report for European Application No. 17192971.4, mailed Feb. 7, 2018, 8 Pages.
Extended European Search Report for European Application No. 17869608.4, mailed Jul. 1, 2020, 10 Pages.
Extended European Search Report for European Application No. 18214393.3, mailed Apr. 12, 2019, 5 Pages.
Extended European Search Report for European Application No. 20857655.3, mailed Mar. 20, 2023, 10 pages.
Fam, A.G., "Strategies and Controversies in the Treatment of Gout and Hyperuricaemia," Bailliere's Clinical Rheumatology: International Practice and Research, Elsevier Science Ltd., Aug. 1990, vol. 4, No. 2, pp. 177-192.
FDA—Drug Safety Brouchure—Ref ID 3116893, Published on the Web for Krystexxa, Apr. 2012, pp. 1-14, Retrieved from URL: http://www.accessdata.fda.gov/drugsatfda_docs/label/2012/125293s034lbl.pdf.
"FDA Approves KRYSTEXXA® (pegloticase) Injection Co-Administered with Methotrexate, Expanding the Labeling to Help More People with Uncontrolled Gout Achieve a Complete Response to Therapy," BENZINGA, Business Wire Press Releases, Jul. 8, 2022, 4 pages.
"FDA Approves KRYSTEXXA® (pegloticase) Injection Co-Administered with Methotrexate, Expanding the Labeling to Help

(56) References Cited

OTHER PUBLICATIONS

More People with Uncontrolled Gout Achieve a Complete Response to Therapy," BioSpace, Jul. 8, 2022, 5 pages.

"FDA Approves KRYSTEXXAR (pegloticase) Injection Co-Administered with Methotrexate, Expanding the Labeling to Help More People with Uncontrolled Gout Achieve a Complete Response to Therapy," StreetInsider, Business Wire, Press Releases, Jul. 8, 2022, 3 pages.

"FDA Approves KRYSTEXXA® (pegloticase) Injection Co-Administered with Methotrexate, Expanding the Labeling to Help More People with Uncontrolled Gout Achieve a Complete Response to Therapy," Yahoo!Finance, Business Wire, Press Releases, Jul. 8, 2022, 4 pages.

"FDA Approves Peglioticase Injection Plus Methotrexate for Patients with Uncontrolled Gout," Rheumatology Network, Jul. 8, 2022, 1 page.

"FDA approves peglioticase, methotrexate combo in patients with uncontrolled gout," Healio Rheumatology, Jul. 8, 2022, 2 pages.

"FDA Approves Peglioticase Plus Methotrexate for Uncontrolled Gout," HCPLive, Jul. 8, 2022, 1 page.

"FDA approves pegloticase injection coadministered with methotrexate for gout," AJMC, Jul. 8, 2022, 2 pages.

"FDA decisions to watch in rheumatology in Second Half of 2022," Rheumatology Network, Jun. 29, 2022, 3 pages.

Flinta, C., et al., "Sequence Determinants of Cytosolic N-Terminal Protein Processing," European Journal of Biochemistry, Jan. 2, 1986, vol. 154, No. 1, pp. 193-196.

Forrest A., et al., "A New Approach for Designing Population Sparse Sampling Strategies—Applied to Ciprofloxacin PKS," Abstracts of Papers, Feb. 1991, vol. 49, No. 2, p. 153.

Francis, G., et al., "PEGylation of Cytokines and other Therapeutic Proteins and Peptides: the Importance of Biological Optimisation of Coupling Techniques," International Journal of Hematology, Jul. 1998, vol. 68, pp. 1-18, 19 pages.

Freyne, B., "A Case Report of Immunosuppressant Medication-Associated Polyarticular Tophaceous Gout Successfully Treated Using the Polyethylene Glycol-Conjugated Uricase Enzyme Pegloticase," Transplantation Proceedings, vol. 50, Dec. 2018, E-published Mar. 9, 2018, pp. 4099-4101.

Fridovich I., "The Competitive Inhibition of Uricase by Oxonate and by Related Derivatives of s-Triazines," The Journal of Biological Chemistry, Jun. 1965, vol. 240, No. 6, pp. 2491-2494.

Friedman T., et al., "The Urate Oxidase Gene of *Drosophila pseudoobscura* and *Drosophila melanogaster*: Evolutionary Changes of Sequence and Regulation," Journal of Molecular Evolution, Jan. 1992, vol. 34, No. 1, pp. 62-77, Abstract only.

Fuertges F., et al., "The Clinical Efficacy of Poly (Ethylene Glycol)-Modified Proteins," Journal of Controlled Release, Elsevier Science, The Netherlands, Jan. 1990, vol. 11, pp. 139-148.

Fujita T., et al., "Tissue Distribution of In-Labeled Uricase Conjugated with Charged Dextrans and Polyethylene Glycol," Journal of Pharmacobio-Dynamics, Pharmaceutical Society of Japan, Nov. 1991, vol. 14, pp. 623-629.

Gaertner H.F., et al., "Site-Specific Attachment of Functionalized Poly(ethylene glycol) to the Amino Terminus of Proteins," Bioconjugate Chemistry, American Chemical Society, United States, Jan. 30, 1996, vol. 7, No. 1, pp. 38-44.

Gaffo et al., "Developing a provisional definition of flare in patients with established gout," May 2012, 64(5), pp. 1508-1517, https://pubmed.ncbi.nlm.nih.gov/22083456/.

Ganson N.J., et al., "Antibodies to Polyethylene Glycol (PEG) during Phase I Investigation of PEG-Urate Oxidase (PEG-uricase; Puricase.RTM.) for Refractory Gout," Presented at American College of Rheumatology Annual Scientific Meeting at San Antonio, TX, Oct. 16-21, 2004, Poster 808, 7 Pages.

Ganson N.J., et al., "Control of Hyperuricemia in Subjects with Refractory Gout, and Induction of Antibody against Poly(ethylene Glycol) (PEG), in a Phase I Trial of Subcutaneous PEGylated Urate Oxidase," Arthritis Research and Therapy, 2005, vol. 8, No. 1 : (R12), pp. 1-10.

Giglione C., et al., "Control of Protein Life-span by N-terminal Methionine Excision," The EMBO—European Molecular Biology Organization Journal, Jan. 2, 2003, vol. 22, No. 1, pp. 13-23.

Goeddel D.V., et al., "Human Leukocyte Interferon Produced by *E. coli* Is Biologically Active," Nature, Oct. 2, 1980, vol. 287, 6 Pages.

Goldman S.C., et al., "A Randomized Comparison Between Rasburicase and Allopurinol in Children with Lymphoma or Leukemia at High Risk for Tumor Lysis," Blood, May 15, 2001, vol. 97, No. 10, pp. 2998-3303.

Goss et al., "Methotrexate Dose in Patients With Early Rheumatoid Arthritis Impacts Methotrexate Polyglutamate Pharmacokinetics, Adalimumab Pharmacokinetics, and Efficacy: Pharmacokinetic and Exposure-response Analysis of the CONCERTO Trial," Clinical Therapeutics, vol. 40, Issue 2, Feb. 2018, pp. 309-319.

Greenberg M.L., et al., "A Radiochemical-High-Performance Liquid Chromatographic Assay for Urate Oxidase in Human Plasma," Analytical Biochemistry, Academic Press, Inc., United States, Feb. 1, 1989, vol. 176, pp. 290-293.

Guttmann A., et al., "Pegloticase in Gout Treatment—Safety Issues, Latest Evidence and Clinical Considerations," Therapeutic Advances in Drug Safety, Dec. 2017, vol. 8, No. 12, pp. 379-388.

Hamburger, S., et al., "Arthritis Advisory Committee Meeting, Pegloticase (Krystexxa) IV fusion," dated Jun. 16, 2009, pp. 1-155, [Retrieved on Aug. 4, 2010], Available on the internet:< url: http=""www.fda.gov/downloads/AdvisoryCommittees/CommitteesMeetingMaterials/DrugsAdvisoryCommittee/UCM167777.pdf, Especially, pp. 108-115.< /url:>.

Hande K.R., et al., "Severe Allopurinol Toxicity. Description and Guidelines for Prevention in Patients in Renal Insufficiency," The American Journal of Medicine, Excerpta Medica, United States, Jan. 1984, vol. 76, pp. 47-56.

Harris J.M., et al., "Effect of Pegylation on Pharmaceuticals," Nature Reviews Drug Discovery, Mar. 2003, vol. 2, No. 3, pp. 214-221.

Hartman et al., Examiner Initiated Interview Summary for U.S. Appl. No. 11/918,297, mailed Jan. 25, 2012, 1 Page.

Hartman et al., Non-Final Office Action for U.S. Appl. No. 11/918,297, dated Aug. 26, 2011; 26 pages.

Hartman et al., Notice of Allowance for U.S. Appl. No. 11/918,297, mailed Jan. 25, 2012, 10 Pages.

Hartmann G., "Exchange In Vitro of Subunits between Enzymes from Different Organisms: Chimeras of Enzymes," Angewandte Chemie International edition in English, Apr. 1976, vol. 15, No. 4, pp. 181-186, JPN6014045522.

Hascall V., et al., "Aggregation of Cartilage Proteoglycans," Journal of Biological Chemistry, Jul. 10, 1974, vol. 249, No. 13, pp. 4232-4241, pp. 4242-4249, and pp. 4250-4256.

Hazen J., "Adjuvants—Terminology, Classification, and Chemistry," Weed Technology, Oct. 2000, vol. 14, pp. 773-784.

Hedlund L., et al., "Magnetic Resonance Microscopy of Toxic Renal Injury by Bromoethylamine in Rats," Fundamental and Applied Toxicology, Academic Press, May 1991, vol. 16, pp. 787-797.

Heftmann E., et al., "Chromatography: Fundamentals and Applications of Chromatographic and Electrophoretic Methods. Part A: Fundamentals and Techniques," Journal of Chromatography, 1983, vol. 22A, pp. A104-A110.

Heinegard D., et al., "Characterization of Chondroitin Sulfate Isolated from Trypsin-Chymotrypsin Digests of Cartilage Proteoglycans," Archives of Biochemistry and Biophysics, Nov. 1974, vol. 165, No. 1, pp. 427-441.

Henney C., et al., "Antibody Production to Aggregated Human gamma.G-Globulin in Acquired Hypogammaglobulinemia," New England Journal of Medicine, Massachusetts Medical Society, United States, May 23, 1968, vol. 278, pp. 1144-1146.

Herbst R., et al., "Folding of Firefly (*Photinus pyralis*) Luciferase: Aggregation and Reactivation of Unfolding Intermediates," Biochemistry, Apr. 17, 1998, vol. 37, No. 18, pp. 6586-6597.

Hershfield et al., Final Office Action for U.S. Appl. No. 09/762,097, mailed Aug. 1, 2005, 5 Pages.

Hershfield et al., U.S. Appl. No. 09/762,097.

Hershfield et al., Non-Final Office Action for U.S. Appl. No. 09/762,097, mailed Oct. 15, 2002, 8 Pages.

(56) References Cited

OTHER PUBLICATIONS

Hershfield et al., Non-Final Office Action for U.S. Appl. No. 09/762,097, mailed Mar. 16, 2005, 6 Pages.
Hershfield et al., Non-Final Office Action for U.S. Appl. No. 09/762,097, mailed Oct. 24, 2003, 6 Pages.
Hershfield et al., Notice of Allowance for U.S. Appl. No. 09/762,097, mailed Nov. 21, 2005, 5 Pages.
Hershfield M., "Biochemistry and Immunology of Poly(ethylene glycol)-Modified Adenosine Deaminase (PEG-ADA)," In: ACS Symposium Series 680, Poly(ethylene glycol), Chemistry and Biological Applications, Harris J.M., and Zaplipsky S., eds., American Chemical Society, Washington, DC, Apr. 1997, pp. 145-154.
Hershfield M et al., "Induced and Pre-Existing Anti-Polyethylene Glycol Antibody in a Trial of Every 3-Week Dosing of Pegloticase for Refractory Gout, including in organ transplant recipients," Arthritis Research & Therapy, Mar. 2014, 16(2), pp. 1-11.
Hershfield M.S., et al., "Use of Site-Directed Mutagenesis to Enhance the Epitope-Shielding Effect of Covalent Modification of Proteins with Polyethylene Glycol," Proceedings of the National Academy of Sciences of the United States of America, Aug. 15, 1991, vol. 88, pp. 7185-7189.
Hess et al., "Cancer metabolism and oxidative stress: Insights into carcinogenesis and checmotherapy via the non-dihydrofolate reductase effects on methotrexate," BB Clinical 3, Jun. 2015, pp. 152-161.
Highlights of Prescribing Information for Allegra (fexofenadine hydrochloride) tablets, ODT 1-18, orally disintegrating tablets) and oral suspension, Jul. 31, 2007 (Apr. 31, 2007, pp. 1-19. Retrieved from the Internet www.accessdata.fda.gov/drugsatfda_docs/label/2008/020872s018,021963s0021bl.pdf on Nov. 7, 2020 (Nov. 7, 2020).
Hinds K., et al., "Synthesis and Characterization of Poly(Ethylene Glycol)-Insuline Conjugates," Bioconjugate Chemistry, American Chemical Society, United States, Feb. 15, 2000, vol. 11, pp. 195-201.
Hirel P., et al., "Extent of N-terminal Methionine Excision from *Escherichia coli* Proteins is Governed by the Side-Chain Length of the Penultimate Amino Acid," Proceedings of the National Academy of Sciences of the United States of America, Jul. 24, 1989, vol. 86, pp. 8247-8251.
"Horizon gets FDA approval for Krystexxa's use with methotrexate for uncontrolled gout," Seeking Alpha, Ravikash, SA News Editor, Jul. 8, 2022, 2 pages.
Horizon, "Horizon Therapeutics plc announces FDA has granted priority review of the supplemental biologics license application (sBLA) for the concomitant use of KRYSTEXXA® (pegloticase injection) plus methotrexate for people living with uncontrolled gout," Mar. 7, 2022, 3 pages.
"Horizon's Krystexxa wins FDA combo nod to fight drug resistance," Fierce Pharm, Jul. 8, 2022, 3 pages.
"Horizon nabs FDA expanded label for gout med Krystexxa," Endpoints, Jul. 8, 2022, 2 pages.
"Horizon Therapeutics: FDA Approves Expanded Labeling for KRYSTEXXA With Methotrexate," Nasdaq, Jul. 8, 2022, 1 page.
"Horizon Therapeutics: FDA approves expanded labeling for KRYSTEXXA with methotrexate," RTTNews, Published Jul. 8, 2022, 5 pages.
"Horizon therapeutics receives FDA approval for uncontrolled gout candidate," BENZINGA, Jul. 8, 2022, 7 pages.
Hortnagl H., et al., "Membrane Proteins of Chromaffin Granules, Dopamine-Hydroxylase, A Major Constituent," Biochemical Journal, Aug. 1972, vol. 129, No. 1, pp. 187-195.
Huang et al., "Specificity of cotranslational amino-terminal processing of proteins in yeast," Biochemistry, Dec. 1987, 26(25), pp. 8242-8246, https://pubmed.ncbi.nlm.nih.gov/3327521/.
Huse W.D., et al., "Generation of a Large Combinatorial Library of the Immunoglobulin Repertoire in Phage Lambda," Research Article, Dec. 8, 1989, vol. 246, pp. 1275-1281.
Huston U.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, Aug. 1988, vol. 85, pp. 5879-5883.
Inada Y., et al. "Biomedical and Biotechnological Applications of PEG- and PM-Modified Proteins," Trends Biotechnology, Elsevier Science Limited, Mar. 1995, vol. 13, pp. 86-91.
Information on EC 1.7.3.3—Urate Oxidase: Retrieved from URL: www.brenda-enzymes.org/php/flat.sub.--result.php4?ecno=1.7.3.3&organisms-ub.--list=&Suchword=, Date Jul. 20, 2009, 53 pages.
International Preliminary Report on Patentability for International Application No. PCT/US1999/017678, mailed Aug. 24, 2000, 5 Pages.
International Preliminary Report on Patentability for International Application No. PCT/US2001/040069, mailed May 24, 2002, 2 Pages.
International Preliminary Report on Patentability for International Application No. PCT/US2006/013502, mailed Jul. 16, 2007, 5 Pages.
International Preliminary Report on Patentability for International Application No. PCT/US2006/013660, mailed Mar. 20, 2012, 5 Pages.
International Preliminary Report on Patentability for International Application No. PCT/US2006/013751, mailed Jun. 2, 2014, 05 Pages.
International Preliminary Report on Patentability for International Application No. PCT/US2010/040082, mailed Jan. 12, 2012, 07 Pages.
International Preliminary Report on Patentability for International Application No. PCT/US2017/061126, mailed May 23, 2019, 08 Pages.
International Preliminary Report on Patentability for International Application No. PCT/US2020/015956, mailed Aug. 12, 2021, 10 Pages.
International Preliminary Report on Patentability for International Application No. PCT/US2020/015958, mailed Aug. 12, 2021, 12 Pages.
International Preliminary Report on Patentability for International Application No. PCT/US2020/015959, mailed Aug. 12, 2021, 13 Pages.
International Preliminary Report on Patentability for International Application No. PCT/US2020/048803, mailed Mar. 10, 2022, 9 Pages.
International Preliminary Report on Patentability for International Application No. PCT/US2021/045350 dated Feb. 23, 2023, 8 pages.
International Search Report and Written Opinion for International Application No. PCT/US2001/040069, mailed Dec. 12, 2001, 4 Pages.
International Search Report and Written Opinion for International Application No. PCT/US2006/013751, mailed Sep. 6, 2006, 10 Pages.
International Search Report and Written Opinion for International Application No. PCT/US2010/040082, mailed Aug. 19, 2010, 08 Pages.
International Search Report and Written Opinion for International Application No. PCT/US2017/061126, mailed Feb. 20, 2018, 11 Pages.
International Search Report and Written Opinion for International Application No. PCT/US2020/015956, mailed May 5, 2020, 13 Pages.
International Search Report and Written Opinion for International Application No. PCT/US2020/015959, date of mailing Apr. 8, 2020, 16 pages.
International Search Report and Written Opinion for International Application No. PCT/US2020/048803, mailed Nov. 24, 2020, 13 Pages.
International Search Report and Written Opinion for International Application No. PCT/US2021/045350, mailed Dec. 27, 2021, 10 Pages.
International Search Report and Written Opinion of the International Search Authority for International Application No. PCT/US2006/013660, mailed Nov. 17, 2006, 10 Pages.

(56) References Cited

OTHER PUBLICATIONS

International Search Report and Written Opinion of the International Searching Authority for International Application No. PCT/US2006/013502, mailed Dec. 13, 2006, 10 Pages.
International Search Report and Written Opinion of the International Searching Authority for International Application No. PCT/US2010/040093, mailed Aug. 19, 2010, 6 Pages.
International Search Report and Written Opinion of the International Searching Authority for International Application No. PCT/US2020/015958, mailed Apr. 14, 2020, 14 Pages.
International Search Report for International Application No. PCT/US1999/017514, mailed Mar. 17, 2000, 5 Pages.
International Search Report for International Application No. PCT/US1999/017678, mailed Feb. 2, 2000, 4 Pages.
International Search Report for International Application No. PCT/US2000/017398, mailed Dec. 6, 2000, 3 Pages.
Ishino, K., et al., "Protein Concentration Dependence on Aggregation Behavior and Properties of Soybean 7S and 11S Globulins during Alkali-Treatment," Agricultural and Biological Chemistry, Jun. 1980, vol. 44, No. 6, pp. 1259-1266.
Ito M., et al., "Identification of an Amino Acid Residue Involved in the Substrate-binding Site of Rat Liver Uricase by Site-directed Mutagenesis," Biochemical and Biophysical Research Communications, Academic Press, United States, Aug. 31, 1992, vol. 187, pp. 101-107.
Jani et al., "The role of DMARDs in reducing the immunogenicity of TNF inhibitors in chronic inflammatory diseases," Rheumatology, 53(2), Feb. 2014, pp. 213-222.
Jaques L., "The Reaction of Heparin with Proteins and Complex Bases," Biochemical Journal, Jul. 1943, vol. 37, pp. 189-195.
Johnson G., et al., "Magnetic Resonance Microscopy in the Life Sciences," Reviews of Magnetic Resonance in Medicine, 1992, vol. 4, pp. 187-219.
Jones A., "The Isolation of Bacterial Nucleic Acids using Cetyltrimethylammonium Bromide," Biochimica et Biophysica Acta, Apr. 1953, vol. 10, pp. 607-612.
Kabat E.A., et al., "Sequences of Proteins of Immunological Interest," US Department of Health and Human Services, 1983, 4 Pages.
Kahn K., et al., "Kinetic Mechanism and Cofactor Content of Soybean Root Nodule Urate Oxidase," Biochemistry, American Chemical Society, United States, Apr. 15, 1997, vol. 36, pp. 4731-4738.
Karri et al., "Methotrexate and Leucovorin exposure modulates biochemical markers in female accessory reproductive organs of albino rats," General Endocrinology, Jul. 2012, pp. 369-386, doi: 10.4183/aeb.2012.369.
Kawata AK., et al., "Validation of the Sf-36 and Haq-Di in Patients With Treatment-Failure Gout," Annals of the Rheumatic Diseases, 2007, 66 (Suppl II), 236, Poster 359, 1 Page.
Keenan et al., "The effect of immunomodulators on the efficacy and tolerability of pegloticase: a systematic review," Seminars in Arthritis and Rheumatism, vol. 51, No. 2, Apr. 2021, pp. 347-352.
Keenan et al., "Use of Pre-Infusion Serum Uric Acid Levels as a Biomarker for Infusion Reaction Risk in Patients on Pegloticase," Rheumatology and Therapy, Jun. 2019, 6(2), pp. 299-304, Epub Mar. 14, 2019, https://pubmed.ncbi.nlm.nih.gov/30875075/.
Kelly S.J., et al., "Diabetes Insipidus in Uricase-Deficient Mice: A Model for Evaluating Therapy with Poly(Ethylene Glycol)-Modified Uricase," Journal of the American Society of Nephrology, Lippincott Williams & Wilkins, United States, May 2001, vol. 12, pp. 1001-1009.
Khanna et al., "2012 American College of Rheumatology Guidelines for Management of Gout Part I: Systematic Non-Pharmacologic and Pharmacologic Therapeutic Approaches to Hyperuricemia," Arthritis Care & Research, Oct. 2012, 64(10), pp. 1431-1466 (28 pages).
Khanna et al., "2012 American College of Rheumatology Guidelines for Management of Gout Part II: Therapy and Anti-Inflammatory Prophylaxis of Acute Gouty Arthritis," Arthritis Care & Research, Oct. 2012, 64(10), pp. 1447-1461 (23 pages).
Khanna et al., "Reducing Immunogenicity of Pegloticase (RECIPE) with Concomitant use of Mycophenolate Mofetil in Patients with Refractory Gout—a Phase II Double Blind Randomized Controlled Trial," ACR Convergence 2020, Abstract #0952, Nov. 2020, 5 pages.
Khanna et al., "Reducing Immunogenicity of Pegloticase (RECIPE) with Concomitant use of Mycophenolate Mofetil in Patients with Refractory Gout—a Phase II Double Blind Randomized Controlled Trial," ACR Convergence Where Rheumatology Meets, Abstract #0952, Nov. 2020, Final Presentation, 17 pages.
Khanna et al., "Reducing Immunogenicity of Pegloticase with Concomitant use of Mycophenolate Mofetil in Patients with Refractory Gout: A Phase II, Randomized, Double-Blind, Placebo-Controlled Trial," Arthritis & Rheumatology, vol. 73, No. 8, Aug. 2021, pp. 1523-1532.
Kidney International, "Kidney Disease: Improving Global Outcomes (KDIGO) Guidelines," Aug. 2009, vol. 76, Supplement 113, 140 pages, https://kdigo.org/wp-content/uploads/2017/02/KDIGO-2009-CKD-MBD-Guideline-English.pdf.
Kinsella, J.E., et al., "Uricase From Fish Liver: Isolation and Some Properties," Comparative Biochemistry and Physiology, American Society of Zoologists, Division of Comparative Physiology, Elsevier, Great Britain, Dec. 30, 1985, vol. 82B, No. 4, pp. 621-624.
Kinstler O.B., et al., "Characterization and Stability of N-Terminally PEGylated rhG-CSF," Pharmaceutical Research, Plenum Publishing Corporation, United States, Jul. 1996, vol. 13, No. 7, pp. 996-1002.
Kishimoto et al., "Improving the efficacy and safety of biologic drugs with tolerogenic nanoparticles," Nature Nanotechnology 11, Aug. 2016, pp. 890-899.
Kissel P., et al., "Modification of Uricaemia and the Excretion of Uric Acid Nitrogen by an Enzyme of Fungal Origin," Nature, Jan. 6, 1968, vol. 217, pp. 72-74.
Kito M., et al., "A Simple and Efficient Method for Preparation of Monomethoxypolyethylene Glycol Activated with p-Nitrophenylchloroformate and its Application to Modification of L-Asparaginase," Journal of Clinical Biochemistry and Nutrition, Institute of Applied Biochemistry, Japan, Sep. 1996, vol. 21, pp. 101-111.
Kohler, G., et al., "Pillars Article: Continuous Cultures of Fused Cells Secreting Antibody of Predefined Specificity," Nature, Mar. 1975, vol. 256, No. 5517, pp. 495-497. The Journal of Immunology, Mar. 2005, 1:174(5):2453-2455.
Kontsek, P., et al., "Forty Years of Interferon," Acta Virologica, Slovak Academic Press, Slovak Republic, Dec. 1997, vol. 41, pp. 349-353.
Kozbor et al., "The production of monoclonal antibodies from human lymphocytes," Immunology Today, Mar. 1983, 4(3), pp. 72-79.
Kozma E.M., et al., "An Accumulation of Proteoglycans in Scarred Fascia," Molecular and Cellular Biochemistry, Jan. 2000, vol. 203, pp. 103-112.
Kozma et al., "Anti-PEG antibodies: Properties, formation, testing and role in adverse immune reactions to PEGylated nano-biopharmaceuticals," Advanced Drug Delivery Reviews, vols. 154-155, 2020, pp. 163-175.
Kral L.G., et al., "Cloning A cDNA for *Drosophila melanogaster* Urate Oxidase," Gene, Elsevier Science Publishers B.V, Netherlands, 1986, vol. 45, pp. 131-137.
Krystexxa (pegloticase) [prescribing information] Horizon, Apr. 2012, 14 pages.
"Krystexxa plus methotrexate approved for uncontrolled gout," MedMDS, Jul. 8, 2022, 4 pages.
"Krystexxa plus methotrexate approved for uncontrolled gout," MPR, Jul. 8, 2022, 4 pages.
Kunitani M., et al., "Classical Light Scattering Quantitation of Protein Aggregates: Off-line Spectroscopy Versus HPLC Detection," Journal of Pharmaceutical and Biomedical Analysis, Elsevier Science B.V., Netherlands, Dec. 1997, vol. 16, 16 Pages.
Kunitani M., et al., "On-Line Characterization of Polyethylene Glycol-Modified Proteins," Journal of Chromatography, Elsevier Science Ltd., Dec. 27, 1991, vol. 588, pp. 125-137.

(56) References Cited

OTHER PUBLICATIONS

Larsen K., "Purification of Nodule-Specific Uricase From Soybean by Arginine-Sepharose Affinity Chromatography," Preparative Biochemistry and Biotechnology, 1990, vol. 20, No. 1, 1 Page, (Abstract Only).
Laurent T.C., et al., "Fractionation of Hyaluronic Acid: The Polydispersity of Hyaluronic Acid from the Bovine Vitreous Body," Biochimica et Biophysica Acta, Aug. 26, 1960, vol. 42, pp. 476-485.
Lawrence R.C., et al., "Estimates of the Prevalence of Arthritis and Selected Musculoskeletal Disorders in the United States," Arthritis & Rheumatology, May 1998, vol. 41, No. 5, pp. 778-799.
Leach, M., et al., "Efficacy of Urate Oxidase (Uricozyme) in Tumor Lysis Induced Urate Nephropathy," Clinical & Laboratory Haematology, Blackwell Science Limited, Jun. 1998, vol. 20, pp. 169-172.
Leaustic M., et al., "Allergic Manifestation of the Bronchospasm Type After Intravenous Injection of Urate Oxidase in a Female Patient Treated for Myeloma," Rev Rhum Mal Osteoartic, 1983, vol. 50, No. 7, 5 Pages.
Lee et al., "Reduction in Serum Uric Acid May Be Related to Methotrexate Efficacy in Early Rheumatoid Arthritis: Data from the Canadian Early Arthritis Cohort (CATCH)," Clinical Medicine Insights: Arthritis and Musculoskeletal Disorders, Jan. 2016, vol. 9, pp. 37-43.
Lee C.C., et al., "Generation of cDNA Probes Directed by Amino Acid Sequence: Cloning of Urate Oxidase," Science, American Association for the Advancement of Science, United States, Mar. 4, 1988, vol. 239, No. 4844, pp. 1288-1291.
Lee et al., "THU0149 does methotrexate lower serum uric acid levels? Data from the catch cohort," Poster Presentations, Annals of the Rheumatic Diseases, Jun. 2015, vol. 74, pp. 248.
Lee, S-S., "Studies on Glycosaminoglycans in Tissues," Fukushima Journal of Medical Sciences, Jan. 1973, vol. 19, No. 1-4, pp. 33-39.
Lee T.H., et al., "A Novel Secretory Tumor Necrosis Factor-Inducible Protein (TSG-6) is a Member of the Family of Hyaluronate Binding Proteins, Closely Related to the Adhesion Receptor CD44," The Journal of Cell Biology, Jan. 1, 1992, vol. 116, No. 2, pp. 545-557.
Legoux R., et al., "Cloning and Expression in *Eschericia coli* of the Gene Encoding Aspergillus Flavus Urate Oxidase," The Journal of Biological Chemistry, American Society for Biochemistry and Molecular Biology, United States, Apr. 25, 1992, vol. 267, No. 12, pp. 8565-8570.
Lie et al., "The effect of comedication with conventional synthetic disease modifying antirheumatic drugs on TNF inhibitor drug survival in patients with ankylosing spondylitis and undifferentiated spondyloarthritis: results from a nationwide prospective study," Annals of the Rheumatic Diseases, Jun. 2015;74(6), pp. 970-978.
Lim S.Y., et al., "Trends in Gout and Rheumatoid Arthritis Hospitalizations in the United States, 1993-2011," The Journal of the American Medical Association, Jun. 7, 2016, vol. 315, No. 21, pp. 2345-2347.
Lipsky P.E., et al., "Pegloticase Immunogenicity: The Relationship Between Efficacy and Antibody Development in Patients Treated for Refractory Chronic Gout," Arthritis Research & Therapy, Mar. 4, 2014, vol. 16, No. 2, R60, 8 Pages.
Lit, J-Y., et al., "Mutations at the S1 Sites of methionine Aminopeptidases From *Escherichia coli* and *Homo sapiens* Reveal the Residues Critical for Substrate Specificity," Journal of Biological Chemistry, May 14, 2004, vol. 279, No. 20, pp. 21128-21134.
Liu C., et al., "Prednisone in Uric Acid Lowering in Symptomatic Heart Failure Patients With Hyperuricemia (PUSH-PATH) Study," Canadian Journal of Cardiology, Sep. 2013, vol. 29, No. 9, pp. 1048-1054, Especially Abstract.
Li-Yu J., et al., "Treatment of Chronic Gout. Can We Determine When Urate Stores Are Depleted Enough to Prevent Attacks of Gout?," The Journal of Rheumatology, Mar. 2001, vol. 28, No. 3, pp. 577-580.
London M., et al., "Uricolytic Activity of Purified Uricase in Two Human Beings," Science, May 10, 1957, vol. 125, pp. 937-938.
Lundquist et al., "Psoriasis and Normouricemic Gout," Dermatology, 1982, vol. 164, No. 2, pp. 104-108.
Macart M., et al., "An Improvement of the Coomassie Blue Dye Binding Method Allowing an Equal Sensitivity to Various Proteins: Application to Cerebrospinal Fluid," Clinica Chimica Acta, Elsevier Biomedical Press, Jun. 16, 1982, vol. 122, pp. 93-101.
Maccari F., et al., "Glycosaminoglycan Blotting on Nitrocellulose Membranes Treated With Cetylpyridinium Chloride After Agarose-Gel Electrophoretic Separation," Electrophoresis, Sep. 2002, vol. 23, pp. 3270-3277.
Mahler H.R., et al., "Studies of Uricase. 1. Preparation, Purification, and Properties of a Cuproprotein," Journal of Biological Chemistry, American Society for Biochemistry and Molecular Biology, United States, Oct. 1955, vol. 216, pp. 625-641.
Mahmoud H.H., et al., "Advances in the Management of Malignancy-Associated Hyperuricaemia," British Journal of Cancer, Supplement 4, Churchill Livingstone, United Kingdom, Jun. 1998, vol. 77, pp. 18-20.
Majjhoo A., et al., "Prophylaxis for Infusion Reactions to Pegloticase: An Analysis of Two Different Corticosteroid Pre-Infusion Regimens in US Community Rheumatology Practices," ACR/ARHP Annual Meeting, Abstract No. 213, Prophylaxis to Pegloticase, Sep. 28, 2016, 4 Pages, Retrieved from URL: https://acrabstracts.org/abstract/.
Majjhoo et al., "Comparison of two corticosteriod pre-infusion regimes for pegloticase in the United States: A retrospective analysis in community rheumatology practices," Drugs Real World Outcomes, Dec. 2019;6(4):165-171.
Majjhoo et al., "Prophylaxis for Infusion Reactions to Pegloticase: An Analysis of Two Different Corticosteroid Pre-Infusion Regimens in US Community Rheumatology Practices," vol. 68, NJ, USA: Wiley, Poster, (2016), 1 page.
Malakhova E.A., et al., "Kinetic Properties of Bacterial Urate Oxidase Entrapped In Hydrated Reversed Micelles," Biologicheskie Membrany, 1991, vol. 8, No. 5, 1 Page, (Abstract Only).
Malamet et al., "SAT0355 Real World Risk of Infusion Reactions with Pegloticase Treatment: Findings from Post-Approval US Safety Data," Annals of the Rheumatic Diseases, Jun. 2013, 72(Suppl 3), pp. A703-A704, https://ard.bmj.com/content/72/Suppl_3/A703.3.
Male et al., "Immunology," 8th edition, Chapter 11, pp. 183-198 and Chapter 19, pp. 307-321, Philadelphia, PA, Elsevier Inc., 2013.
Martin et al., "Methotrexate in Psoriasis: Precipitation of Gout," Arch Dermatol., Oct. 1967, vol. 96, No. 4, pp. 431-433.
Matsumura G., et al., "The Preparation of Hyaluronic Acid from Bovine Synovial Fluid," Short Communications, Biochimica et Biophysica Acta, Mar. 5, 1963, vol. 69, pp. 574-576.
Milgroom, A et al., "Immunosuppressant Use and Gout in the Prevalent Solid Organ Transplant Population," Journal of the American Society of Nephrology, Oct. 2018, 29:152 Abstract TH-P0160, 3 pages.
Miura S., et al., "Urate Oxidase is Imported into Peroxisomes Recognizing the C-terminal SKL Motif of Proteins," European Journal of Biochemistry, Blackwell Science Ltd., United Kingdom, Jul. 1, 1994, vol. 223, pp. 141-146.
Moerschell R.P., et al., "The Specificities of Yeast Methionine Aminopeptidase and Acetylation of Amino-terminal Methionine in Vivo," Journal of Biological Chemistry, Nov. 15, 1990, vol. 265, No. 32, pp. 19638-19643.
Monkarsh, S.P., et al., "Positional Isomers of Monopegylated Interferon Alpha-2a: Isolation, Characterization, and Biological Activity," Analytical Biochemistry, Academic Press, United States, May 1997, vol. 247, pp. 434-440.
Montagna, R., et al., "Letter to Editor," Nephrologie, 1990, vol. 11, No. 4, 259, 3 Pages.
Montalbini, P., et al., "Isolation and Characterization of Uricase From Bean Leaves and Its Comparison With Uredospore Enzymes," Plant Science, Elsevier Science Ireland Ltd., Ireland, Sep. 1999, vol. 147, pp. 139-147.
Montalbini, P., et al., "Uricase From Leaves: Its Purification and Characterization From Three Different Higher Plants," Planta, Springer-Verlag, Germany, Jul. 1997, vol. 202, pp. 277-283.

(56) References Cited

OTHER PUBLICATIONS

Moolenburgh, J.D., et al., "Rasburicase Treatment in Severe Tophaceous Gout: A Novel Therapeutic Option," Clinical Rheumatology, Sep. 2006, vol. 25, pp. 749-752.
Moore, W.V., et al., "Role of Aggregated Human Growth Hormone (hGH) in Development of Antibodies to hGH," The Journal of Clinical Endocrinology and Metabolism, The Endocrine Society, United States, Oct. 1980, vol. 51, pp. 691-697.
Morrison, S. L., et al., "Chimeric human antibody molecules: mouse antigen-binding domains with human constant region domains", Proceedings of the National Academy of Sciences (1984); 81(21): 6851-6855.
Motojima, K., et al., "Cloning And Sequence Analysis of cDNA for Rat Liver Uricase," Journal of Biological Chemistry, Nov. 15, 1988, vol. 263, No. 32, pp. 16677-16681.
Mountain View Pharmaceuticals, Inc., "PURICASE.RTM.," U.S. Trademark Registration No. 2,246,623 (report obtained from U.S. Trademark Electronic Search System (TESS), Dec. 5, 2001), 1 page.
Mourad, G., et al., "Role of Anti-Urate Oxidase Precipitant Antibodies in Urate Oxidase Resistant Hyperuremic," La Presse Medicale, Nov. 24, 1984, vol. 13, No. 42, p. 2585.
Moussy, G., et al., "Inter-Species DNA Polymerase Delta Chimeras Are Functional in *Saccharomyces cerevisiae*," European Journal of Biochemistry, Jul. 1, 1995, vol. 231, No. 1, pp. 45-49.
Muntean et al. "Immunosuppression in kidney transplantation," Clujul Medical, Aug. 5, 2013, (Aug. 5, 2013), vol. 86, pp. 177-180.
"N- and C-Terminally Truncated Pig-Baboon Chimeric Uricase (PBC-NT-CT)," Retrieved from EBI Accession No. GSP: AAY81255, Jun. 19, 2000, 2 Pages.
Nagata, S. et al., "Synthesis in *E. coli* of a polypeptide with human Leukocyte interferon activity," Nature, vol. 284, Mar. 1980, pp. 316-320.
Nahm B.H., et al., "Induction and De Novo Synthesis of Uricase, a Nitrogen-Regulated Enzyme in Neurospora Crassa," Journal for Bacteriology, American Society for Microbiology, United States, May 1987, vol. 169, No. 5, pp. 1943-1948.
Neuberger M.S., et al., "Recombinant Antibodies Possessing Novel Effector Functions," Nature, Dec. 13, 1984, vol. 312, pp. 604-608.
Ngo, J.T., et al., "Computational Complexity, Protein Structure Prediction, and the Levinthal Paradox," The Protein Folding Problem and Tertiary Structure Prediction, Merz et al., (ed.), Birkhauser, Boston, MA, 1994, pp. 491-495.
Nishida Y., et al., "Hypouricaemic Effect After Oral Administration in Chickens of Polyethylene Glycol-modified Uricase Entrapped in Liposomes," Journal of Pharmacy and Pharmacology, Pharmaceutical Press, United Kingdom, May 1984, vol. 36, pp. 354-355.
Nishimura, H., et al., "Improved Modification of Yeast Uricase with Polyethylene Glycol: Accompanied with Nonimmunoreactivity Towards Anti-Uricase Serum and High Enzymic Activity," Enzyme, Karger, Switzerland, 1981, vol. 26, pp. 49-53.
Nishimura H., et al., "Modification of Yeast Uricase with Polyethylene Glycol: Disappearance of Binding Ability towards Anti-Uricase Serum," Enzyme, Karger, Switzerland, 1979, vol. 24, pp. 261-264.
Non-Final Office Action for U.S. Appl. No. 09/839,946, mailed Aug. 2, 2004, 7 Pages.
Non-Final Office Action for U.S. Appl. No. 09/839,946, mailed Aug. 11, 2008, 6 Pages.
Non-Final Office Action for U.S. Appl. No. 09/839,946, mailed May 11, 2009, 8 Pages.
Non-Final Office Action for U.S. Appl. No. 09/839,946, mailed Sep. 11, 2003, 12 Pages.
Non-Final Office Action for U.S. Appl. No. 09/839,946, mailed Jul. 23, 2008, 7 Pages.
Non-Final Office Action for U.S. Appl. No. 09/839,946, mailed Jan. 26, 2005, 12 Pages.
Non-Final Office Action for U.S. Appl. No. 10/928,370, mailed Apr. 9, 2007, 14 Pages.
Non-Final Office Action for U.S. Appl. No. 10/928,370, mailed Dec. 9, 2009, 11 Pages.
Non-Final Office Action for U.S. Appl. No. 10/928,370, mailed Jun. 9, 2011, 14 Pages.
Non-Final Office Action for U.S. Appl. No. 10/928,370, mailed Mar. 18, 2014, 9 Pages.
Non-Final Office Action for U.S. Appl. No. 10/928,370, mailed Sep. 30, 2008, 9 Pages.
Non-Final Office Action for U.S. Appl. No. 11/357,028, mailed Jul. 5, 2016, 4 Pages.
Non-Final Office Action for U.S. Appl. No. 11/357,028, mailed Dec. 6, 2011, 13 Pages.
Non-Final Office Action for U.S. Appl. No. 11/357,028, mailed Feb. 7, 2007, 9 Pages.
Non-Final Office Action for U.S. Appl. No. 11/357,028, mailed Jul. 12, 2013, 9 Pages.
Non-Final Office Action for U.S. Appl. No. 11/357,028, mailed Oct. 13, 2010, 10 Pages.
Non-Final Office Action for U.S. Appl. No. 11/357,028, mailed Mar. 25, 2008, 10 Pages.
Non-Final Office Action for U.S. Appl. No. 11/357,028, mailed May 29, 2009, 16 Pages.
Non-Final Office Action for U.S. Appl. No. 11/539,475, mailed Sep. 9, 2010, 7 Pages.
Non-Final Office Action for U.S. Appl. No. 11/539,475, mailed Jun. 25, 2009, 6 Pages.
Non-Final Office Action for U.S. Appl. No. 11/882,750, mailed Mar. 17, 2010, 9 Pages.
Non-Final Office Action for U.S. Appl. No. 11/899,688, mailed May 6, 2011, 7 Pages.
Non-Final Office Action for U.S. Appl. No. 11/899,688, mailed Oct. 30, 2009, 10 Pages.
Non-Final Office Action for U.S. Appl. No. 11/918,292, mailed Jun. 12, 2014, 12 Pages.
Non-Final Office Action for U.S. Appl. No. 11/918,292, mailed Feb. 17, 2011, 10 Pages.
Non-Final Office Action for U.S. Appl. No. 11/918,292, mailed Feb. 19, 2016, 8 Pages.
Non-Final Office Action for U.S. Appl. No. 12/769,570, mailed Jan. 26, 2011, 9 Pages.
Non-Final Office Action for U.S. Appl. No. 12/769,572, mailed May 9, 2013, 6 Pages.
Non-Final Office Action for U.S. Appl. No. 12/769,572, mailed Dec. 10, 2010, 8 Pages.
Non-Final Office Action for U.S. Appl. No. 12/769,572, mailed Aug. 19, 2014, 9 Pages.
Non-Final Office Action for U.S. Appl. No. 12/769,572, mailed Oct. 20, 2011, 6 Pages.
Non-Final Office Action for U.S. Appl. No. 12/769,572, mailed Aug. 28, 2014, 10 Pages.
Non-Final Office Action for U.S. Appl. No. 13/083,152, mailed Apr. 2, 2013, 10 Pages.
Non-Final Office Action for U.S. Appl. No. 13/085,793, mailed Jan. 3, 2014, 13 Pages.
Non-Final Office Action for U.S. Appl. No. 13/085,793, mailed Oct. 3, 2011, 6 Pages.
Non-Final Office Action for U.S. Appl. No. 13/085,793, mailed Mar. 14, 2012, 9 Pages.
Non-Final Office Action for U.S. Appl. No. 13/306,336, mailed Nov. 14, 2014, 11 Pages.
Non-Final Office Action for U.S. Appl. No. 13/306,336, mailed Jul. 23, 2013, 9 Pages.
Non-Final Office Action for U.S. Appl. No. 13/306,336, mailed Jun. 23, 2014, 9 Pages.
Non-Final Office Action for U.S. Appl. No. 13/379,704, mailed Jul. 5, 2013, 9 Pages.
Non-Final Office Action for U.S. Appl. No. 13/379,704, mailed Feb. 11, 2015, 21 Pages.
Non-Final Office Action for U.S. Appl. No. 13/379,704, mailed Feb. 25, 2014, 11 Pages.
Non-Final Office Action for U.S. Appl. No. 13/461,170, mailed Feb. 4, 2013, 10 Pages.
Non-Final Office Action for U.S. Appl. No. 13/972,167, mailed Aug. 4, 2014, 10 Pages.

(56) References Cited

OTHER PUBLICATIONS

Non-Final Office Action for U.S. Appl. No. 14/462,368, mailed Sep. 2, 2016, 19 Pages.
Non-Final Office Action for U.S. Appl. No. 14/671,246, mailed Apr. 6, 2016, 10 Pages.
Non-Final Office Action for U.S. Appl. No. 15/356,046, mailed Aug. 9, 2018, 68 Pages.
Non-Final Office Action for U.S. Appl. No. 15/356,046, mailed Dec. 27, 2018, 37 Pages.
Non-Final Office Action for U.S. Appl. No. 15/649,398, mailed Aug. 16, 2017, 11 Pages.
Non-Final Office Action for U.S. Appl. No. 15/649,462, mailed Oct. 13, 2017, 10 Pages.
Non-Final Office Action for U.S. Appl. No. 15/649,478, mailed Oct. 16, 2017, 10 Pages.
Non-Final Office Action for U.S. Appl. No. 15/649,488, mailed Sep. 11, 2017, 11 Pages.
Non-Final Office Action for U.S. Appl. No. 16/195,446, mailed Oct. 2, 2019, 53 Pages.
Non-Final Office Action for U.S. Appl. No. 16/202,743, mailed Sep. 10, 2019, 45 Pages.
Non-Final Office Action for U.S. Appl. No. 16/455,073, mailed Apr. 29, 2020, 49 Pages.
Notice of Allowance for U.S. Appl. No. 09/839,946, mailed Dec. 23, 2009, 5 Pages.
Notice of Allowance for U.S. Appl. No. 11/539,475, mailed Oct. 19, 2011, 5 Pages.
Notice of Allowance for U.S. Appl. No. 11/833,590, mailed Dec. 1, 2010, 9 Pages.
Notice of Allowance for U.S. Appl. No. 11/882,750, mailed Dec. 14, 2010, 6 Pages.
Notice of Allowance for U.S. Appl. No. 11/918,292, mailed Aug. 18, 2016, 7 Pages.
Notice of Allowance for U.S. Appl. No. 11/918,296, mailed Jun. 7, 2010, 7 Pages.
Notice of Allowance for U.S. Appl. No. 12/769,570, mailed Jul. 18, 2011, 7 Pages.
Notice of Allowance for U.S. Appl. No. 12/769,572, mailed Apr. 29, 2014, 7 Pages.
Notice of Allowance for U.S. Appl. No. 12/879,084, mailed Feb. 11, 2011, 7 Pages.
Notice of Allowance for U.S. Appl. No. 12/879,084, mailed Feb. 22, 2011, 4 Pages.
Notice of Allowance for U.S. Appl. No. 13/083,152, mailed Aug. 22, 2013, 8 Pages.
Notice of Allowance for U.S. Appl. No. 13/085,793, mailed Aug. 21, 2014, 7 Pages.
Notice of Allowance for U.S. Appl. No. 13/107,498, mailed Jun. 14, 2011, 8 Pages.
Notice of Allowance for U.S. Appl. No. 13/226,891, mailed Jan. 9, 2012, 7 Pages.
Notice of Allowance for U.S. Appl. No. 13/379,704, mailed May 6, 2016, 10 Pages.
Notice of Allowance for U.S. Appl. No. 13/452,151, mailed Jun. 19, 2012, 7 Pages.
Notice of Allowance for U.S. Appl. No. 13/461,170, mailed May 17, 2013, 8 Pages.
Notice of Allowance for U.S. Appl. No. 13/623,512, mailed Feb. 19, 2013, 7 Pages.
Notice of Allowance for U.S. Appl. No. 13/972,167, mailed Dec. 26, 2014, 9 Pages.
Notice of Allowance for U.S. Appl. No. 14/671,246, mailed Nov. 8, 2016, 9 Pages.
Notice of Allowance for U.S. Appl. No. 14/671,246, mailed Jan. 19, 2017, 8 Pages.
Notice of Allowance for U.S. Appl. No. 14/806,494, mailed Jun. 13, 2017, 8 Pages.
Notice of Allowance for U.S. Appl. No. 14/806,494, mailed Sep. 27, 2017, 7 Pages.
Notice of Allowance for U.S. Appl. No. 15/649,462, mailed Jan. 29, 2018, 9 Pages.
Notice of Allowance for U.S. Appl. No. 15/649,478, mailed May 10, 2018, 8 Pages.
Notice of Allowance for U.S. Appl. No. 15/649,478, mailed Sep. 11, 2018, 28 Pages.
Notice of Allowance for U.S. Appl. No. 15/649,488, mailed Jan. 19, 2018, 10 Pages.
Notice of Allowance for U.S. Appl. No. 15/906,839, mailed May 14, 2018, 9 Pages.
Notice of Allowance for U.S. Appl. No. 16/195,446, mailed Jul. 1, 2020, 15 Pages.
Notice of Allowance for U.S. Appl. No. 16/202,743, mailed Mar. 27, 2020, 13 Pages.
Notice of Appeal for U.S. Appl. No. 09/839,946, mailed Dec. 20, 2005, 1 Page.
Notice of Appeal for U.S. Appl. No. 10/928,370, mailed May 1, 2008, 1 Page.
Notice of Appeal for U.S. Appl. No. 11/357,028, mailed Apr. 5, 2010, 1 Page.
Notice of Appeal for U.S. Appl. No. 11/357,028, mailed Dec. 10, 2012, 1 Page.
Notice of Hearing for U.S. Appl. No. 09/839,946, mailed May 15, 2007, 1 Page.
Nucci M.L., et al., "The Therapeutic Value of Poly(Ethylene Glycol)-Modified Proteins," Advanced Drug Delivery Reviews, Elsevier Science Publishers, Netherlands, Mar.-Apr. 1991, vol. 6, No. 2, pp. 133-151.
"$NZNP—Horizon gets FDA approval for Krystexxa's use with methotrexate for uncontrolled gout," Breaking News @MarketCurrents, Jul. 8, 2022, SANews Twitter, 1 page.
Office Action for U.S. Appl. No. 11/833,590, mailed Mar. 22, 2010, 10 Pages.
Osman A.M., et al., "Liver Uricase In Camelus Dromedarius: Purification and Properties," Comparative Biochemistry and Physiology B, Pergamon Press, London, GB, Dec. 6, 1989, vol. 94B, No. 3, pp. 469-474, ISSN 0305-0491, XP002125210.
Otta M.E., et al., "Solubilization of Particle-Linked Urate Oxidase by Different Agents," Acta Physiologica Latinoamericana, 1975, vol. 25, pp. 451-457.
Pakula A.A., et al., "Genetic Analysis of Protein Stability and Function," Annual Review of Genetics, 1989, vol. 23, pp. 289-310.
Palleroni A.V., et al., "Interferon Immunogenicity: Preclinical Evaluation of Interferon-alpha.2a," Journal of Interferon and Cytokine Research, Mary Ann Liebert, Inc., United States, Jul. 1997, vol. 17, Supplement 1, pp. S23-S27.
Patton J., "Mechanisms of Macromolecule Absorption by the Lungs, " Advanced Drug Delivery Reviews, Apr. 30, 1996, vol. 19, No. 1, pp. 3-36.
Pearce R.H., et al., "Quantitative Isolation of Purified Acidic Glycosaminoglycans from Rat Skin," Canadian Journal of Biochemistry and Physiology, Oct. 1967, vol. 45, pp. 1565-1576.
Perez-Ruiz F., et al., "Effect of Urate-Lowering Therapy on the Velocity of Size Reduction of Tophi in Chronic Gout," Arthritis & Rheumatology, Aug. 15, 2002, vol. 47, No. 4, pp. 356-360.
Philippovich, Y.B., "The Fundamentals of Biochemistry," AGAR, Moscow, Russia, 1999, pp. 29-30, (with unverified, Partial English language translation).
Pitts O.M., et al., "Uricase: Subunit Composition and Resistance to Denaturants," Biochemistry, American Chemical Society, United States, Feb. 26, 1974, vol. 13, No. 5, pp. 888-892.
Porstmann, B., et al., "Comparison of Chromogens for the Determination of Horseradish Peroxidase as a Marker in Enzyme Immunoassay," Journal of Clinical Chemistry and Clinical Biochemistry, Walter de Gruyter & Co., Germany, Jul. 1981, vol. 19, pp. 435-439.
Potaux L., et al., "Uricolytic Therapy Value of Urate Oxidase in the Treatment of Hyperuricemia," La Nouvelle Presse Medicale, Apr. 12, 1975, vol. 4, No. 15, 10 Pages.
"Prevent—Definition by Merriam-Webster Online Dictionary," pp. 1-3, [Retrieved on Jun. 27, 2013] Retrieved from URL: http://www.merriam-webster.com/dictionary/prevent.
U.S. Appl. No. 60/670,520, filed Apr. 11, 2005 and titled "Purification of proteins with cationic surfactant," 53 pages.

(56) References Cited

OTHER PUBLICATIONS

Pui et al., "Recombinant Urate Oxidase for the Prophylaxis or Treatment of Hyperuricemia in Patients With Leukemia or Lymphoma," Journal of Clinical Oncology, vol. 19, Issue 3, Feb. 2001, pp. 697-704.
Pui et al., "Recombinant Urate Oxidase (rasburicase) in the prevention and treatment of malignancy-associated hyperuricemia in pediatric and adult patients: results of a compassionate-use trial," Leukemia 15, Oct. 2001, pp. 1505-1509.
Pui et al., "Urate oxidase in prevention and treatment of hyperusicemia associates with lymphoid malignancies," Leukemia 11, Nov. 1997, pp. 1813-1816.
R&D Focus Drug News: "PEG-uricase BioTechnology General, Duke University, Mountain View licensing agreement," DataStar File IPNR/IPNA, Accession No. 1998:2984 DRUGNL, Aug. 24, 1998, 1 Page.
Reinders, M., "Practice Research in the Field of Gout: Clinical Pharmacology of Antihyperuricemic Drugs", University of Groningen, Doctoral Thesis, Nov. 28, 2008, pp. 1-152. p. 18, Table 2; p. 131, para 2.
Restriction requirement for U.S. Appl. No. 17/325,555, mailed Dec. 28, 2022, 7 pages.
Richette P., et al., "Rasburicase for Tophaceous Gout not Treatable with Allopurinol: An Exploratory Study," The Journal of Rheumatology, Oct. 2007, vol. 34, No. 10, pp. 2093-2098.
Richette P., et al., "Successful Treatment with Rasburicase of a Tophaceous Gout in a Patient Allergic to Allopurinol," Nature Clinical Practice Rheumatology, Jun. 2006, vol. 2, No. 6, pp. 338-342.
Rinella J.V., et al., "Elutability of Proteins from Aluminum-Containing Vaccine Adjuvants by Treatment with Surfactants," Journal of Colloid and Interface Science, Jan. 1, 1998, vol. 197, pp. 48-56.
Rosenberg A.S., "Effects of Protein Aggregates: An Immunologic Perspective," The American Association of Pharmaceutical Scientists Journal, United States, Aug. 4, 2006, vol. 8, No. 3, pp. E501-E507.
Rosenberg A.S., et al., "Urate-Oxidase for the Treatment of Tophaceous Gout in Heart Transplant Recipients," Rev Rhum, Eng. Ed., May 1995, vol. 62, No. 5, pp. 392-394.
Rudinger, J., "Characteristics of the Amino Acids as Components of a Peptide Hormone Sequence," Peptide Hormones, JA Parsons Edition, University Park Press, Jun. 1976, pp. 1-7.
Saag et al. "Initial results of a clinical study to determine whether a tolerizing regimen of pegloticase can increase the frequency of subjects having sustained lowering of serum urate," American College of Rheumatology, Abstract 1141, Sep. 2017, 2 pages.
Saag K., et al., "FRI0240: Clinical Trial to Determine Whether Altering the Regimen of Pegloticase Administration Can Increase the Frequency of Subjects Having Sustained Lowering of Serum Urate," Annals of Rheumatic Disease, Friday, Jun. 15, 2018, vol. 77, p. 661.
Saifer M.G.P., et al., "Improved Conjugation of Cytokines Using High Molecular Weight Poly(ethylene glycol): PEG-GM-CSF as a Prototype," Polymer Preprints, American Chemical Society, United States, Apr. 1997, vol. 38, pp. 576-577.
Saifer M.G.P., et al., "Plasma Clearance and Immunologic Properties of Long-Acting Superoxide Dismutase Prepared Using 35,000 to 120,000 Dalton Poly-Ethylene Glycol," Advances in Experimental Medicine and Biology, 1994, vol. 366, pp. 377-387.
Saito, S., "Coagulation and Peptization of Polyelectrolyte Solution by Detergent Ions. I," Kolloid-Zeitschrift, 1955, vol. 143, No. 2, 18 Pages.
Sakane T., et al., "Carboxyl-Directed Pegylation of Brain-Derived Neurotrophic Factor Markedly Reduces Systemic Clearance with Minimal Loss of Biologic Activity," Pharmaceutical Research, Plenum Publishing Corporation, United States, Aug. 1997, vol. 14, pp. 1085-1091.
Sampson et al., "Second symposium on the definition and management of anaphylaxis: summary report—Second National Institute of Allergy and Infectious Disease/Food Allergy and Anaphylaxis Network Symposium," Journal of Allergy and Clinical Immunology, Feb. 2006, 117(2), pp. 391-397, https://pubmed.ncbi.nlm.nih.gov/16461139/.
Sartore L., et al., "Enzyme Modification by mPEG with an Amino Acid or Peptide as Spacer Arms," Applied Biochemistry and Biotechnology, Jan. 1991, vol. 27, No. 1, pp. 45-54.
Savoca K., et al., "Induction of Tolerance in Mice by Uricase and Monomethoxypolyethylene Glycol-Modified Uricase," International Archives of Allergy and Applied Immunology, 1984, vol. 75, pp. 58-67.
Scandella, C.J., et al., "A Membrane-Bound Phospholipase AI Purified from *Escherichia colt*," Biochemistry, Nov. 23, 1971, vol. 10, No. 24, pp. 4447-4456.
Schiavon O., et al., "Therapeutic Proteins: A Comparison of Chemical and Biological Properties of Uricase Conjugated to Linear or Branched Poly(Ethylene Glycol) and Poly(N-Acryloylmorpholine)," Il Farmaco, Apr. 2000, vol. 55, No. 4, pp. 264-269.
Schinzel R., et al., "The Phosphate Recognition Site of *Escherichia coli* Maltodextrin Phosphorylase," Federation of European Biochemical Societies, Jul. 1991, vol. 286, No. 1, 2, pp. 125-128.
Schlensinger et al., "Pegloticase," Nature Reviews: Drug Discovery, vol. 10, Jan. 2011, pp. 17-18.
Schlesinger et al., "Evaluation of proposed criteria for remission and evidence-based development of criteria for complete response in patients with chronic refractory gout," ACR Open Rheumatology, Jun. 2019, vol. 1, No. 4, pp. 236-243, doi: 10.1002/acr2.1025.
Schumacher H.R., et al., "Effects of Febuxostat Versus Allopurinol and Placebo in Reducing Serum Urate in Subjects with Hyperuricemia and Gout: A 28-Week, Phase III, Randomized, Double-Blind, Parallel-Group Trial," Arthritis & Rheumatism (Arthritis Care & Research), Nov. 15, 2008, vol. 59, No. 11, pp. 1540-1548.
Schumacher, H.R., et al., "Outcome Evaluations in Gout," The Journal of Rheumatology, Jun. 2007, vol. 34, No. 6, pp. 1381-1385, XP008158539.
Scott, J., "The Precipitation of Polyanions by Long-Chain Aliphatic Ammonium Salts," Journal of Biochemistry, 1961, vol. 81, pp. 418-424.
Scott, J., "The Reaction of Long-Chain Quarternary Ammonium Salts with Acidic Polysaccharides," Chemistry and Industry, Feb. 12, 1955, pp. 168-169.
Scott, J., "The Solubility of Cetylpyridinium Complexes of Biological Polyanions in Solution of Salts," Biochimica et Biophysica Acta, Nov. 1955, vol. 18, pp. 428-429.
Scott, J.E., "Aliphatic Ammonium Salts in the Assay of Acidic Polysaccharides from Tissues," Methods of Biochemical Analysis, Jan. 1960, vol. 8, pp. 145-197.
Serafini-Fracassini A., et al., "The Protein-Polysaccharide Complex of Bovine Nasal Cartilage," Journal of Biochemistry, Nov. 1967, vol. 105, pp. 569-575.
Sharma B., "Immunogenicity of Therapeutic Proteins. Part 3: Impact of Manufacturing Changes," Biotechnology Advances, Elsevier Inc., Netherlands, Jan. 2007, vol. 25, pp. 325-331.
Shearwater Polymers Inc:, "Functionalized Biocompatible Polymers for Research and Pharmaceuticals," Shearwater Polymers, Inc., Catalog, Jul. 1997, 6 Pages.
Sherman et a., Petition Decision for U.S. Appl. No. 09/501,730, mailed on Jul. 12, 2007, filed Feb. 10, 2000, now U.S. Pat. No. 6,783,965.
Sherman et al., Advisory Action for U.S. Appl. No. 09/501,730, mailed Nov. 17, 2003, 5 Pages.
Sherman et al., Final Office Action for U.S. Appl. No. 09/501,730, mailed Feb. 10, 2004, 8 Pages.
Sherman et al., Final Office Action for U.S. Appl. No. 09/501,730, mailed Jun. 18, 2003, 9 Pages.
Sherman et al., Final Office Action for U.S. Appl. No. 09/501,730, May 22, 2002, 8 Pages.
Sherman et al., Non-Final Office Action for U.S. Appl. No. 09/501,730, mailed Dec. 3, 2002, 11 Pages.
Sherman et al., Non-Final Office Action for U.S. Appl. No. 09/501,730, mailed Dec. 5, 2001, 9 Pages.
Sherman et al., Non-Final Office Action for U.S. Appl. No. 09/501,730, mailed Apr. 6, 2001, 12 Pages.

(56) References Cited

OTHER PUBLICATIONS

Sherman et al., Notice of Allowance for U.S. Appl. No. 09/501,730, mailed Jan. 13, 2004, 8 Pages.
Sherman et al., Notice of Allowance for U.S. Appl. No. 09/501,730, mailed Feb. 24, 2004, 6 Pages.
Sherman et al., Notice of Appeal for U.S. Appl. No. 09/501,730, mailed Sep. 9, 2003, 1 Page.
Sherman, F., et al., "Methionine or Not Methionine at the Beginning of a Protein," Bio Essays, Jul. 1985, vol. 3, Issue 1, pp. 27-31.
Sherman, M., et al., "Conjugation of High-Molecular Weight Poly-(ethylene glycol) to Cytokines: Granulocyte-Macrophage Colony-Stimulating Factors as Model Substrates," ACS Symposium Series 680, Poly(ethylene glycol), Chemistry and Biological Applications, Harris J.M., and Zaplipsky S., eds., American Chemical Society, Washington, DC, Aug. 5, 1997, pp. 155-169.
Sherman, M., et al., "PEG-Uricase in the Management of Treatment-Resistant Gout and Hyperuricemia," Advanced Drug Delivery Reviews, Jan. 3, 2008, vol. 60, No. 1, pp. 59-68.
Shoji A., et al., "A Retrospective Study of the Relationship Between Serum Urate Level and Recurrent Attacks of Gouty Arthritis: Evidence for Reduction of Recurrent Gouty Arthritis With Antihyperuricemic Therapy," Arthritis & Rheumatology, Jun. 15, 2004, vol. 51, No. 3, pp. 321-325.
Sigma Catalog, p. 1008, Product Nos. U 3250, 292-8, U3500, U 9375 or U 3377, (1993), 2 pages.
Sigma Genosys: "Designing Custom Peptides," Accessed on Dec. 16, 2004, pp. 1-2.
Smith T., et al., "Human Lung Tryptase," Journal of Biological Chemistry, Sep. 10, 1984, vol. 259, No. 17, pp. 11046-11051.
Smolenska et al., "Effect of methotrexate on blood purine and pyrimidine levels in patients with rheumatoid arthritis," Rheumatology, Oct. 1999, vol. 38, No. 10, pp. 997-1002.
Somack R., et al., "Preparation of Long-Acting Superoxide Dismutase Using High Molecular Weight Polyethylene Glycol (41,000-72,000 Daltons)," Free Radical Research Communications, Harwood Academic Publishers GmbH, Germany, 1991, vol. 12-13, pp. 553-562.
Sorensen L.B., "Suppression of the Shunt Pathway in Primary Gout by Azathioprine," Proceedings of the National Academy of Science of the USA, Mar. 1966, vol. 55, No. 3, pp. 571-575.
Sparks et al., "Effect of Low-Dose Methotrexate on eGFR and Kidney Adverse Events: A Randomized Clinical Trial," Journal of the American Society of Nephrology, Dec. 2021, 32(12):3197-3207.
Stamp et al., "Expert opinion on emerging urate-lowering therapies," Expert Opinion on Emerging Drugs, vol. 23, 2018, pp. 201-209.
Stamp et al., "Gout in solid organ transplantation: a challenging clinical problem," Drugs, Dec. 2005, 65(18), pp. 2593-2611, https://pubmed.ncbi.nlm.nih.gov/16392875/.
Streuli, M. et al., "Target cell specificity of two species of human interferon-α produced in *Escherichia coli* and of hybrid molecules derived from them," Proceedings of the National Academy of Sciences USA, vol. 78, No. 5, May 1981, pp. 2848-2852.
Sundy J., et al., "A Multicenter Longitudinal Study of Disease Characteristics in Patients With Treatment-Failure Gout," Presented at the EULAR—Annual European Congress of Rheumatology, Amsterdam, Netherlands, Poster 518, Jun. 21-24, 2006, 1 Page.
Sundy J., et al., "A Phase 2 Study of Multiple Doses of Intravenous Polyethylene Glycol (PEG)-uricase in Patients with Hyperuricemia and Refractory Gout," Presented at the EULAR—Annual European Congress of Rheumatology, Amsterdam, Netherlands, Poster 516, Jun. 21-24, 2006, 1 Page.
Sundy, J., et al., "A Phase I Study of Pegylated-Uricase (Puricase. RTM.) in Subjects with Gout," Presented at American College of Rheumatology Annual Scientific Meeting at San Antonio, TX, on Oct. 16-21, 2004, Poster 807, 1 page.
Sundy J., et al., "Efficacy and Tolerability of Pegloticase for the Treatment of Chronic Gout in Patients Refractory to Conventional Treatment: Two Randomized Controlled Trials," American Medical Association, Aug. 17, 2011, vol. 306, No. 7, pp. 711-720.
Sundy J., et al., "Pharmacokinetics and Pharmacodynamics of Intravenous PEGylated Recombinant Mammalian Urate Oxidase in Patients With Refractory Gout," Arthritis & Rheumatology, Mar. 2007, vol. 56, No. 3, pp. 1021-1028.
Sundy J., et al., "Quality of Life in Patients With Treatment-Failure Gout," Presented at the EULAR-Annual European Congress of Rheumatology, Amsterdam, Netherlands, Poster 517, Jun. 21-24, 2006, 1 Page.
Sundy J., et al., "Reduction of Plasma Urate Levels Following Treatment with Multiple Doses of Pegloticase in Patients with Treatment-Failure Gout," Arthritis & Rheumatism, Sep. 2008, vol. 58, No. 9, pp. 2882-2891.
Sundy J., et al., "Uricase and Other Novel Agents for the Management of Patients With Treatment-Failure Gout," Current Rheumatology Reports, Jun. 2007, vol. 9, No. 3, pp. 258-264.
Sundy, U.S., et al., "A Phase 2 Study of Multiple Doses of Intravenous Polyethylene Glycol (PEG)-uricase in Patients with Hyperuricemia and Refractory Gout," Presented at American College of Rheumatology 2005 Annual Scientific Meeting at San Diego, CA, #1836 on Nov. 13-17, 2005, 51 pages.
Sundy S., et al., Arthritis & Rheumatism, Sep. 2005, vol. 52, No. 9 (Supplement), Abstract Supplement, Annual Scientific Meeting, San Diego, California, Nov. 12-17, 2005, Abstract #1836, 3 Pages.
Supplementary Search Report for European Application No. 10792756.8, mailed Oct. 10, 2013, 2 Pages.
Sutterlin, et al., "Mixtures of Quaternary Ammonium Compounds and Anionic Organic Compounds in the Aquatic Environment: Elimination and Biodegradability in the Closed Bottle Test Monitored by LC-MS/MS," Chemosphere, Jun. 2008, vol. 72, No. 3, pp. 479-484, Abstract only.
Suzuki, H., et al., "Soybean Nodule-Specific Uricase (Nodulin-35) is Expressed and Assembled into a Functional Tetrameric Holoenzyme in *Escherichia coli*," Plant Physiology, American Society of Plant Physiologists, United States, Feb. 1991, vol. 95, pp. 384-389.
Takeda, et al., "Construction of Chimaeric Processed Immunoglobulin Genes Containing Mouse Variable and Human Constant Region Sequences," Nature, Apr. 4, 1985, vol. 314, pp. 452-454.
Terkeltaub R., "Gout", Clinical Practice, The New England Journal of Medicine, 2003, vol. 349, No. 17, pp. 1647-1655.
"The @US_FDA's decision on the co-treatment of pegloticase (#Krystexxa) plus methotrexate (#MTX) for patients with uncontrolled #gout was based on the phase 4 MIRROR clinical trial," HCPLive Tweet Twitter, Jul. 8, 2022, 1 page.
"The @US_FDA expanded the #pegloticase label to include the co-treatment of pegloticase (KRYSTEXXA) injection plus methotrexate in patients with uncontrolled #gout. @HorizonNews," Rheumatology Network Tweet Tweeter, Jul. 8, 2022, 1 page.
Thomas et al., "Comparative Immunogenicity of TNF Inhibitors: Impact on Clinical Efficacy and Tolerability in the Management of Autoimmune Diseases. A Systematic review and Meta-Analysis," BioDrugs 29, Aug. 2015, pp. 241-258.
Tla S., et al., "Urate Oxidase from Pig Liver: Biochemical and Immunological Properties," Prikl Biokhim Mikrobiol, Izdatesltvo Nauka, Russia, Jul. 1, 1978, vol. 14, pp. 533-542.
Tomanee P., et al., "Fractionation of Protein, RNA, and Plasmid DNA in Centrifugal Precipitation Chromatography Using Cationic Surfactant CTAB Containing Inorganic Salts NaCl and NH4Cl," Wiley InterScience, Sep. 9, 2004, 8 Pages, DOI: 10.1002/bit.20203.
Top 10 Home Remedies: "How to Control Uric Acid Levels," Accessed on Sep. 22, 2015, pp. 1-6, Retrieved from URL: http://www.top10homeremedies.com/how-to/control-uric-acid-levels.html.
Treuheit M., et al., "Inverse Relationship of Protein Concentration and Aggregation," Pharmaceutical Research, Plenum Publishing Corporation, United States, Apr. 2002, vol. 19, pp. 511-516.
Truscoe R., "Effect of Detergents on Extraction and Activity of Ox-Kidney Urate Oxidase," Enzymologia, Jul. 31, 1967, vol. 33, pp. 119-132.
Truscoe R., et al., "Effect of pH on Extraction and Activity of Ox-kidney Urate Oxidase," Biochimica et Biophysica Acta, Elsevier Publishing Co., Netherlands, Jul. 8, 1964, vol. 89, pp. 179-182.

(56) References Cited

OTHER PUBLICATIONS

Tsuji J., et al., "Studies on Antigenicity of the Polyethylene Glycol (PEG)-Modified Uricase," International Journal of Immunopharmacology, Elsevier Science, 1985, vol. 7, No. 5, pp. 725-730.
Tsunasawa S., et al., "Amino-terminal Processing of Mutant Forms of Yeast Iso-1-cytochrome c, The Specificities of Methionine Aminopeptidase and Acetyltransferase," The Journal of Biological Chemistry, May 10, 1985, vol. 260, No. 9, pp. 5382-5391.
Tutton, R et al., "Pharmacogenomic Biomarkers in Drug Labels: What do they tell us?," Pharmacogenomics, Feb. 2014, 15(3), pp. 297-304.
U.S. Appl. No. 60/670,573, filed Apr. 11, 2005, 76 Pages.
U.S. Appl. No. 16/777,625, filed Jan. 30, 2020, 78 Pages.
U.S. Appl. No. 16/777,634, filed Jan. 30, 2020, 76 Pages.
U.S. Appl. No. 16/777,646, filed Jan. 30, 2020, 295 Pages.
U.S. Appl. No. 16/942,569, filed Jul. 29, 2020, 83 Pages.
U.S. Trademark Registration No. 2,246,623, entitled "Puricase," filed on Jul. 15, 1997, 1 Page.
Van Groen et al., "Application of the health assessment questionnaire disability index to various rheumatic diseases," Quality of Life Research, Nov. 2010, 19, pp. 1255-1263.
Varelas J., et al., "Expression and Characterization of a Single Recombinant Proteoglycan Tandem Repeat Domain of Link Protein That Binds Zinc and Hyaluronate," Archives of Biochemistry and Biophysics, Aug. 1, 1995, vol. 321, No. 1, pp. 21-30.
Venkataseshan V., et al., "Acute Hyperuricemic Nephropathy and Rental Failure after Transplantation," Nephron, Karger AG, Switzerland, 1990, vol. 56, pp. 317-321.
Verhoef et al., "Potential induction of anti-PEG antibodies and complement activation toward PEGylated therapeutics," Drug Discovery Today, vol. 19, Issue 12, Dec. 2014, pp. 1945-1952.
Verma et al., "Folate Conjugated Double Liposomes Bearing Prednisolone and Methotrexate for Targeting Rheumatoid Arthritis," Pharmaceutical Research, Aug. 2019, 36(8):123, pp. 1-13.
Vermeire et al., "Effectiveness of concomitant immunosuppresive therapy in suppressing the formation of antibodies to infliximab in Crohn's disease," Gut, Jan. 2007, vol. 56, pp. 1226-1231.
Veronese F., "Branched and Linear Poly(Ethylene) Glycol: Influence of the Polymer Structure on Ezymological, Pharmacokinetic, and Immunological Properties of Protein Conjugates," Journal of Bioactive and Compatible Polymers, Tectonic Publishing Co., Inc., United States, Jul. 1, 1997, vol. 12, pp. 196-207.
Veronese F., et al., "New Synthetic Polymers for Enzyme and Liposome Modification," In: ACS Symposium Series 580, Poly(Ethylene Glycol) Chemistry and Biological Applications, Harris J.M., and Zaplipsky S., eds., American Chemical Society, Washington, D.C., 1997, pp. 182-192.
Veronese F., et al., "Surface Modification of Proteins. Activation of Monomethoxy-Polyethylene Glycols by Phenylchloroformates and Modification of Ribonuclease and Superoxide Dismutase," Applied Biochemistry and Biotechnology, The Humana Press, Inc., United States, Apr. 1985, vol. 11, pp. 141-152.
Veronese F.M., et al., "Preface: Introduction and Overview of Peptide and Protein Pegylation," Advanced Drug Delivery Reviews, 2002, vol. 54, pp. 453-456.
Voet D., et al., Biochemistry, Second Edition, John Wiley & Sons, Inc., Apr. 1995, pp. 235-241.
Voshaar M et al., "Dutch Translation and Cross-Cultural Adaptation of the PROMIS Physical Function Item Bank and Cognitive Pre-Test in Dutch Arthritis Patients," Arthritis Research & Therapy, Mar. 5, 2012, vol. 14, No. 2, 7 Pages.
Wallrath L., et al., "Molecular Characterization of the *Drosophila melanogaster* Rate Oxidase Gene, an Ecdysone-Repressible Gene Expressed Only in the Malpighian Tubules," Molecular and Cellular Biology, American Society for Microbiology, United States, Oct. 1990, vol. 10, pp. 5114-5127.
Waltrip R., et al., "Pharmacokinetics and Pharmacodynamics of Peg-Uricase in Patients With Hyperuricemia and Treatment Failure Gout," Presented at the EULAR—Annual European Congress of Rheumatology, Barcelona, Spain, Poster 358, Jun. 13-16, 2007, 2 Pages.
Waltrip R., et al., "Weekly Flare Burden Index: A New Metric for Evaluating Gout Treatment," Annals of the Rheumatic Diseases, 2007, vol. 66 (Suppl II), Abstract 748, p. 624.
Wang L., et al., "Purification and Characterization of Uricase, a Nitrogen-Regulated Enzyme, from Neurospora Crassa," Archives of Biochemistry and Biophysics, Academic Press, Inc., United States, Apr. 15, 1980, vol. 201, pp. 185-193.
Wang X., et al., "Rat Urate Oxidase: Cloning and Structural Analysis of the Gene and 5'-Flanking Region," Gene, Elsevier Science Publishers B.V., The Netherlands, Jan. 15, 1991, vol. 97, pp. 223-229.
Wang X.D., et al., NCBI Entrez Protein (PRF) Database, Deposited Sequence for Rat Urate Oxidase (NP 446220), National Library of Medicine, National institutes of Health, Accession No. 20127395, Accessed at http://www.ncbi.nlm.nih.gov/protein/20127395 , Accessed on Dec. 10, 2003, 2 pages.
Ward E.S., et al., "Binding Activities of a Repertoire of Single Immunoglobulin Variable Domains Secreted from *Escherichia coli*," Nature, Oct. 12, 1989, vol. 341, No. 6242, pp. 544-546.
Watanabe T., et al., "A Simple Purification Method for Rat Liver Urate Oxidase," Analytical Biochemistry, Academic Press, Inc., United States, Sep. 1978, vol. 89, No. 2, pp. 343-347.
WHO Drug Information, vol. 21, No. 4, 2007, List 98, p. 344.
Williams et al., Notice of Allowance for U.S. Appl. No. 09/370,084, mailed Sep. 13, 2002, 9 Pages.
Williams, L.D., et al., Examiner's Answer to Appeal Brief for U.S. Appl. No. 09/839,946, filed Apr. 19, 2001, mailed on Jul. 11, 2006, 21 Pages.
Woodworth et al., "Standardizing assessment and reporting of adverse effects in rheumatology clinical trials II: the Rheumatology Common Toxicity Criteria v.2.0," Jun. 2007, 34(6), pp. 1401-1414, https://pubmed.ncbi.nlm.nih.gov/17552067/.
Wortmann R., et al., "Gout and Hyperuricemia," Kelley's Textbook of Rheumatology, Edited by Ruddy S., Harris E., Sledge C., 6th edn. St. Louis: W.B. Saunders, 2001, pp. 1339-1371.
Wu, E.Q., et al., "Comorbidity Burden, Healthcare Resource Utilization, and Costs in Chronic Gout Patients Refractory to Conventional Urate-Lowering Therapy," American Journal of Therapeutics, Nov. 2012, vol. 19, No. 6, pp. e157-e166.
Wu X., et al., "Hyperuricemia and Urate Nephropathy in Urate Oxidase-Deficient Mice," Proceedings of the National Academy of Sciences, USA, National Academy of Sciences, United States, Jan. 18, 1994, vol. 91, No. 2, pp. 742-746.
Wu X., et al., "Two Independent Mutational Events in the Loss of Urate Oxidase during Hominoid Evolution," Journal of Molecular Evolution, Springer-Verlag, Germany, Jan. 1992, vol. 34, No. 1, pp. 78-84.
Wu X., et al., "Urate Oxidase: Primary Structure and Evolutionary Implications," Proceedings of the National Academy of Sciences, USA, Dec. 1989, vol. 86, No. 23, pp. 9412-9416.
Wuthrich, H. et al., "Guidelines for the Treatment of Gout: A Swiss Perspective," Swiss Medical Weekly 146, (Year: 2016), pp. 1-7.
Yamamoto K., et al., "Nucleotide Sequence of the Uricase Gene from *Bacillus* sp. TB-90," Journal of Biochemistry, Oxford University Press, England, Jan. 1996, vol. 119, No. 1, pp. 80-84.
Yamanaka H., et al., "Optimal Range of Serum Urate Concentrations to Minimize Risk of Gouty Attacks during Anti-Hyperuricemic Treatment," Advances in Experimental Medicine and Biology, 1998, vol. 431, pp. 13-18.
Yasuda Y., et al., "Biochemical and Biopharmaceutical Properties of Macromolecular Conjugates of Uricase with Dextran Polyethylene Glycol," Chemical and Pharmaceutical Bulletin, Pharmaceutical Society of Japan, Jul. 1990, vol. 38, No. 7, pp. 2053-2056.
Yeldandi A.V., et al., "Human Urate Oxidase Gene: Cloning and Partial Sequence Analysis Reveal a Stop Codon within the Fifth Exon," Biochemica et Biophysica Research Communication, Academic Press, United States, Sep. 14, 1990, vol. 171, No. 2, pp. 641-646.

(56) References Cited

OTHER PUBLICATIONS

Yelverton, E., et al., "Bacterial Synthesis of a Novel Human Leukocyte Interferon," Nucleic Acids Research, Feb. 11, 1981, vol. 9, No. 3, pp. 731-741.
Yokoyama S., et al., "Rapid Extraction of Uricase from Candida Utilis Cells by Use of Reducing Agent Plus Surfactant," Enzyme and Microbial Technology, Jan. 1988, vol. 10, No. 1, pp. 52-55.
Yue, C.S., et al., Population Pharmacokinetic and Pharmacodynamic Analysis of PEG-uricase in Subjects With Hyperuricemia and Refractory Gout, presented at the American College of Clinical Pharmacy 2006 Annual Meeting on Oct. 26-29, 2006 at St. Louis, Missouri, Poster, 1 page.
Zhang, T., et al., "Affinity Extraction of BSA with Reversed Micellar System Composed of Unbound Cibacron Blue," Biotechnology Progress, Nov.-Dec. 1999, vol. 15, No. 6, pp. 1078-1082.
Zhang, W., et al., "Forward and Backward Extraction of BSA using Mixed Reverse Micellar System of CTAB and Alkyl Halides," Biochemical Engineering Journal, Oct. 2002, vol. 12, No. 1, pp. 1-5.
Zhu J., et al., "Can Dynamic Contrast-Enhanced MRI (DCE-MRI) and Diffusion-Weighted MRI (DW-MRI) Evaluate Inflammation Disease," A Preliminary Study of Crohn's Disease, Medicine (Baltimore), Apr. 2016, vol. 95, No. 14, Article e3239, pp. 1-9.
Document "Study NCT03303989 as of Oct. 30, 2018" is a pdf of the webpage at ClinicaiTrials.gov at https://classic.clinicaltrials.gov/ct2/history/NCT03303989?A=7&8=7&C=merged#StudyPageTop documenting what was available online as of Oct. 30, 2018, accessed Sep. 14, 2023 (Year: 2018), 10 pages.
Anonymous, Krystexxa—EPAR summary for the public, URL: https://www.ema.europa.eu/en/documents/overview/krystexxa-epar-summary-public_en.pdf, Jan. 2013.
Extended European Search Report issued to Application No. 21856554.7, dated Aug. 26, 2024.
Schlesinger et al., Pegloticase treatment of chronic refractory gout: Update on efficacy and safety, Seminars in Arthritis and Rheumatism, vol. 50, No. 3, XP086204018, Jun. 1, 2020.
Search Report issued to application No. RU2023105050, dated May 6, 2025.
Sundy J.S. et al. Pharmacokinetics and pharmacodynamics of intravenous PEGylated recombinant mammalian urate oxidase in patients with refractory gout//Arthritis & Rheumatism vol. 56, No. 3, Mar. 2007, pp. 1021-1028 DOI 10.1002/art.22403.
Toirov E.S. et al. Diagnostics and treatment of gout.—Tashkent, 2019, pp. 85-89, 96-98.
Albert et al., Increased Efficacy and Tolerability of Pegloticase in Patients with Uncontrolled Gout Co-Treated With Methotrexate: A Retrospective Study. Rheumatol Ther., vol. 7, pp. 639-648, Jul. 27, 2020.

* cited by examiner

METHODS OF TREATING GOUT

CROSS REFERENCE TO RELATED APPLICATIONS

This application is a U.S. National Stage Application under 35 U.S.C. § 371 of International Application No. PCT/US2021/045350, filed on Aug. 10, 2021, which claims the benefit of U.S. Provisional Patent Application Nos. 63/063,826, filed Aug. 10, 2020, and 63/148,982, filed Feb. 12, 2021, the disclosures of which are incorporated by reference herein in their entireties.

Gout affects approximately 4% of the U.S. population, is the most common form of inflammatory arthritis in men, and is associated with decreased quality of life. The frequency of gout is increasing worldwide, with prevalence rates estimated to be as high as 7% in older men. It is estimated that up to 400,000 (up to 5% of the estimated 8 million persons with gout) in the United States experience chronic refractory gout, characterized by ongoing symptoms of active disease and a failure to control/maintain serum urate <6 mg/dL with conventional xanthine oxidase inhibitors (i.e., allopurinol and febuxostat) and uricosuric agents (i.e., probenecid). These patients often have significant, disabling urate deposits in soft tissues and bone known as tophi.

Uric acid (UA) is the end metabolite in the human purine catabolic pathway. Unlike most mammalian species, humans lack the urate oxidase enzymatic pathway for the oxidation and disposition of uric acid and are susceptible to the development of gout. To develop an animal model of hyperuricemia and gout for a therapeutic uricase proof-of-concept study, a mouse was genetically modified by knocking out its endogenous uricase gene (Uox). This genetic lesion results in a marked elevation of plasma uric acid levels, leading to deposition of urate in kidney tissue and causing a profound defect in renal concentrating ability and nephrogenic diabetes insipidus. The studies in the mouse Uox−/−system demonstrate the therapeutic potential of pegloticase administration for the treatment of hyperuricemia and provided a "proof of principle" for the clinical use of pegloticase.

A series of pharmacokinetic (PK) studies was conducted in rats, rabbits, dogs and pigs to determine the circulation half-life and bioavailability as a function of the route of pegloticase administration. Plasma pegloticase levels were determined by assaying uricase bioactivity in plasma. As part of the PK studies, antibody levels in plasma were determined 2 weeks after the last injection in the rabbit, dog and rat. Collectively, the results of the PK studies in these animals lend support to the expectation of high bioavailability and prolonged retention of pegloticase after administration in humans. Absorption, distribution, metabolism and excretion of pegloticase were examined in rat studies. Approximately 70% of the dose was excreted in the urine during the course of 7 days after injection.

When the concentration of serum uric acid (SUA) is above the biochemical limit of solubility, 6.8 mg/dL, monosodium urate crystals may precipitate in tissues. It is hypothesized that after many years of persistent hyperuricemia, accumulation of monosodium urate crystals causes symptoms of gout, such as acute inflammation of joints (gout flare), formation of gout tophi, gouty arthritis, and UA nephropathy (including UA renal stones). Control of chronic gout cannot be achieved without maintaining SUA<6 mg/dL. A total of 8.3 million patients have been diagnosed with gout in the United States. The principal pharmaceutical approach to the treatment of gout is the use of the xanthine oxidase inhibitors, allopurinol, and febuxostat, to block the synthesis of UA. Approximately 2% of patients treated with allopurinol develop allergic reactions and a severe hypersensitivity syndrome occurs in about 0.4% of the patients. Patients with medical contraindications to xanthine oxidase inhibitors because of allergy/hypersensitivity, or who have failed to normalize SUA at maximum medically appropriate doses of these medications, can go on to develop chronic gout.

Pegloticase or PEGylated uricase (KRYSTEXXA®; "KXX") is a monomethoxypoly(ethylene glycol) (PEG) modified recombinant mammalian uricase (urate oxidase) which reduces levels of UA in the serum (or plasma) by catalyzing its conversion to allantoin, a water-soluble metabolite more readily excreted in the urine than uric acid. Pegloticase provides a new therapeutic mechanism to reduce SUA in patients with chronic gout refractory to conventional oral therapy. These patients experience a severe burden of gout disease characterized by tophi (approximately 70%), frequent and often crippling flares (approximately 7 per year), and deforming arthritis. Pegloticase provides medical benefits in patients who respond by lowering SUA and by reducing tophus burden in these patients who currently have no therapeutic options.

Seven clinical studies have been conducted with pegloticase in patients with refractory chronic gout. The Phase 1 program established an acceptable profile of tolerability and safety for intravenous (IV) dosing, whereas subcutaneous dose administration was less well tolerated. The Phase 2 program identified a minimally effective dose (4 mg), a dose-response plateau dose (12 mg), a safe and optimally effective dose (8 mg), and a once every 2 weeks or once every 4 weeks dosing regimen.

Two randomized, double-blind, placebo-controlled, multi-center, 6-month safety and efficacy Phase 3 studies have been conducted in a total of 225 hyperuricemic patients (SUA>8 mg/dL) with symptomatic gout who reported contraindication to or who had failed to normalize SUA with allopurinol therapy. The primary endpoint was defined as plasma UA (highly correlated to serum uric acid) reduction to below 6 mg/dL for 80% of the time in Months 3 and 6 combined. The pooled efficacy results showed improvements in tophus burden consistent with urate-lowering effect of pegloticase in both dose groups. Improvements were more rapid in patients who received pegloticase 8 mg every 2 weeks compared to every 4 weeks and met the outcomes data of complete resolution of at least 1 tophus with no new or progressive tophi as assessed by blinded assessment of digital photographs of target tophi.

The pooled safety results from these Phase 3 studies showed that deaths, AEs, SAEs, as well as the laboratory abnormalities were generally equally distributed across placebo and pegloticase treatment groups, with the clear exception of gout flares and IRs. Gout flares were more common in the pegloticase groups than in the placebo group during the first 3 months of therapy, a physiological effect resulting from SUA-lowering which is commonly observed upon the initiation of all urate-lowering therapies. Despite use of prophylactic medications against hypersensitivity including administration of corticosteroids, antihistamine and acetaminophen in advance of each pegloticase infusion, IRs were seen in 22/85 (26%) of subjects receiving the 8 mg 2-week regimen, although it is noted that there was no pre-infusion uric acid monitoring protocol during this study, and the 26% IR rate is higher than that seen in clinical practice/studies with a monitoring protocol, typically about 8%.

During the second 3 months of treatment, a lower proportion of pegloticase-treated patients experienced flares than patients receiving placebo. The incidence of flares during this period was lowest in the group receiving pegloticase 8 mg every 2 weeks than in the group who received pegloticase 8 mg every 4 weeks, as was the incidence of infusion-related reactions (26% with biweekly dosing vs. 40% with the every-4-week dosing regimen). Both infusion reactions (IRs) and gout flares were least common in patients with sustained urate-lowering responses to treatment and those who received bi-weekly treatment. In most pegloticase-treated patients with IRs, a loss of response to pegloticase (return to SUA≥6 mg/dL) preceded the time of the first IR (20/21; 95%).

A relationship between the loss of urate-lowering efficacy, incidence of IRs, and high-titer antibody formation was identified in a post-hoc analysis of the pooled data from the Phase 3 studies. Patients with high anti-pegloticase antibody titers (>1:2430) showed a loss of pegloticase activity attributed to a more rapid clearance of drug in the presence of these antibodies. In one study, 69 (41%) of 169 patients receiving pegloticase developed high titer anti-pegloticase antibodies and subsequently lost response to the drug. In a second study, only 1 of 52 participants with high antibody titers maintained a response to pegloticase (serum urate <6 mg/dL). In addition, 60% participants with high titers developed IR. Anti-pegloticase antibodies were largely directed to the polyethylene glycol (PEG) portion of the molecule and altered the pharmacokinetic clearance of pegloticase, resulting in inhibition of SUA lowering activity. In another study, only 7 of 65 patients (10.8%) with an antibody titer exceeding 1:2430 at any time during treatment maintained a response to pegloticase compared with 89.2% (58/65) who had never had an antibody titer above that level. In addition, 31 of 52 (60%) patients with titers exceeding 1:2430 developed IRs. The ability of pegloticase to induce antibody production demonstrated the antigenic potential of the drug, and thus raised the possibility that relatively large or more frequent doses of pegloticase (antigen) might reduce antibody formation by induction of antigen-specific non-responsiveness (high zone tolerance). By preventing the formation of anti-pegloticase antibodies, a tolerizing dose regimen should prevent loss of response to the drug and decrease the incidence of IRs associated with it.

As described herein, an alternate approach to prevent immunogenicity by pegloticase and therefore reduce the incidence of IRs, as well as to enhance the response rate seen with pegloticase alone in adults with uncontrolled gout, is co-administration or concomitant administration of pegloticase and an immunosuppressive agent. As described herein, one such immunosuppressive agent is methotrexate (MTX). As described herein, a shortened infusion (e.g., about 30, about 45, or about 60 minutes) or administration time may be employed for patients receiving pegloticase+MTX therapy as deemed appropriate and provided that patients do not meet infusion speed-limiting criteria as set forth herein. In some embodiments, pegloticase may also be administered in a reduced volume, such as a volume of 50 mL, rather than the 250 mL volume that is the current standard treatment. Speed-limiting criteria may include, but are not limited to, (i) respiratory symptoms: difficulty breathing with wheezing or stridor; upper airway swelling (lip, tongue, throat, uvula, or larynx); respiratory distress manifested as at least 2 or more of the following: tachypnoea, increased use of accessory respiratory muscles, cyanosis, recession, grunting; (ii) cardiovascular symptoms: hypertension, tachycardia, measured hypotension, a decreased level of consciousness, loss of consciousness; (iii) dermatological or mucosal symptoms: generalized urticaria (hives) or generalized erythema, angioedema, generalized pruritus with skin rash. Patients receiving KXX treatment as described herein, e.g., in a shortened infusion period (e.g., about 30, about 45, or about 60 minutes) or with a reduced infusion volume (e.g., about 50 mL), may not experience an increase in adverse events and/or may experience an adverse event profile similar in nature and severity to patients receiving the PEGylated uricase in a 120-minute infusion period with a 250 mL infusion volume as approved by the FDA.

The long-term safety of pegloticase has been demonstrated in an open-label extension study that enrolled 151 patients: 149 received pegloticase either bi-weekly or every 4 weeks for up to 30 months and 2 chose observation only. No new safety signals were observed and ongoing patient benefit in several clinical outcome measures was maintained beyond the 6-month period of the double-blind studies.

Currently, pegloticase is FDA approved for intravenous administration over no less than 120 minutes in an infusion volume of 250 mL (cc). Pegloticase is re-administered every two weeks to achieve optimal therapeutic outcomes, prevent elevations in sUA levels, and reduce tophus burden. Compliance with such a regimen can be burdensome and pose a barrier to treatment for some patients who may otherwise benefit from the infusion. Therefore, there is an unmet need for patients with uncontrolled gout to have access to a therapy that is effective with limited AEs, amenable to high patient compliance over several months. Administering pegloticase over a shorter duration time, and/or with a reduced infusion volume, may address this unmet need.

One concern, however, is that a shorter infusion duration may lead to increased AEs. Pegloticase has been associated with IRs, including anaphylaxis. In Phase 3 studies (which included IR prophylaxis for all subjects), with pegloticase administered over 120 minutes, IRs occurred in 26% of subjects receiving pegloticase compared to 5% of subjects receiving placebo and anaphylaxis was reported in 5% of subjects receiving pegloticase and 0% of subjects receiving placebo (pegloticase, KRYSTEXXA®, KXX). These AEs are thought to be related to the development of anti-drug antibodies and can be reduced by avoiding infusions in patients who initially respond and then have a rebound of their serum uric acid to 6 mg/mL or greater. These anti-drug antibodies are also associated with loss of efficacy as reflected in this increase in sUA levels.

To address the possibility of increased AEs with a shorter infusion duration, this study will incorporate an IR prophylaxis regimen as well as pre-treatment and concomitant use of MTX with pegloticase.

Individual subject sUA Discontinuation Criteria will also be in place to minimize the potential for AEs in subjects who are non-responders to treatment. Since the risk of anaphylaxis and IRs is higher in patients who have lost therapeutic response, this study will also discontinue treatment if sUA levels increase to 6 mg/dL or above at 2 consecutive study visits to minimize the potential for such AEs.

As described herein, the present study will be initiated enrolling subjects assigned to 60-minute infusion durations. Based on tolerability, this infusion duration may be progressively shortened to 45-minute and 30-minute infusions. The consistent adverse event profile supports initiating this trial with subjects receiving infusions at 60-minute durations and progressively moving to shorter durations of 45 minutes and 30 minutes.

Thus, in one aspect, the disclosure provides a method of treating gout in a patient having a serum uric acid (SUA)

level of ≥6 mg/dL comprising: administering methotrexate (MTX) to said patient at a dose of about 15 mg per week for a period of 2-4 weeks prior to a first administration of a PEGylated uricase; and co-administering the PEGylated uricase and MTX to said patient using a dosage regimen comprising a dose of from about 8 mg to about 32 mg of the PEGylated uricase intravenously every 2-4 weeks for a total of 6-26 doses, and a dose of about 15 mg of MTX per week, wherein the co-administered MTX is administered concurrently with each administration of the PEGylated uricase; wherein the PEGylated uricase is administered within a shortened infusion period of 60 minutes or less; and wherein the infusion is administered in a reduced volume of 50 mL.

In another aspect, the disclosure provides method of reducing immunogenicity to PEGylated uricase and prolonging the urate lowering effect comprising co-administering a PEGylated uricase at a dosage of about 8 mg to about 32 mg intravenously every 2-4 weeks and methotrexate (MTX) at a dosage of about 15 mg per week to a patient having a serum uric acid (SUA) level of ≥6 mg/dL prior to PEGylated uricase treatment initiation, wherein the administration of the PEGylated uricase and MTX result in the SUA level being reduced relative to a patient not receiving co-administration of the PEGylated uricase and MTX immunosuppressive therapy, wherein the PEGylated uricase is administered within a shortened infusion period of about 60 minutes or less; and wherein the infusion is administered in a reduced volume of about 50 mL.

In one embodiment, a method described herein further comprises reducing the administration period of the PEGylated uricase to 45 minutes for subjects who do not meet infusion speed-limiting criteria. In another embodiment, a method described herein further comprises reducing the infusion period of the PEGylated uricase to 30 minutes for subjects who do not meet infusion speed-limiting criteria. In another embodiment, the infusion speed-limiting criteria comprise one or more of: (i) respiratory symptoms: difficulty breathing with wheezing or stridor; upper airway swelling (lip, tongue, throat, uvula, or larynx); respiratory distress manifested as at least 2 or more of the following: tachypnoea, increased use of accessory respiratory muscles, cyanosis, recession, grunting; (ii) cardiovascular symptoms: hypertension, tachycardia, measured hypotension, a decreased level of consciousness, loss of consciousness; (iii) dermatological or mucosal symptoms: generalized urticaria (hives) or generalized erythema, angioedema, generalized pruritus with skin rash. In another embodiment, patients receiving the PEGylated uricase in the shortened infusion period: (i) do not experience an increase in adverse events; or (ii) experience an adverse event profile similar in nature and severity to patients receiving the PEGylated uricase in a 120-minute infusion period.

In some embodiments, a PEGylated uricase (i.e., KXX) as described herein is administered within a shortened infusion period of about 60 minutes or less. In some embodiments, a shortened infusion period for administration of KXX may be, but is not limited to, about 20 minutes, about 25 minutes, about 30 minutes, about 35 minutes, about 40 minutes, about 45 minutes, about 50 minutes, about 55 minutes, about 60 minutes, about 65 minutes, about 70 minutes, or the like.

In some embodiments, KXX may be administered to a patient as described herein in a reduced volume compared to the standard 250 mL known in the art. In some embodiments, a reduced volume refers to a volume of less than 250 mL, such as including, but not limited to, 25 mL, 30 mL, 35 mL, 40 mL, 45 mL, 50 mL, 55 mL, 60 mL, 65 mL, 70 mL, 75 mL, 80 mL, 85 mL, 90 mL, 95 mL, 100 mL, 110 mL, 120 mL, 130 mL, 140 mL, 150 mL, 160 mL, 170 mL, 180 mL, 190 mL, 200 mL, 210 mL, 220 mL, 230 mL, or 240 mL. In some embodiments, KXX is administered at a reduced volume of 50 mL (50 cc), rather than the standard 250 mL known in the art. In some embodiments, and as described herein, a dosage of 16 mg KXX is administered in a volume of 50 mL every 4 weeks or monthly. In some embodiments, such a reduced volume may be given in normal or half-normal saline, or 0.45% or 0.9% Sodium Chloride Injection, USP.

In another embodiment, a method described herein further comprises administering folic acid to said patient at a dosage of 1 mg per day. In another embodiment, a method described herein further comprises an altered dosage of MTX, wherein the altered dosage comprises: administering folic acid to said patient at a dosage of about 1 mg per day; or administering MTX to said patient at a dosage of about 7.5 mg twice per day; or administering MTX to said patient at a dosage of about 10 mg, wherein the altered dosage of MTX is based on laboratory findings. In another embodiment, the altered dosage of MTX comprises a temporary stop for laboratory parameters selected from the group consisting of WBC levels of less than about 3.0×109/L, platelet levels of less than about $50\times10^9$/L, hematocrit levels of less than about 27%, AST/ALT levels of greater than about 2×upper limit of normal (ULN), and eGFR levels of less than 30 mL/min/1.73 $m^2$, wherein the altered dosage of MTX comprises a reduction in the dosage of MTX to 10 mg per week for laboratory parameters selected from the group consisting of: WBC levels of from about $3.0\times10^9$/L to about $3.5\times10^9$/L and AST/ALT levels of between about 1.5 and about 2×ULN. In another embodiment, a method described herein further comprises a prophylactic regimen of colchicine for a period of at least 2 weeks prior to the first administration of the PEGylated uricase. In another embodiment, the SUA levels of the patient are determined prior to each dose of the PEGylated uricase. In another embodiment, a method described herein further comprises measuring one or more of trough PEGylated uricase levels, anti-PEGylated uricase antibody levels, and anti-PEG antibody levels, prior to each dose of the PEGylated uricase after the first dose. In another embodiment, a method described herein further comprises measuring hematology and liver function during treatment.

In another embodiment, co-administration of the PEGylated uricase and MTX results in normalization of the SUA level in the patient relative to a patient not receiving co-administration of the PEGylated uricase and MTX immunosuppressive therapy. In another embodiment, the SUA level is reduced to less than 6 mg/dL as a result of co-administration of the PEGylated uricase and MTX immunosuppressive therapy. In another embodiment, the SUA level is reduced to less than 5 mg/dL as a result of co-administration of the PEGylated uricase and MTX immunosuppressive therapy. In another embodiment, the SUA level is reduced to less than 2 mg/dL as a result of co-administration of the PEGylated uricase and MTX immunosuppressive therapy. In another embodiment, the incidence of infusion reaction, gout flare, or anaphylaxis is reduced as a result of co-administration of the PEGylated uricase and MTX immunosuppressive therapy. In another embodiment, the level of MTX metabolite is increased relative to a patient not receiving co-administration of the PEGylated uricase and MTX immunosuppressive therapy. In another embodiment, the mean titer of anti-PEGylated uricase antibodies is less than or equal to 1:6000 as a result of co-administration of the PEGylated uricase and MTX immunosuppressive therapy. In another embodiment, the serum uric acid level is normalized by week 12 after co-administration of PEGylated uricase and MTX treatment begins.

Provided is a method of treating gout in a patient having a serum uric acid (SUA) level of ≥6 mg/dL comprising: administering methotrexate (MTX) to said patient at a dose of about 15 mg per week for a period of 2 to 4 weeks prior to a first administration of a PEGylated uricase; and co-administering the PEGylated uricase and MTX to said patient using a dosage regimen comprising a dose of about 8 mg to about 32 mg of the PEGylated uricase intravenously every 2 to 4 weeks for a total of 6 to 26 doses, and a dose of about 15 mg of MTX per week, wherein the co-administered MTX is administered concurrently with each administration of the PEGylated uricase; wherein the PEGylated uricase is administered over an infusion period of 60 minutes or less; and wherein the infusion volume is about 50 mL.

Also provided is a method of reducing immunogenicity to PEGylated uricase and prolonging the urate lowering effect comprising co-administering a PEGylated uricase at a dosage of about 8 mg to about 32 mg intravenously every 2 to 4 weeks and methotrexate (MTX) at a dosage of about 15 mg per week to a patient having a serum uric acid (SUA) level of ≥6 mg/dL prior to PEGylated uricase treatment initiation, wherein the administration of the PEGylated uricase and MTX result in the SUA level being reduced relative to a patient not receiving co-administration of the PEGylated uricase and MTX immunosuppressive therapy, wherein the PEGylated uricase is administered over an infusion period of 60 minutes or less; and wherein the infusion volume is about 50 mL.

In some embodiments, the infusion period is 45 minutes and the infusion volume is 50 mL.

In some embodiments, the infusion period is 30 minutes.

In some embodiments, the patient lacks one or more of the following symptoms: (i) respiratory symptoms: difficulty breathing with wheezing or stridor; upper airway swelling (lip, tongue, throat, uvula, or larynx); respiratory distress manifested as at least 2 or more of the following: tachypnoea, increased use of accessory respiratory muscles, cyanosis, recession, grunting; or (ii) cardiovascular symptoms: hypertension, tachycardia, measured hypotension, a decreased level of consciousness, loss of consciousness; or (iii) dermatological or mucosal symptoms: generalized urticaria (hives) or generalized erythema, angioedema, generalized pruritus with skin rash.

In some embodiments, patients: (i) do not experience an increase in adverse events; or (ii) experience an adverse event profile similar in nature and severity to patients receiving the PEGylated uricase over a 120-minute infusion period and an infusion volume of 250 mL.

In some embodiments, the method further comprises administering folic acid to said patient at a dosage of 1 mg per day.

In some embodiments, the method further comprises an altered dosage of MTX, wherein the altered dosage comprises: administering folic acid to said patient at a dosage of about 1 mg per day; or administering MTX to said patient at a dosage of about 7.5 mg twice per day; or administering MTX to said patient at a dosage of about 10 mg, wherein the altered dosage of MTX is based on laboratory findings.

In some embodiments, the altered dosage of MTX comprises a temporary stop for laboratory parameters selected from the group consisting of WBC levels of less than about $3.0\times10^9$/L, platelet levels of less than about $50\times10^9$/L, hematocrit levels of less than about 27%, AST/ALT levels of greater than about 2×upper limit of normal (ULN), and eGFR levels of less than 30 mL/min/1.73 $m^2$, wherein the altered dosage of MTX comprises a reduction in the dosage of MTX to 10 mg per week for laboratory parameters selected from the group consisting of: WBC levels of from about $3.0\times10^9$/L to about $3.5\times10^9$/L and AST/ALT levels of between about 1.5 and about 2×ULN.

In some embodiments, the method further comprises a prophylactic regimen of colchicine for a period of at least 2 weeks prior to the first administration of the PEGylated uricase.

In some embodiments, the SUA levels of the patient are determined prior to each dose of the PEGylated uricase.

In some embodiments, the method further comprises measuring one or more of trough PEGylated uricase levels, anti-PEGylated uricase antibody levels, and anti-PEG antibody levels, prior to each dose of the PEGylated uricase after the first dose.

In some embodiments, the method further comprises measuring hematology and liver function during treatment.

In some embodiments, said co-administration of the PEGylated uricase and MTX results in normalization of the SUA level in the patient relative to a patient not receiving co-administration of the PEGylated uricase and MTX immunosuppressive therapy.

In some embodiments, the SUA level is reduced to less than 6 mg/dL as a result of co-administration of the PEGylated uricase and MTX immunosuppressive therapy.

In some embodiments, the SUA level is reduced to less than 5 mg/dL as a result of co-administration of the PEGylated uricase and MTX immunosuppressive therapy.

In some embodiments, the SUA level is reduced to less than 2 mg/dL as a result of co-administration of the PEGylated uricase and MTX immunosuppressive therapy.

In some embodiments, the incidence of infusion reaction, gout flare, or anaphylaxis is reduced as a result of co-administration of the PEGylated uricase and MTX immunosuppressive therapy.

In some embodiments, the level of MTX metabolite is increased relative to a patient not receiving co-administration of the PEGylated uricase and MTX immunosuppressive therapy.

In some embodiments, the mean titer of anti-PEGylated uricase antibodies is less than or equal to 1:6000 as a result of co-administration of the PEGylated uricase and MTX immunosuppressive therapy.

In some embodiments, the serum uric acid level is normalized by week 12 after co-administration of PEGylated uricase and MTX treatment begins.

In some embodiments, the MTX is administered orally.

In some embodiments, MTX is administered for a period of 2 weeks prior to a first administration of a PEGylated uricase.

In some embodiments, MTX is administered for a period of 3 weeks prior to a first administration of a PEGylated uricase.

In some embodiments, MTX is administered for a period of 4 weeks prior to a first administration of a PEGylated uricase.

In some embodiments, the PEGylated uricase is administered over an infusion period of 30, 45, or 60 minutes.

In some embodiments, the PEGylated uricase is administered at a dose of about 8 mg.

In some embodiments, the PEGylated uricase is administered at a dose of about 12 mg.

In some embodiments, the PEGylated uricase is administered at a dose of about 16 mg.

In some embodiments, the PEGylated uricase is administered at a dose of about 20 mg.

In some embodiments, the PEGylated uricase is administered at a dose of about 24 mg.

In some embodiments, the PEGylated uricase is administered at a dose of about 28 mg.

In some embodiments, the PEGylated uricase is administered at a dose of about 32 mg.

Also provided is a method of treating gout in a patient having a serum uric acid (SUA) level of ≥6 mg/dL comprising: administering methotrexate (MTX) to said patient at a dose of about 15 mg per week for a period of 2 to 4 weeks prior to a first administration of a PEGylated uricase; and co-administering the PEGylated uricase and MTX to said patient using a dosage regimen comprising a dose of about 8 mg to about 32 mg of the PEGylated uricase intravenously every 2 to 4 weeks for a total of 6 to 26 doses, and a dose of about 15 mg of MTX per week, wherein the co-administered MTX is administered concurrently with each administration of the PEGylated uricase; wherein the PEGylated uricase is administered over an infusion period of 60 minutes or less.

These and other embodiments of the disclosure are described in detail below.

DETAILED DESCRIPTION

Overview

Figure 1:
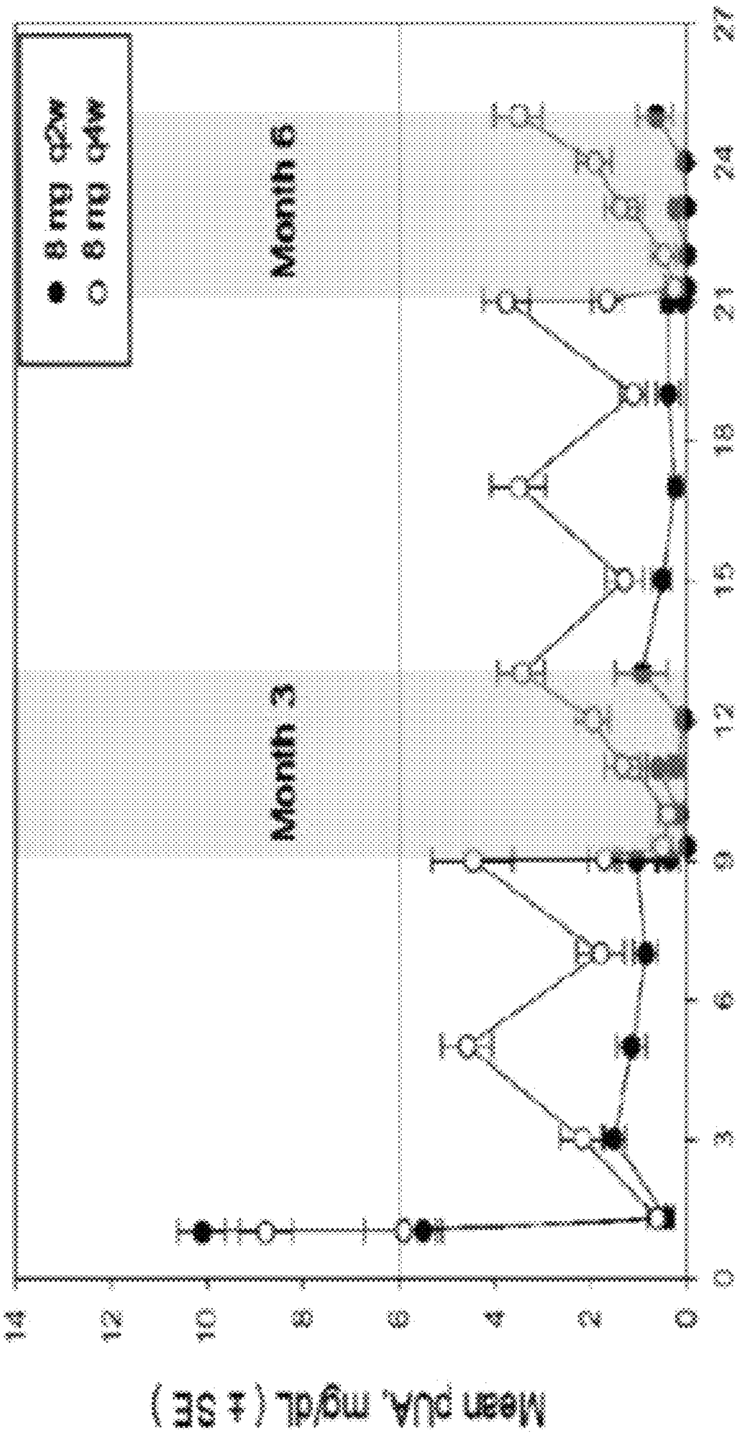
FIG. 1 depicts a graph of the urate reducing efficacy of pegloticase.

In one embodiment, the disclosure provides a method of treating gout in a patient having a serum uric acid (SUA) level of ≥6 mg/dL comprising: administering methotrexate (MTX) to said patient at a dose of 15 mg per week for a period of 2-4 weeks prior to the first administration of a PEGylated uricase; and co-administering the PEGylated uricase and MTX to said patient using a dosage regimen comprising a dose of 8, 16, 24, or 32 mg of the PEGylated uricase intravenously every 2-4 weeks for a total of 6-26 doses, and a dose of 15 mg of MTX per week, wherein the co-administered MTX is administered concurrently with each administration of the PEGylated uricase; wherein the PEGylated uricase is administered within a shortened infusion period of about 60 minutes or less, and wherein the infusion is administered in a reduced volume of 50 mL. In another embodiment, the disclosure provides a method of reducing or preventing a loss of response to PEGylated uricase and prolonging the urate lowering effect comprising co-administering a PEGylated uricase at a dosage of 8, 16, 24, or 32 mg intravenously every 2-4 weeks and methotrexate (MTX) at a dosage of 15 mg per week to a patient having a serum uric acid (SUA) level of ≥6 mg/dL prior to PEGylated uricase treatment initiation, wherein the administration of the PEGylated uricase and MTX result in the SUA level being reduced or normalized relative to a patient not receiving co-administration of the PEGylated uricase and MTX immunosuppressive therapy, wherein the PEGylated uricase is administered within a shortened infusion period of about 60 minutes or less, and wherein the infusion is administered in a reduced volume of 50 mL.

KRYSTYEXXA® (Pegloticase)

KRYSTEXXA® ("KXX," pegloticase) is a uric acid specific enzyme, which is a PEGylated product that consists of recombinant modified mammalian urate oxidase (uricase) produced by a genetically modified strain of *Escherichia coli*. KXX is indicated for the treatment of chronic gout in patients that are refractory to conventional therapy. KXX is described at least in U.S. Pat. Nos. 8,188,224; 7,811,800; 9,534,013; 6,576,235; 9,377,454; 6,783,965; as well as PCT Publ. No. WO 2018/089808, each of which is incorporated herein in its entirety. In some embodiments, non-mammalian uricases may be used as deemed appropriate, or a uricase from any species. In other embodiments, muteins of a uricase as described herein, having an altered amino acid sequence, may be used and are encompassed within the present disclosure.

Certain uricases are useful for preparing conjugates with various forms of poly(ethylene glycol) or poly(ethylene oxide) (both referred to as PEG) to produce therapeutically efficacious forms of uricase having increased protein half-life and reduced immunogenicity. Thus, in some embodiments, uricase is covalently conjugated to monomethoxy-poly(ethylene glycol) [mPEG] (10 kDa molecular weight). The cDNA coding for uricase is based on mammalian sequences. Each uricase subunit has a molecular weight of approximately 34 kDa per subunit. The average molecular weight of pegloticase (tetrameric enzyme conjugated to mPEG) is approximately 545 kDa.

In some embodiments, a uricase as described herein may be conjugated to any desired number of PEG or mPEG molecules, such as 1, 2, 3, 4, 5, 6, 7, 8, 9, 10, 11, 12, 13, 14, or the like. In other embodiments, a uricase as described herein may be conjugated to other modifiers in addition to, or alternatively to, PEG or mPEG. Such PEG or mPEG molecules may be attached to a uricase using any means appropriate in accordance with the disclosure. For example, a PEG or mPEG molecule may be conjugated to a uricase as described herein by a cysteine residue, or a serine residue, or a lysine residue. A PEG or mPEG may be attached to a uricase as described herein using any specific amino acid in accordance with the disclosure.

In other embodiments, a uricase of the present disclosure may be modified with a non-PEG modification. For example, one or more residues of proline, alanine, and/or serine (PAS), or combinations thereof, referred to herein as PASylation. In other embodiments, a uricase as described herein may be modified by conjugation with an antibody, a protein, or a small molecule, or may be conjugated to poly(2-ethyl-2-oxazoline) referred to herein as POZylation. In other embodiments, a uricase may be modified at the amine end or the carboxy end, or both. In other embodiments, any other modifiers deemed appropriate may be used to extend the half-life in circulation in accordance with the present disclosure.

Clinical Pharmacokinetics of KXX

Pegloticase levels were determined in serum based on measurements of uricase enzyme activity. Following single IV infusions of 0.5 mg to 12 mg pegloticase in 23 patients with symptomatic gout, maximum serum concentrations of pegloticase increased in proportion to the dose administered. The PK of pegloticase has not been studied in children and adolescents.

In patients undergoing hemodialysis (Study M0403), pegloticase serum concentrations were not clinically meaningfully affected by 2 hemodialysis sessions. Pre- and post-dialyzer samples, as well as samples taken during dialysis, demonstrated that study drug was not removed by the dialysis process. No formal studies have been conducted to examine the effects of hepatic impairment on pegloticase PK.

Risks of Pegloticase

Pegloticase is efficacious in reducing sUA levels and improving clinical signs and symptoms of gout. The risks of pegloticase use are detailed in the full prescribing information and include: (1) IRs, including anaphylaxis; (2) Hemolysis and methemoglobinemia in patients with glucose-6-phosphate dehydrogenase (G6PD) deficiency; (3) Gout flares; (4) Congestive heart failure exacerbation.

Subjects with diseases or conditions (e.g., non-compensated congestive heart failure) that could potentially place them at increased risk for these events will be excluded from the study.

It is required that all subjects receive prophylactic treatment to reduce the risk of acute gout flares, unless medically contraindicated or not tolerated, as noted in the pegloticase prescribing information. Subjects should begin a regimen of colchicine (0.6 mg/day) and/or NSAID and/or low-dose prednisone (10 mg/day) prophylaxis ≥1 week before the first dose of pegloticase and continuing flare prophylaxis throughout the pegloticase treatment period per American College of Rheumatology guidelines (Khanna D et al., 2012). All subjects who experience a gout flare during the study will be prescribed anti-inflammatory treatment (e.g., NSAIDs, colchicine), as deemed clinically indicated by the study physician.

Since IRs can occur, all subjects will receive pre-treatment prophylaxis consisting of an antihistamine, acetaminophen and a corticosteroid prior to each infusion of pegloticase. To standardize this regimen, subjects will receive fexofenadine (180 mg orally) the day before each infusion; fexofenadine (180 mg orally) and acetaminophen (1000 mg orally) the morning of each infusion; and methylprednisolone (125 mg IV) given over the infusion duration 10-30 minutes (recommended) will be administered immediately prior to each infusion.

The risk of anaphylaxis and IRs is higher in patients whose sUA level increases to ≥6 mg/dL. Therefore, as described herein in the Examples, beginning with Week 2, 2 pre-dose blood samples (within 48 hours prior to dosing pegloticase) will be obtained to verify the sUA level is <6 mg/dL prior to infusion of pegloticase. A subject with sUA level ≥6 mg/dL at 2 consecutive study visits, beginning with the Week 2 Visit, will be classified as a non-responder and will be discontinued from pegloticase treatment, but continue on study.

The principal safety risks associated with pegloticase include anaphylaxis, IRs and gout flares. Pegloticase has not been formally studied in patients with congestive heart failure, but some subjects in the clinical trials experienced exacerbation.

The data support that monitoring of sUA and discontinuation of pegloticase therapy in patients who lose the ability to maintain uric acid <6 mg/dL can lead to the avoidance of the majority of IRs and unnecessary exposure to drug. The longer-term exposure evidenced by the open-label extension study supports the benefit-to-risk assessment of 8 mg of pegloticase IV every 2 weeks as an effective therapy in chronic gout patients, particularly those with tophi who are unresponsive to other therapies.

Mode of Action of KXX

KXX achieves its therapeutic effect by catalyzing the oxidation of uric acid to allantoin, thereby lowering serum uric acid. Allantoin is an inert and water-soluble purine metabolite. It is readily eliminated, primarily by renal excretion.

KXX (pegloticase) concentrations are expressed as concentrations of uricase protein. Each mL of KXX contains 8 mg of uricase protein (conjugated to 24 mg of 10 kDa mPEG), 2.18 mg Disodium Hydrogen Phosphate Dihydrate ($Na_2HPO_4 \cdot 2H_2O$), 8.77 mg Sodium Chloride (NaCl), 0.43 mg Sodium Dihydrogen Phosphate Dihydrate ($NaH_2PO_4 \cdot 2H_2O$), and Water for Injection to deliver 8 mg of pegloticase (as uricase protein).

KXX was granted orphan designation by the FDA on Feb. 21, 2001 (ODA #00-1356) and KXX 8 mg every 2 weeks by IV infusion was approved by the United States (US) FDA on Sep. 14, 2010 for the treatment of adult patients with chronic gout refractory to conventional therapy. Since pegloticase was approved in the US, there have been no new safety signals reported to Horizon Pharma, PLC (Horizon) the manufacturer of KXX. The most common adverse events continue to be IRs, anaphylaxis, and gout flares. Post-marketing safety information suggests that the concomitant use of pegloticase with urate-lowering agents may mask the detection of patients who have lost therapeutic response to the drug and increase the risk of IR and/or anaphylaxis. Pegloticase is contraindicated in patients with glucose-6-phosphate dehydrogenase (G6PD) deficiency because of the risk of hemolysis and methemoglobinemia.

Treatment of Patients with KXX

KXX treatment may be initiated with monitoring of SUA levels prior to each infusion. In some embodiments, KXX therapy may be discontinued if the SUA levels increase to above 6 mg/dL, particularly when 2 consecutive levels of above 6 mg/dL are observed, or when SUA levels at 2 consecutive visits are above 6 mg/dL.

In addition, to reduce the incidence of infusion reactions, adverse events (AEs), such as gout flare, or serious adverse events (SAEs) such as anaphylaxis, patients may be premedicated with antihistamines and/or corticosteroids. AEs and SAEs are described in detail below. Anaphylaxis or other IRs may occur with any infusion, including a first infusion, or any subsequent infusion, and generally manifests within 2 hours of the infusion. Delayed-type hypersensitivity reactions may also occur. The most common adverse reactions (occurring in about 5% or more of KXX-treated patients) are gout flares, infusion reactions, nausea, contusion or ecchymosis, nasopharyngitis, constipation, chest pain, anaphylaxis, and vomiting. Additional monitoring of patients during and after infusion may be beneficial to prevent or detect such reactions. In some embodiments, patients are monitored for one hour or more following administration of KXX. In some embodiments, gout flare prophylaxis may be recommended for patients when treating with KXX. For example, gout flare prophylaxis may be recommended for a period of about the first six months of KXX therapy.

In some embodiments, patients or subjects receiving KXX therapy, either alone or co-administered with an immunosuppressive agent, may experience exacerbation of congestive heart failure. For such patients, close monitoring after infusion may be beneficial.

In some embodiments, and to prevent or manage reactions to KXX therapy, such as anaphylaxis and/or infusion reactions, KXX may be administered in a healthcare setting and by a healthcare provider. The KXX admixture may be administered by intravenous infusion over a period of about 60 minutes, or about 45 minutes or about 30 minutes. The KXX admixture may be administered by intravenous infusion over a period of about 45 minutes. The KXX admixture may be administered by intravenous infusion over a period of about 30 minutes. The KXX admixture may be administered by intravenous infusion over a period of about 60 minutes.

In some embodiments, a patient who tolerates a shortened infusion time may be administered pegloticase at a further reduced infusion time as deemed appropriate by a clinician. In some embodiments, a subject or patient receiving pegloticase in about 60, about 45, or about 30 minutes may not experience an increase in adverse events as described herein and therefore may experience an adverse event profile similar in nature and severity to patients receiving the PEGylated uricase in the FDA-approved 120-minute infusion period. Regardless of infusion time, pegloticase is administered via gravity feed, syringe-type pump, or infusion pump. As described in detail below, KXX may be administered alone to a patient, or may be co-administered to a patient or subject with an immunosuppressive agent such as methotrexate (MTX). In some embodiments, KXX may be administered in a healthcare setting as described herein, and an immunosuppressive agent may be administered at home. In other embodiments, both KXX and an immunosuppressive agent such as MTX may be administered in a healthcare setting.

In some embodiments, pre-screening of patients or subjects to be administered KXX, either alone of co-administered with an immunosuppressive agent, such as MTX, for the presence of, or a risk for developing glucose-6-phosphate dehydrogenase (G6PD) deficiency may be beneficial. Such patients may be excluded from treatment with KXX because of a risk of hemolysis and/or methemoglobinemia.

In some embodiments, KXX, either alone, or in combination with an immunosuppressive agent or therapy, may be used to treat a patient with gout or an elevated serum uric acid (SUA) level as described herein.

Dosage of KXX

In some embodiments, KXX may be administered at any dosage deemed appropriate by a clinician or study director. In some embodiments, KXX may be administered at a dosage of about 0.5 mg to about 24 mg of uricase in solution every 2 to 4 weeks. For example, a dosage of KXX as described herein may include, but is not limited to, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, or the like.

In some embodiments, KXX may be administered every 2-4 weeks, such as every 2 weeks, every 3 weeks, or every 4 weeks. In some embodiments, KXX may be administered once per month, or monthly, or twice per month, or bimonthly.

The uricase may be administered in any appropriate way known to one of skill in the art, for example intravenously, intramuscularly, or subcutaneously. In some embodiments, when the administration is intravenous, about 0.5 mg to about 12 mg of uricase is administered, including, but not limited to, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, or the like.

In some embodiments, when the administration is subcutaneous, about 4 mg to about 24 mg of uricase is administered, such as including, but not limited to, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, or the like.

In some embodiments, the uricase is administered by intravenous infusion over a period of about 30 minutes to about 240 minutes, such as including about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, about 180 minutes, about 185 minutes, about 190 minutes, about 195 minutes, about 200 minutes, about 205 minutes, about 210 minutes, about 215 minutes, about 220 minutes, about 225 minutes, about 230 minutes, about 235 minutes, about 240 minutes, or the like, including any specific length of time falling within the 30-240-minute range. In some embodiments, the uricase is administered rapidly, i.e., in a shortened infusion time, e.g., over about 30 minutes to about 240 minutes, or about 30 minutes to about 120 minutes, or about 30 minutes to about 90 minutes, or about 30 minutes to about 60 minutes, or about 30 minutes to about 45 minutes, or about 45 minutes to about 240 minutes, or about 45 minutes to about 120 minutes, or about 45 minutes to about 90 minutes, or about 45 minutes to about 60 minutes, or about 60 minutes to about 240 minutes, or about 60 minutes to about 120 minutes, or about 60 minutes to about 90 minutes, or the like. In other embodiments, KXX is administered over a period of about 30 minutes, or about 45 minutes, or about 60 minutes, or about 75 minutes, or about 90 minutes. Infusion times may be altered, i.e., reduced or extended, from any time period recited herein as deemed appropriate by a clinician or physician.

In some embodiments, a dose of KXX described herein, such as a dose of about 8 mg, or about 12 mg, or about 16 mg, or about 20 mg, or about 24 mg, or about 28 mg, or about 32 mg of uricase is administered once about every 2 weeks, or once about every 3 weeks, or once about every 4 weeks, or once about every 5 weeks, or once about every 6 weeks, or once about every 7 weeks, or once about every 8 weeks. In some embodiments, a dose of KXX as described herein, such as a dose of about 8 mg, or about 12 mg, or about 16 mg, or about 20 mg, or about 24 mg, or about 28 mg, or about 32 mg of KXX may be administered once about every month, or about monthly, or once about every 2 weeks, or about bi-monthly, or once about every 2 months, or the like. In some embodiments, about 8 mg of uricase is administered once every 2 weeks or bi-monthly. In some embodiments, about 32 mg of uricase is administered once every 4 weeks or monthly.

The recommended dose and regimen of KXX for adult patients is 8 mg (uricase protein) given as an intravenous (IV) infusion every two weeks. The optimal treatment duration with KXX has not been established. KXX is a sterile, clear, colorless solution containing 8 mg/mL pegloticase in phosphate-buffered saline, and it intended for intravenous infusion. In other embodiments, KXX is administered in a reduced volume of 50 mL as described herein.

In some embodiments, KXX may be administered to a patient at a dosage of about 8 mg every 2 weeks, or about 8 mg every 3 weeks, or about 8 mg every 4 weeks, or about 8 mg once per month, or about 8 mg bi-monthly, or about 16 mg every 2 weeks, or about 16 mg every 3 weeks, or about 16 mg every 4 weeks, or about 16 mg once per month, or about 16 mg bi-monthly, or about 24 mg every 2 weeks, or about 24 mg every 3 weeks, or about 24 mg every 4 weeks, or about 24 mg once per month, or about 24 mg bi-monthly, or about 32 mg every 2 weeks, or about 32 mg every 3 weeks, or about 32 mg every 4 weeks, or about 32 mg once per month, or about 32 mg bi-monthly. In any of the embodiments described here, in addition to KXX administered at about 8 mg, about 12 mg, about 16 mg, about 20 mg, about 24 mg, or about 32 mg, MTX is also administered to a patient along with MTX at an oral dosage of 15 mg weekly.

In some embodiments, a dosage of KXX described herein, such as including, but not limited to, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg KXX, is administered once every 4 weeks, or once per month or monthly, at a shortened infusion time as described herein, such as about 30 minutes to about 240 minutes, or about 30 minutes to about 120 minutes, or about 30 minutes to about 90 minutes, or about 30 minutes to about 60 minutes, or about 30 minutes to about 45 minutes, or about 45 minutes to about 240 minutes, or about 45 minutes to about 120 minutes, or about 45 minutes to about 90 minutes, or about 45 minutes to about 60 minutes, or about 60 minutes to about 240 minutes, or about 60 minutes to about 120 minutes, or about 60 minutes to about 90 minutes, or the like. In other embodiments, KXX is administered over a period of about 30 minutes, or about 45 minutes, or about 60 minutes, or about 75 minutes, or about 90 minutes. In any of the embodiments described here, in addition to administration of KXX, MTX is also administered to a patient along with MTX at an oral dosage of 15 mg weekly.

Dosage Forms of KXX

KXX may be provided in a 1-mL sterile concentrate for dilution containing 8 mg of pegloticase protein, expressed in uricase protein amounts.

Toxicology of KXX

An observation in the chronic toxicology studies is the finding of a dose-dependent increase in vacuolated cells. There were no associated clinical manifestations in any animals in which vacuolated cells were present. Evidence of vacuolated cells, especially in the spleen, has been observed with pegloticase administration in all the chronic toxicity studies as well as the embryo/fetal development and absorption, distribution, metabolism and excretion studies in the rat. It is thought that vacuolation of spleen macrophages is a result of lysosomal overloading following phagocytosis of persistent circulating macromolecules of high molecular weight. In the 39-week, long-term toxicity studies in dogs, vacuolated cells were also present in the basal area of the lamina propria within the duodenum and jejunum, adrenal cortical cells, hepatic Kupffer cells and the intimal cells within the aortic outflow area of the heart. The vacuolated cells in the heart and adrenal gland did not stain as macrophages. In the aortic outflow tract of the heart, vacuoles were seen in the cytoplasm of endothelial cells in the intimal lining of the aorta. In the adrenal gland, vacuoles were located within cortical cells in the zona *reticularis* and zona *fasciculata*.

Methotrexate (MTX)

It some embodiments, as described herein, KXX may be administered alone as a treatment, or may be co-administered with an immunosuppressive or immunomodulatory agent, such as MTX. In some embodiments, a course of MTX can mitigate immunogenicity to pegloticase, and/or enhance the response rate seen with pegloticase alone in adults with uncontrolled gout. In some embodiments, MTX may be administered to patients receiving KXX to prevent the formation of anti-KXX antibodies. Development of anti-KXX antibodies may increase the clearance of KXX, thereby causing loss of a drug response in the patient.

For this study, MTX was co-administered with KXX to patients or subjects to improve treatment efficacy and reduce IR in patients being treated for chronic refractory gout as an innovative approach to gout management with pegloticase. New strategies to deal with the growing burden of gout and to improve use of existing therapies are urgently needed and the present disclosure represents a novel approach addressing both clinical and immunological questions. In some embodiments, MTX may be administered for a specified period before KXX treatment begins (i.e., pre-dosing of MTX), which may be referred to herein as an MTX "lead-in" period. A lead-in period may begin, for example, 8 weeks, 7 weeks, 6 weeks, 5 weeks, 4 weeks, 3 weeks, 2 weeks, 1 week, 6 days, 5 days, 4 days, 3 days, 2 days, or 1 day prior to KXX treatment, at a dosage as described herein, e.g., 15 mg. In some embodiments, such a pre-dosing period may begin at week −4 (i.e., 4 weeks prior to KXX treatment begins) and continue for as long as deemed appropriate or beneficial. In some embodiments, an MTX lead-in period may continue from week −4 through day 1 of KXX treatment. In some embodiments, an MTX lead-in period may continue from week −3 through day 1 of KXX treatment. In some embodiments, an MTX lead-in period may continue from week −2 through day 1 of KXX treatment. In some embodiments, an MTX lead-in period may continue from week −1 through day 1 of KXX treatment. In some embodiments, MTX may be administered after the lead-in period and for the duration of K×X treatment as described herein.

In some embodiments, MTX may be administered to the patient in any form, either orally or subcutaneously, and at any dose deemed appropriate by a clinician or practitioner. For subcutaneous administration, an auto-injector (e.g., in dosages of 7.5 mg, 10 mg, 15 mg, 20 mg, or 25 mg) may be used by a patient or subject, or may be used by a clinician or practitioner. In some embodiments, oral MTX exposure plateaus at doses of greater than or equal to 15 mg/week. Thus, in some embodiments, the dosage of MTX used in the present study is 15 mg per week, administered orally. In other embodiments, MTX may be administered at a dosage of 15 mg to 25 mg per week, administered subcutaneously. In some embodiments, a patient may be administered increasing doses of MTX to reach a final dosage of 15 mg or 25 mg as described herein, e.g., titrate up to the final MTX dosage. One of skill in the art will understand that different routes of administration may be used without deviating from the scope of the disclosure.

Such a dosage may be administered to a patient to prevent or control immunogenicity to KXX or associated AEs, SAEs, or IRs occurring as a result of KXX treatment. In some embodiments, such a dosage may also be administered to enhance the response rate seen with pegloticase alone in adults with uncontrolled gout. In some embodiments, MTX may be administered to a patient starting when the serum uric acid level is 6 mg/dL or greater. Alternate dosages of MTX may be used as deemed appropriate by a clinician. For example, MTX may be administered at a dosage of 1.0 mg, 1.5 mg, 2.0 mg, 2.5 mg, 3.0 mg, 3.3 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg. 12.0 mg, 12.5 mg, 13.0 mg, 13.5 mg, 14.0 mg, 14.5 mg, 15.0 mg, 15.5 mg, 16.5 mg, 17.0 mg, 17.5 mg, 18.0 mg, 18.5 mg, 19.0 mg, 19.5 mg, 20.0 mg, 20.5 mg, 21.0 mg, 21.5 mg, 22.0 mg, 22.5 mg, 23.0 mg, 23.5 mg, 24.0 mg, 24.5 mg, 25 mg, 50 mg, 75 mg, 100 mg, 125 mg, 150 mg, 175 mg, 200 mg, or the like. In some embodiments, the dosage may be from 10 mg to 25 mg, 15 mg to 30 mg, 5 mg to 50 mg, or the like.

In some embodiments, a maximum dose of 20 mg of MTX may be administered to a patient per week.

Risks of Methotrexate

MTX is a folic acid reductase inhibitor used as a disease-modifying, anti-rheumatic drug for the treatment of autoimmune diseases. Methotrexate is a drug well-known to rheumatologists, has a well-established and understood safety profile and is known to prevent the formation of antidrug antibodies.

Adverse events (AEs) that may be experienced by subjects treated with MTX include: (1) Gastrointestinal: nausea, vomiting, diarrhea, stomatitis; (2) Hematologic and oncologic: leukopenia, thrombocytopenia; (3) Hepatic: hepatotoxicity, increased serum alkaline phosphatase, increased serum bilirubin, increased serum transaminases; (4) Infection: increased susceptibility to infection; (5) General: malaise, fatigue, dizziness, alopecia, photosensitivity.

In some embodiments, MTX dosages may be altered or down-titrated as necessary in the event of gastrointestinal distress, central nervous system symptoms, or elevation in liver function tests. In some embodiments, for subjects experiencing adverse symptoms as described above, folic acid supplementation may be initiated or increased, or the dosage of MTX may be divided into two doses on the same day. In some embodiments, the dosage of MTX may be reduced to, for example, 10 mg in such subjects. In some embodiments, a temporary stop of MTX may be ordered for the patient or subject.

Table 1 below provides lab parameters that may be used to determine the dosage of MTX. The most common reasons to have a temporary stop are typically laboratory based (e.g., increased liver function tests, a decline in renal function, or a decline in white blood cells) or clinical, such as for gastrointestinal-related symptoms, infections, or other intolerance. Additional information relating to MTX is provided herein in the Examples below.

In some embodiments, if liver tests or renal tests become slightly abnormal or changed from baseline, the dosage of MTX may be reduced or temporarily stopped for 2-4 weeks. After re-evaluation of the laboratory tests, MTX may be restarted if appropriate. In other embodiments, a temporary stop of MTX may be ordered if an infection occurs, and maintained while the patient is on antibiotics, which is often 7-14 days unless the infection is severe. MTX may then be resumed if still clinically indicated.

For gastrointestinal symptoms or other tolerance issues, the dose of folic acid, which is given as a supplement to MTX to reduce side effects, may be reduced, or MTX may be held for 1-2 weeks if necessary.

TABLE 1

MTX Dose Guidance During Run-In Period and KXX + MTX Treatment Period

| Lab Parameters | Value | MTX Dose Change |
|---|---|---|
| WBC | $3.0 \times 10^9$/L~$3.5 \times 10^9$/L | Decrease to 10 mg |
| | <$3.0 \times 10^9$/L | Temporary stop |
| Platelets | <$50 \times 10^9$/L | Temporary stop |
| Hematocrit | <27% | Temporary stop |
| AST/ALT | Between 1.5~2 × ULN | Decrease to 10 mg |
| | >2 × ULN | Temporary stop |
| eGFR | <30 ml/min/1.73 $m^2$ | Temporary stop |
| New clinically important symptoms/signs* | Yes | Temporary stop |

In some embodiments, new clinically important symptoms or signs may also affect the dosage of MTX, such as rash or oral ulceration, persistent nausea, vomiting and diarrhea, new or increasing dyspnea or dry cough, or unexplained cough with fever, severe sore throat, abnormal bruising, severe headaches, fatigue, and problems concentrating, any other important medical events that might increase methotrexate toxicity or pre-dispose to new or worsening infection (e.g., undergoing surgery, hospitalization, being treated with antibiotics, having a clinical infection, developing new clinically significant pericardial/pleural effusion or ascites). In such cases, MTX may be temporarily stopped as deemed appropriate.

If minor clinical symptoms emerge, such as mild stomatitis, mild GI discomfort, etc., the folic acid dose may be increased to 2 mg daily or the dose of MTX may be divided (e.g., 3 tabs of 2.5 mg in the morning and evening on the day of dosing).

Emergence of any one of the following criteria should be reviewed: (1) ALT/AST>1.5×ULN on 3 of any 5 consecutive measures; (2) Albumin <0.8×LLN on 2 consecutive measures; (3) Any laboratory or clinical symptoms leading to temporary stop on 3 consecutive measures, in which case consideration for re-initiation, continued temporary stop, or a permanent stop should be taken.

Guidance for increasing MTX back towards 15 mg after dose reduction, based on improvement or resolution of abnormal liver enzymes (>2×ULN) is as follows: (1) When liver enzymes return to values ≤1.5×ULN, increase MTX or dose by 2.5 mg and reassess in 2 weeks; (2) If liver enzymes remain ≤1.5×ULN, increase MTX or dose by 2.5 mg and reassess in 2 weeks.

Improvement of other laboratory abnormalities potentially attributed to MTX may also warrant titration back up to 15 mg weekly.

One of skill in the art will understand that dosages of drugs as described herein may be altered as needed for a patient or subject without deviating from the scope of the disclosure.

In other embodiments, MTX may be administered once per day, twice per day, 3 times per day, or more times per day as needed. In other embodiments, MTX may be administered every 2 days, or every 3 days, or every 4 days, or every 5 days, or every 6 days, or every 7 days, or every 8 days, or every 9 days, or every 10 days, or every 11 days, or every 12 days, or every 13 days, or every 14 days. In other embodiments, the drug may be administered one per week, twice per week, 3 times per week, 4 times per week, 5 times per week, 6 times per week, 7 times per week, 8 times per week, 9 times per week, 10 times per week, 11 times per week, 12 times per week, 13 times per week, 14 times per week, or the like. In some embodiments, different dosages or frequencies may be used on different days, as described herein.

Pharmacokinetic (PK) Analysis

In some embodiments, patients or subjects of the present disclosure may have blood samples taken for PK analysis during treatment with KXX, either alone, or co-administered with an immunosuppressive or immunomodulatory agent, such as MTX. For all subjects, serum samples for pegloticase PK analysis will be collected approximately 15 minutes to 2 hours after the end of infusion on Day 1, or any other infusion days; and prior to infusion and approximately 15 minutes to 2 hours after the end of the infusion. An additional PK sample may be collected at the End-of-Study/Early Termination Visit as applicable. Each sample collection date and time will be recorded.

Although limited PK results have been reported in subjects receiving pegloticase, and no PK studies have been performed in subjects weighing ≥120 kg, the present disclosure provides PK analysis in patients receiving KXX treatment, either alone or co-administered with an immunosuppressive agent or therapy. Sundy et al. (*JAMA* 306(7): 711-20, 2011) reported results from 24 subjects with refractory gout who received single doses from 0.5 to 12 mg of pegloticase. PK parameters included plasma uricase activity (pUox) and the plasma urate concentration (pUAc). In this study, the pUox half-life was 6.4 to 13.8 days. After doses of 4 to 12 mg, the pUAc fell within 24 to 72 hours, from a mean±SD value of 11.1±0.6 mg/dL to 1.0±0.5 mg/dL; the AUC value for the pUAc was equivalent to maintaining the pUAc at 1.2 to 4.7 mg/dL for 21 days post-infusion. It remains uncertain whether body mass affects drug distribution. Since pegloticase is administered as a single dose regardless of body mass, this is important to assess.

Joint Imaging

In some embodiments, joint imaging may be performed for patients or subjects receiving KXX, either alone or co-administered with immunosuppressive therapy, such as MTX. Clinical research has shown that measuring tophus volume alone in gout is incomplete as successful therapy also needs to be associated with a reduction in inflammation, chronic synovitis, acute flares and slowing the progression or even healing of bone erosion, and thus, application of all-inclusive measurements that can measure all parameters of the physiologic impact of urate deposition will allow for comprehensive assessment of chronic gout and the impact of treatment. In some embodiments, a sub-study may also be performed to assess the ability of DECT and DCE-MRI to measure treatment response to pegloticase in subjects with chronic refractory gout.

Co-Administration of KXX and Immunosuppressive Therapy

Immunogenicity in response to pegloticase therapy (anti-pegloticase antibodies) may give rise to low serum drug levels, loss of therapeutic response, poor drug survival, and/or adverse events (e.g., IR). The development of anti-drug antibodies can be influenced by drug- and treatment-related factors, as well as participant characteristics. A potential prophylactic strategy to manage anti-drug antibody response with biologic response modifiers is the co-administration of immune modulating therapy. Reduction of immunogenicity with concomitant administration of other biologic agents (e.g., methotrexate use with adalimumab, infliximab) has been attributed to two mechanisms: (1) an immune modulating effect downregulating B cell activation, differentiation, and immunoglobulin production, and (2) alteration in Fc gamma R-mediated clearance mechanisms leading to prolongation of the half-life of monoclonal antibodies.

Thus, in some embodiments, the addition of immune modulating therapy (i.e., co-administration of KXX with an immunosuppressive or immunomodulatory agent) with an induction regimen or loading dose provides additive benefit in abrogating immunogenicity associated with biologics. As described herein, the immune modulating agent, methotrexate (MTX), is beneficial for use as a therapy to improve treatment efficacy and reduce IR in patients being treated for chronic gout with KXX, and to enhance the response rate seen with pegloticase alone in adults with uncontrolled gout.

Various embodiments of the disclosure provide for treatment of gout or gout related symptoms by administering KXX, either alone or co-administered with an immunosuppressive or immunomodulatory agent, such as MTX. In some embodiments, KXX may be administered alone to a patient for treatment of gout. In other embodiments, KXX may be co-administered with an immunosuppressant, such as MTX, for a combined immunosuppressive therapy.

As used herein, "immunosuppressive agent" may also be referred to as "immunosuppressant" or "immunosuppressive therapy." In some embodiments, an "immunosuppressant" may also be referred to herein as an "immunomodulatory agent." Examples of immunosuppressants include azathioprine, chloroquine, ciclosporin, cyclophosphamide, etanercept, hydroxychloroquine tablets, leflunomide, methotrexate, mycophenolate mofetil, penicillamine, prednisolone, prednisone, sirolimus, sodium aurothiomalate, and tacrolimus.

Administration of an immunosuppressive drug may reduce or eliminate any immune reactions that may occur in the patient. An immune reaction that may be encountered in a drug treatment as described herein may be an allergic reaction or any associated symptoms, including, but not limited to, hives, itching, nasal congestion, rash, scratchy throat, watery or itchy eyes. Severe allergic reactions may have additional symptoms, including, but not limited to abdominal cramping or pain, pain or tightness in the chest, intestinal upset, dizziness, nausea, weakness, or the like. In some embodiments, a severe allergic reaction may include symptoms of anaphylaxis as described herein. Drug reactions may be referred to herein as adverse events (AEs), and may be mild AEs or may be serious AEs (SAEs). Such combination of KXX and another drug, such as MTX, may reduce adverse events in a patient or subject. Thus, in some embodiments, administration of an immunosuppressive therapy with KXX may be beneficial for patients having gout or symptoms thereof. In some embodiments, a patient or subject may be an individual having a serum uric acid level of ≥6 mg/dL.

In some embodiments, co-administration of a PEGylated uricase as described herein and MTX results in normalization of the serum uric acid level in a patient relative to a patient not receiving co-administration of the PEGylated uricase and MTX. In some embodiments, the serum uric acid level may be reduced to less than 6 mg/dL as a result of co-administration of the PEGylated uricase and MTX. In other embodiments, the serum uric acid level may be reduced to less than 5 mg/dL as a result of co-administration of the PEGylated uricase and MTX. In another embodiment, the serum uric acid level is reduced to less than 2 mg/dL as a result of co-administration of the PEGylated uricase and MTX.

In some embodiments, patients or subjects may benefit from a particular dosage of KXX, or a particular dosage regiment, as described herein. For example, patients may be initially treated with a tolerizing dose of KXX, such as a dose of 8 mg KXX on a weekly basis for 3 weeks for a total of 3 doses. In some embodiments, such tolerizing dosage may be altered as deemed necessary by a clinician or practitioner.

In some embodiments, KXX may be administered to a patient following a tolerizing dose at a dosage such as about 8 mg, or 12 mg, or about 16 mg, or about 20 mg, or about 24 mg, or about 32 mg by intravenous infusion about every 2 weeks or about every 3 weeks or about every 4 weeks, or about once per month or monthly, or about twice per month or bi-monthly. In some embodiments, KXX may be administered to a patient following a tolerizing dose at a dosage such as about 8 mg, or about 12 mg, or about 16 mg, or about 20 mg, or about 24 mg, or about 32 mg by intravenous infusion about every 2 weeks or about every 3 weeks or about every 4 weeks, or about once per month or monthly, or about twice per month or bi-monthly. This dosage may be continued for any period of time deemed appropriate by a clinician or practitioner. For example, about 8 mg, or about 12 mg, or about 16 mg, or about 20 mg, or about 24 mg, or about 32 mg KXX may be given to a particular patient about every 2 weeks, or about every 3 weeks, or about every 4 weeks, or about once per month or monthly, or about twice per month or bi-monthly about following a tolerizing dosage regimen and lasting for a period of time totaling about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 53 weeks, about 54 weeks, about 55 weeks, about 60 weeks, about 65 weeks, about 70 weeks, or the like. Likewise, KXX+MTX therapy may continue for any specific number of treatment or infusions as deemed appropriate by a clinician or study director. For example, during KXX+MTX treatment, KXX may be administered in 5 infusions, or 6 infusions, or 7 infusions, or 8 infusions, or 9 infusions, or 10 infusions, or 11 infusions, or 12 infusions, or 13 infusions, or 14 infusions, or 15 infusions, or 16 infusions, or 17 infusions, or 18 infusions, or 19 infusions, or 20 infusions, or 21 infusions, or 22 infusions, or 23 infusions, or 24 infusions, or 25 infusions, or 26 infusions, or 27 infusions, or 28 infusions, or 29 infusions, or 30 infusions. In some embodiments, KXX may be administered in 6-26 infusions. In some embodiments, KXX may be given to a patient for more than about 6 months, or more than about 7 months, or more than about 8 months, or more than about 9 months, or more than about 10 months, or more than about 11 months, or more than about 12 months, or more than about 13 months, or more than about 14 months, or more than about 15 months, or more than about 18 months, or more than about 24 months. In other embodiments, KXX may be given to a patient for any length of time deemed appropriate by a clinician or practitioner, and as described herein, for the remainder of the patient's life.

In some embodiments, the patient may be treated with KXX plus an immunosuppressive or immunomodulatory agent or therapy for at least one month. In some embodiments, the patient is treated for 2 months, 3 months, 4 months, 5 months, 6 months, 7 months, 8 months, 9 months, 10 months, 11 months, 12 months, 13 months, 14 months, 15 months, 18 months, 21 months, 24 months, 30 months, 36 months, or more. In some embodiments, the patient may be treated for up to 52 weeks, or 51 weeks, or 50 weeks, or 49 weeks, or 48 weeks, or 47 weeks, or 46 weeks, or 45 weeks, or 44 weeks, or 43 weeks, or 42 weeks, or 41 weeks, or 40 weeks, or 39 weeks, or 38 weeks, or 37 weeks, or 36 weeks, or 35 weeks, or 34 weeks, or 33 weeks, or 32 weeks, or 31 weeks, or 30 weeks, or 25 weeks, or 20 weeks, or 17 weeks, or 12 weeks, or 6 weeks, or 4 weeks, or 2 weeks, or 24 months, or up to 36 months, or up to 48 months. In some embodiments, the patient may be treated for more than 24 months. In some embodiments, the patient is treated with for the rest of the patient's life.

In some embodiments, a tolerizing dosage regimen as described herein may be combined with the use or co-administration of an immunosuppressive agent or therapy. Such a tolerizing dosage regimen may involve escalation of a dose of KXX and an immunosuppressive agent or therapy such that the patient or subject is able to better tolerate KXX or the dosage thereof. In other embodiments, such a tolerizing dosage regimen may involve increasing or escalating doses of KXX with a particular dose of an immunosuppressive agent or therapy. Such treatments may be employed for any duration as described herein.

In some embodiments, treatment with KXX either alone or co-administered with an immunosuppressive or immunomodulatory agent, may be continued as appropriate for any length of time, as long as the patient experiences an improvement in the symptoms or signs of gout. Such signs/symptoms of gout that may serve as a metric for improvement in disease severity may include, but are not limited to, serum uric acid level, peripheral joint urate deposition volume, and inflammatory volume. For example, KXX treatment, either alone, or co-administered with an immunosuppressive agent, such as MTX, may be monitored with regular assessment of the patient or subject before, during, and following treatment. Any number of diagnostic or evaluative testing procedures may be performed at any time, and at any frequency as deemed necessary by a clinician or practitioner.

KXX treatment typically is monitored using regular determination of the patient's SUA levels. A reduction in the serum uric acid level relative to the SUA in the patient before KXX treatment may generally be indicative of successful treatment with KXX, alone, or co-administered with an immunosuppressive agent or therapy, such as MTX, as described herein. Collection and measurement of a patient's serum uric acid levels are known to those of skill in the art. In some embodiments, the patient's serum uric acid levels are assayed before each KXX therapy. In some embodiments, any suitable method for collecting appropriate samples and methods of measuring or quantifying uric acid levels may be used in accordance with the disclosure.

Additional measurements to assess the efficacy and safety of KXX treatment may be used in accordance with the disclosure. These may include trough KXX levels, anti-KXX antibody levels, and/or anti-PEG antibody levels. In some embodiments, these measurements may be taken prior to each dose of KXX after the first dose. In other words, an initial dose of KXX may be administered to a patient without measurement of KXX levels, anti-KXX antibody levels, and/or anti-PEG antibody levels. Then, prior to each subsequent dose of KXX, such measurements may be taken as described herein. For treatment regiments wherein KXX is co-administered with an immunosuppressive agent or therapy, the same measurements may be taken at the same time periods, without deviating from the scope of the disclosure. Such measurements may be obtained from each patient as necessary to evaluate response to the treatment, or a lack thereof. Specific criteria for responders and non-responders to treatment with KXX are described in the Examples.

For example, in some embodiments, serum uric acid levels may be evaluated to assess the response rate of the patient to the KXX+MTX therapy or treatment, as well as the response of a patient or subject to a shortened infusion period as described herein. Some embodiments provide for lowering or normalization of the SUA levels to below 6 mg/dL as described herein. Other embodiments provide for lowering or normalization of the SUA levels to 5 mg/dL or below as described herein. Some embodiments provide for lowering or normalization of the SUA levels to 6 mg/dL or below as described herein. Other embodiments provide for lowering or normalization of the SUA levels to 5 mg/dL or below as described herein. In some embodiments, certain objectives of the present disclosure and the studies described herein may include estimation of response rate during Month 3 (e.g., Weeks 10, 12 and 14) of KXX+MTX therapy, as measured by the sustained normalization of SUA to <6 mg/dL for at least 80% of the time during Month 3 in subjects receiving pegloticase with MTX. In some embodiments, estimation may be performed of the overall response rate, as measured by the sustained normalization of SUA to <6 mg/dL for at least 80% of the time during both Month 3 (e.g., Weeks 10, 12 and 14) and Month 6 (e.g., Weeks 20, 22 and 24) combined of KXX+MTX therapy in subjects receiving pegloticase with MTX. In other embodiments, estimation may be performed of the 5 mg/dL response rate during Month 3, during Month 6, and Overall (Months 3 and 6 combined), as measured by the sustained normalization of SUA to <5 mg/dL for at least 80% of the time in subjects receiving pegloticase with MTX. In some embodiments, estimation may be performed of the mean change from baseline to a certain time point, e.g., including, but not limited to, Weeks 14, 24, 36, and 52 in SUA for subjects receiving KXX+MTX. Such measurements and the methods for their collection and evaluation are described in detail in the Examples.

In some embodiments, when KXX is co-administered with an immunosuppressive agent or therapy, such as MTX, additional measurements for assessing the efficacy of treatment may be obtained. For example, trough methotrexate metabolite levels may be obtained for each patient or subject prior to each dose of KXX, as described herein. In other embodiments, measurement of hematology and liver function may be obtained for each patient on a weekly basis during treatment. This type of measurement may provide information to clinicians relating to the breakdown of the immunosuppressive agent in the patient's body.

In some embodiments, co-administration of KXX and methotrexate immunosuppressive therapy results in normalization of the serum uric acid level in the patient relative to a patient not receiving KXX and MTX immunosuppressive therapy. As used herein, "normalization" refers to lowering of the serum uric acid level similar to that found in normal healthy patients. In other embodiments, normalization may refer to SUA levels being reduced to levels similar to that found in patients not requiring KXX treatment or therapy. In some embodiments, the serum uric acid level is normalized after KXX and methotrexate immunosuppressive therapy begins.

In some embodiments, as described herein, the serum uric acid level in patients treated with KXX and an immunosuppressive therapy such as MTX is reduced to less than 6 mg/dL as a result of treatment, including, but not limited to, 6 mg/dL, 5.9 mg/dL, 5.8 mg/dL, 5.7 mg/dL, 5.6 mg/dL, 5.5 mg/dL, 5.4 mg/dL, 5.3 mg/dL, 5.2 mg/dL, 5.1 mg/dL, 5 mg/dL, 4.9 mg/dL, 4.8 mg/dL, 4.7 mg/dL, 4.6 mg/dL, 4.5 mg/dL, 4.4 mg/dL, 4.3 mg/dL, 4.2 mg/dL, 4.1 mg/dL, 4 mg/dL, 3.9 mg/dL, 3.8 mg/dL, 3.7 mg/dL, 3.6 mg/dL, 3.5 mg/dL, 3.4 mg/dL, 3.3 mg/dL, 3.2 mg/dL, 3.1 mg/dL, 3 mg/dL, 2.9 mg/dL, 2.8 mg/dL, 2.7 mg/dL, 2.6 mg/dL, 2.5 mg/dL, 2.4 mg/dL, 2.3 mg/dL, 2.2 mg/dL, 2.1 mg/dL, 2 mg/dL, 1.9 mg/dL, 1.8. mg/dL, 1.7 mg/dL, 1.6 mg/dL, 1.5 mg/dL, 1.4 mg/dL, 1.3 mg/dL, 1.2 mg/dL, 1.1 mg/dL, 1 mg/dL, or the like. In other embodiments, the serum uric acid level may be reduced to less than 5 mg/dL as a result of treatment. In still further embodiments, the serum uric acid level is reduced to less than 2 mg/dL as a result of KXX and methotrexate immunosuppressive therapy. Treatment with KXX plus an immunosuppressive therapy may be able to reduce the serum uric acid levels to levels that result in improvement of symptoms associated with gout as described herein.

In some embodiments, normalization of the SUA levels in a subject may be achieved within a specific amount of time as a measurement of success or efficacy. For example, in some embodiments, normalization of the SUA may be achieved by 2 weeks after initiation of treatment with KXX+MTX, such as by week 1, or week 2, or week 3, or week 4, or week 5, or week 6, or week 7, or week 8, or week 9, week 10, or week 11, or week 12, or week 13, or week 14, or week 15, week 16, or week 17, or week 18, or week 19, or week 20, or week 21, or week 22, or week 23, or week 24, or week 25, or week 26, or week 27, or week 28, or week 29, or week 30, or week 31, or week 32, or week 33, or week 34, or week 35, or week 36, or week 37, or week 38, or week 39, or week 40, or week 41, or week 42, or week 43, or week 44, or week 45, or week 46, or week 47, or week 48, or week 49, or week 50, or week 51, or week 52, or week 53, or week 54, or week 55, or week 56, or week 57, or week 58, or week 59, or week 60, or the like.

In some embodiments, treatment of a patient or subject with KXX plus an immunosuppressive or immunomodulatory agent such as MTX results in a reduction of the incidence of infusion reaction, gout flare, or anaphylaxis.

In some embodiments, the level of MTX metabolite is increased relative to a patient not receiving KXX and methotrexate immunosuppressive therapy.

In some embodiments, analysis of the efficacy of a method as described herein for treating gout may further comprise measurements to assess disease severity. For example, a diagnostic imaging test, such as including, but not limited to, computed tomography (CT), magnetic resonance imaging (MRI), X-ray, ultrasound, positron emission tomography (PET), fluoroscopy, or the like.

In some embodiments, peripheral joint urate deposition volume and inflammatory volume may be measured in a patient and used to evaluate disease severity or to evaluate efficacy of the drug treatment. For example, in some embodiments, peripheral joint urate deposition volume is reduced in the patient relative to a patient not receiving KXX and methotrexate immunosuppressive therapy. In other embodiments, peripheral joint urate deposition volume is determined by dual-energy computed tomography (DECT) scanning. In other embodiments, inflammatory volume is reduced in the patient relative to a patient not receiving KXX and methotrexate immunosuppressive therapy. In other embodiments, inflammatory volume is determined by Dynamic Contrast Enhanced-Magnetic Resonance Imaging (DCE-MRI) or MRI without contrast, or both.

In some embodiments, administration of KXX alone or co-administration of KXX with an immunosuppressive therapy or agent or with a drug having monomethoxypoly (ethylene glycol) (PEG) may elicit an immune reaction in the patient or subject. Evaluation of antibodies in a subject or patient receiving KXX therapy may provide an assessment of such an immune reaction to the drug treatment. For example, in some embodiments, determination of a mean titer of anti-KXX antibodies or anti-monomethoxypoly(ethylene glycol) (PEG) antibodies may be performed to determine an immune reaction in the patient or subject, or to determine the efficacy of immunosuppressive therapy. In some embodiments, a mean titer of anti-KXX antibodies may be determined for a patient. In other embodiments, a mean titer of anti-monomethoxypoly (ethylene glycol) (PEG) antibodies may be determined. In some embodiments, antibody titers may be any value determined by any appropriate measurements or analyses. Antibody titers in a patient as used herein are a metric for and may indicate an immune response to a drug such as KXX. In some embodiments, an antibody titer as described herein may refer to antibodies in a patient directed against KXX or PEG. In some embodiments, an anti-KXX or anti-PEG mean antibody titer may be less than or equal to about 1:6000 as a result of KXX administration. For example, an antibody titer for a patient receiving KXX therapy, either alone or in combination with MTX, may be less than or equal to about 1:100, about 1:200, about 1:300, about 1:400, about 1:500, about 1:600, about 1:700, about 1:800, about 1:900, about 1:1000, about 1:2000, about 1:3000, about 1:4000, about 1:5000, about 1:6000, about 1:7000, about 1:8000, about 1:9000, about 1:10000, or the like. In some embodiments, a responder may have an anti-KXX antibody titer of about 1:837±1687, or about 1:4211, or about 1:5898. In other embodiments, the antibody titers recited above may generally be found in patients who exhibit a positive response to KXX therapy (i.e., a responder). In some embodiments, a non-responder may have substantially or significantly higher antibody titers, for example, less than or equal to about 1:30000, about 1:40000, about 1:50000, about 1:60000, about 1:70000, about 1:80000, about 1:90000, about 1:100000, about 1:150000, about 1:200000, about 1:250000, about 1:300000, about 1:350000, about 1:400000, about 1:450000, about 1:500000, or the like. In some embodiments, a non-responder may have an anti-KXX antibody titer of about 1:34528±42,228. In other embodiments, such antibody titers may be determined for KXX treatment alone or may be determined for KXX+MTX immunosuppressive therapy. Anti-KXX or anti-PEG mean antibody titers as a result of KXX and MTX immunosuppressive therapy may be beneficially maintained at or below any threshold value tolerable for the patient.

In some embodiments, anti-drug antibody titers may be reduced as a result of use of an immunosuppressive agent or therapy, such as MTX as described herein. In other embodiments, the titer of specific types of antibodies may be reduced. For example, in some embodiments, the levels or titer of any specific type of antibodies may be reduced as a result of KXX co-administered with an immunosuppressive agent or therapy, such as IgG antibodies, IgA antibodies, IgM antibodies, IgD antibodies, IgE antibodies, or combinations thereof.

In some embodiments, evaluation of antibody titers may be beneficial for patients receiving KXX, either alone, or co-administered with an immunosuppressive agent or therapy such as MTX, for the first time. In other embodiments, evaluation of antibody titers may be beneficial for patients who have developed anti-KXX antibodies, or who have been classified as non-responders to KXX treatment. Criteria for classifying a patient or subject as a responder or a non-responder are described herein elsewhere.

In some embodiments, heavier and/or younger patients may have a higher incidence of anti-KXX antibodies, or may have higher anti-KXX drug titers, than lighter and/or older patients. In other embodiments, lighter and/or older patients may have higher drug loading of KXX than heavier and/or younger patients. In some embodiments, lighter patients may have higher exposures of KXX than heavier patients. For example, in some embodiments, lighter patients may have greater than 2-fold exposure to KXX than heavier patients. In some embodiments, lower drug levels in a patient may result in anti-KXX antibodies. For example, the mean area under the curve (AUC) for lighter patients may be about 8.92 mg/L versus about 4.04 mg/L in heavier patients. In other embodiments, older patients may have higher exposures of KXX than younger patients. For example, in some embodiments, older patients may have greater than 2-fold exposure to KXX than younger patients. In some embodiments, the mean area AUC for older patients may be about 8.86 mg/L versus about 3.93 mg/L in younger patients, indicating that younger patients may have a more robust immune system. Thus, in some embodiments, additional 8-mg doses of KXX (e.g., 16 mg, 24 mg, or 32 mg) may be beneficial for younger and/or heavier patients. In other embodiments, younger and/or heavier patients may benefit from one or more loading doses of 16 mg of KXX.

In some embodiments, production of anti-drug antibodies, such as antibodies to KXX, may be reduced or eliminated by increasing the amount of KXX delivered to a patient, i.e., maintaining higher trough levels of KXX in a patient. Higher trough levels of KXX may reduce anti-drug antibody production. In some embodiments, possible dosing strategies for increasing the amount of KXX delivered to a patient, and thus producing higher trough levels in the patient, may include reducing the interval between doses of KXX, or using higher doses at the beginning of and/or during treatment. Another possible strategy for reducing anti-KXX antibodies is the use of immunomodulators, such as MTX, as described herein. Immunomodulators may reduce or eliminate an immune response to unfamiliar proteins. One of skill in the art will understand that other immunomodulators may be used with similar results, including, but not limited to, corticosteroids (i.e., prednisone), Rapimmune, myophenolate, methotrexate, or the like.

The methods disclosed herein presume that the patient is effectively receiving all the prescribed dose. In some embodiments, depending on the age of the patient, it may be difficult to deliver a drug to a patient, for example when administering a drug to an infant and, therefore, the compliance and effectiveness of drug delivery by the patient's parent(s), guardian(s), or health care provider(s) may also be assessed.

Definitions

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and can also cover other unlisted steps. Similarly, any composition or device that "comprises," "has," or "includes" one or more features is not limited to possessing only those one or more features and can cover other unlisted features.

As used in this specification and the appended claims, the singular forms "a," "an," and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like.

As used herein, "KXX" may be used interchangeably with KRYSTEXXA® or pegloticase. Likewise, as used herein, "Pegloticase+IMM Period" may also be referred to herein as "KXX+IMM Period" or "KXX+MTX Period." As used herein, "KXX+MTX Period" or "Pegloticase+MTX Period" may be for any length of time deemed appropriate by a clinician or study director.

"IMM" as used herein refers to an immunomodulatory agent, such as MTX as described herein. As such, IMM may also be used interchangeably herein with MTX. Therefore, "Pegloticase+IMM Period" or other similar terminology refers to the presently described co-administration or concomitant administration of KXX and MTX.

As used herein, an "adverse event" or "AE" refers to any untoward medical occurrence associated with the use of a drug in humans, whether it is considered drug-related or not. An AE or suspected adverse reaction is considered a "serious adverse event" or "SAE" if, it results in any of the following outcomes: (1) Death, (2) Life-threatening: an AE is considered "life-threatening" if its occurrence places the subject or subject at immediate risk of death. It does not include an AE that, had it occurred in a more severe form, might have caused death; (3) Inpatient hospitalization or prolongation of existing hospitalization (treatment on an emergency, outpatient basis for an event not fulfilling any of the definitions of SAEs and not resulting in hospital admission does not qualify); (4) A persistent or significant incapacity or substantial disruption of the ability to conduct normal life functions. (5) A congenital anomaly/birth defect; (6) A suspected transmission of any infectious agent via a medicinal product; (7) Important medical events that may not result in death, be life-threatening, or require hospitalization may be considered serious when, based upon appropriate medical judgment, they may jeopardize the patient or subject and may require medical or surgical intervention to prevent one of the outcomes listed in this definition. Examples of such medical events include invasive cancers, allergic bronchospasm requiring intensive treatment in an emergency room or at home, blood dyscrasias or convulsions that do not result in hospitalization, or the development of drug dependency or drug abuse. AEs that do not result in any of these outcomes are considered non-serious.

As used herein, "anaphylaxis" refers to a severe, acute onset allergic reaction that may occur over minutes to several hours. Anaphylaxis may involve the skin, mucosal tissue, or both, and may have one or more symptoms including, but not limited to, generalized hives, pruritus (itching), flushing, swelling of the lips, tongue, throat or uvula, shortness of breath, vomiting, lightheadedness, wheezing, hemodynamic instability, and rash or urticaria. In addition, anaphylaxis may be accompanied by at least one of the following: respiratory compromise (e.g., dyspnea, wheeze-bronchospasm, stridor, reduced peak expiratory flow, hypoxemia), and reduced blood pressure (i.e., systolic blood pressure <90 mm Hg or greater than 30% decrease from that person's baseline) or associated symptoms of end-organ failure (e.g., hypotonia [collapse], syncope, incontinence). Anaphylaxis in accordance with the disclosure is defined by the National Institute of Allergy and Infectious Disease/Food Allergy and Anaphylaxis Network (NIAID/FAAN) clinical criteria for diagnosing anaphylaxis (Sampson et al., 2006). Anaphylaxis reactions were reported as a serious adverse event (SAE) for the present disclosure. The Criteria are as follows: (1) Acute onset of an illness (minutes to several hours) with involvement of the skin, mucosal tissue, or both (e.g., generalized hives; pruritus or flushing; urticaria and angioedema (of lips, tongue, or uvula) and >1 of the following: (a) Respiratory compromise (e.g., dyspnea, wheeze-bronchospasm, stridor, reduced peak expiratory flow, hypoxemia); (b) Reduced BP or associated symptoms of end-organ dysfunction (e.g., hypotonia [collapse], syncope, incontinence). (2) Two or more of the following that occur rapidly after exposure to a likely allergen for that subject (minutes to several hours): (a) Involvement of the skin-mucosal tissue (e.g., generalized hives, itch-flush, swollen lips-tongue, uvula); (b) Respiratory compromise (e.g., dyspnea, wheeze-bronchospasm, stridor, reduced peak expiratory flow, hypoxemia); (c) Reduced BP or associated symptoms (e.g., hypotonia [collapse], syncope, incontinence); (d) Persistent gastrointestinal symptoms (e.g., crampy, abdominal pain, vomiting). (3) Reduced BP after exposure to known allergen for that subject (minutes to several hours): systolic BP<90 mmHg or >30% decrease from that subject's baseline.

Anti-drug Antibody Measurements Immunogenicity of pegloticase will be assessed via serum samples for evaluation of anti-PEG and anti-uricase IgG antibodies. Samples will be collected prior to the pegloticase infusion on Day 1 and at regular intervals throughout the treatment period, e.g., Weeks 2, 6, 12, 20, the End-of-study/Early Termination Visit and 3- or 6-month Post-Treatment Follow-up Visits. In other embodiments, assessment of anti-drug antibody measurements may be obtained at any time before, during, or after infusion of KXX. In the event of an AE suspected to be an IR, a serum sample will be collected at that time or at the subsequent visit for evaluation of pegloticase antibodies. Each sample collection date and time will be recorded.

As used herein, "bi-monthly" refers to a period of time, e.g., for administration of KXX as described herein, occurring every 2 weeks or twice per month. In some embodiments, "monthly" refers to a period of time, e.g., for administration of KXX as described herein, occurring every 4 weeks or once per month.

Cardiovascular Events: The following cardiovascular events were collected. Major Adverse Cardiovascular Events (MACE) defined as: Non-Fatal Myocardial Infarction: The presence of at least 2 of the 3 following criteria: (1) chest pain consistent with angina, (2) abnormal values of cardiac enzymes (>upper limit of normal of the MB fraction of creatinine phosphokinase and/or troponin that follows a pattern of myocardial injury), (3) myocardial injury current (ST segment elevation) or the development of new Q waves in 2 contiguous leads of the electrocardiogram. Non-Fatal Stroke: ischemic or hemorrhagic stroke defined as an acute, focal neurologic event that persisted for >24 hours. If neurologic symptoms last for <24 hours but magnetic resonance imaging (MRI) confirms an infarct, it was considered as a stroke. Cardiovascular deaths: including any death from a cardiovascular cause including: myocardial infarction, stroke, heart failure, arrhythmic death, aortic dissection or rupture, any fatal thromboembolic event, sudden cardiac death, any death of unknown cause and unwitnessed death. Congestive heart failure defined as: hospitalization or prolonged (>12 hours) emergency department visit due to dyspnea, shortness of breath, with progressive edema accompanied by clinical findings of pulmonary vascular congestion.

As used herein, "co-administration" refers to the simultaneous administration of one or more drugs with another in a treatment regimen. For example, as described herein, co-administration of KXX with MTX may refer to administration of MTX at the same time as KXX or may refer to administration of MTX at a specific period of time before or after KXX administration. In some embodiments, MTX may be administered before KXX. In other embodiments, KXX may be administered before MTX. In other embodiments, both drugs are administered at the same time. As described herein elsewhere, co-administration may also refer to any particular time period of administration of either KXX or MTX, or both. For example, as described herein, MTX may be administered hours, days, weeks, or months before KXX treatment, as long as both drugs are to be provided to a patient or subject in a particular treatment regimen. In other embodiments, MTX may be administered to a patient hours, days, weeks, or months after KXX treatment. In some embodiments, co-administration may refer to any time of administration of KXX and/or MTX such that both drugs are present in the body of a patient at the same. In some embodiments, either drug may be administered before or after the other, so long as they are both present within the patient for enough time that the patient received the intended clinical or pharmacological benefits.

As used herein, "concomitant administration" refers to a therapeutic or drug regimen in which one or more medications are given together. i.e., at the same time. In some embodiments, concomitant administration and co-administration may be referred to interchangeably.

By the terms "effective amount" and "therapeutically effective amount" of an agent, compound, drug, composition or combination which is nontoxic and effective for producing some desired therapeutic effect upon administration to a subject or patient (e.g., a human subject or patient).

As used herein, "gout" or "uncontrolled gout" refers to chronic gout in adult patients refractory to conventional management. As described herein, pegloticase (KXX) is indicated for the treatment of chronic gout in adult patients refractory to conventional management.

As used herein, a "gout flare" refers to a manifestation of physiological or biochemical symptoms of gout, which is a possible side effect or AE associated with treatment with KXX. A gout flare may produce burning itching, tingling, or stiffness in the joints, particularly the peripheral joints. An individual may also experience redness, swelling, and pain in the joints. In accordance with the disclosure, gout flares may initially increase when starting treatment with KXX. For such individuals, medications to help reduce flares may be taken regularly for the first few months after KXX is started. Prophylactic treatment for gout flares may include, but is not limited to, anti-inflammatory treatment (e.g., corticosteroids, colchicine, intra-articular steroid injections, non-steroidal anti-inflammatory drugs (NSAID), a or low-dose prednisone (e.g., ≤10 mg/day).

In some embodiments, prophylactic treatment may be given prior to an infusion of KXX, for example one week prior to treatment with KXX.

As used herein, "glucose-6-phosphate dehydrogenase (G6PD) Deficiency" or "G6PD" refers to a condition caused by an inborn error of metabolism that predisposes an individual to red blood cell breakdown. Individuals with G6PD deficiency are not included in the present study and are generally advised not to take KXX.

As used herein, "immuno-tolerance" refers to the lack of an immune response in a patient as a result of a drug treatment such as KXX. In some embodiments, establishing immune-tolerance may also refer to reducing immunogenicity to KXX, or to reduce or prevent loss of a response to KXX. Such loss of response may be the result of the formation of anti-drug antibodies, which may increase clearance of KXX, causing a loss of response.

Individual Tophi Response: All measurable tophi were measured bi-dimensionally (using the longest diameter and the longest perpendicular to that diameter) and the response of each individual tophus was categorized according to the change from baseline in area of each tophus at each visit as follows: Complete Response (CR)—A 100% decrease in the area of the tophus; Marked Response (MR)—At least a 75% decrease in the area of the tophus; Stable Disease (SD)—Neither a 50% decrease nor a 25% increase in the area of the tophus can be demonstrated; Progressive Disease (PD)—A 25% or more increase in the area of the tophus; Unable to Evaluate (UE)—The tophus cannot be accurately measured for any reason at any given post-baseline time point (e.g., image missing or of poor quality, obvious infection of the tophus).

Each individual unmeasured tophus was semi-quantitatively assessed based upon the impression of the central reader using the following guideline: Complete Response—the disappearance of the tophus; Improved—an approximate 50% or more reduction from baseline in the size of the tophus; Stable Disease—neither improvement nor progression from baseline can be determined; Progressive Disease—an approximate 50% or more increase from baseline in the area of the tophus. Unable to Evaluate—the tophus cannot be assessed for any reason at any given post-baseline time point (e.g., image missing or of poor quality, or obvious infection of the tophus).

The overall response for a subject was based upon the best response among all tophi (including measurable and unmeasured) for that subject (e.g., if any one tophus shows complete response, the overall response is Complete Response). If any single tophus shows progression, or if a new tophus appears during the study, the overall response for that subject was Progressive Disease, regardless of the response of any other tophi. New tophi arising outside of the regions photographed at baseline were captured and also resulted in an overall response assessment of Progressive Disease.

As used herein, an "infusion reaction" or "IR" refers to a reaction of a patient or subject to a drug. An IR will be defined as any infusion-related AE or cluster of temporally-related AEs, not attributable to another cause, which occur during the pegloticase infusion and for 2 hours post infusion. Infusion reactions generally refer to drugs administered by intravenous (IV) infusion. The most common signs and symptoms of an infusion reaction, including urticaria (skin rash), erythema (redness of the skin), dyspnea (difficulty breathing), flushing, chest discomfort, chest pain, and rash. For the present disclosure, IRs were recorded as Infusion Reaction AEs. If the IR meets the definition for "Serious" as described herein, it is also reported as an SAE. In some embodiments, an IR was defined as any infusion-related AE or cluster of temporally-related AEs, not attributable to another cause, which occur during or within 2 hours after the infusion of pegloticase. Other AEs that occur outside of the 2-hour window following the infusion may also be categorized as an IR per the discretion of each study site. Signs and symptoms of the IR, and treatments administered, were documented. Examples of AEs not considered possible IRs include but are not limited to: laboratory abnormalities that are unlikely to have occurred during or within 2 hours following the infusion (e.g., anemia, hypercholesterolemia), gout flares, most infectious diseases, or the recurrence or worsening of a known chronic medical problem identified in the participant's medical history.

As used herein, "IR Prophylaxis" refers to a treatment regimen to prevent infusion reactions. In some embodiments, all participants received pre-treatment IR prophylaxis consisting of at least an antihistamine and corticosteroid prior to each infusion of pegloticase. In some embodiments, to standardize this prophylaxis regimen, participants may take (60 mg) fexofenadine orally the night before and again on the morning of the infusion with 1000 mg/day of acetaminophen. Prior to the infusion, hydrocortisone 200 mg IV was administered and a targeted physical exam was performed. The name, dose, route, date, and time of administration of each prophylactic medication were recorded in the medical record and in the CRF. In some embodiments, IR prophylaxis may include fexofenadine (180 mg orally) and prednisone (50 mg orally) may be taken the night before each KXX infusion; fexofenadine (180 mg orally), famotidine (20 mg orally), montelukast (10 mg orally), and acetaminophen (1000 mg orally) may be taken the morning of each KXX infusion; methylprednisolone (125 mg IV) may also be administered prior to each KXX infusion, e.g., over an infusion duration of 10 to 30 minutes. In some embodiments, IR prophylaxis may include, but is not limited to, hydrocortisone (200 mg IV) immediately preceding infusions and fexofenadine (60 mg PO) the night before and the morning of infusions.

As used herein, "KRYSTEXXA®" or "KXX" or "pegloticase" or "PEGylated uricase" refers to a covalent conjugate of uricase produced by a genetically modified strain of *Escherichia coli* and monomethoxypoly (ethylene glycol). Although the term "uricase" or "PEGylated uricase" may be used herein to refer to a PEGylated uricase such as KRYSTEXXA®, one of skill in the art would understand that many different forms of a uricase may be known and used in accordance with the disclosure, and therefore any PEGylated uricase, such as KRYSTEXA or KXX, may be used for treatment of a patient with elevated SUA as described herein. Per the prescribing information, KRYSTEXXA® (pegloticase) concentrations are expressed as concentrations of uricase protein. Each mL of KRYSTEXXA contains 8 mg of uricase protein (conjugated to 24 mg of 10 kDa mPEG), 2.18 mg Disodium Hydrogen Phosphate Dihydrate ($Na_2HPO_4 \cdot 2H_2O$), 8.77 mg Sodium Chloride (NaCl), 0.43 mg Sodium Dihydrogen Phosphate Dihydrate ($NaH_2PO_4 \cdot 2H_2O$), and Water for Injection to deliver 8 mg of pegloticase (as uricase protein).

MTX Polyglutamate Measurements: Blood samples will be collected prior to pegloticase infusion on, e.g., Day 1, Weeks 14, 22, End of Pegloticase Infusions Visit (if applicable) and any number of Visits during the Pegloticase+MTX Period, e.g., 6 visits, 12 visits, 18 visits, 24 visits, 26 visits, or the like. Each sample collection date and time will be recorded.

As used herein, the term "normal uric acid level" refers to a patient's blood plasma uric acid concentration in a range that does not cause physiological or biochemical symptoms or signs of gout. In some embodiments, a normal uric acid level may not exceed the biochemical limit of solubility. For females, a normal uric acid range may fall between about 2.4 mg/dL and about 6 mg dL, and for males, about 3.4 mg/dL to about 7 mg/dL. One of skill in the art will recognize that these values may vary slightly depending on the subject or patient, as well as on the laboratory. As used herein, the term "elevated uric acid levels" refers to a patient's blood plasma or serum uric acid concentration equal to or greater than about 6 mg/dL. In some embodiments, the uric acid level in a patient may be normalized to less than about 6 mg/dL, or less than about 5 mg/dL, or less than about 2 mg/dL, following treatment with KXX, either alone or co-administered with an immunosuppressive agent or therapy. To this effect, uric acid levels can vary based on the particular testing methodology and from laboratory to laboratory.

As used herein, an "overdose" is defined as a known deliberate or accidental administration of investigational drug, to, or by a study subject, at a dose above that which is assigned to that individual subject according to the study protocol. All cases of medication errors and overdose (with or without associated AEs) will be documented on the eCRF in order to capture this important safety information consistently in the database. AEs associated with an overdose and SAEs of overdose are to be reported. In the event of drug overdose, the subject is to be treated as appropriate.

Patient Global Assessment: The Patient Global Assessment was collected at the Screening and Week −4, −3, −2 (prior to the first dose of MTX) Visits during the MTX Run-in Period; prior to KXX infusion, e.g., at the Day 1 and Weeks 14, 24, and 36 Visits during the KXX+MTX Period; at the End of Pegloticase Infusions Visit (if applicable); the End of Study/Early Termination Visit and the Post Treatment Periods 3 and 6 Month Follow-up Visits.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Pharmacokinetic and Anti-drug Antibody Measurements: Serum samples for PK analysis of pegloticase were collected prior to the pegloticase infusion and after the end of infusion (prior to discharge) on, e.g., Day 1 and Week 2, 4, 6, 8 and 36 Visits, or Weeks 2, 6, 14, 24, 36, for the open-label and randomized studies, respectively, and prior to the pegloticase infusion only at Weeks 10, 14, 18, 22, 24 (open-label study); at the End of Pegloticase Infusions Visit (if applicable); and the End of Study/Early Termination Visits. One of skill in the art will understand that serum, blood, urine, etc. samples may be obtained at any time or before/during/after any visit during the enrollment period, run-in period, treatment period (e.g., KXX+MTX period) or follow-up period for assessment of patient status, sUA, IRs, or the like. Visits for frequent sampling of a subset of subjects who consent for additional non-infusion visit PK sampling can occur at any time, e.g., Weeks 1 and 7 or at week 21 for the open-label and randomized studies, respectively.

Immunogenicity of pegloticase was assessed via serum samples for evaluation of anti-PEG and anti-uricase IgG antibodies. Samples were collected prior to the pegloticase infusion on, e.g., Day 1, and at the Weeks 2, 4, 6, 8, 10, 14, 18, 22, 24, 36, or weeks 2, 6, 14, 22, 24, 36 for the open-label and randomized studies, respectively; at the End of Pegloticase Infusions Visit (if applicable); and End of Study/Early Termination Visits and Post Treatment 3- or 6-month Follow-up Visits. Visits for frequent sampling of a subset of subjects who consent for additional non-infusion visit PK sampling occurred at Weeks 1 and 7 (open-label study). In the event of an AE suspected to be an infusion reaction, a serum sample may be collected at that time or at the subsequent visit for evaluation of pegloticase antibodies.

Physician Global Assessment: The physician global assessment was collected at the Screening and Week −4, −3, −2, −1, or Week −6 (prior to the first dose of MTX) Visits during the MTX Run-in Period for the open-label and randomized studies, respectively; prior to pegloticase infusion at any time, e.g., the Day 1 and Weeks 14, 24, and 36 Visits, and the Day 1 and Week 6, 14, 20, 24, 30, 36, and 44 visits during the Pegloticase+IMM Period for the open-label and randomized studies, respectively.

As used herein, "prolonging" refers to extending the duration of the treatment effects of KXX therapy, either alone or co-administered with MTX. For example, as described herein, treatment of a patient with KXX co-administered with MTX, may result in a more enhanced response to the drug in the patient, resulting in a lowered SUA, when compared with treatment with KXX alone.

As used herein, "reducing" refers to a lowering or lessening, such as reducing immunogenicity to KXX in a patient. In some embodiments, co-administration of KXX and MTX results in "reducing" immunogenicity to KXX, indicating that the patient does not produce anti-KXX antibodies, or produces fewer anti-KXX antibodies than would be expected for a patient not receiving the same treatment. "Reducing" may also refer to a reduction in disease symptoms as a result of KXX treatment, either alone, or co-administered with MTX. "Reducing" immunogenicity to KXX may also be referred to herein as increasing or enhancing "immuno-tolerance."

As used herein, "relatedness" or "causality" assessment is required for AEs (and SAEs) that occur during clinical investigations. The following terms were used during this study.

Likely: Reasons to consider an AE likely related to treatment may include but are not limited to the following: (1) Timing of the event relative to the administration of the investigational product. (2) Location of the AE relative to the site of investigational product administration. (3) Likelihood based on experience with similar products. (4) There is a biologically plausible explanation based on the mechanism of action or mode of delivery of the treatment. (5) The AE is repeated on subsequent treatments. (6) No other explanation is likely.

Quality-of-Life Assessment: The HAQ was administered at any point during the study. The HAQ-DI is a self-report functional status instrument that can be filled out by a subject in less than 5 minutes and requires 1 minute to score. The index measures disability over the past week by asking a total of 20 questions covering 8 domains of function: dressing and grooming, arising, eating, walking, hygiene, reach, grip, and usual activities. There are at least 2 questions in each domain and the 8 domains represent a comprehensive set of functional activities. The HAQ-DI is calculated by scoring the answer to each question in the HAQ from 0 to 3, with 0 representing the ability to do without any difficulty, and 3 representing inability to do. Any activity that requires assistance from another individual or requires the use of an assistive device raises a 0 or 1 score to a 2. The highest score for each of the 8 domains is summed (range from 0 to 24) and divided by 8 to yield, on a scale with 25 possible values, a Functional Disability Index with a range from 0 to 3. The disability index is based on the number of domains answered and is computed only if the subject completes answers to at least 6 domains. The HAQ pain scale asks subjects to record how much pain they have had in the past week on a scale of 0 to 100, where zero represents "no pain" and 100 represents "severe pain". The HAQ health scale is a measure of overall health. Subjects are asked to rate how well they are doing on a score of 0 to 100, where zero represents "very well" and 100 represents "very poor" health.

As used herein, a "reduced volume" refers to an infusion volume for pegloticase or solutions or compositions thereof that is lower than the standard 250-mL (250 cc) infusion volume. In some embodiments, a reduced volume may be 50 mL (50 cc). In some embodiments, such a reduced volume may be given in normal or half-normal saline, or 0.45% or 0.9% Sodium Chloride Injection, USP.

As used herein, a "screening period" refers to a period of time in which prospective participants of a study may be evaluated for participation in the study. A screening period may last as long as necessary to enroll a sufficient number of participants in the study. In some embodiments, a screening period may be any length of time deemed appropriate by a clinician or study director, such as including, but not limited to, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, or the like, 1 week, 2 weeks, 3 weeks, 4 weeks, 5 weeks, 6, weeks, 7, weeks, 8 weeks, or the like. In some embodiments, a screening period as described herein may be a period of up to 2 weeks. In some embodiments, a screening period as described herein may be a period of time lasting up to 35 days.

As used herein, a "severe adverse event" or "severe AE" refers to a sign, symptom, or event that causes severe discomfort to the participant and significantly affects clinical status or the ability to perform usual life activities, whether the event is considered related to the study drug or not. In some embodiments, treatment intervention may be warranted for a severe AE.

Examples of an AE include: (1) Conditions newly detected or diagnosed after the signing of the ICF, including conditions that may have been present but undetected prior to the start of the study; (2) Conditions known to have been present prior to the start of the study that worsen after the signing of the ICF; (3) Signs, symptoms, or the clinical sequelae of a suspected drug interaction; (4) Signs, symptoms, or the clinical sequelae of a suspected overdose of either investigational product or a concomitant medication (overdose per se was not reported as an AE). Adverse events of special interest may include IRs, anaphylaxis, gout flares, and cardiovascular events.

All AEs, both serious and non-serious, will be assessed for severity using the Rheumatology Common Toxicity Criteria v2.0. The scale displays Grades 1 through 4 with unique clinical descriptions of severity for each AE (including abnormal laboratory values) based on this general guideline: Grade 1 (Mild)—asymptomatic or transient, short duration (<1 week), no change in lifestyle, no medication or over-the-counter. Grade 2 (Moderate)—symptomatic, duration 1 to 2 weeks, alter lifestyle occasionally, medications give relief (may be prescription). Grade 3 (Severe)—prolonged symptoms, reversible, major functional impairment, prescription medications/partial relief, hospitalized <24 hours, temporary or permanent study drug discontinuation. Grade 4 (Includes Life-threatening)—at risk of death, substantial disability, especially if permanent, hospitalized >24 hours, permanent study drug discontinuation.

As used herein, a "shortened infusion period" refers to an infusion or administration time for pegloticase that is shorter than the FDA-approved 120-minute infusion period. In some embodiments, a shortened infusion period may be about 60 minutes, about 45 minutes, or about 30 minutes.

As used herein, "stopping rule" refers to subjects with an SUA≥6 mg/dL at 2 consecutive study visits beginning with the week 2 visit (not including post-infusion samples). Individuals for whom this condition is met discontinued treatment and remained in the study.

As used herein, "subject" or "individual" or "patient" refers to any patient for whom or which therapy is desired, and generally refers to the recipient of the therapy.

As used herein, a "temporary stop" refers to a short-term interruption in a dosing regimen as described herein, such as for KXX and/or MTX. A temporary stop typically lasts 2 to 4 weeks, after which the patient or subject resumes taking the drug or discontinues the drug completely. For example, as provided in Table 1, a patient taking MTX as described herein, and for whom WBC levels fall below $3\times10^9$/L, was instructed to stop taking MTX for a short period of time. Following a temporary stop, the patient or subject may either resume taking the drug or may be instructed to discontinue the drug completely.

As used herein, "MTX tolerability assessment period" or "MTX run-in period" refers to a period of time in which participants of a study may be evaluated for tolerability of MTX. Such a period may be any length of time deemed appropriate by a clinician or study director, such as including, but not limited to, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, or the like, or 1 week, 2 weeks, 3 weeks, 4 weeks, 5 weeks, 6, weeks, 7 weeks, 8 weeks, or the like. In some embodiments, an MTX run-in period as described herein may be a period of 4 weeks, for example lasting from Week −4 through Day 1. In some embodiments, an MTX run-in period as described herein may be a period of 3 weeks, for example lasting from Week −3 through Day 1. In some embodiments, an MTX run-in period as described herein may be a period of 2 weeks, for example lasting from Week −2 through Day 1. In some embodiments, an MTX run-in period as described herein may be a period of 1 weeks, for example lasting from Week −1 through Day 1. In some embodiments, MTX is administered to a subject during the MTX run-in period at a dosage of 15 mg MTX per day in a form suitable for oral administration. In some embodiments, titrating up of MTX may have a target dose of 25 mg MTX for patients having an estimated glomerular filtration rate (eGFR) of ≥45 mL/min/1.73 $m^2$, or a target dose of 15 mg MTX for patient having an eGFR of ≥45 mL/min/1.73 $m^2$.

As used herein, a "tolerizing dosage regimen" refers to a dosage or treatment regimen with KXX that induces immunological tolerance to the drug. A tolerizing dosage regimen prevents the loss of response to a drug in a patient by preventing the formation of anti-KXX antibodies. A tolerizing dosage regimen may also decrease the incidence of IRs associated with the drug.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. The phrase "administering to a patient" refers to the process of introducing a composition or dosage form into the patient via an art-recognized means of introduction.

As used herein, "trough" refers to the lowest concentration of a drug in a patient before the next dose of the drug is administered. For example, trough KXX levels refer to the lowest levels of KXX in a patient before the next infusion of KXX. Trough levels may be used by clinicians or practitioners to determine the efficacy of the drug, or the response of the patient to the drug treatment. Trough levels of KXX or MTX may be determined or measured at any point during a treatment period as described herein, such as before any infusion of KXX, or before any administration of MTX.

As used herein, an "unexpected adverse event" or "unexpected AE" refers to any AE, the specificity, frequency or severity of which is not consistent with either: The known or foreseeable risk of AEs associated with the procedures involved in the research that are described in the protocol-related documents, such as the IRB-approved research protocol, any applicable investigator brochure, the current IRB-approved informed consent document, and other relevant sources of information (e.g., product labeling and package inserts); or the expected natural progression of any underlying disease or condition of the participant(s) experiencing the AE.

An AE or suspected adverse reaction is considered unexpected if it is not listed in the Reference Safety Information section of the Investigator's Brochure or is not listed with the specificity or severity that has been observed. Unexpected, as used in this definition, also refers to AEs or suspected adverse reactions that are mentioned in the Reference Safety Information as occurring with a class of drugs or as anticipated from the pharmacological properties of the drug, but are not specifically mentioned as occurring with the particular drug under investigation.

Unlikely: An AE with no temporal association with the study drug but rather related to other etiologies such as concomitant medications or conditions, or subject's known clinical state.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Unless defined otherwise, all technical and scientific terms used herein have the meaning commonly understood by one of ordinary skill in the art to which the disclosure pertains. Specific terminology of importance to the description of the present disclosure is defined below.

Having described the present disclosure in detail, it will be apparent that modifications, variations, and equivalent embodiments are possible without departing the scope of the present disclosure defined in the appended claims. Further-more, it should be appreciated that all examples in the present disclosure are provided as non-limiting examples.

EXAMPLES

Examples of embodiments of the present disclosure are provided in the following examples. The following examples are presented only by way of illustration and to assist one of ordinary skill in using the disclosure. The examples are not intended in any way to otherwise limit the scope of the disclosure.

Example 1— Clinical Trial: Shorter Infusion Duration

The present disclosure describes a study in subjects initiating pegloticase for treatment of chronic refractory gout. The purpose of the present study was to assess the tolerability of pegloticase administered on a monthly (e.g., every 4 weeks) administered with a shorter infusion duration and in a reduced volume of 50 mL (50 cc) in subjects with uncontrolled gout receiving methotrexate. One concern with shortened infusion is that a shorter infusion duration may lead to increased AEs. Pegloticase has been associated with IRs, including anaphylaxis. In a Phase 2 study in which pegloticase was administered in 30 minutes in the majority of subjects, 44% of subjects experienced an IR (no subjects experienced anaphylaxis). Methotrexate was not administered as part of the protocol and the majority of subjects did not receive any IR prophylaxis. In Phase 3 studies (which included IR prophylaxis for all subjects), with pegloticase administered over 120 minutes, IRs occurred in 26% of subjects receiving pegloticase compared to 5% of subjects receiving placebo and anaphylaxis was reported in 5% of subjects receiving pegloticase and 0% of subjects receiving placebo (pegloticase (KRYSTEXXA®). The nature and the severity of the IRs in the Phase 2 and Phase 3 studies were relatively similar. These AEs are thought to be related to the development of anti-drug antibodies and can be reduced by avoiding infusions in patients who initially respond and then have a rebound of their serum uric acid above 6 mg/mL. These anti-drug antibodies are also associated with loss of efficacy as reflected in this increase in sUA levels.

Pretreatment and co-administration with the study dose of methotrexate 15 mg orally once weekly has been shown to reduce failure rates in pegloticase treated patients with chronic gout.

To address the possibility of increased AEs with a shorter infusion duration, the present study will incorporate an IR prophylaxis regimen as well as pre-treatment and concomitant use of MTX with pegloticase.

This study is an open-label, non-randomized, single-arm design in which all subjects will receive the same study drugs (i.e., MTX and pegloticase) in the same volume (50 mL). The study will be initiated enrolling patients assigned to 60-minute infusion durations. Infusion duration assignment may be progressively shortened to 45-minute or 30-minute infusion durations based on tolerability of previous subjects.

The present disclosure describes a Phase 4, multicenter, open-label, infusion duration, proof-of-concept study of pegloticase administered over <120 minutes in a volume of 50 mL with MTX in adult subjects with uncontrolled gout. Approximately 30-50 subjects will be enrolled. Treatment duration with pegloticase will be approximately 24 weeks.

The current approved dose of pegloticase for intravenous infusions, i.e., 8 mg every 2 weeks, will be tested in this study. In other aspects of this study, alternate dosages of KXX (e.g., about 8 mg, about 12 mg, about 16 mg, about 20 mg, about 24 mg, about 28 mg, or about 32 mg) will be administered at shortened infusion times (e.g., 30 minutes, 45 minutes, 60 minutes, etc.) and/or in reduced infusion volumes (e.g., 50 mL) every 2-4 weeks. In some embodiments, a reduced volume of pegloticase solution as described herein may result in an increased concentration of the administered solution, i.e., 8 mg of pegloticase in a final volume to be administered of 50 mL normal or half-normal saline or 0.45% or 0.9% Sodium Chloride Injection, USP, as compared to the standard 8 mg of pegloticase in a final volume to be administered of 250 mL normal or half-normal saline or 0.45% or 0.9% Sodium Chloride Injection, USP.

The study design will include: (1) a Screening Period, lasting up to 35 days; and (2) a 4-week MTX Run-in Period; (3) a 24-week Pegloticase+MTX Period which includes an End-of study Week 24/Early Termination Visit. In some aspects of the study, the study may be continued for a total of 12 months, with the primary endpoint evaluated at 6 months or 24 weeks.

All subjects who meet eligibility criteria at Screening will begin oral MTX at a dose of 15 mg weekly for 4 weeks prior to the first dose of pegloticase.

Subjects will also take folic acid 1 mg orally every day beginning at Week −4 (the start of MTX) continuing until prior to the End of Pegloticase Infusion Visit (if applicable) or the Week 24/End of Study/Early Termination Visit. Subjects must be able to tolerate MTX at a dose of 15 mg during the 4-week MTX Run-in Period (prior to Day 1) to be eligible to participate in the Pegloticase+MTX Period.

Subjects who are unable to tolerate MTX at a dose of 15 mg during the MTX Run-in Period will be considered screen failures.

Prior to the Treatment Period, subjects will begin taking at least one of the per protocol standard gout flare prophylaxis regimen (colchicine 0.6 mg/day and/or nonsteroidal anti-inflammatory drug (NSAID) and/or low dose prednisone <10 mg/day) for ≥1 week before the first dose of pegloticase and continues flare prophylaxis throughout the pegloticase treatment period per American College of Rheumatology guidelines.

For IR prophylaxis, fexofenadine (180 mg orally) will be taken the night before each infusion; fexofenadine (180 mg orally) and acetaminophen (1000 mg orally) will be taken the morning of each infusion; and methylprednisolone (125 mg IV) over an infusion duration between 10 and 30 minutes, will be administered immediately prior to each infusion.

During the Pegloticase+MTX Period, all subjects will receive pegloticase 8 mg every 2 weeks administered IV for a total of 12 infusions of 50 mL each from Day 1 through Week 22, inclusive. In other aspects of the study, subjects may receive a dosage of pegloticase as described herein, e.g., 8 mg, 12 mg, 16 mg, 20 mg, 24 mg, 28 mg, or 32 mg, every 2-4 weeks, e.g., monthly, for a treatment period described herein, e.g., monthly for 12 months. Pegloticase will be administered after all pre-dose study visit assessments have been completed at each visit. The date and start and stop time of infusion will be recorded. sUA Discontinuation Criteria will be applied: subjects with sUA level ≥6 mg/dL at 2 consecutive study visits beginning with the Week 2 Visit will discontinue treatment but continue on with the study as described herein.

Figure 2:
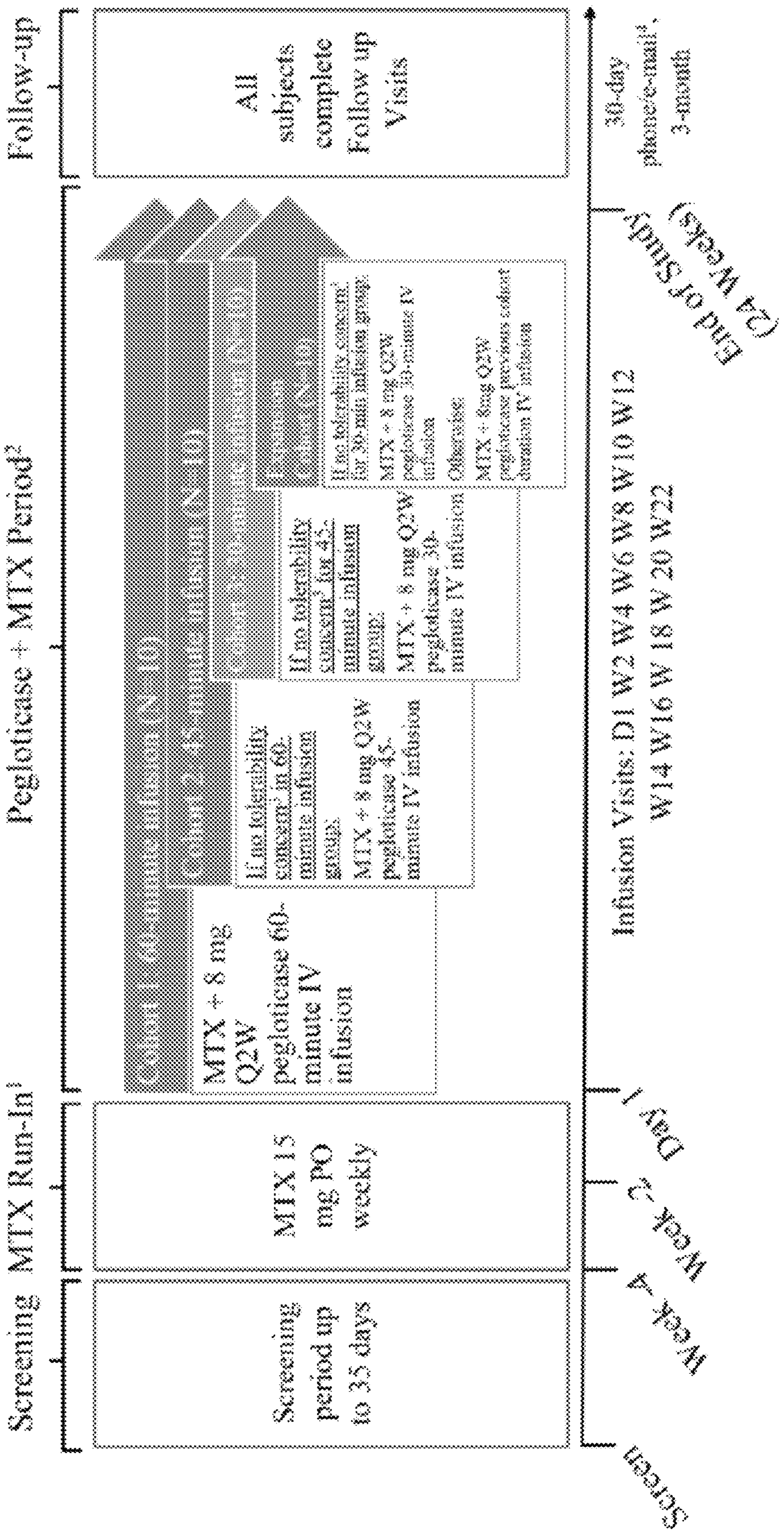
FIG. 2 depicts a study design for the present study. IV=intravenous; MTX=methotrexate; PO=oral; Q2W=every 2 weeks; W=week. Study visits were completed within ±3 days of the target visit date. (1) Prior to the Treatment Period, subjects will begin taking at least one of the per protocol standard gout flare prophylaxis regimen (colchicine 0.6 mg/day and/or NSAID and/or low dose prednisone <10 mg/day) for ≥1 week before the first dose of pegloticase and continuing flare prophylaxis throughout the pegloticase treatment period per American College of Rheumatology guidelines. For IR prophylaxis, fexofenadine (180 mg orally) will be taken the day before each infusion; fexofenadine (180 mg orally) and acetaminophen (1000 mg orally) will be taken the morning of each infusion; and methylprednisolone (125 mg IV) over an infusion duration between 10 and 30 minutes, will be administered immediately prior to each infusion. (2) Stopping rules will be implemented: Subjects with 2 sUA levels ≥6 mg/dL at 2 consecutive study visits beginning with the Week 2 Visit will discontinue from pegloticase therapy and complete the End of Pegloticase Infusions Visit and remain on study. (3) The determination on whether to enroll the next cohort of subjects to a lower infusion duration level will be based on whether the previous cohort meets the Infusion Speed-Limiting Criteria as well as the Safety Review Committee decision. Expansion Cohort may follow Cohort 2 or Cohort 3, depending on tolerability assessment decision.

Up to three pegloticase infusion durations will be assessed in the Pegloticase+MTX Period: (1) 60-minute infusion, (2) 45-minute infusion, and (3) 30-minute infusion. Cohorts of 10 subjects will be enrolled sequentially at progressively shorter infusion durations, beginning with the 60-minute infusion duration, progressing down to the 45-minute infusion duration and then to the 30-minute infusion duration. All infusions will be given in a volume of 50 mL. An additional cohort of 10 subjects will be enrolled following the last infusion duration cohort. The study plan is outlined in FIG. 2.

The overall objective of the study is to assess the tolerability of pegloticase administered with a shorter infusion duration and reduced volume in subjects with uncontrolled gout receiving methotrexate.

The primary objective is to assess the tolerability of pegloticase infusions administered over <120 minutes and in a volume of 50 mL with methotrexate (MTX) from Day 1 through Week 24, as measured by the incidence of infusion reactions (including anaphylaxis) related to pegloticase.

Secondary objectives of the present disclosure include the following:

(1) Assess the proportion of subjects receiving pegloticase with MTX who experienced any of the following events: infusion reaction (IR) leading to discontinuation of treatment, anaphylaxis, or meeting Individual Subject sUA Discontinuation Criteria.

(2) Assess the time to any of the following events: IR leading to discontinuation of treatment, anaphylaxis, or meeting Individual Subject sUA Discontinuation Criteria (two consecutive pre-infusion sUAs≥6 mg/dL).

(3) Assess the proportion of subjects who experienced IR leading to slowing down of the infusion rate or discontinuation of treatment.

(4) Assess the time to first IR leading to slowing down of the infusion rate or discontinuation of treatment.

(5) Assess the time to first IR.

(6) Assess the proportion of subjects who were able to complete all infusions over the assigned treatment duration length or a lesser time, without clinically requiring an increased infusion time.

(7) Assess the proportion of infusions completed over the assigned duration length or a lesser time, without clinically requiring an increased infusion time.

Exploratory objectives of the present disclosure include the following:

(1) Assess the rate of interrupted infusions from Day 1 to Week 24.

(2) Assess the incidence of subjects with at least one interrupted infusion from Day 1 to Week 24.

(3) Assess the proportion of subjects meeting Individual Subject sUA Discontinuation Criteria (two consecutive pre-infusion sUAs≥6 mg/dL).

(4) Estimate the response rate at Month 6 (Weeks 20, 22 and 24), as measured by the sustained normalization of sUA to <6 mg/dL for at least 80% of the time during Month 6.

(5) Assess the proportion of subjects with sUA<6 mg/dL for each visit.

(6) Estimate the mean change from baseline to Weeks 14 and 24 in patient global assessment of gout.

(7) Estimate the mean change from baseline to Weeks 14 and 24 in physician global assessment of gout.

(8) Assess the pharmacokinetics of pegloticase.

(9) Assess the profile of anti-uricase antibodies and anti-poly (ethylene glycol) antibodies.

Safety objectives of the present disclosure include the following:

(1) Assess the incidence of adverse events of special interest (AESI), including IRs, anaphylaxis, gout flares, cardiovascular events, and the AE/SAE profile overall.

(2) Laboratory tests and 12-lead electrocardiogram (ECG).

(3) Vital signs and physical examinations.

Subjects diagnosed with gout eligible for this study will have sUA≥6 mg/dL and inability to maintain sUA<6 mg/dL on other urate-lowering therapy, or intolerable side effects associated with current urate-lowering therapy, or with a contraindication to xanthine oxidase inhibitor therapy.

Eligible subjects must meet/provide all the following criteria:

Uncontrolled gout, defined as meeting the following criteria: (a) Hyperuricemia during the screening period defined as SUA≥6 mg/dL, and; (b) Failure to maintain normalization of SUA with xanthine oxidase inhibitors at the maximum medically appropriate dose, or with intolerable side effects or a contraindication to xanthine oxidase inhibitor therapy based on medical record review or subject interview, and; (c) Symptoms of gout including at least 1 of the following: (i) Presence of at least one tophus; (ii) Recurrent flares defined as 2 or more flares in the past 12 months prior to screening; and (iii) Presence of chronic gouty arthritis.

Willing to discontinue any oral urate lowering therapy for at least 7 days prior to MTX dosing at Week−4 and remain off of urate lowering therapy when receiving pegloticase infusions during the study.

Able to tolerate MTX 15 mg for 4 weeks during the MTX Run-in period prior to the first dose of pegloticase.

Subjects were ineligible for study participation if they meet any of the following criteria:

Weight >160 kg (352 pounds) at Screening.

Any serious acute bacterial infection, unless treated and completely resolved with antibiotics at least 2 weeks prior to the Week −4 Visit.

Severe chronic or recurrent bacterial infections, such as recurrent pneumonia or chronic bronchiectasis.

Current or chronic treatment with systemic immunosuppressive agents such as MTX, azathioprine, or mycophenolate mofetil; prednisone ≥10 mg/day or equivalent dose of other corticosteroid on a chronic basis (3 months or longer) would also meet exclusion criteria.

Known history of any solid organ transplant surgery requiring maintenance immunosuppressive therapy unless treated and no chronic or active infection confirmed by HBV serology.

Known history of hepatitis B virus surface antigen positivity or hepatitis B DNA positivity, unless treated and viral load is negative and no chronic or active infection confirmed by HBV serology.

Known history of hepatitis C virus RNA positivity unless treated and viral load is negative.

Known history of Human Immunodeficiency Virus (HIV) positivity.

Glucose-6-phosphate dehydrogenase (G6PD) deficiency (tested at the Screening Visit).

Severe chronic renal impairment, defined as an estimated glomerular filtration rate (eGFR)<40 mL/min/1.73 $m^2$ at the Screening Visit based on 4 variable-Modification of Diet in Renal Disease [MDRD] formula or currently on dialysis.

Non-compensated congestive heart failure or hospitalization for congestive heart failure or treatment for acute coronary syndrome (myocardial infarction or unstable angina) within 3 months of the Screening Visit, or current uncontrolled arrhythmia, or current uncontrolled blood pressure (BP) (>160/100 mmHg) prior to Week −4.

Prior treatment with pegloticase, another recombinant uricase (rasburicase), or concomitant therapy with a polyethylene glycol-conjugated drug.

Known allergy to pegylated products or history of anaphylactic reaction to a recombinant protein or porcine product.

Contraindication to MTX treatment or MTX treatment considered inappropriate.

Known intolerance to MTX.

Liver transaminase levels (AST or ALT)>upper limit of normal (ULN) or albumin <the lower limit of normal (LLN) at the Screening Visit.

Chronic liver disease.

White blood cell count <4,000/μl, hematocrit <32%, or platelet count <75,000/μl.

Currently receiving systemic or radiologic treatment for ongoing cancer.

History of malignancy within 5 years other than non-melanoma skin cancer or in situ carcinoma of cervix.

Uncontrolled hyperglycemia with a plasma glucose value >240 mg/dL at Screening that is not subsequently controlled by the end of the Screening.

Diagnosis of osteomyelitis.

Known history of hypoxanthine-guanine phosphoribosyltransferase deficiency, such as Lesch-Nyhan and Kelley-Seegmiller syndrome.

A known intolerance to all protocol standard gout flare prophylaxis regimen (i.e., colchicine and/or non-steroidal anti-inflammatory drugs and/or low-dose prednisone ≤10 mg/day).

Currently receiving urate-lowering therapies and unable to discontinue treatment at least 7 days prior to MTX dosing at Week −4 and remain off of urate lowering therapy when receiving pegloticase infusions during the study.

Current pulmonary fibrosis, bronchiectasis or interstitial pneumonitis.

During the MTX Run-in Period, which begins 4 weeks prior to the first dose of pegloticase, subjects will take oral MTX at a dose of 15 mg weekly.

Subjects will also take folic acid 1 mg orally every day beginning at Week −4 (the start of MTX) until prior to the Week 24 Visit.

All subjects who meet the inclusion/exclusion criteria and tolerate oral MTX 15 mg weekly during the MTX Run-in Period will receive pegloticase at a dose of 8 mg administered IV every 2 weeks in a volume of 50 mL for a total of 12 infusions from Day 1 through Week 22 inclusive (Pegloticase+MTX Period).

All subjects will receive standardized prophylactic treatment to reduce the risk of acute gout flares, beginning ≥1 week before the first dose of pegloticase and continuing throughout the pegloticase treatment per American College of Rheumatology guidelines (Khanna et al., 2012).

Standardized IR prophylaxis consisting of pre-treatment with an antihistamine, acetaminophen and a corticosteroid will accompany each infusion.

During the Pegloticase+MTX Period, MTX should be taken 1 to 3 days prior to the pegloticase infusion and one additional weekly dose after the last infusion (at Week 22) for subjects who have not stopped pegloticase due to study sUA Discontinuation Criteria. If a subject is not able to take the MTX 1 to 3 days prior to the pegloticase infusion, MTX must be taken ≥60 minutes prior to the pegloticase infusion.

During the Pegloticase+MTX Period, if a subject becomes unable to tolerate the MTX the dosage may be decreased.

Subjects will also take folic acid 1 mg orally every day beginning at Week −4 (the start of MTX) until prior to the Week 24 Visit.

Pegloticase is a clear, colorless, sterile solution in phosphate-buffered saline intended for IV infusion after dilution. Each mL of pegloticase contains 8 mg of uricase protein conjugated to 24 mg of 10 kDa monomethoxypoly(ethylene glycol). Excipients include disodium hydrogen phosphate dihydrate, sodium chloride, sodium dihydrogen phosphate dihydrate and water for injection.

Before preparation for use, pegloticase will be stored in the carton, maintained under refrigeration between 2° C. and 8° C. (36° F. and 46° F.), protected from light and will not be shaken or frozen. Pegloticase diluted in infusion bags is stable for 4 hours at 2° C. to 8° C. (36° F. to 46° F.) and for 4 hours at room temperature (20° C. to 25° C., 68° F. to 77° F.).

Syringe contents will be injected into a single 50 mL bag of 0.45% or 0.9% Sodium Chloride Injection, USP for IV infusion and will not be mixed or diluted with other drugs. The infusion bag containing the dilute pegloticase solution will be inverted a number of times to ensure thorough mixing but will not be shaken. In accordance with good pharmacy practice, gloves will be worn during preparation of the dose.

Pegloticase must be started within 4 hours of dilution. Before administration, the diluted solution of pegloticase will be allowed to reach room temperature. Pegloticase must never be subjected to artificial heating.

Pegloticase will be administered as an admixture of 8 mg in 50 mL of 0.45% or 0.9% Sodium Chloride Injection, USP for IV infusion by gravity feed or infusion pump. Pegloticase will not be administered as an IV push or bolus. In some embodiments, KXX will be administered as a drug alone, i.e., no admixture or additives (e.g., excipients or adjuvants).

In a patent IV site, using tubing with no in-line filter, the pegloticase preparation will be infused over approximately 30 to 60±5 minutes, depending on cohort assignment, while the subject is under close observation for any signs of distress. If an in-line filter is used, it should be 0.2 μm or larger. At the end of the infusion, the IV line will be flushed with 10 mL of normal saline to ensure the full dose is administered. The date and time of infusion start and stop (inclusive of the IV flush) will be recorded.

In the event of an IR, the infusion should be slowed, or stopped and restarted at a slower rate. Infusions subsequent to an IR in an individual subject may be given in a larger volume of diluent, not to exceed 500 mL. In this case, the infusion duration will also be extended to a minimum of 3 hours.

All subjects who meet the inclusion/exclusion criteria and tolerate oral MTX 15 mg weekly during the MTX Run-in Period will receive pegloticase at a dose of 8 mg administered IV every 2 weeks for a total of 12 infusions from Day 1 through Week 22 inclusive (Pegloticase+MTX Period). The date and start and stop time of infusion will be recorded. Subjects will not be fasting on the day of infusion and will be encouraged to have a snack or normal meal before or after the infusion.

All subjects will receive standardized prophylactic treatment to reduce the risk of acute gout flares, beginning ≥1 week before the first dose of pegloticase and continuing flare prophylaxis throughout the pegloticase treatment period per American College of Rheumatology guidelines.

Standardized IR prophylaxis consisting of pre-treatment with an antihistamine, acetaminophen and a corticosteroid will accompany each infusion.

It is required that before a subject begins the Pegloticase+MTX Period, he or she has been taking at least one protocol standard gout flare prophylaxis regimen (i.e., colchicine and/or NSAIDs and/or low-dose prednisone 10 mg/day) for ≥1 week before the first dose of pegloticase and continuing flare prophylaxis throughout the pegloticase treatment period per American College of Rheumatology guidelines.

Since IRs can occur with pegloticase, all subjects will receive IR prophylaxis prior to each infusion, consisting of an antihistamine, acetaminophen and a corticosteroid. To standardize this regimen, subjects will receive fexofenadine (180 mg orally) the day before each infusion; fexofenadine (180 mg orally) and acetaminophen (1000 mg orally) the morning of each infusion; and methylprednisolone (125 mg IV) given over an infusion duration between 10-30 minutes, immediately prior to each infusion. Substitution of the corticosteroid is not allowed. The name, dose, route, date and time of administration of each prophylactic medication will be recorded. The Solumedrol used for IR prophylaxis will be supplied by the site. Other IR medications administered prior to each infusion may also be supplied by the site.

Infusions subsequent to an IR in an individual subject may be given in a larger volume of diluent, not to exceed 500 mL. In this case, the infusion duration will also be extended to a minimum of 3 hours.

During the MTX Run-in a subject will be considered a screen failure if any of the following new laboratory findings or symptoms reflecting MTX intolerance occur:

(1) Abnormal Hematology findings: (a) WBC $<3.5\times10^9$/L; (b) Platelets $<75\times10^9$/L; (c) Hematocrit <32%

(2) Abnormal hepatic function findings: (a) AST/ALT>1.5×upper limit of reference range and (b) Albumin<lower limit (LLN) of reference range.

(3) Abnormal renal function: eGFR<30 ml/min/1.73 $m^2$ (as estimated with the MDRD equation).

(4) New clinically important signs and symptoms, such as the following: (a) Rash or oral ulceration; (b) Persistent nausea, vomiting and diarrhea; (c) New or increasing dyspnea or dry cough, or unexplained cough with fever; (d) Severe sore throat, abnormal bruising; (e) Severe headaches, fatigue and problems concentrating.

If minor clinical symptoms emerge, such as mild stomatitis, mild GI discomfort, etc., the folic acid dose may be increased (e.g., 2 mg daily) or a divided dose of MTX (e.g., 3 tabs of 2.5 mg in the morning and evening on the day of dosing) may be administered; if symptoms improve, subject will not be considered a screen failure on the basis of that symptom.

Screening: Up to 35 days prior to the Pegloticase+MTX Period.

MTX Run-in Period (Week −4 to Day 1): 4 weeks of MTX dosing prior to initial pegloticase dose.

Pegloticase+MTX Period (Day 1 through Week 24): 24 weeks (infusion visits every 2 weeks) plus the End-of study/Early Termination Visit (Week 24).

Week 24/End-of-study/Early Termination Visit: Week 24 or earlier if the subject withdraws consent to participate in the study.

Subjects will be directed to discontinue current urate-lowering therapy prior to screening. Other medications used at the time of study initiation may be continued as deemed appropriate.

Subjects should not receive the following medications from the time of Screening through the end of pegloticase and MTX treatment:

(1) Oral urate-lowering therapies including allopurinol, febuxostat, probenecid, lesinurad, or other ULT for gout; re-introduction of oral ULTs should not start until after the End of Pegloticase Visit (or End of Study) laboratory tests are collected.

(2) Any PEG-conjugated drug.

(3) Any other investigational agent.

(4) Methotrexate (other than study investigational product), azathioprine, mycophenolate mofetil, or other systemic immunosuppressants aside from glucocorticoids for gout flare prophylaxis (<10 mg prednisone or equivalent per day) or intermittent gout flare treatment.

(5) If a subject is treated with antibiotics, a temporary stop may be ordered as described herein.

(6) Systemic immunosuppressive agents.

(7) Systemic radiologic treatment for ongoing cancer, excluding non-melanoma skin cancer.

Concomitant medications are defined as drug or biological products other than the study drugs (or prior gout medications) taken by a subject from Screening through the Post-Treatment Follow-up Visits. This includes other prescription medications (including preventive vaccines), over the counter medications, herbal medications, vitamins and food supplements.

Subjects will be directed to discontinue current urate-lowering therapy prior to initiation of pegloticase therapy as per the current package insert. Other medications used at the time of study initiation may be continued as deemed appropriate.

The primary endpoint is the incidence of subjects experiencing IRs (including anaphylaxis) related to pegloticase from Day 1 to Week 24.

Secondary Endpoints

The proportion of subjects who experienced any of the following events: IR leading to discontinuation of treatment, anaphylaxis, or meeting Individual Subject sUA Discontinuation Criteria.

Time to any of the following events: IR leading to discontinuation of treatment, anaphylaxis, or meeting Individual Subject sUA Discontinuation Criteria (two consecutive pre-infusion sUAs≥6 mg/dL).

The proportion of subjects who experienced IR leading to slowing down of the infusion rate or discontinuation of treatment.

The time to first IR leading to slowing down of the infusion rate or discontinuation of treatment.

Time to first IR.

The proportion of subjects who were able to complete all infusions over the assigned treatment duration length or a lesser time, without clinically requiring an increased infusion time The proportion of infusions completed over the assigned duration length or a lesser time, without clinically requiring an increased infusion time.

Exploratory Endpoints

The proportion of interrupted infusions from Day 1 to Week 24.

The incidence of subjects with at least one interrupted infusion from Day 1 to Week 24.

The proportion of subjects meeting Individual Subject sUA Discontinuation Criteria (two consecutive pre-infusion sUAs≥6 mg/dL).

The proportion of Month 6 (Weeks 20, 22 and 24) responders, defined as subjects achieving and maintaining sUA<6 mg/dL for at least 80% of the time during Month 6.

The proportion of subjects with sUA<6 mg/dL for each visit.

The mean change from baseline to Weeks 14 and 24 in patient global assessment of gout.

The mean change from baseline to Weeks 14 and 24 in physician global assessment of gout.

Pharmacokinetic and Anti-Drug Antibody Endpoints

PK of pegloticase.

The incidence and titer of anti-PEG and anti-Uricase IgG antibodies.

Safety Objectives

Incidence of IRs, anaphylaxis, gout flares, cardiovascular events and the AE/SAE profile overall and potentially attributed to the combination of pegloticase and MTX.

Efficacy will be assessed based on measurement of sUA from blood samples.

Example 2—Clinical Trial

In addition to the study described above, an open-label study was performed in subjects starting pegloticase for treatment of chronic refractory gout. The purpose of the study was to determine the efficacy and safety of using immune modulating therapy with MTX to prevent immunogenicity conferred by pegloticase and to enhance the response rate seen with pegloticase alone in adults with uncontrolled gout. This was a multicenter, open-label, efficacy and safety study of pegloticase with MTX in adult subjects with uncontrolled gout.

The study design included: (1) up to a 2-week Screening Period (screening was completed within 2 weeks prior to Week −4); (2) a 4-week MTX Run-in Period (week −4 through day 1); (3) a 52-week Pegloticase+MTX Period (day 1 through week 52), MTX dosed weekly and 50 weeks of KXX infusions visits every 2 weeks; non-infusion visits at Weeks 1, 7 and 52); (4) a Safety Follow-up (Phone/Email/Site Visit); and (5) a 3- and 6-month Post Treatment Follow-up.

In addition, if applicable, the following additional study periods applied:

End of Pegloticase Infusions Visit—completed within approximately 2 weeks of the last infusion if the subject discontinued pegloticase treatment prior to infusion Week 50, such as due to the SUA stopping rules. Subjects continued in the study.

Week 52/End-of-study/Early Termination Visit: Week 52 or earlier if the subject withdrew consent to participate in the study.

The subjects also took folic acid 1 mg orally every day beginning at Week −4 (the start of MTX) continuing until prior to the Week 52/End of Study/Early Termination Visit. Subjects had to be able to tolerate MTX at a dose of 15 mg during the 4-week MTX Run-in Period (prior to Day 1) to be eligible to participate in the KXX+MTX Period. Subjects who were unable to tolerate MTX at a dose of 15 mg during the MTX Run-in Period were considered screen failures.

Criteria for Evaluation: Efficacy was assessed by SUA levels, tender and swollen joint counts, patient and physician global assessments of gout, joint pain, and DECT.

Quality of life was assessed using the HAQ.

The PK of pegloticase and pegloticase immunogenicity as assessed by the incidence of anti-PEG and anti-uricase IgG antibodies were assessed at specified time points.

Safety assessments included monitoring and recording of all AEs, whether drug-related or not, measurement of vital signs, physical examinations, and monitoring of hematology and blood chemistry.

The overall objective of the study is to assess the efficacy, safety, tolerability, and pharmacokinetics (PK) of the concomitant use of KXX with MTX to enhance the response rate seen with pegloticase alone in adults with uncontrolled gout.

Primary Objectives/Outcomes

The primary objective is to estimate the response rate during Month 6 (Weeks 20, 22, and 24), as measured by the sustained normalization of serum uric acid (SUA) to <6 mg/dL for at least 80% of the time during Month 6 in subjects receiving KXX with MTX.

The primary efficacy outcome endpoint is the sustained normalization of SUA to <6 mg/dL for at least 80% of the time during month 6 (weeks 20, 22, and 24) in subjects receiving KXX with MTX. This is slightly below the urate solubility threshold and this threshold has been the accepted standard for nearly all modern gout trials. Participants who achieve this endpoint were classified as “responders.” Serum uric acid (SUA) responders may also be defined as participants achieving and maintaining SUA<6 mg/dL for at least 80% of the time during Month 6 (Weeks 20, 22, and 24).

Secondary Objectives/Outcomes

Secondary endpoints may examine anti-pegloticase Ab titers/types, different definitions of SUA level for specific later time points of success, and patient reported outcomes (PROs).

For example, in some embodiments, secondary outcomes may include one or more of the following:

- Estimation of the response rate during month 3 (weeks 10, 12, and 14), as measured by the sustained normalization of serum uric acid (SUA) to <6 mg/dL for at least 80% of the time during month 3 in subjects receiving pegloticase with MTX;
- Estimation of the overall response rate as measured by the sustained normalization of SUA to <6 mg/dL for at least 80% of the time during month 3 (weeks 10, 12, and 14) and month 6 (weeks 20, 22, and 24) combined in subjects receiving pegloticase with MTX;
- Estimation of the 5 mg/dL response rate during month 3, during month 6, and overall (months 3 and 6 combined), as measured by the sustained normalization of SUA to <5 mg/dL for at least 80% of the time during month 3, during month 6, and months 3 and 6 combined in subjects receiving pegloticase with MTX;
- Estimation of the mean change in serum uric acid from baseline to weeks 14, 24, 36, and 52 in SUA in subjects receiving pegloticase with MTX.

Exploratory Objectives/Outcomes

Exploratory objectives may include one or more of the following:

Estimation of the response rate during month 9 (weeks 32, 34 and 36), as measured by the sustained normalization of SUA to <6 mg/dL for at least 80% of the time during month 9 in subjects receiving pegloticase with MTX.

Estimation of the response rate during month 12 (weeks 48, 50 and 52), as measured by the sustained normalization of SUA to <6 mg/dL for at least 80% of the time during month 12 in subjects receiving pegloticase with MTX.

Estimation of the 5 mg/dL response rate during Month 9 (Weeks 32, 34 and 36), as measured by the sustained normalization of SUA to <5 mg/dL for at least 80% of the time during Month 9 in subjects receiving pegloticase with MTX.

Estimation of the 5 mg/dL response rate during Month 12 (Weeks 48, 50 and 52), as measured by the sustained normalization of SUA to <5 mg/dL for at least 80% of the time during Month 12 in subjects receiving pegloticase with MTX.

Estimation of the time to first SUA>6 mg/dL in subjects receiving pegloticase with MTX.

Estimation of the time to SUA>6 mg/dL (stopping rule) at 2 consecutive study visits beginning with the week 2 visit (not including post-infusion samples) in subjects receiving pegloticase with MTX.

Estimation of the mean change from baseline to Week 24, 36 and 52 in urate volume and gout erosions using dual-energy computed tomography (DECT) scan of the hands and feet in subjects receiving pegloticase with MTX.

Estimation of the mean change from baseline in number of joints affected by tophi in subjects receiving pegloticase with MTX.

Estimation of the mean change from baseline to Weeks 14, 24, 36, and 52 in tender joint count (68-point scale) in subjects receiving pegloticase with MTX.

Estimation of the mean change from baseline to Weeks 14, 24, 36, and 52 in swollen joint count (66-point scale) in subjects receiving pegloticase with MTX.

Estimation of the mean change from baseline to Weeks 14, 24, 36, and 52 in the Health Assessment Questionnaire-Disability Index (HAQ-DI) in subjects receiving pegloticase with MTX.

Estimation of the mean change from baseline to Weeks 14, 24, 36, and 52 in the HAQ Pain score in subjects receiving pegloticase with MTX.

Estimation of the mean change from baseline to Weeks 14, 24, 36, and 52 in the HAQ Health score in subjects receiving pegloticase with MTX.

Estimation of the mean change from baseline to Weeks 14, 24, 36, and 52 in patient global assessment of gout in subjects receiving pegloticase with MTX.

Estimation of the mean change from baseline to Weeks 14, 24, 36, and 52 in physician global assessment of gout in subjects receiving pegloticase with MTX.

Estimation of the mean change from baseline to Weeks 14, 24, 36, and 52 in subject assessment of average, least, and worst joint pain in subjects receiving pegloticase with MTX.

Estimation of the proportion of subjects achieving 20%, 50%, or 70% improvement based on gout chronic response criteria at Weeks 14, 24, 36, and 52 in subjects receiving pegloticase with MTX.

Pharmacokinetic and Anti-Drug Antibody Objectives/Outcomes

Assessment of the PK of pegloticase in subjects receiving concomitant MTX.

Assessment of the incidence of anti-PEG and anti-Uricase IgG antibodies.

Safety and Tolerability Objectives/Outcomes

Safety and Tolerability objectives/outcomes may include assessment of the incidence of infusion reactions (IRs), anaphylaxis, gout flares, cardiovascular events, and the adverse event (AE)/serious AE profile overall and potentially attributed to the combination of pegloticase and MTX.

Inclusion Criteria

Men and women ≥18 years of age. Participants may also be selected based on an age range between 18 and 65 years of age.

Hyperuricemic at screening visit, week −4, or week −2 of the screening or run-in period as documented by SUA≥6 mg/dL.

Chronic refractory gout*, defined as subjects who failed to achieve a sustained SUA of <6 mg/dL and whose signs and symptoms were inadequately controlled with xanthine oxidase inhibitors at a medically appropriate dose or for whom these drugs were contraindicated. Uncontrolled gout may be defined as meeting the following criteria: SUA≥6 mg/dL prior to entry into the KXX+MTX Period (any laboratory tests during screening up to and including during the MTX Run in Period) and at least 1 of the following: inability to maintain SUA<6 mg/dL on other urate-lowering therapy; intolerable side effects associated with current urate lowering therapy; functionally limiting tophaceous deposits (including those detected clinically or by DECT imaging).

Able to tolerate MTX at a dosage of 15 mg for 4 weeks during the Screening/MTX Run-in Period prior to the first dose of KXX.

Exclusion Criteria

Weight >160 kg (352 pounds).

Any serious acute bacterial infection, unless treated and complete resolved with antibiotics at least 2 weeks prior to the week −4 Visit of the MTX run-in period.

Severe chronic or recurrent bacterial infections (such as recurrent pneumonia, chronic bronchiectasis)

Current immunocompromised condition, including current or chronic treatment with immunosuppressive agents (prednisone or equivalent dose >5 mg/day). Prednisone >10 mg/day or equivalent dose of other corticosteroid may also exclude certain patients.

Subjects at risk for tuberculosis (TB). Specifically, subjects with i) current clinical, radiographic or laboratory evidence of active or latent TB; ii) a history of active TB within the last 3 years even if it was treated; iii) a history of active TB greater than 3 years ago unless there is documentation that the prior anti-TB treatment was appropriate in duration and type.

Known history of Hepatitis-B surface antigen-positive or Hepatitis B DNA positive subjects.

Known history of Hepatitis C RNA-positive subjects.

Human Immunodeficiency Virus (HIV) infection positive

G6PD deficiency (tested at Screening Visit 1)

Severe chronic renal impairment (glomerular filtration rate [GFR]<25 mL/min/1.73 $m^2$) or currently on dialysis Subjects having any transplant surgery requiring maintenance immunosuppressive therapy.

Non-compensated congestive heart failure, uncontrolled arrhythmia, treatment for acute coronary syndrome (myocardial infarction or unstable angina), or hospitalization for congestive heart failure within 3 months of screening or uncontrolled blood pressure (>160/100 mm Hg) at the end of the screening and MTX run-in period Prior treatment with pegloticase, another recombinant uricase, or concomitant therapy with a polyethylene glycol (PEG)-conjugated drug Known allergy to pegylated products or history of anaphylactic reaction to a recombinant protein or porcine product Contraindication to MTX treatment or MTX treatment considered inappropriate Known immunogenicity to MTX Recipient of an investigational drug within 4 weeks or 5 half-lives prior to study drug or MTX administration or plans to take an investigational agent during the study Current liver disease as determined by alanine transaminase ALT or aspartate transaminase (AST) levels >3 times upper limit of normal Currently receiving treatment for ongoing cancer, excluding non-melanoma skin cancer History of malignancy within 5 years other than skin cancer or in situ carcinoma of cervix Uncontrolled hyperglycemia with a plasma glucose value >240 mg/dL at screening that is not subsequently controlled by the end of the Screening/MTX Run-in Period.

Diagnosed Osteomyelitis

Individuals with hypoxanthine-guanine phosphoribosyltransferase (HGPRT) deficiency such as Lesch-Nyhan and Kelley-Seegmiller syndrome Currently receiving allopurinol and unable to discontinue medication 7 days prior to MTX dosing at Week −4 and unable to discontinue treatment during the duration of the study.

Administration—Pegloticase was administered as an admixture of 8 mg in 250 mL of 0.45% or 0.9% Sodium Chloride Injection, USP for IV infusion over a target infusion time of 120 minutes by gravity feed or infusion pump. Pegloticase was not administered as an IV push or bolus. Standardized IR prophylaxis consisting of pre-treatment with antihistamines and corticosteroids accompanied each infusionPrior to pegloticase infusion participants received infusion prophylaxis (e.g., oral fexofenadine (60 mg) the night before and fexofenadine (60 mg/PO) and acetaminophen (1000 mg/PO) the morning of the infusion; and hydrocortisone IV (200 mg) immediately prior to the infusion).

In a patent IV site, using tubing with no in-line filter, infuse the drug preparation over approximately 120 minutes (within ±15 minutes) while the participant was under close observation for any signs of distress. Administration of drug was immediately discontinued if respiratory distress, agitation, chest or back pain, urticaria, or another clinically significant event occurs during infusion.

Infusions after an infusion-related reaction in an individual participant may be given in a larger volume of diluent, not to exceed 500 mL. In such a case, the infusion duration was also extended to a minimum of 3 hours. The total volume and duration of infusion was captured in the medical record and CRF.

Methotrexate (MTX)—MTX, the immune modulator therapy for the study, is an antifolate drug, and thus inhibits the activation of folic acid in the body. MIX is structurally, similar to folic acid, which is important for making new cells. MTX inhibits the enzyme dihydrofolate reductase, which activates folic acid.

Concomitant Medications—Concomitant medications were defined as drug or biological products other than the study drug(s) taken by a participant during the clinical trial. This includes other prescription medications (including preventive vaccines), over-the-counter medications, herbal medications, vitamins, and food supplements.

Gout Flare Prophylaxis—All participants received prophylactic treatment to reduce the risk of acute gout flares, unless medically contraindicated or not tolerated as noted in the FDA-approved pegloticase full prescribing information. The participant began a regime of colchicine (0.6 mg/day) or NSAID prophylaxis at least 1 week before the first dose of pegloticase and continued for the duration of pegloticase therapy. Colchicine prophylaxis was not interrupted during the clinical trial unless medically contraindicated or if the participant became intolerant of colchicine, regardless of whether a gout flare occurs.

Gout Flare Treatment—An increase in gout flares was frequently observed upon initiation of anti-hyperuricemic therapy, including treatment with pegloticase. Participants were instructed to contact the site within 12 hours of the onset of symptoms. Gout flares were confirmed through questioning or direct observation. All participants who experience a gout flare during the study were prescribed anti-inflammatory treatment (e.g., corticosteroids, NSAIDs, colchicine) as deemed clinically indicated by the study physician.

Colchicine may be prescribed in a medically appropriate dose range of 0.6 to 1.8 mg/day, usually dosed as 0.6 mg orally twice per day unless reduced dosing was necessitated by renal insufficiency or gastrointestinal intolerance. The precise dose and regimen of colchicine was individualized for each participant, such as in the case of renal insufficiency where colchicine was appropriately started at 0.6 mg/day and increased to three times a day as tolerated.

Example 3—Randomized, Double-Blind, Placebo-Controlled, Multicenter, Efficacy and Safety Study of MTX to Increase Response Rates in Patients with Uncontrolled Gout Receiving KXX The overall objective of this study was to assess the potential for pegloticase with MTX to increase the response rate seen with pegloticase alone, and to characterize the safety, tolerability and pharmacokinetics (PK) of the concomitant use of pegloticase with MTX, by comparing pegloticase co-administered with MTX to pegloticase co-administered with placebo for MTX in adults with uncontrolled gout.

The primary objective was to evaluate the effect of pegloticase with MTX vs. pegloticase with placebo for MTX on the response rate during Month 6 (Weeks 20, 21, 22, 23 and 24), as measured by the sustained normalization of SUA) to <6 mg/dL for at least 80% of the time during Month 6.

Secondary objectives may include:

- Evaluate the effect of pegloticase with MTX vs. pegloticase with placebo for MTX on the response rate during Month 9 (Weeks 32, 34, and 36), as measured by the sustained normalization of SUA to <6 mg/dL for at least 80% of the time during Month 9.
- Evaluate the effect of pegloticase with MTX vs. pegloticase with placebo for MTX on the response rate during Month 12 (Weeks 48, 50, and 52), as measured by the sustained normalization of SUA to <6 mg/dL for at least 80% of the time during Month 12.
- Evaluate the effect of pegloticase with MTX vs. pegloticase with placebo for MTX on the complete resolution of ≥1 tophi (using digital photography) at Week 52 in subjects with tophi at baseline.

Exploratory Objectives

- Evaluate the effect of pegloticase with MTX vs. pegloticase with placebo for MTX on the mean change from baseline in urate deposition volume and bone erosions due to gout to Weeks 14, 24, and 52 based on dual-energy computed tomography (DECT) of the hands and feet.
- Evaluate the effect of pegloticase with MTX vs. pegloticase with placebo for MTX on the mean change from baseline in bone erosions due to gout to Weeks 24 and 52 based on X-rays of the hands and feet.
- Evaluate the effect of pegloticase with MTX vs. pegloticase with placebo for MTX on the complete resolution of ≥1 tophi (using digital photography) at Weeks 24 and 36 in subjects with tophi at baseline.
- Evaluate the effect of pegloticase with MTX vs. pegloticase with placebo for MTX on the mean change from baseline in tophus size (long axis measured using digital photography) to Weeks 14, 24, 36 and 52 in subjects with tophus present at baseline.

Evaluate the effect of pegloticase with MTX vs. pegloticase with placebo for MTX on the response rate during Month 3 (Weeks 10, 12 and 14), as measured by the sustained normalization of SUA to <6 mg/dL for at least 80% of the time during Month 3.

Evaluate the effect of pegloticase with MTX vs. pegloticase with placebo for MTX on the overall response rate, as measured by the sustained normalization of SUA to <6 mg/dL for at least 80% of the time during Month 3 (Weeks 10, 12, and 14) and Month 6 (Weeks 20, 21, 22, 23, and 24) combined.

Evaluate the effect of pegloticase with MTX vs. pegloticase with placebo for MTX on reducing SUA to <5 mg/dL for at least 80% of the time during Months 3, 6, 9 and 12, individually.

Evaluate the effect of pegloticase with MTX vs. pegloticase with placebo for MTX on the mean change from baseline in SUA at Weeks 14, 24, 36 and 52.

Evaluate the effect of pegloticase with MTX vs. pegloticase with placebo for MTX on the time to first SUA>6 mg/dL.

Evaluate the effect of pegloticase with MTX vs. pegloticase with placebo for MTX on the time to two consecutive SUA>6 mg/dL (SUA stopping rule).

Evaluate the effect of pegloticase with MTX vs. pegloticase with placebo for MTX on the percentage of non-hyperuricemic (SUA<6 mg/dL) time during Months 3, 6, 9 and 12.

Evaluate the effect of pegloticase with MTX vs. pegloticase with placebo for MTX on the mean change from baseline in HAQ Pain Score at Weeks 14, 24, 36 and 52.

Evaluate the effect of pegloticase with MTX vs. pegloticase with placebo for MTX on the mean change from baseline in HAQ Health Score at Weeks 14, 24, 36 and 52.

Evaluate the effect of pegloticase and MTX vs. pegloticase and placebo for MTX on the mean change from baseline in HAQ-DI Score at Weeks 14, 24, 36 and 52.

Evaluate the effect of pegloticase with MTX vs. pegloticase with placebo for MTX on the mean change from baseline in tender joint count (68-point scale) at Weeks 14, 24, 36 and 52.

Evaluate the effect of pegloticase with MTX vs. pegloticase with placebo for MTX on the mean change from baseline in swollen joint count (66-point scale) at Weeks 14, 24, 36 and 52.

Evaluate the effect of pegloticase with MTX vs. pegloticase with placebo for MTX on the mean change from baseline in number of tender or swollen joints at Weeks 14, 24, 36 and 52.

Evaluate the effect of pegloticase with MTX vs. pegloticase with placebo for MTX on the mean change from baseline in physician global assessment of gout at Weeks 14, 24, 36 and 52.

Evaluate the effect of pegloticase with MTX vs. pegloticase with placebo for MTX on the proportion of subjects achieving 20%, 50%, or 70% improvement based on gout chronic response criteria at Weeks 14, 24, 36 and 52.

Evaluate the effect of pegloticase with MTX vs. pegloticase with placebo for MTX on the proportion of subjects whose treatment goals were met at Weeks 24 and 52.

Evaluate the effect of pegloticase with MTX vs. pegloticase with placebo for MTX on the mean change from baseline in systolic blood pressure (SBP) and diastolic blood pressure (DBP) to each visit.

Assess the PK of pegloticase.

Assess the incidence of anti-PEG and anti-Uricase IgG antibodies.

The study design included: 1) a Screening Period (screening should be completed within 4 weeks prior to Week −6); 2) a 2-week MTX Tolerability Assessment Period consisting of 2 weeks oral MTX for all subjects; 3) a Run-In Period consisting of randomization followed by 4 weeks of blinded oral MTX or placebo for MTX; 4) a 52-week Pegloticase+IMM Period; 5) a Safety Follow-up (Phone/Email/Site Visit) and 6) a 3 and 6 month Post Treatment Follow-up.

All subjects who met eligibility criteria at Screening began 15 mg MTX orally weekly at the Week −6 visit. Subjects also took folic acid 1 mg orally every day beginning during the MTX Tolerability Assessment Period (Week −6 to Week −4) and continuing until prior to the Week 52 Visit.

Subjects had to be able to tolerate the weekly dose of MTX 15 mg for 2 weeks to be eligible to be randomized at Week −4. Subjects who tolerate the weekly 15 mg MTX dose during the 2 weeks preceding Week −4 Visit and continue to meet eligibility criteria were randomized at the Week −4 Visit in a 2:1 ratio (stratified by presence of tophi) to receive either blinded oral 15 mg MTX or blinded oral placebo for MTX. Subjects continued to take the blinded MTX or placebo for MTX from Week −4 to Day 1 (the Run-in period) at the 15 mg MTX or placebo for MTX dose. If a subject does not tolerate the 15 mg MTX or placebo for MTX dose after randomization at the Week −4 Visit and prior to Day 1, the MTX or placebo for MTX may be dose-reduced or discontinued. After Day 1, MTX or placebo for MTX may be re-initiated. The subject was re-initiated to the same treatment they were randomized to at Week −4. The re-initiated MTX or placebo for MTX remained blinded.

It was required that before a subject begins the pegloticase+IMM Period, he or she had been taking at least one protocol standard gout flare prophylaxis regimen (i.e., colchicine and/or non-steroidal anti-inflammatory drugs and/or low-dose prednisone ≤10 mg/day) for ≥1 week before the first dose of pegloticase and continues flare prophylaxis per American College of Rheumatology guidelines for the greater of 1) 6 months, 2) 3 months after achieving target serum urate (SUA<6 mg/dL) for patients with no tophi detected on physical exam, or 3) 6 months after achieving target serum urate (SUA<5 mg/dL) for patients with one or more tophi detected on initial physical exam that had since resolved. For IR prophylaxis, fexofenadine (180 mg orally) was taken the day before each infusion; fexofenadine (180 mg orally) and acetaminophen (1000 mg orally) were taken the morning of each infusion; and methylprednisolone (125 mg IV) given over an infusion duration between 10-30 minutes, immediately prior to each infusion.

During the Pegloticase+IMM Period, pegloticase 8 mg was administered intravenously (IV) every 2 weeks from Day 1 through the Week 50 Visit for a total of 26 infusions; pegloticase was administered after all pre-dose study visit assessments were completed at each visit. The date and start and stop time of infusion were recorded. Serum uric acid stopping rules were applied: subjects with SUA level >6 mg/dL at 2 consecutive study visits beginning with the Week 2 Visit discontinued treatment, complete the End of Pegloticase Infusion Visit procedures within 2 weeks, and continued the subject visits according to the protocol (without treatment).

During the Pegloticase+IMM Period, subjects were instructed to take MTX or placebo for MTX weekly on the same day each week, within 1 to 3 days prior to each pegloticase infusion and one additional weekly dose after the last infusion for subjects who had not stopped pegloticase due to SUA stopping rules; however, if a subject does not do so, MTX or placebo for MTX were taken ≥60 minutes prior to each pegloticase infusion.

After Day 1, if a subject became unable to tolerate MTX or placebo for MTX, the MTX or placebo for MTX dose was reduced and/or discontinued based on pre-defined criteria, and the subject remained in the study.

Subjects eligible for this study had SUA≥7 mg/dL and gout refractory to conventional therapy characterized by failure to normalize serum uric acid despite conventional therapy or contraindication to conventional therapy, and ongoing symptoms of gout including one of the following: visible tophi, recurrent gout flares, or chronic gouty arthropathy.

Eligible subjects must meet/provide all the following criteria:

- Uncontrolled gout, defined as meeting the following criteria:
- Hyperuricemia during the screening period defined as SUA≥7 mg/dL, and;
- Failure to maintain normalization of SUA with xanthine oxidase inhibitors at the maximum medically appropriate dose, or with a contraindication to xanthine oxidase inhibitor therapy based on medical record review or subject interview, and;
- Symptoms of gout including at least 1 of the following:
- Presence of at least one tophus
- Recurrent flares defined as 2 or more flares in the past 12 months prior to screening
- Presence of chronic gouty arthritis
- Willing to discontinue any oral urate lowering therapy for at least 7 days prior to MTX dosing at Week−6 and remain off when receiving pegloticase infusions.
- Able to tolerate MTX 15 mg orally for 2 to 4 weeks during the screening/MTX Run-in period prior to the first dose of KXX.

Subjects were ineligible for study participation if they meet any of the following criteria:

- Weight >160 kg (352 pounds) at Screening.
- Any serious acute bacterial infection, unless treated and completely resolved with antibiotics at least 2 weeks prior to the Week −6 Visit.
- Severe chronic or recurrent bacterial infections, such as recurrent pneumonia or chronic bronchiectasis.
- Current or chronic treatment with systemic immunosuppressive agents such as MTX, azathioprine, or mycophenolate mofetil; prednisone ≥10 mg/day or equivalent dose of other corticosteroid on a chronic basis (3 months or longer) would also meet exclusion criteria.
- History of any transplant surgery requiring maintenance immunosuppressive therapy.
- Known history of hepatitis B virus surface antigen positivity or hepatitis B DNA positivity.
- Known history of hepatitis C virus RNA positivity.
- Known history of Human Immunodeficiency Virus (HIV) positivity.
- Glucose-6-phosphate dehydrogenase deficiency (tested at the Screening Visit).
- Chronic renal impairment defined as estimated glomerular filtration rate (eGFR)<40 mL/min/1.73 $m^2$ or currently on dialysis.
- Non-compensated congestive heart failure or hospitalization for congestive heart failure within 3 months of the Screening Visit, uncontrolled arrhythmia, treatment for acute coronary syndrome (myocardial infarction or unstable angina), or uncontrolled blood pressure (>160/100 mmHg) prior to Randomization at Week −4.
- Prior treatment with pegloticase, another recombinant uricase (rasburicase), or concomitant therapy with a polyethylene glycol-conjugated drug.
- Known allergy to pegylated products or history of anaphylactic reaction to a recombinant protein or porcine product.
- Contraindication to MTX treatment or MTX treatment considered inappropriate.
- Known immunogenicity of MTX.
- Receipt of an investigational drug within 4 weeks or 5 half-lives, whichever was longer, prior to MTX administration at Week −6 or plans to take an investigational drug during the study.
- Liver transaminase levels (AST or ALT)>upper limit of normal (ULN) or albumin <the lower limit of normal (LLN) at the Screening Visit.
- Chronic liver disease.
- White blood cell count <4,000/ul, hematocrit <32 percent, or platelet count <75,000/ul.
- Currently receiving systemic or radiologic treatment for ongoing cancer.
- History of malignancy within 5 years other than non-melanoma skin cancer or in situ carcinoma of cervix.
- Diagnosis of osteomyelitis.
- Known history of hypoxanthine-guanine phosphoribosyltransferase deficiency, such as Lesch-Nyhan and Kelley-Seegmiller syndrome.
- A known intolerance to at least one protocol standard gout flare prophylaxis regimen (i.e., colchicine and/or non-steroidal anti-inflammatory drugs and/or low-dose prednisone ≤10 mg/day).
- Current pulmonary fibrosis, bronchiectasis or interstitial pneumonitis.

Pegloticase was administered as an admixture of 8 mg in 250 mL of 0.45% or 0.9% Sodium Chloride Injection, United States Pharmacopeia (USP) for IV infusion by gravity feed or infusion pump. Pegloticase was not administered as an IV push or bolus.

MTX 2.5 mg tablets for oral administration during the MTX Tolerability Assessment Period (Week −6 through Week −4) were provided to subjects as a commercially available generic.

MTX 2.5 mg tablets for oral administration during the Run-In Period (Week −4 through Day 1) and the Pegloticase+IMM Period (Day 1 through Week 52) were provided to subjects as a methotrexate 2.5 mg tablet over-encapsulated in a size zero Swedish Orange capsule.

Placebo for methotrexate 2.5 mg for oral administration during the Run-In Period (Week −4 through Day 1) and the Pegloticase+IMM Period (Day 1 through Week 52) were provided as a size zero Swedish Orange capsule with Avicel® filling Efficacy was assessed by SUA levels, tophus resolution, tophus size, tender and swollen joint counts, physician global assessment of gout, and DECT and X-ray of hands and feet.

Quality of life was assessed using the HAQ.

The PK of pegloticase was assessed prior to and after the pegloticase infusion at specified time points.

Pegloticase immunogenicity was assessed by the incidence of anti-PEG and anti-uricase IgG antibodies prior to the pegloticase infusion at specified time points.

Safety assessments included monitoring and recording of all AEs, whether drug-related or not, measurement of vital signs, physical examinations, and monitoring of hematology and blood chemistry.

Example 4— Results from Open-Label Clinical Trial in Patients with Uncontrolled Gout-Mirror OL Adult patients with uncontrolled gout who were beginning pegloticase therapy were considered for enrollment in this ongoing multicenter, open-label, efficacy and safety study of pegloticase with MTX co-treatment (NCT03635957). Patients were administered oral MTX (15 mg/week) and folate (1 mg/day) 4 weeks prior to the first pegloticase infusion (Day 1) and throughout the pegloticase treatment period. Blood was drawn prior to each infusion to measure sUA level, monitor clinical parameters, and examine for ADA development. All patients followed typical IR prophylaxis protocols (fexofenadine one day before and the morning of each infusion and acetaminophen and IV corticosteroid the morning of each infusion). Patients also received gout flare prophylaxis with either NSAIDs, colchicine or prednisone initiated at least 1 week prior to Day 1. The primary study outcome was the proportion of responders, defined as sUA<6 mg/dL for at least 80% of the time during month 6 (weeks 20, 22, and 24). All analyses were performed on a modified intent-to-treat population, defined as patients who received ≥1 pegloticase infusion.

A total of 17 patients were screened and 14 patients (all men, average age: 49.3±8.7 years) were enrolled. Patient characteristics are provided in Table 2. On Day 1, mean sUA was 9.2±2.5 mg/dL and 12 of the 14 patients had visible tophi. At the 6 months timepoint, 11/14 (78.6%, 95% CI 49.2-95.3%) met the responder definition, with 3 patients discontinuing after meeting stopping rules (pre-infusion sUA values greater than 6 mg/dL at 2 consecutive scheduled visits). All patients tolerated MTX. One serious AE of bacterial sepsis occurred (unrelated to study drug, resolved). AEs that occurred in >1 patient were: diarrhea and upper respiratory tract infection in 3 patients each, nasopharyngitis, sinusitis, muscle strain, and hypertension in 2 patients each. Gout flares occurred in 10/14 (71.4%) patients. No new safety concerns were identified.

Results are provided in Tables 3-10. An increased proportion of patients maintained therapeutic response at 6 months when treated concomitantly with MTX and pegloticase (78.6%) when compared to the previously reported 42% using pegloticase alone. These results support and reflect the improved response rates demonstrated in two prior case series.

For the following tables, abbreviations as follows may apply: ITT=Intent-to-Treat, Max=Maximum, Min=Minimum, mITT=Modified Intent-to-Treat, SD=Standard Deviation, sUA=serum Uric Acid, IMM=Immunomodulator, MTX=Methotrexate, PK=Pharmacokinetic, CI=Confidence Interval, NE=Not Estimable, eCRF=electronic case report form.

Percentages were based on the number of subjects in each population. Month 6 includes pre-infusion and post-infusion sUA assessments at Week 20, pre-infusion and post-infusion sUA assessments at Week 22, pre-infusion assessments at Week 24, and pre-infusion unscheduled sUA assessments between Week 20 and Week 24. Local laboratory-reported pre-infusion sUA values were included only when the sUA result from the central laboratory at the same time point was unavailable.

[1] Treatment stopping Rule: Subjects with a sUA level >6 mg/dL at 2 consecutive scheduled study visits beginning with Week 2

[2] If the subject's proportion of hours that sUA was <6 mg/dL was greater than or equal to 80% the subject was called a responder.

Subjects meeting the stopping rule were counted as non-responders. If only one sUA result was collected during Month 6 period, response was based on the single value. A subject with the proportion of hours less than 80% was counted as non-responders.

Any other subject was counted as a non-responder if sUA values were not collected during the Month 6 period.

[3] Two-sided 95% Exact Clopper-Pearson confidence interval.

TABLE 2

Subject Disposition

| Number of Subjects | Overall n (%) |
|---|---|
| Screened | 17 |
| Screen Failures | 3 |
| Received MTX [1] | 1 |
| Did not receive MTX | 2 |
| ITT Population | 15 |
| mITT Population | 14 |
| PK Population | 0 |
| Entered the MTX Run-in Period | 15 |
| Completed the MTX Run-in Period | 14 (93.3) |
| Discontinued from MTX Run-in Period [1] | 1 (6.7) |
| Entered Pegloticase + IMM Period | 14 (100) |
| Completed Treatment [2] | 3 (21.4) |
| 24 Weeks (Amendment 1) | 1 (7.1) |
| 52 Weeks (Amendment 2) | 2 (14.3) |
| Discontinued Treatment [3] | 5 |
| Reasons for Discontinuation | |
| Adverse Events | 0 |
| Lack of Efficacy (sUA stopping criteria met) | 3 (60.0) |
| Unacceptable Risk to Patient | 0 |
| Subject refusal of additional therapy | 2 (40.0) |
| Study Terminated by Sponsor | 0 |
| Pregnancy | 0 |
| Death | 0 |
| Completed Study | 4 (28.6) |
| At Week 24 (Amendment 1) | 1 (7.1) |
| At Week 52 (Amendment 2) | 3 (21.4) |
| Discontinued Study | 3 |
| Reasons for Discontinuation | |
| Death | 0 |
| Lack of Efficacy (sUA stopping criteria met) [4] | 3 (100) |
| Lost to Follow-Up | 0 |
| Study Terminated by Sponsor | 0 |
| Withdrawal by Subject | 0 |
| Have 3 month follow-up | 0 |
| Have 6 month follow-up | 0 |

TABLE 3

SUA < 6 mg/dL Responders during Month 3 and Overall (Months 3 and 6 Combined) (ITT and mITT Populations)

| Time Point | | ITT Population N = 15 | mITT Population N = 14 |
|---|---|---|---|
| Month 3 (Weeks 10, 12, 14) | Responder, n (%) [2] | 11 (73.3) | 11 (78.6) |
| | 95% Clopper-Pearson Confidence Interval [3] | 44.9, 92.2 | 49.2, 95.3 |
| | Non-Responder, n (%) | 4 (26.7) | 3 (21.4) |
| | Proportion of Time during Period that sUA < 6 mg/dL | | |
| | n | 11 | 11 |
| | Mean (SD) | 100.0 (0.00) | 100.0 (0.00) |
| | Median | 100.0 | 100.0 |
| | Min, Max | 100, 100 | 100, 100 |
| Month 3 (Weeks 10, 12, 14) | Discontinued due to stopping rule prior to Week 14, n (%) [1] | 3 (20.0) | 3 (21.4) |
| | Subjects missing all data in analysis period, n (%) | 3 (20.0) | 2 (14.3) |
| | Subjects with only one measurement (above cutoff) in analysis period, n (%) | 1 (6.7) | 1 (7.1) |
| | Subjects with only one measurement (below cutoff) in analysis period, n (%) | 0 | 0 |
| Overall (Month 3 and Month 6 Combined) [4] | Responder, n (%) [2] | 11 (73.3) | 11 (78.6) |
| | 95% Clopper-Pearson Confidence Interval [3] | 44.9, 92.2 | 49.2, 95.3 |
| | Non-Responder, n (%) | 4 (26.7) | 3 (21.4) |
| Overall (Month 3 and Month 6 Combined) [4] | Proportion of Time during Period that sUA < 6 mg/dL | | |
| | n | 11 | 11 |
| | Mean (SD) | 100.0 (0.00) | 100.0 (0.00) |
| | Median | 100.0 | 100.0 |
| | Min, Max | 100, 100 | 100, 100 |
| | Discontinued due to stopping rule prior to Week 14, n (%) [1] | 3 (20.0) | 3 (21.4) |

TABLE 4

Serum Uric Acid < 5 mg/dL Responders during Month 3, Month 6, and Overall (Month 3 and Month 6 Combined) (ITT Population and mITT Population)

| Time Point | | ITT Population N = 15 | mITT Population N = 14 |
|---|---|---|---|
| Month 3 (Weeks 10, 12, 14) | Responder, n (%) [2] | 11 (73.3) | 11 (78.6) |
| | 95% Clopper-Pearson Confidence Interval [3] | 44.9, 92.2 | 49.2, 95.3 |
| | Non-Responder, n (%) | 4 (26.7) | 3 (21.4) |
| | Proportion of Time during Period that sUA < 5 mg/dL | | |
| | n | 11 | 11 |
| | Mean (SD) | 100.0 (0.00) | 100.0 (0.00) |
| | Median | 100.0 | 100.0 |
| | Min, Max | 100, 100 | 100, 100 |
| Month 3 (Weeks 10, 12, 14) | Discontinued due to stopping rule prior to Week 14, n (%) [1] | 3 (20.0) | 3 (21.4) |
| | Subjects missing all data in analysis period, n (%) | 3 (20.0) | 2 (14.3) |
| | Subjects with only one measurement (above cutoff) in analysis period, n (%) | 1 (6.7) | 1 (7.1) |
| | Subjects with only one measurement (below cutoff) in analysis period, n (%) | 0 | 0 |
| Month 6 (Weeks 20, 22, 24) | Responder, n (%) [2] | 11 (73.3) | 11 (78.6) |
| | 95% Clopper-Pearson Confidence Interval [3] | 44.9, 92.2 | 49.2, 95.3 |
| | Non-Responder, n (%) | 4 (26.7) | 3 (21.4) |

TABLE 4-continued

Serum Uric Acid < 5 mg/dL Responders during Month 3, Month 6, and Overall (Month 3 and Month 6 Combined) (ITT Population and mITT Population)

| Time Point | | ITT Population N = 15 | mITT Population N = 14 |
|---|---|---|---|
| Month 6 (Weeks 20, 22, 24) | Proportion of Time during Period that sUA < 5 mg/dL | | |
| | n | 11 | 11 |
| | Mean (SD) | 100.0 (0.00) | 100.0 (0.00) |
| | Median | 100.0 | 100.0 |
| | Min, Max | 100, 100 | 100, 100 |
| | Discontinued due to stopping rule prior to Week 24, n (%) [1] | 3 (20.0) | 3 (21.4) |
| | Subjects missing all data in analysis period, n (%) | 4 (26.7) | 3 (21.4) |
| | Subjects with only one measurement (above cutoff) in analysis period, n (%) | 0 | 0 |
| | Subjects with only one measurement (below cutoff) in analysis period, n (%) | 0 | 0 |
| Overall (Month 3 and Month 6 Combined) [4] | Responder, n (%) [4] | 11 (73.3) | 11 (78.6) |
| | 95% Clopper-Pearson Confidence Interval [3] | 44.9, 92.2 | 49.2, 95.3 |
| | Non-Responder, n (%) | 4 (26.7) | 3 (21.4) |
| | Proportion of Time during Period that sUA < 5 mg/dL | | |
| | n | 11 | 11 |
| | Mean (SD) | 100.0 (0.00) | 100.0 (0.00) |
| | Median | 100.0 | 100.0 |
| | Min, Max | 100, 100 | 100, 100 |
| | Discontinued due to stopping rule prior to Week 24, n (%) [1] | 3 (20.0) | 3 (21.4) |

TABLE 5

Serum Uric Acid (mg/dL): Observed Values and Change from Methotrexate Baseline Values (mITT Population)

| | mITT Population (N = 14) | | |
|---|---|---|---|
| Visit Statistics | Baseline [1] | Observed | Change from Baseline |
| Baseline [2] | | | |
| n | | 14 | |
| Mean (SD) | | 8.91 (1.877) | |
| Median | | 9.05 | |
| Min, Max | | 5.4, 12.4 | |
| 95% CI [3] | | (7.82, 9.99) | |
| sUA < 6 mg/dL, n (%) | | 1 (7.1%) | |
| Week −2 | | | |
| n | 14 | 14 | 14 |
| Mean (SD) | 8.91 (1.877) | 9.45 (2.211) | 0.54 (0.839) |
| Median | 9.05 | 9.30 | 0.50 |
| Min, Max | 5.4, 12.4 | 5.2, 14.6 | 0.9, 2.2 |
| 95% CI [3] | (7.82, 9.99) | (8.17, 10.73) | (0.06, 1.03) |
| sUA < 6 mg/dL, n (%) | | 1 (7.1%) | |
| Day 1 - Pre-Infusion | | | |
| n | 14 | 14 | 14 |
| Mean (SD) | 8.91 (1.877) | 9.16 (2.486) | 0.25 (1.283) |
| Median | 9.05 | 9.00 | −0.25 |
| Min, Max | 5.4, 12.4 | 4.7, 15.8 | −1.2, 3.4 |
| 95% CI [3] | (7.82, 9.99) | (7.72, 10.59) | (−0.49, 0.99) |
| sUA < 6 mg/dL, n (%) | | 1 (7.1%) | |
| Day 1 - Post-Infusion | | | |
| n | 11 | 11 | 11 |
| Mean (SD) | 8.48 (1.758) | 1.18 (1.417) | −7.30 (2.081) |
| Median | 8.70 | 0.30 | −7.30 |
| Min, Max | 5.4, 11.6 | 0.3, 4.9 | −11.3, −3.8 |
| 95% CI [3] | (7.30, 9.66) | (0.23, 2.13) | (−8.70, −5.90) |
| sUA < 6 mg/dL, n (%) | | 11 (100%) | |

TABLE 5-continued

Serum Uric Acid (mg/dL): Observed Values and Change from Methotrexate Baseline Values (mITT Population)

| Visit Statistics | mITT Population (N = 14) | | |
|---|---|---|---|
| | Baseline [1] | Observed | Change from Baseline |
| **Week 1** | | | |
| n | 6 | 6 | 6 |
| Mean (SD) | 8.10 (1.541) | 0.30 (0.000) | −7.80 (1.541) |
| Median | 8.30 | 0.30 | −8.00 |
| Min, Max | 5.4, 9.6 | 0.3, 0.3 | −9.3, −5.1 |
| 95% CI [3] | (6.48, 9.72) | (0.30, 0.30) | (−9.42, −6.18) |
| sUA < 6 mg/dL, n (%) | | 6 (100%) | |
| **Week 2 - Pre-Infusion** | | | |
| n | 14 | 14 | 14 |
| Mean (SD) | 8.91 (1.877) | 1.26 (2.163) | −7.65 (2.496) |
| Median | 9.05 | 0.30 | −8.00 |
| Min, Max | 5.4, 12.4 | 0.3, 7.7 | −11.3, −1.0 |
| 95% CI [3] | (7.82, 9.99) | (0.01, 2.51) | (−9.09, −6.21) |
| sUA < 6 mg/dL, n (%) | | 13 (92.9%) | |
| **Week 2 - Post-Infusion** | | | |
| n | 14 | 14 | 14 |
| Mean (SD) | 8.91 (1.877) | 0.30 (0.000) | −8.61 (1.877) |
| Median | 9.05 | 0.30 | −8.75 |
| Min, Max | 5.4, 12.4 | 0.3, 0.3 | −12.1, −5.1 |
| 95% CI [3] | (7.82, 9.99) | (0.30, 0.30) | (−9.69, −7.52) |
| sUA < 6 mg/dL, n (%) | | 14 (100%) | |
| **Week 4 - Pre-Infusion** | | | |
| n | 14 | 14 | 14 |
| Mean (SD) | 8.91 (1.877) | 1.61 (2.637) | −7.29 (3.137) |
| Median | 9.05 | 0.30 | −7.45 |
| Min, Max | 5.4, 12.4 | 0.3, 8.2 | −12.1, −0.5 |
| 95% CI [3] | (7.82, 9.99) | (0.09, 3.14) | (−9.10, −5.48) |
| sUA < 6 mg/dL, n (%) | | 12 (85.7%) | |
| **Week 4 - Post-Infusion** | | | |
| n | 13 | 13 | 13 |
| Mean (SD) | 8.92 (1.953) | 0.30 (0.000) | −8.62 (1.953) |
| Median | 9.40 | 0.30 | −9.10 |
| Min, Max | 5.4, 12.4 | 0.3, 0.3 | −12.1, −5.1 |
| 95% CI [3] | (7.74, 10.10) | (0.30, 0.30) | (−9.80, −7.44) |
| sUA < 6 mg/dL, n (%) | | 13 (100%) | |
| **Week 6 - Pre-Infusion** | | | |
| n | 13 | 13 | 13 |
| Mean (SD) | 8.92 (1.953) | 0.91 (2.191) | −8.02 (2.779) |
| Median | 9.40 | 0.30 | −8.40 |
| Min, Max | 5.4, 12.4 | 0.3, 8.2 | −12.1, −1.4 |
| 95% CI [3] | (7.74, 10.10) | (0.00, 2.23) | (−9.69, −6.34) |
| sUA < 6 mg/dL, n (%) | | 12 (92.3%) | |
| **Week 6 - Post-Infusion** | | | |
| n | 12 | 12 | 12 |
| Mean (SD) | 8.87 (2.029) | 0.30 (0.000) | −8.57 (2.029) |
| Median | 9.05 | 0.30 | −8.75 |
| Min, Max | 5.4, 12.4 | 0.3, 0.3 | −12.1, −5.1 |
| 95% CI [3] | (7.58, 10.16) | (0.30, 0.30) | (−9.86, −7.28) |
| sUA < 6 mg/dL, n (%) | | 12 (100%) | |
| **Week 7** | | | |
| n | 4 | 4 | 4 |
| Mean (SD) | 8.70 (2.960) | 0.30 (0.000) | −8.40 (2.960) |
| Median | 8.50 | 0.30 | −8.20 |
| Min, Max | 5.4, 12.4 | 0.3, 0.3 | −12.1, −5.1 |
| 95% CI [3] | (3.99, 13.41) | (0.30, 0.30) | (−13.11, −3.69) |
| sUA < 6 mg/dL, n (%) | | 4 (100%) | |
| **Week 8 - Pre-Infusion** | | | |
| n | 12 | 12 | 12 |
| Mean (SD) | 8.87 (2.029) | 1.08 (2.472) | −7.79 (3.227) |
| Median | 9.05 | 0.30 | −7.98 |
| Min, Max | 5.4, 12.4 | 0.3, 8.9 | −12.1, 0.2 |
| 95% CI [3] | (7.58, 10.16) | (0.00, 2.65) | (−9.84, −5.74) |
| sUA < 6 mg/dL, n (%) | | 11 (91.7%) | |

TABLE 5-continued

Serum Uric Acid (mg/dL): Observed Values and Change from Methotrexate Baseline Values (mITT Population)

| Visit<br>Statistics | mITT Population (N = 14)<br>Baseline [1] | <br>Observed | <br>Change from Baseline |
|---|---|---|---|
| Week 8 - Post-Infusion | | | |
| n | 12 | 12 | 12 |
| Mean (SD) | 8.87 (2.029) | 0.30 (0.000) | −8.57 (2.029) |
| Median | 9.05 | 0.30 | −8.75 |
| Min, Max | 5.4, 12.4 | 0.3, 0.3 | −12.1, −5.1 |
| 95% CI [3] | (7.58, 10.16) | (0.30, 0.30) | (−9.86, −7.28) |
| sUA < 6 mg/dL, n (%) | | 12 (100%) | |
| Week 10 - Pre-Infusion | | | |
| n | 12 | 12 | 12 |
| Mean (SD) | 8.87 (2.029) | 0.95 (2.252) | −7.92 (3.069) |
| Median | 9.05 | 0.30 | −8.35 |
| Min, Max | 5.4, 12.4 | 0.3, 8.1 | −12.1, −0.6 |
| 95% CI [3] | (7.58, 10.16) | (0.00, 2.38) | (−9.87, −5.97) |
| sUA < 6 mg/dL, n (%) | | 11 (91.7%) | |
| Week 10 - Post-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 12 - Pre-Infusion | | | |
| n | 11 | 11 | 11 |
| Mean (SD) | 8.88 (2.127) | 0.30 (0.015) | −8.59 (2.124) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.29, 0.31) | (−10.01, −7.16) |
| sUA < 6 mg/dL, n (%) | | 11 (100%) | |
| Week 12 - Post-Infusion | | | |
| n | 10 | 10 | 10 |
| Mean (SD) | 8.98 (2.216) | 0.30 (0.000) | −8.68 (2.216) |
| Median | 9.50 | 0.30 | −9.20 |
| Min, Max | 5.4, 12.4 | 0.3, 0.3 | −12.1, −5.1 |
| 95% CI [3] | (7.40, 10.56) | (0.30, 0.30) | (−10.26, −7.10) |
| sUA < 6 mg/dL, n (%) | | 10 (100%) | |
| Week 14 - Pre-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 14 - Post-Infusion | | | |
| n | 10 | 10 | 10 |
| Mean (SD) | 8.80 (2.224) | 0.30 (0.000) | −8.50 (2.224) |
| Median | 8.65 | 0.30 | −8.35 |
| Min, Max | 5.4, 12.4 | 0.3, 0.3 | −12.1, −5.1 |
| 95% CI [3] | (7.21, 10.39) | (0.30, 0.30) | (−10.09, −6.91) |
| sUA < 6 mg/dL, n (%) | | 10 (100%) | |
| Week 16 - Pre-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 16 - Post-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |

TABLE 5-continued

Serum Uric Acid (mg/dL): Observed Values and Change from Methotrexate Baseline Values (mITT Population)

| Visit<br>Statistics | mITT Population (N = 14)<br>Baseline [1] | <br>Observed | <br>Change from Baseline |
|---|---|---|---|
| Week 18 - Pre-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 18 - Post-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 20 - Pre-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 20 - Post-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 22 - Pre-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 22 - Post-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 24 - Pre-Infusion | | | |
| n | 11 | 11 | 11 |
| Mean (SD) | 8.88 (2.127) | 0.30 (0.000) | −8.58 (2.127) |
| Median | 9.40 | 0.30 | −9.10 |
| Min, Max | 5.4, 12.4 | 0.3, 0.3 | −12.1, −5.1 |
| 95% CI [3] | (7.45, 10.31) | (0.30, 0.30) | (−10.01, −7.15) |
| sUA < 6 mg/dL, n (%) | | 11 (100%) | |
| Week 24 - Post-Infusion | | | |
| n | 5 | 5 | 5 |
| Mean (SD) | 9.02 (2.648) | 0.30 (0.000) | −8.72 (2.648) |
| Median | 9.60 | 0.30 | −9.30 |
| Min, Max | 5.4, 12.4 | 0.3, 0.3 | −12.1, −5.1 |
| 95% CI [3] | (5.73, 12.31) | (0.30, 0.30) | (−12.01, −5.43) |
| sUA < 6 mg/dL, n (%) | | 5 (100%) | |
| Week 26 - Pre-Infusion | | | |
| n | 8 | 8 | 8 |
| Mean (SD) | 9.10 (2.449) | 0.30 (0.000) | −8.80 (2.449) |
| Median | 9.65 | 0.30 | −9.35 |
| Min, Max | 5.4, 12.4 | 0.3, 0.3 | −12.1, −5.1 |
| 95% CI [3] | (7.05, 11.15) | (0.30, 0.30) | (−10.85, −6.75) |
| sUA < 6 mg/dL, n (%) | | 8 (100%) | |

TABLE 5-continued

Serum Uric Acid (mg/dL): Observed Values and Change from Methotrexate Baseline Values (mITT Population)

| | mITT Population (N = 14) | | |
|---|---|---|---|
| Visit<br>Statistics | Baseline [1] | Observed | Change from Baseline |
| **Week 28 - Pre-Infusion** | | | |
| n | 8 | 8 | 8 |
| Mean (SD) | 9.10 (2.449) | 0.30 (0.000) | −8.80 (2.449) |
| Median | 9.65 | 0.30 | −9.35 |
| Min, Max | 5.4, 12.4 | 0.3, 0.3 | −12.1, −5.1 |
| 95% CI [3] | (7.05, 11.15) | (0.30, 0.30) | (−10.85, −6.75) |
| sUA < 6 mg/dL, n (%) | | 8 (100%) | |
| **Week 30 - Pre-Infusion** | | | |
| n | 8 | 8 | 8 |
| Mean (SD) | 9.10 (2.449) | 0.30 (0.000) | −8.80 (2.449) |
| Median | 9.65 | 0.30 | −9.35 |
| Min, Max | 5.4, 12.4 | 0.3, 0.3 | −12.1, −5.1 |
| 95% CI [3] | (7.05, 11.15) | (0.30, 0.30) | (−10.85, −6.75) |
| sUA < 6 mg/dL, n (%) | | 8 (100%) | |
| **Week 32 - Pre-Infusion** | | | |
| n | 10 | 10 | 10 |
| Mean (SD) | 8.83 (2.235) | 0.30 (0.000) | −8.53 (2.235) |
| Median | 8.75 | 0.30 | −8.45 |
| Min, Max | 5.4, 12.4 | 0.3, 0.3 | −12.1, −5.1 |
| 95% CI [3] | (7.23, 10.43) | (0.30, 0.30) | (−10.13, −6.93) |
| sUA < 6 mg/dL, n (%) | | 10 (100%) | |
| **Week 32 - Post-Infusion** | | | |
| n | 8 | 8 | 8 |
| Mean (SD) | 9.10 (2.449) | 0.30 (0.000) | −8.80 (2.449) |
| Median | 9.65 | 0.30 | −9.35 |
| Min, Max | 5.4, 12.4 | 0.3, 0.3 | −12.1, −5.1 |
| 95% CI [3] | (7.05, 11.15) | (0.30, 0.30) | (−10.85, −6.75) |
| sUA < 6 mg/dL, n (%) | | 8 (100%) | |
| **Week 34 - Pre-Infusion** | | | |
| n | 10 | 10 | 10 |
| Mean (SD) | 8.83 (2.235) | 0.82 (1.046) | −8.01 (2.709) |
| Median | 8.75 | 0.30 | −8.20 |
| Min, Max | 5.4, 12.4 | 0.3, 2.9 | −12.1, −4.9 |
| 95% CI [3] | (7.23, 10.43) | (0.07, 1.57) | (−9.95, −6.07) |
| sUA < 6 mg/dL, n (%) | | 10 (100%) | |
| **Week 34 - Post-Infusion** | | | |
| n | 8 | 8 | 8 |
| Mean (SD) | 9.10 (2.449) | 0.30 (0.000) | −8.80 (2.449) |
| Median | 9.65 | 0.30 | −9.35 |
| Min, Max | 5.4, 12.4 | 0.3, 0.3 | −12.1, −5.1 |
| 95% CI [3] | (7.05, 11.15) | (0.30, 0.30) | (−10.85, −6.75) |
| sUA < 6 mg/dL, n (%) | | 8 (100%) | |
| **Week 36 - Pre-Infusion** | | | |
| n | 9 | 9 | 9 |
| Mean (SD) | 9.10 (2.190) | 1.58 (2.425) | −7.52 (3.769) |
| Median | 9.60 | 0.30 | −9.14 |
| Min, Max | 5.4, 12.4 | 0.1, 6.4 | −12.1, −1.2 |
| 95% CI [3] | (7.42, 10.78) | (0.00, 3.44) | (−10.42, −4.63) |
| sUA < 6 mg/dL, n (%) | | 8 (88.9%) | |
| **Week 36 - Post-Infusion** | | | |
| n | 6 | 6 | 6 |
| Mean (SD) | 9.38 (2.577) | 0.30 (0.000) | −9.08 (2.577) |
| Median | 9.65 | 0.30 | −9.35 |
| Min, Max | 5.4, 12.4 | 0.3, 0.3 | −12.1, −5.1 |
| 95% CI [3] | (6.68, 12.09) | (0.30, 0.30) | (−11.79, −6.38) |
| sUA < 6 mg/dL, n (%) | | 6 (100%) | |
| **Week 38 - Pre-Infusion** | | | |
| n | 5 | 5 | 5 |
| Mean (SD) | 8.94 (2.613) | 0.93 (1.583) | −8.01 (3.904) |
| Median | 9.60 | 0.30 | −9.30 |
| Min, Max | 5.4, 12.4 | 0.0, 3.8 | −12.1, −1.6 |
| 95% CI [3] | (5.70, 12.18) | (0.00, 2.90) | (−12.86, −3.16) |
| sUA < 6 mg/dL, n (%) | | 5 (100%) | |

TABLE 5-continued

Serum Uric Acid (mg/dL): Observed Values and Change from Methotrexate Baseline Values (mITT Population)

| Visit Statistics | mITT Population (N = 14) Baseline [1] | Observed | Change from Baseline |
|---|---|---|---|
| Week 40 - Pre-Infusion | | | |
| n | 3 | 3 | 3 |
| Mean (SD) | 10.57 (1.589) | 0.30 (0.000) | −10.27 (1.589) |
| Median | 9.70 | 0.30 | −9.40 |
| Min, Max | 9.6, 12.4 | 0.3, 0.3 | −12.1, −9.3 |
| 95% CI [3] | (6.62, 14.51) | (0.30, 0.30) | (−14.21, −6.32) |
| sUA < 6 mg/dL, n (%) | | 3 (100%) | |
| Week 42 - Pre-Infusion | | | |
| n | 3 | 3 | 3 |
| Mean (SD) | 10.57 (1.589) | 0.30 (0.000) | −10.27 (1.589) |
| Median | 9.70 | 0.30 | −9.40 |
| Min, Max | 9.6, 12.4 | 0.3, 0.3 | −12.1, −9.3 |
| 95% CI [3] | (6.62, 14.51) | (0.30, 0.30) | (−14.21, −6.32) |
| sUA < 6 mg/dL, n (%) | | 3 (100%) | |
| Week 44 - Pre-Infusion | | | |
| n | 3 | 3 | 3 |
| Mean (SD) | 10.57 (1.589) | 1.05 (1.305) | −9.51 (2.487) |
| Median | 9.70 | 0.30 | −9.30 |
| Min, Max | 9.6, 12.4 | 0.3, 2.6 | −12.1, −7.1 |
| 95% CI [3] | (6.62, 14.51) | (0.00, 4.29) | (−15.69, −3.34) |
| sUA < 6 mg/dL, n (%) | | 3 (100%) | |
| Week 46 - Pre-Infusion | | | |
| n | 2 | 2 | 2 |
| Mean (SD) | 11.00 (1.980) | 0.30 (0.000) | −10.70 (1.980) |
| Median | 11.00 | 0.30 | −10.70 |
| Min, Max | 9.6, 12.4 | 0.3, 0.3 | −12.1, −9.3 |
| 95% CI [3] | (0.00, 28.79) | (0.30, 0.30) | (−28.49, −7.09) |
| sUA < 6 mg/dL, n (%) | | 2 (100%) | |
| Week 48 - Pre-Infusion | | | |
| n | 2 | 2 | 2 |
| Mean (SD) | 11.00 (1.980) | 0.30 (0.000) | −10.70 (1.980) |
| Median | 11.00 | 0.30 | −10.70 |
| Min, Max | 9.6, 12.4 | 0.3, 0.3 | −12.1, −9.3 |
| 95% CI [3] | (0.00, 28.79) | (0.30, 0.30) | (−28.49, −7.09) |
| sUA < 6 mg/dL, n (%) | | 2 (100%) | |
| Week 48 - Post-Infusion | | | |
| n | 3 | 3 | 3 |
| Mean (SD) | 9.87 (2.411) | 1.60 (2.252) | −8.27 (4.441) |
| Median | 9.60 | 0.30 | −9.30 |
| Min, Max | 7.6, 12.4 | 0.3, 4.2 | −12.1, −3.4 |
| 95% CI [3] | (3.88, 15.86) | (0.00, 7.19) | (−19.30, −2.77) |
| sUA < 6 mg/dL, n (%) | | 3 (100%) | |
| Week 50 - Pre-Infusion | | | |
| n | 2 | 2 | 2 |
| Mean (SD) | 11.00 (1.980) | 0.30 (0.000) | −10.70 (1.980) |
| Median | 11.00 | 0.30 | −10.70 |
| Min, Max | 9.6, 12.4 | 0.3, 0.3 | −12.1, −9.3 |
| 95% CI [3] | (0.00, 28.79) | (0.30, 0.30) | (−28.49, −7.09) |
| sUA < 6 mg/dL, n (%) | | 2 (100%) | |
| Week 50 - Post-Infusion | | | |
| n | 3 | 3 | 3 |
| Mean (SD) | 9.87 (2.411) | 1.37 (1.848) | −8.50 (4.060) |
| Median | 9.60 | 0.30 | −9.30 |
| Min, Max | 7.6, 12.4 | 0.3, 3.5 | −12.1, −4.1 |
| 95% CI [3] | (3.88, 15.86) | (0.00, 5.96) | (−18.58, 1.58) |
| sUA < 6 mg/dL, n (%) | | 3 (100%) | |
| Week 52/ET | | | |
| n | 2 | 2 | 2 |
| Mean (SD) | 11.00 (1.980) | 0.30 (0.000) | −10.70 (1.980) |
| Median | 11.00 | 0.30 | −10.70 |
| Min, Max | 9.6, 12.4 | 0.3, 0.3 | −12.1, −9.3 |
| 95% CI [3] | (0.00, 28.79) | (0.30, 0.30) | (−28.49, −7.09) |
| sUA < 6 mg/dL, n (%) | | 2 (100%) | |

TABLE 5-continued

Serum Uric Acid (mg/dL): Observed Values and Change from Methotrexate Baseline Values (mITT Population)

| Visit<br>Statistics | mITT Population (N = 14)<br>Baseline [1] | <br>Observed | <br>Change from Baseline |
|---|---|---|---|
| End of Pegloticase Infusions Visit | | | |
| n | 2 | 2 | 2 |
| Mean (SD) | 7.75 (0.212) | 0.30 (0.000) | −7.45 (0.212) |
| Median | 7.75 | 0.30 | −7.45 |
| Min, Max | 7.6, 7.9 | 0.3, 0.3 | −7.6, −7.3 |
| 95% CI [3] | (5.84, 9.66) | (0.30, 0.30) | (−9.36, −5.54) |
| sUA < 6 mg/dL, n (%) | | 2 (100%) | |
| Early Termination Visit | | | |
| n | 3 | 3 | 3 |
| Mean (SD) | 9.00 (0.520) | 8.17 (0.058) | −0.83 (0.493) |
| Median | 8.70 | 8.20 | −0.60 |
| Min, Max | 8.7, 9.6 | 8.1, 8.2 | −1.4, −0.5 |
| 95% CI [3] | (7.71, 10.29) | (8.02, 8.31) | (−2.06, −0.39) |
| sUA < 6 mg/dL, n (%) | | 0 | |

TABLE 6

Serum Uric Acid (mg/dL): Observed Values and Change from Pegloticase Baseline Values (mITT Population)

| Visit<br>Statistics | mITT Population (N = 14)<br>Baseline [1] | <br>Observed | <br>Change from Baseline |
|---|---|---|---|
| Baseline [2] | | | |
| n | | 14 | |
| Mean (SD) | | 9.16 (2.486) | |
| Median | | 9.00 | |
| Min, Max | | 4.7, 15.8 | |
| 95% CI [3] | | (7.72, 10.59) | |
| sUA < 6 mg/dL, n (%) | | 1 (7.1%) | |
| Day 1 - Post-Infusion | | | |
| n | 11 | 11 | 11 |
| Mean (SD) | 8.47 (1.736) | 1.18 (1.417) | −7.29 (2.254) |
| Median | 8.40 | 0.30 | −7.30 |
| Min, Max | 4.7, 11.4 | 0.3, 4.9 | −11.1, −3.5 |
| 95% CI [3] | (7.31, 9.64) | (0.23, 2.13) | (−8.80, −5.78) |
| sUA < 6 mg/dL, n (%) | | 11 (100%) | |
| Week 1 | | | |
| n | 6 | 6 | 6 |
| Mean (SD) | 7.58 (1.556) | 0.30 (0.000) | −7.28 (1.556) |
| Median | 8.05 | 0.30 | −7.75 |
| Min, Max | 4.7, 9.1 | 0.3, 0.3 | −8.8, −4.4 |
| 95% CI [3] | (5.95, 9.22) | (0.30, 0.30) | (−8.92, −5.65) |
| sUA < 6 mg/dL, n (%) | | 6 (100%) | |
| Week 2 - Pre-Infusion | | | |
| n | 14 | 14 | 14 |
| Mean (SD) | 9.16 (2.486) | 1.26 (2.163) | −7.90 (2.878) |
| Median | 9.00 | 0.30 | −8.70 |
| Min, Max | 4.7, 15.8 | 0.3, 7.7 | −11.9, −0.7 |
| 95% CI [3] | (7.72, 10.59) | (0.01, 2.51) | (−9.56, −6.24) |
| sUA < 6 mg/dL, n (%) | | 13 (92.9%) | |

TABLE 6-continued

Serum Uric Acid (mg/dL): Observed Values and Change from Pegloticase Baseline Values (mITT Population)

| Visit<br>Statistics | mITT Population (N = 14)<br>Baseline [1] | <br>Observed | <br>Change from Baseline |
|---|---|---|---|
| Week 2 - Post-Infusion | | | |
| n | 14 | 14 | 14 |
| Mean (SD) | 9.16 (2.486) | 0.30 (0.000) | −8.86 (2.486) |
| Median | 9.00 | 0.30 | −8.70 |
| Min, Max | 4.7, 15.8 | 0.3, 0.3 | −15.5, −4.4 |
| 95% CI [3] | (7.72, 10.59) | (0.30, 0.30) | (−10.29, −7.42) |
| sUA < 6 mg/dL, n (%) | | 14 (100%) | |
| Week 4 - Pre-Infusion | | | |
| n | 14 | 14 | 14 |
| Mean (SD) | 9.16 (2.486) | 1.61 (2.637) | −7.54 (3.768) |
| Median | 9.00 | 0.30 | −8.00 |
| Min, Max | 4.7, 15.8 | 0.3, 8.2 | −15.5, −0.2 |
| 95% CI [3] | (7.72, 10.59) | (0.09, 3.14) | (−9.72, −5.37) |
| sUA < 6 mg/dL, n (%) | | 12 (85.7%) | |
| Week 4 - Post-Infusion | | | |
| n | 13 | 13 | 13 |
| Mean (SD) | 9.22 (2.577) | 0.30 (0.000) | −8.92 (2.577) |
| Median | 9.10 | 0.30 | −8.80 |
| Min, Max | 4.7, 15.8 | 0.3, 0.3 | −15.5, −4.4 |
| 95% CI [3] | (7.66, 10.77) | (0.30, 0.30) | (−10.47, −7.36) |
| sUA < 6 mg/dL, n (%) | | 13 (100%) | |
| Week 6 - Pre-Infusion | | | |
| n | 13 | 13 | 13 |
| Mean (SD) | 9.22 (2.577) | 0.91 (2.191) | −8.31 (3.538) |
| Median | 9.10 | 0.30 | −8.80 |
| Min, Max | 4.7, 15.8 | 0.3, 8.2 | −15.5, −0.2 |
| 95% CI [3] | (7.66, 10.77) | (0.00, 2.23) | (−10.45, −6.17) |
| sUA < 6 mg/dL, n (%) | | 12 (92.3%) | |

TABLE 6-continued

Serum Uric Acid (mg/dL): Observed Values and Change from Pegloticase Baseline Values (mITT Population)

| Visit Statistics | mITT Population (N = 14) Baseline [1] | Observed | Change from Baseline |
|---|---|---|---|
| Week 6 - Post-Infusion | | | |
| n | 12 | 12 | 12 |
| Mean (SD) | 9.28 (2.679) | 0.30 (0.000) | −8.98 (2.679) |
| Median | 9.25 | 0.30 | −8.95 |
| Min, Max | 4.7, 15.8 | 0.3, 0.3 | −15.5, −4.4 |
| 95% CI [3] | (7.58, 10.99) | (0.30, 0.30) | (−10.69, −7.28) |
| sUA < 6 mg/dL, n (%) | | 12 (100%) | |
| Week 7 | | | |
| n | 4 | 4 | 4 |
| Mean (SD) | 9.20 (4.755) | 0.30 (0.000) | −8.90 (4.755) |
| Median | 8.15 | 0.30 | −7.85 |
| Min, Max | 4.7, 15.8 | 0.3, 0.3 | −15.5, −4.4 |
| 95% CI [3] | (1.63, 16.77) | (0.30, 0.30) | (−16.47, −1.33) |
| sUA < 6 mg/dL, n (%) | | 4 (100%) | |
| Week 8 - Pre-Infusion | | | |
| n | 12 | 12 | 12 |
| Mean (SD) | 9.28 (2.679) | 1.08 (2.472) | −8.20 (3.624) |
| Median | 9.25 | 0.30 | −8.33 |
| Min, Max | 4.7, 15.8 | 0.3, 8.9 | −15.5, −0.5 |
| 95% CI [3] | (7.58, 10.99) | (0.00, 2.65) | (−10.51, −5.90) |
| sUA < 6 mg/dL, n (%) | | 11 (91.7%) | |
| Week 8 - Post-Infusion | | | |
| n | 12 | 12 | 12 |
| Mean (SD) | 9.28 (2.679) | 0.30 (0.000) | −8.98 (2.679) |
| Median | 9.25 | 0.30 | −8.95 |
| Min, Max | 4.7, 15.8 | 0.3, 0.3 | −15.5, −4.4 |
| 95% CI [3] | (7.58, 10.99) | (0.30, 0.30) | (−10.69, −7.28) |
| sUA < 6 mg/dL, n (%) | | 12 (100%) | |
| Week 10 - Pre-Infusion | | | |
| n | 12 | 12 | 12 |
| Mean (SD) | 9.28 (2.679) | 0.95 (2.252) | −8.33 (3.476) |
| Median | 9.25 | 0.30 | −8.70 |
| Min, Max | 4.7, 15.8 | 0.3, 8.1 | −15.5, −1.3 |
| 95% CI [3] | (7.58, 10.99) | (0.00, 2.38) | (−10.54, −6.12) |
| sUA < 6 mg/dL, n (%) | | 11 (91.7%) | |
| Week 10 - Post-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 12 - Pre-Infusion | | | |
| n | 11 | 11 | 11 |
| Mean (SD) | 9.27 (2.810) | 0.30 (0.015) | −8.98 (2.806) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.29, 0.31) | (−10.86, −7.09) |
| sUA < 6 mg/dL, n (%) | | 11 (100%) | |

TABLE 6-continued

Serum Uric Acid (mg/dL): Observed Values and Change from Pegloticase Baseline Values (mITT Population)

| Visit Statistics | mITT Population (N = 14) Baseline [1] | Observed | Change from Baseline |
|---|---|---|---|
| Week 12 - Post-Infusion | | | |
| n | 10 | 10 | 10 |
| Mean (SD) | 9.43 (2.911) | 0.30 (0.000) | −9.13 (2.911) |
| Median | 9.35 | 0.30 | −9.05 |
| Min, Max | 4.7, 15.8 | 0.3, 0.3 | −15.5, −4.4 |
| 95% CI [3] | (7.35, 11.51) | (0.30, 0.30) | (−11.21, −7.05) |
| sUA < 6 mg/dL, n (%) | | 10 (100%) | |
| Week 14 - Pre-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 14 - Post-Infusion | | | |
| n | 10 | 10 | 10 |
| Mean (SD) | 9.31 (2.959) | 0.30 (0.000) | −9.01 (2.959) |
| Median | 9.35 | 0.30 | −9.05 |
| Min, Max | 4.7, 15.8 | 0.3, 0.3 | −15.5, −4.4 |
| 95% CI [3] | (7.19, 11.43) | (0.30, 0.30) | (−11.13, −6.89) |
| sUA < 6 mg/dL, n (%) | | 10 (100%) | |
| Week 16 - Pre-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 16 - Post-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 18 - Pre-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 18 - Post-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |

TABLE 6-continued

Serum Uric Acid (mg/dL): Observed Values and Change from Pegloticase Baseline Values (mITT Population)

| Visit Statistics | mITT Population (N = 14) Baseline [1] | Observed | Change from Baseline |
|---|---|---|---|
| Week 20 - Pre-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 20 - Post-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 22 - Pre-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 22 - Post-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 24 - Pre-Infusion | | | |
| n | 11 | 11 | 11 |
| Mean (SD) | 9.27 (2.810) | 0.30 (0.000) | −8.97 (2.810) |
| Median | 9.10 | 0.30 | −8.80 |
| Min, Max | 4.7, 15.8 | 0.3, 0.3 | −15.5, −4.4 |
| 95% CI [3] | (7.38, 11.16) | (0.30, 0.30) | (−10.86, −7.08) |
| sUA < 6 mg/dL, n (%) | | 11 (100%) | |
| Week 24 - Post-Infusion | | | |
| n | 5 | 5 | 5 |
| Mean (SD) | 9.48 (4.135) | 0.30 (0.000) | −9.18 (4.135) |
| Median | 9.60 | 0.30 | −9.30 |
| Min, Max | 4.7, 15.8 | 0.3, 0.3 | −15.5, −4.4 |
| 95% CI [3] | (4.35, 14.61) | (0.30, 0.30) | (−14.31, −4.05) |
| sUA < 6 mg/dL, n (%) | | 5 (100%) | |
| Week 26 - Pre-Infusion | | | |
| n | 8 | 8 | 8 |
| Mean (SD) | 9.41 (3.293) | 0.30 (0.000) | −9.11 (3.293) |
| Median | 9.25 | 0.30 | −8.95 |
| Min, Max | 4.7, 15.8 | 0.3, 0.3 | −15.5, −4.4 |
| 95% CI [3] | (6.66, 12.17) | (0.30, 0.30) | (−11.87, −6.36) |
| sUA < 6 mg/dL, n (%) | | 8 (100%) | |
| Week 28 - Pre-Infusion | | | |
| n | 8 | 8 | 8 |
| Mean (SD) | 9.41 (3.293) | 0.30 (0.000) | −9.11 (3.293) |
| Median | 9.25 | 0.30 | −8.95 |
| Min, Max | 4.7, 15.8 | 0.3, 0.3 | −15.5, −4.4 |
| 95% CI [3] | (6.66, 12.17) | (0.30, 0.30) | (−11.87, −6.36) |
| sUA < 6 mg/dL, n (%) | | 8 (100%) | |
| Week 30 - Pre-Infusion | | | |
| n | 8 | 8 | 8 |
| Mean (SD) | 9.41 (3.293) | 0.30 (0.000) | −9.11 (3.293) |
| Median | 9.25 | 0.30 | −8.95 |
| Min, Max | 4.7, 15.8 | 0.3, 0.3 | −15.5, −4.4 |
| 95% CI [3] | (6.66, 12.17) | (0.30, 0.30) | (−11.87, −6.36) |
| sUA < 6 mg/dL, n (%) | | 8 (100%) | |
| Week 32 - Pre-Infusion | | | |
| n | 10 | 10 | 10 |
| Mean (SD) | 9.29 (2.961) | 0.30 (0.000) | −8.99 (2.961) |
| Median | 9.25 | 0.30 | −8.95 |
| Min, Max | 4.7, 15.8 | 0.3, 0.3 | −15.5, −4.4 |
| 95% CI [3] | (7.17, 11.41) | (0.30, 0.30) | (−11.11, −6.87) |
| sUA < 6 mg/dL, n (%) | | 10 (100%) | |
| Week 32 - Post-Infusion | | | |
| n | 8 | 8 | 8 |
| Mean (SD) | 9.41 (3.293) | 0.30 (0.000) | −9.11 (3.293) |
| Median | 9.25 | 0.30 | −8.95 |
| Min, Max | 4.7, 15.8 | 0.3, 0.3 | −15.5, −4.4 |
| 95% CI [3] | (6.66, 12.17) | (0.30, 0.30) | (−11.87, −6.36) |
| sUA < 6 mg/dL, n (%) | | 8 (100%) | |
| Week 34 - Pre-Infusion | | | |
| n | 10 | 10 | 10 |
| Mean (SD) | 9.29 (2.961) | 0.82 (1.046) | −8.47 (3.248) |
| Median | 9.25 | 0.30 | −7.95 |
| Min, Max | 4.7, 15.8 | 0.3, 2.9 | −15.5, −4.4 |
| 95% CI [3] | (7.17, 11.41) | (0.07, 1.57) | (−10.79, −6.15) |
| sUA < 6 mg/dL, n (%) | | 10 (100%) | |
| Week 34 - Post-Infusion | | | |
| n | 8 | 8 | 8 |
| Mean (SD) | 9.41 (3.293) | 0.30 (0.000) | −9.11 (3.293) |
| Median | 9.25 | 0.30 | −8.95 |
| Min, Max | 4.7, 15.8 | 0.3, 0.3 | −15.5, −4.4 |
| 95% CI [3] | (6.66, 12.17) | (0.30, 0.30) | (−11.87, −6.36) |
| sUA < 6 mg/dL, n (%) | | 8 (100%) | |
| Week 36 - Pre-Infusion | | | |
| n | 9 | 9 | 9 |
| Mean (SD) | 9.48 (3.077) | 1.58 (2.425) | −7.90 (4.094) |
| Median | 9.60 | 0.30 | −8.60 |
| Min, Max | 4.7, 15.8 | 0.1, 6.4 | −15.5, −2.5 |
| 95% CI [3] | (7.11, 11.84) | (0.00, 3.44) | (−11.05, −4.75) |
| sUA < 6 mg/dL, n (%) | | 8 (88.9%) | |

TABLE 6-continued

Serum Uric Acid (mg/dL): Observed Values and Change from Pegloticase Baseline Values (mITT Population)

| Visit Statistics | mITT Population (N = 14) Baseline [1] | Observed | Change from Baseline |
|---|---|---|---|
| Week 36 - Post-Infusion | | | |
| n | 6 | 6 | 6 |
| Mean (SD) | 9.68 (3.799) | 0.30 (0.000) | −9.38 (3.799) |
| Median | 9.50 | 0.30 | −9.20 |
| Min, Max | 4.7, 15.8 | 0.3, 0.3 | −15.5, −4.4 |
| 95% CI [3] | (5.70, 13.67) | (0.30, 0.30) | (−13.37, −5.40) |
| sUA < 6 mg/dL, n (%) | | 6 (100%) | |
| Week 38 - Pre-Infusion | | | |
| n | 5 | 5 | 5 |
| Mean (SD) | 9.34 (4.142) | 0.93 (1.583) | −8.41 (5.229) |
| Median | 8.90 | 0.30 | −8.60 |
| Min, Max | 4.7, 15.8 | 0.0, 3.8 | −15.5, −0.9 |
| 95% CI [3] | (4.20, 14.48) | (0.00, 2.90) | (−14.90, −1.92) |
| sUA < 6 mg/dL, n (%) | | 5 (100%) | |
| Week 40 - Pre-Infusion | | | |
| n | 3 | 3 | 3 |
| Mean (SD) | 11.60 (3.686) | 0.30 (0.000) | −11.30 (3.686) |
| Median | 10.10 | 0.30 | −9.80 |
| Min, Max | 8.9, 15.8 | 0.3, 0.3 | −15.5, −8.6 |
| 95% CI [3] | (2.44, 20.76) | (0.30, 0.30) | (−20.46, −2.14) |
| sUA < 6 mg/dL, n (%) | | 3 (100%) | |
| Week 42 - Pre-Infusion | | | |
| n | 3 | 3 | 3 |
| Mean (SD) | 11.60 (3.686) | 0.30 (0.000) | −11.30 (3.686) |
| Median | 10.10 | 0.30 | −9.80 |
| Min, Max | 8.9, 15.8 | 0.3, 0.3 | −15.5, −8.6 |
| 95% CI [3] | (2.44, 20.76) | (0.30, 0.30) | (−20.46, −2.14) |
| sUA < 6 mg/dL, n (%) | | 3 (100%) | |
| Week 44 - Pre-Infusion | | | |
| n | 3 | 3 | 3 |
| Mean (SD) | 11.60 (3.686) | 1.05 (1.305) | −10.55 (4.625) |
| Median | 10.10 | 0.30 | −9.80 |
| Min, Max | 8.9, 15.8 | 0.3, 2.6 | −15.5, −6.3 |
| 95% CI [3] | (2.44, 20.76) | (0.00, 4.29) | (−22.04, 0.94) |
| sUA < 6 mg/dL, n (%) | | 3 (100%) | |
| Week 46 - Pre-Infusion | | | |
| n | 2 | 2 | 2 |
| Mean (SD) | 12.95 (4.031) | 0.30 (0.000) | −12.65 (4.031) |
| Median | 12.95 | 0.30 | −12.65 |
| Min, Max | 10.1, 15.8 | 0.3, 0.3 | −15.5, −9.8 |
| 95% CI [3] | (0.00, 49.16) | (0.30, 0.30) | (−48.86, 23.56) |
| sUA < 6 mg/dL, n (%) | | 2 (100%) | |
| Week 48 - Pre-Infusion | | | |
| n | 2 | 2 | 2 |
| Mean (SD) | 12.95 (4.031) | 0.30 (0.000) | −12.65 (4.031) |
| Median | 12.95 | 0.30 | −12.65 |
| Min, Max | 10.1, 15.8 | 0.3, 0.3 | −15.5, −9.8 |
| 95% CI [3] | (0.00, 49.16) | (0.30, 0.30) | (−48.86, 23.56) |
| sUA < 6 mg/dL, n (%) | | 2 (100%) | |
| Week 48 - Post-Infusion | | | |
| n | 3 | 3 | 3 |
| Mean (SD) | 11.93 (3.350) | 1.60 (2.252) | −10.33 (4.922) |
| Median | 10.10 | 0.30 | −9.80 |
| Min, Max | 9.9, 15.8 | 0.3, 4.2 | −15.5, −5.7 |
| 95% CI [3] | (3.61, 20.26) | (0.00, 7.19) | (−22.56, 1.89) |
| sUA < 6 mg/dL, n (%) | | 3 (100%) | |
| Week 50 - Pre-Infusion | | | |
| n | 2 | 2 | 2 |
| Mean (SD) | 12.95 (4.031) | 0.30 (0.000) | −12.65 (4.031) |
| Median | 12.95 | 0.30 | −12.65 |
| Min, Max | 10.1, 15.8 | 0.3, 0.3 | −15.5, −9.8 |
| 95% CI [3] | (0.00, 49.16) | (0.30, 0.30) | (−48.86, 23.56) |
| sUA < 6 mg/dL, n (%) | | 2 (100%) | |
| Week 50 - Post-Infusion | | | |
| n | 3 | 3 | 3 |
| Mean (SD) | 11.93 (3.350) | 1.37 (1.848) | −10.57 (4.598) |
| Median | 10.10 | 0.30 | −9.80 |
| Min, Max | 9.9, 15.8 | 0.3, 3.5 | −15.5, −6.4 |
| 95% CI [3] | (3.61, 20.26) | (0.00, 5.96) | (−21.99, 0.86) |
| sUA < 6 mg/dL, n (%) | | 3 (100%) | |
| Week 52/ET | | | |
| n | 2 | 2 | 2 |
| Mean (SD) | 12.95 (4.031) | 0.30 (0.000) | −12.65 (4.031) |
| Median | 12.95 | 0.30 | −12.65 |
| Min, Max | 10.1, 15.8 | 0.3, 0.3 | −15.5, −9.8 |
| 95% CI [3] | (0.00, 49.16) | (0.30, 0.30) | (−48.86, 23.56) |
| sUA < 6 mg/dL, n (%) | | 2 (100%) | |
| End of Pegloticase Infusions Visit | | | |
| n | 2 | 2 | 2 |
| Mean (SD) | 8.80 (1.556) | 0.30 (0.000) | −8.50 (1.556) |
| Median | 8.80 | 0.30 | −8.50 |
| Min, Max | 7.7, 9.9 | 0.3, 0.3 | −9.6, −7.4 |
| 95% CI [3] | (0.00, 22.78) | (0.30, 0.30) | (−22.48, 5.48) |
| sUA < 6 mg/dL, n (%) | | 2 (100%) | |
| Early Termination Visit | | | |
| n | 3 | 3 | 3 |
| Mean (SD) | 8.73 (0.577) | 8.17 (0.058) | −0.57 (0.635) |
| Median | 8.40 | 8.20 | −0.20 |
| Min, Max | 8.4, 9.4 | 8.1, 8.2 | −1.3, −0.2 |
| 95% CI [3] | (7.30, 10.17) | (8.02, 8.31) | (−2.14, 1.01) |
| sUA < 6 mg/dL, n (%) | | 0 | |

TABLE 7

Serum Uric Acid (mg/dL): Observed Values and Change from Pegloticase Baseline Values by Month 6 sUA Responder Subgroup (mITT Population)

| | Month 6 sUA Responders [1] (N = 11) | | | Month 6 sUA Non-Responders [1] (N = 3) | | |
|---|---|---|---|---|---|---|
| Visit<br>Statistics | Baseline [2] | Observed | Change from Baseline | Baseline [2] | Observed | Change from Baseline |
| Baseline [3] | | | | | | |
| n | | 11 | | | 3 | |
| Mean (SD) | | 9.27 (2.810) | | | 8.73 (0.577) | |
| Median | | 9.10 | | | 8.40 | |
| Min, Max | | 4.7, 15.8 | | | 8.4, 9.4 | |
| 95% CI [4] | | (7.38, 11.16) | | | (7.30, 10.17) | |
| sUA < 6 mg/dL, n (%) | | 1 (9.1%) | | | 0 | |
| Day 1 - Post-Infusion | | | | | | |
| n | 8 | 8 | 8 | 3 | 3 | 3 |
| Mean (SD) | 8.38 (2.042) | 0.83 (0.798) | −7.55 (2.158) | 8.73 (0.577) | 2.13 (2.438) | −6.60 (2.848) |
| Median | 8.30 | 0.30 | −7.50 | 8.40 | 1.20 | −7.20 |
| Min, Max | 4.7, 11.4 | 0.3, 2.4 | −11.1, −4.4 | 8.4, 9.4 | 0.3, 4.9 | −9.1, −3.5 |
| 95% CI [4] | (6.67, 10.08) | (0.16, 1.49) | (−9.35, −5.75) | (7.30, 10.17) | (0.00, 8.19) | (−13.67, 0.47) |
| sUA < 6 mg/dL, n (%) | | 8 (100%) | | | 3 (100%) | |
| Week 1 | | | | | | |
| n | 4 | 4 | 4 | 2 | 2 | 2 |
| Mean (SD) | 7.18 (1.836) | 0.30 (0.000) | −6.88 (1.836) | 8.40 (0.000) | 0.30 (0.000) | −8.10 (0.000) |
| Median | 7.45 | 0.30 | −7.15 | 8.40 | 0.30 | −8.10 |
| Min, Max | 4.7, 9.1 | 0.3, 0.3 | −8.8, −4.4 | 8.4, 8.4 | 0.3, 0.3 | −8.1, −8.1 |
| 95% CI [4] | (4.25, 10.10) | (0.30, 0.30) | (−9.80, −3.95) | (8.40, 8.40) | (0.30, 0.30) | (−8.10, −8.10) |
| sUA < 6 mg/dL, n (%) | | 4 (100%) | | | 2 (100%) | |
| Week 2 - Pre-Infusion | | | | | | |
| n | 11 | 11 | 11 | 3 | 3 | 3 |
| Mean (SD) | 9.27 (2.810) | 0.63 (1.096) | −8.64 (2.086) | 8.73 (0.577) | 3.57 (3.775) | −5.17 (4.225) |
| Median | 9.10 | 0.30 | −8.80 | 8.40 | 2.70 | −5.70 |
| Min, Max | 4.7, 15.8 | 0.3, 3.9 | −11.9, −4.4 | 8.4, 9.4 | 0.3, 7.7 | −9.1, −0.7 |
| 95% CI [4] | (7.38, 11.16) | (0.00, 1.37) | (−10.04, −7.24) | (7.30, 10.17) | (0.00, 12.95) | (−15.66, 5.33) |
| sUA < 6 mg/dL, n (%) | | 11 (100%) | | | 2 (66.7%) | |
| Week 2 - Post-Infusion | | | | | | |
| n | 11 | 11 | 11 | 3 | 3 | 3 |
| Mean (SD) | 9.27 (2.810) | 0.30 (0.000) | −8.97 (2.810) | 8.73 (0.577) | 0.30 (0.000) | −8.43 (0.577) |
| Median | 9.10 | 0.30 | −8.80 | 8.40 | 0.30 | −8.10 |
| Min, Max | 4.7, 15.8 | 0.3, 0.3 | −15.5, −4.4 | 8.4, 9.4 | 0.3, 0.3 | −9.1, −8.1 |
| 95% CI [4] | (7.38, 11.16) | (0.30, 0.30) | (−10.86, −7.08) | (7.30, 10.17) | (0.30, 0.30) | (−9.87, −7.00) |
| sUA < 6 mg/dL, n (%) | | 11 (100%) | | | 3 (100%) | |
| Week 4 - Pre-Infusion | | | | | | |
| n | 11 | 11 | 11 | 3 | 3 | 3 |
| Mean (SD) | 9.27 (2.810) | 0.68 (1.043) | −8.59 (2.884) | 8.73 (0.577) | 5.03 (4.177) | −3.70 (4.744) |
| Median | 9.10 | 0.30 | −8.60 | 8.40 | 6.60 | −1.80 |
| Min, Max | 4.7, 15.8 | 0.3, 3.8 | −15.5, −4.4 | 8.4, 9.4 | 0.3, 8.2 | −9.1, −0.2 |
| 95% CI [4] | (7.38, 11.16) | (0.00, 1.38) | (−10.53, −6.65) | (7.30, 10.17) | (0.00, 15.41) | (−15.49, 8.09) |
| sUA < 6 mg/dL, n (%) | | 11 (100%) | | | 1 (33.3%) | |
| Week 4 - Post-Infusion | | | | | | |
| n | 11 | 11 | 11 | 2 | 2 | 2 |
| Mean (SD) | 9.27 (2.810) | 0.30 (0.000) | −8.97 (2.810) | 8.90 (0.707) | 0.30 (0.000) | −8.60 (0.707) |
| Median | 9.10 | 0.30 | −8.80 | 8.90 | 0.30 | −8.60 |
| Min, Max | 4.7, 15.8 | 0.3, 0.3 | −15.5, −4.4 | 8.4, 9.4 | 0.3, 0.3 | −9.1, −8.1 |
| 95% CI [4] | (7.38, 11.16) | (0.30, 0.30) | (−10.86, −7.08) | (2.55, 15.25) | (0.30, 0.30) | (−14.95, −2.25) |
| sUA < 6 mg/dL, n (%) | | 11 (100%) | | | 2 (100%) | |
| Week 6 - Pre-Infusion | | | | | | |
| n | 11 | 11 | 11 | 2 | 2 | 2 |
| Mean (SD) | 9.27 (2.810) | 0.30 (0.000) | −8.97 (2.810) | 8.90 (0.707) | 4.25 (5.586) | −4.65 (6.293) |
| Median | 9.10 | 0.30 | −8.80 | 8.90 | 4.25 | −4.65 |
| Min, Max | 4.7, 15.8 | 0.3, 0.3 | −15.5, −4.4 | 8.4, 9.4 | 0.3, 8.2 | −9.1, −0.2 |
| 95% CI [4] | (7.38, 11.16) | (0.30, 0.30) | (−10.86, −7.08) | (2.55, 15.25) | (0.00, 54.44) | (−61.19, 51.89) |
| sUA < 6 mg/dL, n (%) | | 11 (100%) | | | 1 (50.0%) | |
| Week 6 - Post-Infusion | | | | | | |
| n | 11 | 11 | 11 | 1 | 1 | 1 |
| Mean (SD) | 9.27 (2.810) | 0.30 (0.000) | −8.97 (2.810) | 9.40 (NE) | 0.30 (NE) | −9.10 (NE) |
| Median | 9.10 | 0.30 | −8.80 | 9.40 | 0.30 | −9.10 |
| Min, Max | 4.7, 15.8 | 0.3, 0.3 | −15.5, −4.4 | 9.4, 9.4 | 0.3, 0.3 | −9.1, −9.1 |
| 95% CI [4] | (7.38, 11.16) | (0.30, 0.30) | (−10.86, −7.08) | (NE, NE) | (NE, NE) | (NE, NE) |
| sUA < 6 mg/dL, n (%) | | 11 (100%) | | | 1 (100%) | |

TABLE 7-continued

Serum Uric Acid (mg/dL): Observed Values and Change from Pegloticase Baseline Values by Month 6 sUA Responder Subgroup (mITT Population)

| | Month 6 sUA Responders [1] (N = 11) | | | Month 6 sUA Non-Responders [1] (N = 3) | | |
|---|---|---|---|---|---|---|
| Visit<br>Statistics | Baseline [2] | Observed | Change from Baseline | Baseline [2] | Observed | Change from Baseline |
| Week 7 | | | | | | |
| n | 4 | 4 | 4 | 0 | 0 | 0 |
| Mean (SD) | 9.20 (4.755) | 0.30 (0.000) | −8.90 (4.755) | | | |
| Median | 8.15 | 0.30 | −7.85 | | | |
| Min, Max | 4.7, 15.8 | 0.3, 0.3 | −15.5, −4.4 | | | |
| 95% CI [4] | (1.63, 16.77) | (0.30, 0.30) | (−16.47, −1.33) | | | |
| sUA < 6 mg/dL, n (%) | | 4 (100%) | | | 0 | |
| Week 8 - Pre-Infusion | | | | | | |
| n | 11 | 11 | 11 | 1 | 1 | 1 |
| Mean (SD) | 9.27 (2.810) | 0.37 (0.224) | −8.91 (2.824) | 9.40 (NE) | 8.90 (NE) | −0.50 (NE) |
| Median | 9.10 | 0.30 | −8.60 | 9.40 | 8.90 | −0.50 |
| Min, Max | 4.7, 15.8 | 0.3, 1.0 | −15.5, −4.4 | 9.4, 9.4 | 8.9, 8.9 | −0.5, −0.5 |
| 95% CI [4] | (7.38, 11.16) | (0.22, 0.52) | (−10.80, −7.01) | (NE, NE) | (NE, NE) | (NE, NE) |
| sUA < 6 mg/dL, n (%) | | 11 (100%) | | | 0 | |
| Week 8 - Post-Infusion | | | | | | |
| n | 11 | 11 | 11 | 1 | 1 | 1 |
| Mean (SD) | 9.27 (2.810) | 0.30 (0.000) | −8.97 (2.810) | 9.40 (NE) | 0.30 (NE) | −9.10 (NE) |
| Median | 9.10 | 0.30 | −8.80 | 9.40 | 0.30 | −9.10 |
| Min, Max | 4.7, 15.8 | 0.3, 0.3 | −15.5, −4.4 | 9.4, 9.4 | 0.3, 0.3 | −9.1, −9.1 |
| 95% CI [4] | (7.38, 11.16) | (0.30, 0.30) | (−10.86, −7.08) | (NE, NE) | (NE, NE) | (NE, NE) |
| sUA < 6 mg/dL, n (%) | | 11 (100%) | | | 1 (100%) | |
| Week 10 - Pre-Infusion | | | | | | |
| n | 11 | 11 | 11 | 1 | 1 | 1 |
| Mean (SD) | 9.27 (2.810) | 0.30 (0.000) | −8.97 (2.810) | 9.40 (NE) | 8.10 (NE) | −1.30 (NE) |
| Median | 9.10 | 0.30 | −8.80 | 9.40 | 8.10 | −1.30 |
| Min, Max | 4.7, 15.8 | 0.3, 0.3 | −15.5, −4.4 | 9.4, 9.4 | 8.1, 8.1 | −1.3, −1.3 |
| 95% CI [4] | (7.38, 11.16) | (0.30, 0.30) | (−10.86, −7.08) | (NE, NE) | (NE, NE) | (NE, NE) |
| sUA < 6 mg/dL, n (%) | | 11 (100%) | | | 0 | |
| Week 10 - Post-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 12 - Pre-Infusion | | | | | | |
| n | 11 | 11 | 11 | 0 | 0 | 0 |
| Mean (SD) | 9.27 (2.810) | 0.30 (0.015) | −8.98 (2.806) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.29, 0.31) | (−10.86, −7.09) | | | |
| sUA < 6 mg/dL, n (%) | | 11 (100%) | | | 0 | |
| Week 12 - Post-Infusion | | | | | | |
| n | 10 | 10 | 10 | 0 | 0 | 0 |
| Mean (SD) | 9.43 (2.911) | 0.30 (0.000) | −9.13 (2.911) | | | |
| Median | 9.35 | 0.30 | −9.05 | | | |
| Min, Max | 4.7, 15.8 | 0.3, 0.3 | −15.5, −4.4 | | | |
| 95% CI [4] | (7.35, 11.51) | (0.30, 0.30) | (−11.21, −7.05) | | | |
| sUA < 6 mg/dL, n (%) | | 10 (100%) | | | 0 | |
| Week 14 - Pre-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 14 - Post-Infusion | | | | | | |
| n | 10 | 10 | 10 | 0 | 0 | 0 |
| Mean | (SD) (2.959) | 0.30 (0.000) | −9.01 (2.959) | | | |
| Median | 9.35 | 0.30 | −9.05 | | | |
| Min, Max | 4.7, 15.8 | 0.3, 0.3 | −15.5, −4.4 | | | |
| 95% CI [4] | (7.19, 11.43) | (0.30, 0.30) | (−11.13, −6.89) | | | |
| sUA < 6 mg/dL, n (%) | | 10 (100%) | | | 0 | |

TABLE 7-continued

Serum Uric Acid (mg/dL): Observed Values and Change from Pegloticase Baseline Values by Month 6 sUA Responder Subgroup (mITT Population)

| | Month 6 sUA Responders [1] (N = 11) | | | Month 6 sUA Non-Responders [1] (N = 3) | | |
|---|---|---|---|---|---|---|
| Visit<br>Statistics | Baseline [2] | Observed | Change from<br>Baseline | Baseline [2] | Observed | Change from<br>Baseline |
| Week 16 - Pre-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 16 - Post-Infusion | | | | | | |
| n | 11 | 11 | 11 | 0 | 0 | 0 |
| Mean | (SD) (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 18 - Pre-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 18 - Post-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 20 - Pre-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 20 - Post-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 22 - Pre-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 22 - Post-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |
| Week 24 - Pre-Infusion | | | | | | |
| n | 11 | 11 | 11 | 0 | 0 | 0 |
| Mean (SD) | 9.27 (2.810) | 0.30 (0.000) | −8.97 (2.810) | | | |
| Median | 9.10 | 0.30 | −8.80 | | | |
| Min, Max | 4.7, 15.8 | 0.3, 0.3 | −15.5, −4.4 | | | |
| 95% CI [4] | (7.38, 11.16) | (0.30, 0.30) | (−10.86, −7.08) | | | |
| sUA < 6 mg/dL, n (%) | | 11 (100%) | | | 0 | |

TABLE 7-continued

Serum Uric Acid (mg/dL): Observed Values and Change from Pegloticase Baseline Values by Month 6 sUA Responder Subgroup (mITT Population)

| Visit Statistics | Month 6 sUA Responders [1] (N = 11) Baseline [2] | Observed | Change from Baseline | Month 6 sUA Non-Responders [1] (N = 3) Baseline [2] | Observed | Change from Baseline |
|---|---|---|---|---|---|---|
| Week 24 - Post-Infusion | | | | | | |
| n | 5 | 5 | 5 | 0 | 0 | 0 |
| Mean (SD) | 9.48 (4.135) | 0.30 (0.000) | −9.18 (4.135) | | | |
| Median | 9.60 | 0.30 | −9.30 | | | |
| Min, Max | 4.7, 15.8 | 0.3, 0.3 | −15.5, −4.4 | | | |
| 95% CI [4] | (4.35, 14.61) | (0.30, 0.30) | (−14.31, −4.05) | | | |
| sUA < 6 mg/dL, n (%) | | 5 (100%) | | | 0 | |
| Week 26 - Pre-Infusion | | | | | | |
| n | 8 | 8 | 8 | 0 | 0 | 0 |
| Mean (SD) | 9.41 (3.293) | 0.30 (0.000) | −9.11 (3.293) | | | |
| Median | 9.25 | 0.30 | −8.95 | | | |
| Min, Max | 4.7, 15.8 | 0.3, 0.3 | −15.5, −4.4 | | | |
| 95% CI [4] | (6.66, 12.17) | (0.30, 0.30) | (−11.87, −6.36) | | | |
| sUA < 6 mg/dL, n (%) | | 8 (100%) | | | 0 | |
| Week 28 - Pre-Infusion | | | | | | |
| n | 8 | 8 | 8 | 0 | 0 | 0 |
| Mean (SD) | 9.41 (3.293) | 0.30 (0.000) | −9.11 (3.293) | | | |
| Median | 9.25 | 0.30 | −8.95 | | | |
| Min, Max | 4.7, 15.8 | 0.3, 0.3 | −15.5, −4.4 | | | |
| 95% CI [4] | (6.66, 12.17) | (0.30, 0.30) | (−11.87, −6.36) | | | |
| sUA < 6 mg/dL, n (%) | | 8 (100%) | | | 0 | |
| Week 30 - Pre-Infusion | | | | | | |
| n | 8 | 8 | 8 | 0 | 0 | 0 |
| Mean (SD) | 9.41 (3.293) | 0.30 (0.000) | −9.11 (3.293) | | | |
| Median | 9.25 | 0.30 | −8.95 | | | |
| Min, Max | 4.7, 15.8 | 0.3, 0.3 | −15.5, −4.4 | | | |
| 95% CI [4] | (6.66, 12.17) | (0.30, 0.30) | (−11.87, −6.36) | | | |
| sUA < 6 mg/dL, n (%) | | 8 (100%) | | | 0 | |
| Week 32 - Pre-Infusion | | | | | | |
| n | 10 | 10 | 10 | 0 | 0 | 0 |
| Mean (SD) | 9.29 (2.961) | 0.30 (0.000) | −8.99 (2.961) | | | |
| Median | 9.25 | 0.30 | −8.95 | | | |
| Min, Max | 4.7, 15.8 | 0.3, 0.3 | −15.5, −4.4 | | | |
| 95% CI [4] | (7.17, 11.41) | (0.30, 0.30) | (−11.11, −6.87) | | | |
| sUA < 6 mg/dL, n (%) | | 10 (100%) | | | 0 | |
| Week 32 - Post-Infusion | | | | | | |
| n | 8 | 8 | 8 | 0 | 0 | 0 |
| Mean (SD) | 9.41 (3.293) | 0.30 (0.000) | −9.11 (3.293) | | | |
| Median | 9.25 | 0.30 | −8.95 | | | |
| Min, Max | 4.7, 15.8 | 0.3, 0.3 | −15.5, −4.4 | | | |
| 95% CI [4] | (6.66, 12.17) | (0.30, 0.30) | (−11.87, −6.36) | | | |
| sUA < 6 mg/dL, n (%) | | 8 (100%) | | | 0 | |
| Week 34 - Pre-Infusion | | | | | | |
| n | 10 | 10 | 10 | 0 | 0 | 0 |
| Mean (SD) | 9.29 (2.961) | 0.82 (1.046) | −8.47 (3.248) | | | |
| Median | 9.25 | 0.30 | −7.95 | | | |
| Min, Max | 4.7, 15.8 | 0.3, 2.9 | −15.5, −4.4 | | | |
| 95% CI [4] | (7.17, 11.41) | (0.07, 1.57) | (−10.79, −6.15) | | | |
| sUA < 6 mg/dL, n (%) | | 10 (100%) | | | 0 | |
| Week 34 - Post-Infusion | | | | | | |
| n | 8 | 8 | 8 | 0 | 0 | 0 |
| Mean (SD) | 9.41 (3.293) | 0.30 (0.000) | −9.11 (3.293) | | | |
| Median | 9.25 | 0.30 | −8.95 | | | |
| Min, Max | 4.7, 15.8 | 0.3, 0.3 | −15.5, −4.4 | | | |
| 95% CI [4] | (6.66, 12.17) | (0.30, 0.30) | (−11.87, −6.36) | | | |
| sUA < 6 mg/dL, n (%) | | 8 (100%) | | | 0 | |
| Week 36 - Pre-Infusion | | | | | | |
| n | 9 | 9 | 9 | 0 | 0 | 0 |
| Mean (SD) | 9.48 (3.077) | 1.58 (2.425) | −7.90 (4.094) | | | |
| Median | 9.60 | 0.30 | −8.60 | | | |
| Min, Max | 4.7, 15.8 | 0.1, 6.4 | −15.5, −2.5 | | | |
| 95% CI [4] | (7.11, 11.84) | (0.00, 3.44) | (−11.05, −4.75) | | | |
| sUA < 6 mg/dL, n (%) | | 8 ( 88.9%) | | | 0 | |

TABLE 7-continued

Serum Uric Acid (mg/dL): Observed Values and Change from Pegloticase Baseline Values by Month 6 sUA Responder Subgroup (mITT Population)

| Visit Statistics | Month 6 sUA Responders [1] (N = 11) Baseline [2] | Month 6 sUA Responders [1] (N = 11) Observed | Month 6 sUA Responders [1] (N = 11) Change from Baseline | Month 6 sUA Non-Responders [1] (N = 3) Baseline [2] | Month 6 sUA Non-Responders [1] (N = 3) Observed | Month 6 sUA Non-Responders [1] (N = 3) Change from Baseline |
|---|---|---|---|---|---|---|
| Week 36 - Post-Infusion | | | | | | |
| n | 6 | 6 | 6 | 0 | 0 | 0 |
| Mean (SD) | 9.68 (3.799) | 0.30 (0.000) | −9.38 (3.799) | | | |
| Median | 9.50 | 0.30 | −9.20 | | | |
| Min, Max | 4.7, 15.8 | 0.3, 0.3 | −15.5, −4.4 | | | |
| 95% CI [4] | (5.70, 13.67) | (0.30, 0.30) | (−13.37, −5.40) | | | |
| sUA < 6 mg/dL, n (%) | | 6 (100%) | | | 0 | |
| Week 38 - Pre-Infusion | | | | | | |
| n | 5 | 5 | 5 | 0 | 0 | 0 |
| Mean (SD) | 9.34 (4.142) | 0.93 (1.583) | −8.41 (5.229) | | | |
| Median | 8.90 | 0.30 | −8.60 | | | |
| Min, Max | 4.7, 15.8 | 0.0, 3.8 | −15.5, −0.9 | | | |
| 95% CI [4] | (4.20, 14.48) | (0.00, 2.90) | (−14.90, −1.92) | | | |
| sUA < 6 mg/dL, n (%) | | 5 (100%) | | | 0 | |
| Week 40 - Pre-Infusion | | | | | | |
| n | 3 | 3 | 3 | 0 | 0 | 0 |
| Mean (SD) | 11.60 (3.686) | 0.30 (0.000) | −11.30 (3.686) | | | |
| Median | 10.10 | 0.30 | −9.80 | | | |
| Min, Max | 8.9, 15.8 | 0.3, 0.3 | −15.5, −8.6 | | | |
| 95% CI [4] | (2.44, 20.76) | (0.30, 0.30) | (−20.46, −2.14) | | | |
| sUA < 6 mg/dL, n (%) | | 3 (100%) | | | 0 | |
| Week 42 - Pre-Infusion | | | | | | |
| n | 3 | 3 | 3 | 0 | 0 | 0 |
| Mean (SD) | 11.60 (3.686) | 0.30 (0.000) | −11.30 (3.686) | | | |
| Median | 10.10 | 0.30 | −9.80 | | | |
| Min, Max | 8.9, 15.8 | 0.3, 0.3 | −15.5, −8.6 | | | |
| 95% CI [4] | (2.44, 20.76) | (0.30, 0.30) | (−20.46, −2.14) | | | |
| sUA < 6 mg/dL, n (%) | | 3 (100%) | | | 0 | |
| Week 44 - Pre-Infusion | | | | | | |
| n | 3 | 3 | 3 | 0 | 0 | 0 |
| Mean (SD) | 11.60 (3.686) | 1.05 (1.305) | −10.55 (4.625) | | | |
| Median | 10.10 | 0.30 | −9.80 | | | |
| Min, Max | 8.9, 15.8 | 0.3, 2.6 | −15.5, −6.3 | | | |
| 95% CI [4] | (2.44, 20.76) | (0.00, 4.29) | (−22.04, 0.94) | | | |
| sUA < 6 mg/dL, n (%) | | 3 (100%) | | | 0 | |
| Week 46 - Pre-Infusion | | | | | | |
| n | 2 | 2 | 2 | 0 | 0 | 0 |
| Mean (SD) | 12.95 (4.031) | 0.30 (0.000) | −12.65 (4.031) | | | |
| Median | 12.95 | 0.30 | −12.65 | | | |
| Min, Max | 10.1, 15.8 | 0.3, 0.3 | −15.5, −9.8 | | | |
| 95% CI [4] | (0.00, 49.16) | (0.30, 0.30) | (−48.86, 23.56) | | | |
| sUA < 6 mg/dL, n (%) | | 2 (100%) | | | 0 | |
| Week 48 - Pre-Infusion | | | | | | |
| n | 2 | 2 | 2 | 0 | 0 | 0 |
| Mean (SD) | 12.95 (4.031) | 0.30 (0.000) | −12.65 (4.031) | | | |
| Median | 12.95 | 0.30 | −12.65 | | | |
| Min, Max | 10.1, 15.8 | 0.3, 0.3 | −15.5, −9.8 | | | |
| 95% CI [4] | (0.00, 49.16) | (0.30, 0.30) | (−48.86, 23.56) | | | |
| sUA < 6 mg/dL, n (%) | | 2 (100%) | | | 0 | |
| Week 48 - Post-Infusion | | | | | | |
| n | 3 | 3 | 3 | 0 | 0 | 0 |
| Mean (SD) | 11.93 (3.350) | 1.60 (2.252) | −10.33 (4.922) | | | |
| Median | 10.10 | 0.30 | −9.80 | | | |
| Min, Max | 9.9, 15.8 | 0.3, 4.2 | −15.5, −5.7 | | | |
| 95% CI [4] | (3.61, 20.26) | (0.00, 7.19) | (−22.56, 1.89) | | | |
| sUA < 6 mg/dL, n (%) | | 3 (100%) | | | 0 | |
| Week 50 - Pre-Infusion | | | | | | |
| n | 2 | 2 | 2 | 0 | 0 | 0 |
| Mean (SD) | 12.95 (4.031) | 0.30 (0.000) | −12.65 (4.031) | | | |
| Median | 12.95 | 0.30 | −12.65 | | | |
| Min, Max | 10.1, 15.8 | 0.3, 0.3 | −15.5, −9.8 | | | |
| 95% CI [4] | (0.00, 49.16) | (0.30, 0.30) | (−48.86, 23.56) | | | |
| sUA < 6 mg/dL, n (%) | | 2 (100%) | | | 0 | |

TABLE 7-continued

Serum Uric Acid (mg/dL): Observed Values and Change from Pegloticase Baseline Values by Month 6 sUA Responder Subgroup (mITT Population)

| Visit Statistics | Month 6 sUA Responders [1] (N = 11) Baseline [2] | Month 6 sUA Responders [1] (N = 11) Observed | Month 6 sUA Responders [1] (N = 11) Change from Baseline | Month 6 sUA Non-Responders [1] (N = 3) Baseline [2] | Month 6 sUA Non-Responders [1] (N = 3) Observed | Month 6 sUA Non-Responders [1] (N = 3) Change from Baseline |
|---|---|---|---|---|---|---|
| Week 50 - Post-Infusion | | | | | | |
| n | 3 | 3 | 3 | 0 | 0 | 0 |
| Mean (SD) | 11.93 (3.350) | 1.37 (1.848) | −10.57 (4.598) | | | |
| Median | 10.10 | 0.30 | −9.80 | | | |
| Min, Max | 9.9, 15.8 | 0.3, 3.5 | −15.5, −6.4 | | | |
| 95% CI [4] | (3.61, 20.26) | (0.00, 5.96) | (−21.99, 0.86) | | | |
| sUA < 6 mg/dL, n (%) | | 3 (100%) | | | 0 | |
| Week 52/ET | | | | | | |
| n | 2 | 2 | 2 | 0 | 0 | 0 |
| Mean (SD) | 12.95 (4.031) | 0.30 (0.000) | −12.65 (4.031) | | | |
| Median | 12.95 | 0.30 | −12.65 | | | |
| Min, Max | 10.1, 15.8 | 0.3, 0.3 | −15.5, −9.8 | | | |
| 95% CI [4] | (0.00, 49.16) | (0.30, 0.30) | (−48.86, 23.56) | | | |
| sUA < 6 mg/dL, n (%) | | 2 (100%) | | | 0 | |
| End of Pegloticase Infusions Visit | | | | | | |
| n | 2 | 2 | 2 | 0 | 0 | 0 |
| Mean (SD) | 8.80 (1.556) | 0.30 (0.000) | −8.50 (1.556) | | | |
| Median | 8.80 | 0.30 | −8.50 | | | |
| Min, Max | 7.7, 9.9 | 0.3, 0.3 | −9.6, −7.4 | | | |
| 95% CI [4] | (0.00, 22.78) | (0.30, 0.30) | (−22.48, 5.48) | | | |
| sUA < 6 mg/dL, n (%) | | 2 (100%) | | | 0 | |
| Early Termination Visit | | | | | | |
| n | 0 | 0 | 0 | 3 | 3 | 3 |
| Mean (SD) | | | | 8.73 (0.577) | 8.17 (0.058) | −0.57 (0.635) |
| Median | | | | 8.40 | 8.20 | −0.20 |
| Min, Max | | | | 8.4, 9.4 | 8.1, 8.2 | −1.3, −0.2 |
| 95% CI [4] | | | | (7.30, 10.17) | (8.02, 8.31) | (−2.14, 1.01) |
| sUA < 6 mg/dL, n (%) | | 0 | | | 0 | |

TABLE 8

Serum Uric Acid < 6 mg/dL Responders during Month 9 and Month 12 (ITT Population and mITT Population)

| Time Point | | ITT Population N = 15 | mITT Population N = 14 |
|---|---|---|---|
| Month 9 (Weeks 32, 34, 36) | Responder, n (%) [3] | 10 (71.4) | 10 (76.9) |
| | 95% Clopper-Pearson Confidence Interval [4] | 41.9, 91.6 | 46.2, 95.0 |
| | Non-Responder, n (%) | 4 (28.6) | 3 (23.1) |
| | Number of subjects eligible for analysis [1] | 14 | 13 |
| | Proportion of Time during Period that sUA < 6 mg/dL | | |
| | n | 10 | 10 |
| | Mean (SD) | 99.48 (1.656) | 99.48 (1.656) |
| | Median | 100.00 | 100.00 |
| | Min, Max | 94.8, 100.0 | 94.8, 100.0 |
| Month 9 (Weeks 32, 34, 36) | Discontinued treatment due to stopping rule prior to Week 36, n (%) [2] | 3 (21.4) | 3 (23.1) |
| | Subjects missing all data in analysis period, n (%) | 4 (28.6) | 3 (23.1) |
| | Subjects with only one measurement (above cutoff) in analysis period, n (%) | 0 | 0 |
| | Subjects with only one measurement (below cutoff) in analysis period, n (%) | 0 | 0 |
| Month 12 (Weeks 48, 50, 52) | Responder, n (%) [5] | 3 (21.4) | 3 (23.1) |
| | 95% Clopper-Pearson Confidence Interval [4] | 4.7, 50.8 | 5.0, 53.8 |
| | Non-Responder, n (%) | 11 (78.6) | 10 (76.9) |

TABLE 8-continued

Serum Uric Acid < 6 mg/dL Responders during Month 9 and Month 12 (ITT Population and mITT Population)

| Time Point | | ITT Population N = 15 | mITT Population N = 14 |
|---|---|---|---|
| Month 12 (Weeks 48, 50, 52) | Number of subjects eligible for analysis [1] | 14 | 13 |
| | Proportion of Time during Period that sUA < 6 mg/dL | | |
| | n | 3 | 3 |
| | Mean (SD) | 100.00 (0.000) | 100.00 (0.000) |
| | Median | 100.00 | 100.00 |
| | Min, Max | 100.0, 100.0 | 100.0, 100.0 |
| Month 12 (Weeks 48, 50, 52) | Discontinued treatment due to stopping rule prior to Week 52, n (%) [2] | 3 (21.4) | 3 (23.1) |
| | Subjects missing all data in analysis period, n (%) | 11 (78.6) | 10 (76.9) |
| | Subjects with only one measurement (above cutoff) in analysis period, n (%) | 0 | 0 |
| | Subjects with only one measurement (below cutoff) in analysis period, n (%) | 0 | 0 |

TABLE 9

Serum Uric Acid < 5 mg/dL Responders during Month 9 and Month 12 (ITT Population and mITT Population)

| Time Point | | ITT Population N = 15 | mITT Population N = 14 |
|---|---|---|---|
| Month 9 (Weeks 32, 34, 36) | Responder, n (%) [3] | 10 (71.4) | 10 (76.9) |
| | 95% Clopper-Pearson Confidence Interval [4] | 41.9, 91.6 | 46.2, 95.0 |
| | Non-Responder, n (%) | 4 (28.6) | 3 (23.1) |
| | Number of subjects eligible for analysis 111 | 14 | 13 |
| | Proportion of Time during Period that sUA < 5 mg/dL | | |
| | n | 10 | 10 |
| | Mean (SD) | 97.73 (5.805) | 97.73 (5.805) |
| | Median | 100.00 | 100.00 |
| | Min, Max | 81.7, 100.0 | 81.7, 100.0 |
| Month 9 (Weeks 32, 34, 36) | Discontinued treatment due to stopping rule prior to Week 36, n (%) [2] | 3 (21.4) | 3 (23.1) |
| | Subjects missing all data in analysis period, n (%) | 4 (28.6) | 3 (23.1) |
| | Subjects with only one measurement (above cutoff) in analysis period, n (%) | 0 | 0 |
| | Subjects with only one measurement (below cutoff) in analysis period, n (%) | 0 | 0 |
| Month 12 (Weeks 48, 50, 52) | Responder, n (%) [5] | 3 (21.4) | 3 (23.1) |
| | 95% Clopper-Pearson Confidence Interval [4] | 4.7, 50.8 | 5.0, 53.8 |
| | Non-Responder, n (%) | 11 (78.6) | 10 (76.9) |
| Month 12 (Weeks 48, 50, 52) | Number of subjects eligible for analysis [1] | 14 | 13 |
| | Proportion of Time during Period that sUA < 5 mg/dL | | |
| | n | 3 | 3 |
| | Mean (SD) | 100.00 (0.000) | 100.00 (0.000) |
| | Median | 100.00 | 100.00 |
| | Min, Max | 100.0, 100.0 | 100.0, 100.0 |
| Month 12 (Weeks 48, 50, 52) | Discontinued treatment due to stopping rule prior to Week 52, n (%) [2] | 3 (21.4) | 3 (23.1) |
| | Subjects missing all data in analysis period, n (%) | 11 (78.6) | 10 (76.9) |
| | Subjects with only one measurement (above cutoff) in analysis period, n (%) | 0 | 0 |
| | Subjects with only one measurement (below cutoff) in analysis period, n (%) | 0 | 0 |

TABLE 10

Time to First Pre-infusion Serum Uric Acid > 6 mg/dU and Time to 2 Consecutive Pre-infusion Serum Uric Acid > 6 mg/dU (mITT Population)

| | mITT Population N = 14 |
|---|---|
| Had pre-Infusion sUA > 6 mg/dL post-Day 1 Pegloticase Infusion, n (%) | |
| Yes | 4 (28.6) |
| No | 10 (71.4) |
| Time to pre-infusion sUA > 6 mg/dL post-Day 1 Pegloticase Infusion (days) [1] | |
| Mean (SD) | 218.3 (110.41) |
| Min, Max | 16, 353 |
| Kaplan-Meier Estimate | |
| Median | NE |
| 95% CI | 57.0, NE |
| Had 2 Consecutive Pre-Infusion sUA > 6 mg/dL post-Day 1 Pegloticase Infusion, n (%) | |
| Yes | 3 (21.4) |
| No | 11 (78.6) |
| Time to 2 Consecutive Pre-Infusion sUA > 6 mg/dL post-Day 1 Pegloticase Infusion (days) [2] | |
| Mean (SD) | 218.3 (110.41) |
| Min, Max | 16, 353 |
| Kaplan-Meier Estimate | |
| Median | NE |
| 95% CI | 57.0, NE |

TABLE 11

Assessment of Number of Joints Affected by Tophi (mITT Population)

| | | mITT Population (N = 14) | | |
|---|---|---|---|---|
| Visit | Statistics | Baseline [1] | Observed | Change from Baseline |
| Screening | n | 13 | | |
| | Mean (SD) | 6.9 (7.94) | | |
| | Median | 4.0 | | |
| | Min, Max | 1, 31 | | |
| Week 24 | n | 9 | 9 | 9 |
| | Mean (SD) | 8.7 (9.10) | 4.0 (3.64) | −4.7 (6.36) |
| | Median | 7.0 | 3.0 | −3.0 |
| | Min, Max | 1, 31 | 1, 12 | −19, 2 |
| Week 36 | n | 4 | 4 | 4 |
| | Mean (SD) | 14.8 (11.15) | 3.3 (3.86) | −11.5 (7.33) |
| | Median | 10.5 | 1.5 | −9.0 |
| | Min, Max | 7, 31 | 1, 9 | −22, −6 |
| Week 52/ET | n | 2 | 2 | 2 |
| | Mean (SD) | 22.0 (12.73) | 5.0 (2.83) | −17.0 (9.90) |
| | Median | 22.0 | 5.0 | −17.0 |
| | Min, Max | 13, 31 | 3, 7 | −24, −10 |

TABLE 12

Tender Joint Count and Swollen Joint Count: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| Tender Joint Count | Baseline [2] | | | |
| | n | | 14 | |
| | Mean (SD) | | 11.6 (15.06) | |
| | Median | | 7.5 | |
| | Min, Max | | 0, 51 | |
| | Day 1 | | | |
| | n | 14 | 14 | 14 |
| | Mean (SD) | 11.6 (15.06) | 9.6 (11.03) | −1.9 (9.75) |
| | Median | 7.5 | 7.0 | 0.0 |
| | Min, Max | 0, 51 | 0, 37 | −23, 11 |
| | 95% CI [3] | | | −7.6, 3.7 |
| | Week 14 | | | |
| | n | 14 | 14 | 14 |
| | Mean (SD) | 11.6 (15.06) | 4.6 (6.16) | −7.0 (14.20) |
| | Median | 7.5 | 2.0 | 0.0 |
| | Min, Max | 0, 51 | 0, 18 | −43, 5 |
| | 95% CI [3] | | | −15.2, 1.2 |
| Tender Joint Count | Week 24 | | | |
| | n | 11 | 11 | 11 |
| | Mean (SD) | 12.8 (16.68) | 2.6 (3.88) | −10.2 (14.27) |
| | Median | 7.0 | 0.0 | −4.0 |
| | Min, Max | 0, 51 | 0, 11 | −40, 0 |
| | 95% CI [3] | | | −19.8, −0.6 |
| | Week 36 | | | |
| | n | 9 | 9 | 9 |
| | Mean (SD) | 14.4 (18.12) | 2.1 (4.54) | −12.3 (14.56) |
| | Median | 7.0 | 0.0 | −7.0 |
| | Min, Max | 0, 51 | 0, 14 | −37, 0 |
| | 95% CI [3] | | | −23.5, −1.1 |
| | Week 52/ET | | | |
| | n | 3 | 3 | 3 |
| | Mean (SD) | 29.3 (18.93) | 5.3 (3.21) | −24.0 (21.38) |
| | Median | 21.0 | 4.0 | −17.0 |
| | Min, Max | 16, 51 | 3, 9 | −48, −7 |
| | 95% CI [3] | | | −77.1, 29.1 |
| Tender Joint Count | End of Pegloticase Infusions Visit | | | |
| | n | 2 | 2 | 2 |
| | Mean (SD) | 14.0 (9.90) | 2.0 (2.83) | −12.0 (7.07) |
| | Median | 14.0 | 2.0 | −12.0 |
| | Min, Max | 7, 21 | 0, 4 | −17, −7 |
| | 95% CI [3] | | | −75.5, 51.5 |
| | Early Termination Visit | | | |
| | n | 3 | 3 | 3 |
| | Mean (SD) | 7.0 (6.56) | 7.7 (8.96) | 0.7 (5.13) |
| | Median | 8.0 | 3.0 | 2.0 |
| | Min, Max | 0, 13 | 2, 18 | −5, 5 |
| | 95% CI [3] | | | −12.1, 13.4 |
| Swollen Joint Count | Baseline [2] | | | |
| | n | | 14 | |
| | Mean (SD) | | 6.0 (9.25) | |
| | Median | | 2.0 | |
| | Min, Max | | 0, 28 | |
| Swollen Joint Count | Day 1 | | | |
| | n | 14 | 14 | 14 |
| | Mean (SD) | 6.0 (9.25) | 5.3 (6.94) | −0.7 (5.21) |
| | Median | 2.0 | 3.5 | 0.5 |
| | Min, Max | 0, 28 | 0, 26 | −12, 6 |
| | 95% CI [3] | | | −3.7, 2.3 |
| | Week 14 | | | |
| | n | 14 | 14 | 14 |
| | Mean (SD) | 6.0 (9.25) | 1.7 (3.73) | −4.3 (7.38) |
| | Median | 2.0 | 0.0 | −2.0 |

TABLE 12-continued

Tender Joint Count and Swollen Joint Count: Observed Values and Change from Methotrexate Baseline Values (mITT Population)

| Parameter | Visit Statistics | mITT Population (N = 14) Baseline [1] | Observed | Change from Baseline |
|---|---|---|---|---|
| | Min, Max | 0, 28 | 0, 13 | −27, 0 |
| | 95% CI [3] | | | −8.5, 0.0 |
| | Week 24 | | | |
| | n | 11 | 11 | 11 |
| | Mean (SD) | 7.2 (10.16) | 0.5 (1.21) | −6.6 (9.03) |
| | Median | 3.0 | 0.0 | −3.0 |
| | Min, Max | 0, 28 | 0, 3 | −25, 0 |
| | 95% CI [3] | | | −12.7, −0.6 |
| Swollen Joint Count | Week 36 | | | |
| | n | 9 | 9 | 9 |
| | Mean (SD) | 7.9 (11.04) | 0.1 (0.33) | −7.8 (10.81) |
| | Median | 3.0 | 0.0 | −3.0 |
| | Min, Max | 0, 28 | 0, 1 | −27, 0 |
| | 95% CI [3] | | | −16.1, 0.5 |
| | Week 52/ET | | | |
| | n | 3 | 3 | 3 |
| | Mean (SD) | 21.0 (9.64) | 0.0 (0.00) | −21.0 (9.64) |
| | Median | 25.0 | 0.0 | −25.0 |
| | Min, Max | 10, 28 | 0, 0 | −28, −10 |
| | 95% CI [3] | | | −45.0, 3.0 |
| | End of Pegloticase Infusions Visit | | | |
| | n | 2 | 2 | 2 |
| | Mean (SD) | 7.0 (4.24) | 0.0 (0.00) | −7.0 (4.24) |
| | Median | 7.0 | 0.0 | −7.0 |
| | Min, Max | 4, 10 | 0, 0 | −10, −4 |
| | 95% CI [3] | | | −45.1, 31.1 |
| Swollen Joint Count | Early Termination Visit | | | |
| | n | 3 | 3 | 3 |
| | Mean (SD) | 1.7 (2.08) | 0.7 (0.58) | −1.0 (1.73) |
| | Median | 1.0 | 1.0 | 0.0 |
| | Min, Max | 0, 4 | 0, 1 | −3, 0 |
| | 95% CI [3] | | | −5.3, 3.3 |

TABLE 13

Tender Joint Count and Swollen Joint Count: Observed Values and Change from Pegloticase Baseline Values (mITT Population)

| Parameter | Visit Statistics | mITT Population (N = 14) Baseline [1] | Observed | Change from Baseline |
|---|---|---|---|---|
| Tender Joint Count | Baseline [2] | | | |
| | n | | 14 | |
| | Mean (SD) | | 9.6 (11.03) | |
| | Median | | 7.0 | |
| | Min, Max | | 0, 37 | |
| | Week 14 | | | |
| | n | 14 | 14 | 14 |
| | Mean (SD) | 9.6 (11.03) | 4.6 (6.16) | −5.1 (8.12) |
| | Median | 7.0 | 2.0 | −5.0 |
| | Min, Max | 0, 37 | 0, 18 | −29, 6 |
| | 95% CI [3] | | | −9.8, −0.4 |
| | Week 24 | | | |
| | n | 11 | 11 | 11 |
| | Mean (SD) | 9.5 (11.29) | 2.6 (3.88) | −6.8 (8.16) |
| | Median | 7.0 | 0.0 | −4.0 |

TABLE 13-continued

Tender Joint Count and Swollen Joint Count: Observed Values and Change from Pegloticase Baseline Values (mITT Population)

| Parameter | Visit Statistics | mITT Population (N = 14) Baseline [1] | Observed | Change from Baseline |
|---|---|---|---|---|
| | Min, Max | 0, 37 | 0, 11 | −26, 1 |
| | 95% CI [3] | | | −12.3, −1.3 |
| Tender Joint Count | Week 36 | | | |
| | n | 9 | 9 | 9 |
| | Mean (SD) | 9.9 (12.57) | 2.1 (4.54) | −7.8 (8.94) |
| | Median | 4.0 | 0.0 | −4.0 |
| | Min, Max | 0, 37 | 0, 14 | −23, 0 |
| | 95% CI [3] | | | −14.7, −0.9 |
| | Week 52/ET | | | |
| | n | 3 | 3 | 3 |
| | Mean (SD) | 21.3 (17.16) | 5.3 (3.21) | −16.0 (17.52) |
| | Median | 24.0 | 4.0 | −15.0 |
| | Min, Max | 3, 37 | 3, 9 | −34, 1 |
| | 95% CI [3] | | | −59.5, 27.5 |
| | End of Pegloticase Infusions Visit | | | |
| | n | 2 | 2 | 2 |
| | Mean (SD) | 5.0 (2.83) | 2.0 (2.83) | −3.0 (5.66) |
| | Median | 5.0 | 2.0 | −3.0 |
| | Min, Max | 3, 7 | 0, 4 | −7, 1 |
| | 95% CI [3] | | | −53.8, 47.8 |
| Tender Joint Count | Early Termination Visit | | | |
| | n | 3 | 3 | 3 |
| | Mean (SD) | 10.3 (12.34) | 7.7 (8.96) | −2.7 (4.16) |
| | Median | 7.0 | 3.0 | −4.0 |
| | Min, Max | 0, 24 | 2, 18 | −6, 2 |
| | 95% CI [3] | | | −13.0, 7.7 |
| Swollen Joint Count | Baseline [2] | | | |
| | n | | 14 | |
| | Mean (SD) | | 5.3 (6.94) | |
| | Median | | 3.5 | |
| | Min, Max | | 0, 26 | |
| | Week 14 | | | |
| | n | 14 | 14 | 14 |
| | Mean (SD) | 5.3 (6.94) | 1.7 (3.73) | −3.6 (7.04) |
| | Median | 3.5 | 0.0 | −2.5 |
| | Min, Max | 0, 26 | 0, 13 | −25, 7 |
| | 95% CI [3] | | | −7.6, 0.5 |
| Swollen Joint Count | Week 24 | | | |
| | n | 11 | 11 | 11 |
| | Mean (SD) | 5.6 (7.71) | 0.5 (1.21) | −5.1 (6.66) |
| | Median | 3.0 | 0.0 | −3.0 |
| | Min, Max | 0, 26 | 0, 3 | −23, 0 |
| | 95% CI [3] | | | −9.6, −0.6 |
| | Week 36 | | | |
| | n | 9 | 9 | 9 |
| | Mean (SD) | 6.3 (8.44) | 0.1 (0.33) | −6.2 (8.15) |
| | Median | 4.0 | 0.0 | −4.0 |
| | Min, Max | 0, 26 | 0, 1 | −25, 0 |
| | 95% CI [3] | | | −12.5, 0.0 |
| | Week 52/ET | | | |
| | n | 3 | 3 | 3 |
| | Mean (SD) | 13.0 (13.00) | 0.0 (0.00) | −13.0 (13.00) |
| | Median | 13.0 | 0.0 | −13.0 |
| | Min, Max | 0, 26 | 0, 0 | −26, 0 |
| | 95% CI [3] | | | −45.3, 19.3 |

TABLE 13-continued

Tender Joint Count and Swollen Joint Count: Observed Values and Change from Pegloticase Baseline Values (mITT Population)

| Parameter | Visit Statistics | mITT Population (N = 14) Baseline [1] | Observed | Change from Baseline |
|---|---|---|---|---|
| Swollen Joint Count | End of Pegloticase Infusions Visit | | | |
| | n | 2 | 2 | 2 |
| | Mean (SD) | 2.0 (2.83) | 0.0 (0.00) | −2.0 (2.83) |
| | Median | 2.0 | 0.0 | −2.0 |
| | Min, Max | 0, 4 | 0, 0 | −4, 0 |
| | 95% CI [3] | | | −27.4, 23.4 |
| | Early Termination Visit | | | |
| | n | 3 | 3 | 3 |
| | Mean (SD) | 4.0 (3.61) | 0.7 (0.58) | −3.3 (3.06) |
| | Median | 5.0 | 1.0 | −4.0 |
| | Min, Max | 0, 7 | 0, 1 | −6, 0 |
| | 95% CI [3] | | | −10.9, 4.3 |

TABLE 14

Health Assessment Questionnaire: Observed Values and Change from Methotrexate Baseline Values (mITT Population)

| Parameter | Visit Statistics | mITT Population (N = 14) Baseline [1] | Observed | Change from Baseline |
|---|---|---|---|---|
| HAQ-DI | Baseline [2] | | | |
| | n | | 14 | |
| | Mean (SD) | | 0.7 (0.71) | |
| | Median | | 0.6 | |
| | Min, Max | | 0, 2 | |
| | Day 1 | | | |
| | n | 13 | 13 | 13 |
| | Mean (SD) | 0.8 (0.71) | 0.8 (0.77) | 0.1 (0.27) |
| | Median | 0.6 | 0.5 | 0.0 |
| | Min, Max | 0, 2 | 0, 2 | −0, 1 |
| | 95% CI [3] | | | −0.1, 0.2 |
| | Week 14 | | | |
| | n | 14 | 14 | 14 |
| | Mean (SD) | 0.7 (0.71) | 0.5 (0.41) | −0.2 (0.77) |
| | Median | 0.6 | 0.5 | 0.0 |
| | Min, Max | 0, 2 | 0, 1 | −2, 1 |
| | 95% CI [3] | | | −0.7, 0.2 |
| HAQ-DI | Week 24 | | | |
| | n | 11 | 11 | 11 |
| | Mean (SD) | 0.8 (0.77) | 0.2 (0.33) | −0.5 (0.74) |
| | Median | 0.6 | 0.1 | −0.1 |
| | Min, Max | 0, 2 | 0, 1 | −2, 0 |
| | 95% CI [3] | | | −1.0, 0.0 |
| | Week 36 | | | |
| | n | 9 | 9 | 9 |
| | Mean (SD) | 0.8 (0.86) | 0.3 (0.49) | −0.5 (0.80) |
| | Median | 0.4 | 0.1 | 0.0 |
| | Min, Max | 0, 2 | 0, 1 | −2, 0 |
| | 95% CI [3] | | | −1.1, 0.1 |
| | Week 52/ET | | | |
| | n | 3 | 3 | 3 |
| | Mean (SD) | 1.0 (0.76) | 0.4 (0.29) | −0.6 (0.87) |
| | Median | 0.9 | 0.3 | −0.1 |
| | Min, Max | 0, 2 | 0, 1 | −2, −0 |
| | 95% CI [3] | | | −2.8, 1.5 |

TABLE 14-continued

Health Assessment Questionnaire: Observed Values and Change from Methotrexate Baseline Values (mITT Population)

| Parameter | Visit Statistics | mITT Population (N = 14) Baseline [1] | Observed | Change from Baseline |
|---|---|---|---|---|
| HAQ-DI | End of Pegloticase Infusions Visit | | | |
| | n | 2 | 2 | 2 |
| | Mean (SD) | 0.3 (0.18) | 0.1 (0.18) | −0.1 (0.35) |
| | Median | 0.3 | 0.1 | −0.1 |
| | Min, Max | 0, 0 | 0, 0 | −0, 0 |
| | 95% CI [3] | | | −3.3, 3.1 |
| | Early Termination Visit | | | |
| | n | 3 | 3 | 3 |
| | Mean (SD) | 0.5 (0.45) | 0.7 (0.51) | 0.2 (0.90) |
| | Median | 0.6 | 0.6 | −0.3 |
| | Min, Max | 0, 1 | 0, 1 | −0, 1 |
| | 95% CI [3] | | | −2.0, 2.5 |
| HAQ-Pain | Baseline [2] | | | |
| | n | | 14 | |
| | Mean (SD) | | 40.9 (23.30) | |
| | Median | | 47.5 | |
| | Min, Max | | 0, 75 | |
| HAQ-Pain | Day 1 | | | |
| | n | 13 | 13 | 13 |
| | Mean (SD) | 40.2 (24.10) | 42.5 (22.24) | 2.3 (19.93) |
| | Median | 45.0 | 40.0 | 0.0 |
| | Min, Max | 0, 75 | 3, 80 | −27, 47 |
| | 95% CI [3] | | | −9.7, 14.4 |
| | Week 14 | | | |
| | n | 14 | 14 | 14 |
| | Mean (SD) | 40.9 (23.30) | 27.1 (26.25) | −13.9 (30.48) |
| | Median | 47.5 | 15.0 | −12.5 |
| | Min, Max | 0, 75 | 0, 90 | −60, 60 |
| | 95% CI [3] | | | −31.5, 3.7 |
| | Week 24 | | | |
| | n | 11 | 11 | 11 |
| | Mean (SD) | 44.5 (22.96) | 25.4 (27.50) | −19.2 (35.13) |
| | Median | 50.0 | 20.0 | −10.0 |
| | Min, Max | 0, 75 | 0, 80 | −75, 55 |
| | 95% CI [3] | | | −42.8, 4.4 |
| HAQ-Pain | Week 36 | | | |
| | n | 9 | 9 | 9 |
| | Mean (SD) | 43.9 (23.02) | 21.0 (27.60) | −22.9 (28.41) |
| | Median | 50.0 | 10.0 | −20.0 |
| | Min, Max | 0, 75 | 0, 80 | −74, 30 |
| | 95% CI [3] | | | −44.7, −1.1 |
| | Week 52/ET | | | |
| | n | 3 | 3 | 3 |
| | Mean (SD) | 46.7 (22.55) | 4.0 (5.20) | −42.7 (18.04) |
| | Median | 45.0 | 1.0 | −44.0 |
| | Min, Max | 25, 70 | 1, 10 | −60, −24 |
| | 95% CI [3] | | | −87.5, 2.1 |
| | End of Pegloticase Infusions Visit | | | |
| | n | 2 | 2 | 2 |
| | Mean (SD) | 37.5 (17.68) | 40.0 (56.57) | 2.5 (74.25) |
| | Median | 37.5 | 40.0 | 2.5 |
| | Min, Max | 25, 50 | 0, 80 | −50, 55 |
| | 95% CI [3] | | | −664.6, 669.6 |

TABLE 14-continued

Health Assessment Questionnaire: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| HAQ-Pain | Early Termination Visit | | | |
| | n | 3 | 3 | 3 |
| | Mean (SD) | 27.7 (23.59) | 46.7 (40.41) | 19.0 (36.51) |
| | Median | 30.0 | 40.0 | 7.0 |
| | Min, Max | 3, 50 | 10, 90 | −10, 60 |
| | 95% CI [3] | | | −71.7, 109.7 |
| HAQ-Health | Baseline [2] | | | |
| | n | | 14 | |
| | Mean (SD) | | 49.1 (30.79) | |
| | Median | | 55.0 | |
| | Min, Max | | 0, 90 | |
| | Day 1 | | | |
| | n | 13 | 13 | 13 |
| | Mean (SD) | 46.7 (30.68) | 37.8 (27.06) | −8.8 (38.29) |
| | Median | 50.0 | 25.0 | 10.0 |
| | Min, Max | 0, 90 | 2, 75 | −70, 55 |
| | 95% CI [3] | | | −32.0, 14.3 |
| HAQ-Health | Week 14 | | | |
| | n | 14 | 14 | 14 |
| | Mean (SD) | 49.1 (30.79) | 36.6 (33.87) | −12.5 (36.79) |
| | Median | 55.0 | 16.5 | −5.0 |
| | Min, Max | 0, 90 | 0, 90 | −75, 60 |
| | 95% CI [3] | | | −33.7, 8.7 |
| | Week 24 | | | |
| | n | 11 | 11 | 11 |
| | Mean (SD) | 54.5 (29.02) | 21.4 (26.65) | −33.2 (36.01) |
| | Median | 60.0 | 10.0 | −40.0 |
| | Min, Max | 0, 90 | 0, 80 | −80, 20 |
| | 95% CI [3] | | | −57.4, −9.0 |
| | Week 36 | | | |
| | n | 9 | 9 | 9 |
| | Mean (SD) | 55.0 (30.41) | 27.3 (35.18) | −27.7 (42.59) |
| | Median | 60.0 | 10.0 | −10.0 |
| | Min, Max | 0, 90 | 0, 100 | −85, 20 |
| | 95% CI [3] | | | −60.4, 5.1 |
| HAQ-Health | Week 52/ET | | | |
| | n | 3 | 3 | 3 |
| | Mean (SD) | 76.7 (15.28) | 60.0 (48.22) | −16.7 (59.23) |
| | Median | 80.0 | 80.0 | 15.0 |
| | Min, Max | 60, 90 | 5, 95 | −85, 20 |
| | 95% CI [3] | | | −163.8, 130.5 |
| | End of Pegloticase Infusions Visit | | | |
| | n | 2 | 2 | 2 |
| | Mean (SD) | 80.0 (0.00) | 0.0 (0.00) | −80.0 (0.00) |
| | Median | 80.0 | 0.0 | −80.0 |
| | Min, Max | 80, 80 | 0, 0 | −80, −80 |
| | 95% CI [3] | | | −80.0, −80.0 |
| | Early Termination Visit | | | |
| | n | 3 | 3 | 3 |
| | Mean (SD) | 29.0 (34.39) | 28.3 (40.72) | −0.7 (16.77) |
| | Median | 20.0 | 10.0 | 8.0 |
| | Min, Max | 0, 67 | 0, 75 | −20, 10 |
| | 95% CI [3] | | | −42.3, 41.0 |

TABLE 15

Health Assessment Questionnaire: Observed Values and Change from Pegloticase Baseline Values (mITT Population)

| | | mITT Population (N = 14) | | |
|---|---|---|---|---|
| Parameter | Visit Statistics | Baseline [1] | Observed | Change from Baseline |
| HAQ-DI | Baseline [2] | | | |
| | n | | 14 | |
| | Mean (SD) | | 0.8 (0.76) | |
| | Median | | 0.5 | |
| | Min, Max | | 0, 2 | |
| | Week 14 | | | |
| | n | 14 | 14 | 14 |
| | Mean (SD) | 0.8 (0.76) | 0.5 (0.41) | −0.3 (0.80) |
| | Median | 0.5 | 0.5 | 0.0 |
| | Min, Max | 0, 2 | 0, 1 | −2, 1 |
| | 95% CI [3] | | | −0.7, 0.2 |
| | Week 24 | | | |
| | n | 11 | 11 | 11 |
| | Mean (SD) | 0.8 (0.86) | 0.2 (0.33) | −0.6 (0.85) |
| | Median | 0.4 | 0.1 | −0.1 |
| | Min, Max | 0, 2 | 0, 1 | −2, 0 |
| | 95% CI [3] | | | −1.2, 0.0 |
| HAQ-DI | Week 36 | | | |
| | n | 9 | 9 | 9 |
| | Mean (SD) | 0.9 (0.93) | 0.3 (0.49) | −0.5 (0.86) |
| | Median | 0.4 | 0.1 | −0.1 |
| | Min, Max | 0, 2 | 0, 1 | −2, 0 |
| | 95% CI [3] | | | −1.2, 0.1 |
| | Week 52/ET | | | |
| | n | 3 | 3 | 3 |
| | Mean (SD) | 1.2 (0.97) | 0.4 (0.29) | −0.8 (1.08) |
| | Median | 0.9 | 0.3 | −0.1 |
| | Min, Max | 0, 2 | 0, 1 | −2, −0 |
| | 95% CI [3] | | | −3.4, 1.9 |
| | End of Pegloticase Infusions Visit | | | |
| | n | 2 | 2 | 2 |
| | Mean (SD) | 0.3 (0.18) | 0.1 (0.18) | −0.1 (0.35) |
| | Median | 0.3 | 0.1 | −0.1 |
| | Min, Max | 0, 0 | 0, 0 | −0, 0 |
| | 95% CI [3] | | | −3.3, 3.1 |
| HAQ-DI | Early Termination Visit | | | |
| | n | 3 | 3 | 3 |
| | Mean (SD) | 0.5 (0.07) | 0.7 (0.51) | 0.2 (0.56) |
| | Median | 0.5 | 0.6 | 0.1 |
| | Min, Max | 1, 1 | 0, 1 | −0, 1 |
| | 95% CI [3] | | | −1.2, 1.6 |
| HAQ-Pain | Baseline [2] | | | |
| | n | | 14 | |
| | Mean (SD) | | 43.1 (21.46) | |
| | Median | | 45.0 | |
| | Min, Max | | 3, 80 | |
| | Week 14 | | | |
| | n | 14 | 14 | 14 |
| | Mean (SD) | 43.1 (21.46) | 27.1 (26.25) | −16.0 (30.65) |
| | Median | 45.0 | 15.0 | −12.5 |
| | Min, Max | 3, 80 | 0, 90 | −65, 50 |
| | 95% CI [3] | | | −33.7, 1.7 |
| HAQ-Pain | Week 24 | | | |
| | n | 11 | 11 | 11 |
| | Mean (SD) | 42.1 (24.23) | 25.4 (27.50) | −16.7 (38.53) |
| | Median | 30.0 | 20.0 | −10.0 |
| | Min, Max | 3, 80 | 0, 80 | −66, 55 |
| | 95% CI [3] | | | −42.6, 9.2 |

TABLE 15-continued

Health Assessment Questionnaire: Observed Values and Change from Pegloticase Baseline Values (mITT Population)

| Parameter | Visit Statistics | mITT Population (N = 14) Baseline [1] | Observed | Change from Baseline |
|---|---|---|---|---|
| | Week 36 | | | |
| | n | 9 | 9 | 9 |
| | Mean (SD) | 40.9 (25.46) | 21.0 (27.60) | −19.9 (20.25) |
| | Median | 30.0 | 10.0 | −20.0 |
| | Min, Max | 3, 80 | 0, 80 | −59, 10 |
| | 95% CI [3] | | | −35.5, −4.3 |
| | Week 52/ET | | | |
| | n | 3 | 3 | 3 |
| | Mean (SD) | 45.0 (30.41) | 4.0 (5.20) | −41.0 (25.24) |
| | Median | 30.0 | 1.0 | −29.0 |
| | Min, Max | 25, 80 | 1, 10 | −70, −24 |
| | 95% CI [3] | | | −103.7, 21.7 |
| HAQ-Pain | End of Pegloticase Infusions Visit | | | |
| | n | 2 | 2 | 2 |
| | Mean (SD) | 37.5 (17.68) | 40.0 (56.57) | 2.5 (74.25) |
| | Median | 37.5 | 40.0 | 2.5 |
| | Min, Max | 25, 50 | 0, 80 | −50, 55 |
| | 95% CI [3] | | | −664.6, 669.6 |
| | Early Termination Visit | | | |
| | n | 3 | 3 | 3 |
| | Mean (SD) | 46.7 (5.77) | 46.7 (40.41) | 0.0 (45.83) |
| | Median | 50.0 | 40.0 | −10.0 |
| | Min, Max | 40, 50 | 10, 90 | −40, 50 |
| | 95% CI [3] | | | −113.8, 113.8 |
| HAQ-Health | Baseline [2] | | | |
| | n | | 14 | |
| | Mean (SD) | | 40.9 (28.33) | |
| | Median | | 32.5 | |
| | Min, Max | | 2, 80 | |
| HAQ-Health | Week 14 | | | |
| | n | 14 | 14 | 14 |
| | Mean (SD) | 40.9 (28.33) | 36.6 (33.87) | −4.3 (43.82) |
| | Median | 32.5 | 16.5 | −1.0 |
| | Min, Max | 2, 80 | 0, 90 | −75, 75 |
| | 95% CI [3] | | | −29.6, 21.0 |
| | Week 24 | | | |
| | n | 11 | 11 | 11 |
| | Mean (SD) | 41.1 (29.29) | 21.4 (26.65) | −19.7 (43.38) |
| | Median | 40.0 | 10.0 | −10.0 |
| | Min, Max | 2, 80 | 0, 80 | −80, 55 |
| | 95% CI [3] | | | −48.9, 9.4 |
| | Week 36 | | | |
| | n | 9 | 9 | 9 |
| | Mean (SD) | 43.6 (31.78) | 27.3 (35.18) | −16.2 (50.72) |
| | Median | 50.0 | 10.0 | −10.0 |
| | Min, Max | 2, 80 | 0, 100 | −80, 90 |
| | 95% CI [3] | | | −55.2, 22.8 |
| HAQ-Health | Week 52/ET | | | |
| | n | 3 | 3 | 3 |
| | Mean (SD) | 36.7 (34.03) | 60.0 (48.22) | 23.3 (54.85) |
| | Median | 25.0 | 80.0 | 5.0 |
| | Min, Max | 10, 75 | 5, 95 | −20, 85 |
| | 95% CI [3] | | | −112.9, 159.6 |
| | End of Pegloticase Infusions Visit | | | |
| | n | 2 | 2 | 2 |
| | Mean (SD) | 45.0 (49.50) | 0.0 (0.00) | −45.0 (49.50) |
| | Median | 45.0 | 0.0 | −45.0 |

TABLE 15-continued

Health Assessment Questionnaire: Observed Values and Change from Pegloticase Baseline Values (mITT Population)

| Parameter | Visit Statistics | mITT Population (N = 14) Baseline [1] | Observed | Change from Baseline |
|---|---|---|---|---|
| | Min, Max | 10, 80 | 0, 0 | −80, −10 |
| | 95% CI [3] | | | −489.7, 399.7 |
| | Early Termination Visit | | | |
| | n | 3 | 3 | 3 |
| | Mean (SD) | 40.0 (30.41) | 28.3 (40.72) | −11.7 (62.52) |
| | Median | 25.0 | 10.0 | −10.0 |
| | Min, Max | 20, 75 | 0, 75 | −75, 50 |
| | 95% CI [3] | | | −167.0, 143.6 |

TABLE 16

Patient Global Assessment of Gout and Physician Global Assessment of Gout: Observed Values and Change from Methotrexate Baseline Values (mITT Population)

| Parameter | Visit Statistics | mITT Population (N = 14) Baseline [1] | Observed | Change from Baseline |
|---|---|---|---|---|
| Patient Global Assessment of Gout | Baseline [2] | | | |
| | n | | 14 | |
| | Mean (SD) | | 5.6 (2.21) | |
| | Median | | 6.0 | |
| | Min, Max | | 1, 10 | |
| | Day 1 | | | |
| | n | 14 | 14 | 14 |
| | Mean (SD) | 5.6 (2.21) | 5.8 (1.76) | 0.2 (1.85) |
| | Median | 6.0 | 6.0 | 0.0 |
| | Min, Max | 1, 10 | 3, 8 | −3, 4 |
| | 95% CI [3] | | | −0.9, 1.3 |
| | Week 14 | | | |
| | n | 14 | 14 | 14 |
| | Mean (SD) | 5.6 (2.21) | 3.1 (2.27) | −2.5 (2.77) |
| | Median | 6.0 | 3.0 | −2.5 |
| | Min, Max | 1, 10 | 0, 9 | −6, 4 |
| | 95% CI [3] | | | −4.1, −0.9 |
| Patient Global Assessment of Gout | Week 24 | | | |
| | n | 11 | 11 | 11 |
| | Mean (SD) | 5.7 (2.45) | 2.0 (1.79) | −3.7 (3.23) |
| | Median | 6.0 | 3.0 | −3.0 |
| | Min, Max | 1, 10 | 0, 4 | −10, 0 |
| | 95% CI [3] | | | −5.9, −1.6 |
| | Week 36 | | | |
| | n | 9 | 9 | 9 |
| | Mean (SD) | 5.6 (2.07) | 2.1 (2.80) | −3.4 (2.92) |
| | Median | 6.0 | 1.0 | −4.0 |
| | Min, Max | 1, 8 | 0, 8 | −8, 2 |
| | 95% CI [3] | | | −5.7, −1.2 |
| | Week 52/ET | | | |
| | n | 3 | 3 | 3 |
| | Mean (SD) | 5.3 (1.53) | 1.0 (1.00) | −4.3 (0.58) |
| | Median | 5.0 | 1.0 | −4.0 |
| | Min, Max | 4, 7 | 0, 2 | −5, −4 |
| | 95% CI [3] | | | −5.8, −2.9 |

TABLE 16-continued

Patient Global Assessment of Gout and Physician Global Assessment of Gout: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| Patient Global Assessment of Gout | End of Pegloticase Infusions Visit | | | |
| | n | 2 | 2 | 2 |
| | Mean (SD) | 6.0 (1.41) | 2.0 (2.83) | −4.0 (4.24) |
| | Median | 6.0 | 2.0 | −4.0 |
| | Min, Max | 5, 7 | 0, 4 | −7, −1 |
| | 95% CI [3] | | | −42.1, 34.1 |
| | Early Termination Visit | | | |
| | n | 3 | 3 | 3 |
| | Mean (SD) | 5.0 (1.00) | 5.7 (3.06) | 0.7 (2.89) |
| | Median | 5.0 | 5.0 | −1.0 |
| | Min, Max | 4, 6 | 3, 9 | −1, 4 |
| | 95% CI [3] | | | −6.5, 7.8 |
| Physician Global Assessment of Gout | Baseline [2] | | | |
| | n | | 14 | |
| | Mean (SD) | | 6.1 (2.25) | |
| | Median | | 7.0 | |
| | Min, Max | | 1, 9 | |
| Physician Global Assessment of Gout | Day 1 | | | |
| | n | 14 | 14 | 14 |
| | Mean (SD) | 6.1 (2.25) | 6.0 (2.45) | −0.1 (2.35) |
| | Median | 7.0 | 7.0 | 0.0 |
| | Min, Max | 1, 9 | 0, 9 | −6, 4 |
| | 95% CI [3] | | | −1.5, 1.2 |
| | Week 14 | | | |
| | n | 14 | 14 | 14 |
| | Mean (SD) | 6.1 (2.25) | 1.9 (1.64) | −4.2 (2.22) |
| | Median | 7.0 | 2.0 | −5.0 |
| | Min, Max | 1, 9 | 0, 6 | −8, −1 |
| | 95% CI [3] | | | −5.5, −2.9 |
| | Week 24 | | | |
| | n | 11 | 11 | 11 |
| | Mean (SD) | 6.1 (2.39) | 0.8 (0.87) | −5.3 (2.10) |
| | Median | 7.0 | 1.0 | −6.0 |
| | Min, Max | 1, 9 | 0, 3 | −8, −1 |
| | 95% CI [3] | | | −6.7, −3.9 |
| Physician Global Assessment of Gout | Week 36 | | | |
| | n | 9 | 9 | 9 |
| | Mean (SD) | 6.6 (2.40) | 0.7 (1.00) | −5.9 (2.03) |
| | Median | 7.0 | 0.0 | −6.0 |
| | Min, Max | 1, 9 | 0, 2 | −8, −1 |
| | 95% CI [3] | | | −7.4, −4.3 |
| | Week 52/ET | | | |
| | n | 3 | 3 | 3 |
| | Mean (SD) | 8.3 (0.58) | 1.0 (0.00) | −7.3 (0.58) |
| | Median | 8.0 | 1.0 | −7.0 |
| | Min, Max | 8, 9 | 1, 1 | −8, −7 |
| | 95% CI [3] | | | −8.8, −5.9 |
| | End of Pegloticase Infusions Visit | | | |
| | n | 2 | 2 | 2 |
| | Mean (SD) | 7.5 (0.71) | 0.5 (0.71) | −7.0 (0.00) |
| | Median | 7.5 | 0.5 | −7.0 |
| | Min, Max | 7, 8 | 0, 1 | −7, −7 |
| | 95% CI [3] | | | −7.0, −7.0 |

TABLE 16-continued

Patient Global Assessment of Gout and Physician Global Assessment of Gout: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| Physician Global Assessment of Gout | Early Termination Visit | | | |
| | n | 3 | 3 | 3 |
| | Mean (SD) | 6.3 (2.08) | 3.7 (2.08) | −2.7 (2.08) |
| | Median | 7.0 | 3.0 | −2.0 |
| | Min, Max | 4, 8 | 2, 6 | −5, −1 |
| | 95% CI [3] | | | −7.8, 2.5 |

TABLE 17

Patient Global Assessment of Gout and Physician Global Assessment of Gout: Observed Values and Change from Pegloticase Baseline Values (mITT Population)

| | | mITT Population (N = 14) | | |
|---|---|---|---|---|
| Parameter | Visit Statistics | Baseline [1] | Observed | Change from Baseline |
| Patient Global Assessment of Gout | Baseline [2] | | | |
| | n | | 14 | |
| | Mean (SD) | | 5.8 (1.76) | |
| | Median | | 6.0 | |
| | Min, Max | | 3, 8 | |
| | Week 14 | | | |
| | n | 14 | 14 | 14 |
| | Mean (SD) | 5.8 (1.76) | 3.1 (2.27) | −2.7 (2.43) |
| | Median | 6.0 | 3.0 | −3.0 |
| | Min, Max | 3, 8 | 0, 9 | −6, 4 |
| | 95% CI [3] | | | −4.1, −1.3 |
| | Week 24 | | | |
| | n | 11 | 11 | 11 |
| | Mean (SD) | 5.9 (1.97) | 2.0 (1.79) | −3.9 (2.51) |
| | Median | 7.0 | 3.0 | −4.0 |
| | Min, Max | 3, 8 | 0, 4 | −8, 0 |
| | 95% CI [3] | | | −5.6, −2.2 |
| Patient Global Assessment of Gout | Week 36 | | | |
| | n | 9 | 9 | 9 |
| | Mean (SD) | 5.6 (2.01) | 2.1 (2.80) | −3.4 (2.46) |
| | Median | 6.0 | 1.0 | −3.0 |
| | Min, Max | 3, 8 | 0, 8 | −7, 0 |
| | 95% CI [3] | | | −5.3, −1.6 |
| | Week 52/ET | | | |
| | n | 3 | 3 | 3 |
| | Mean (SD) | 5.3 (2.08) | 1.0 (1.00) | −4.3 (1.15) |
| | Median | 6.0 | 1.0 | −5.0 |
| | Min, Max | 3, 7 | 0, 2 | −5, −3 |
| | 95% CI [3] | | | −7.2, −1.5 |
| | End of Pegloticase Infusions Visit | | | |
| | n | 2 | 2 | 2 |
| | Mean (SD) | 6.5 (0.71) | 2.0 (2.83) | −4.5 (3.54) |
| | Median | 6.5 | 2.0 | −4.5 |
| | Min, Max | 6, 7 | 0, 4 | −7, −2 |
| | 95% CI [3] | | | −36.3, 27.3 |
| Patient Global Assessment of Gout | Early Termination Visit | | | |
| | n | 3 | 3 | 3 |
| | Mean (SD) | 5.3 (0.58) | 5.7 (3.06) | 0.3 (3.51) |
| | Median | 5.0 | 5.0 | 0.0 |
| | Min, Max | 5, 6 | 3, 9 | −3, 4 |
| | 95% CI [3] | | | −8.4, 9.1 |

TABLE 17-continued

Patient Global Assessment of Gout and Physician Global Assessment of Gout: Observed Values and Change from Pegloticase Baseline Values (mITT Population)

| | | mITT Population (N = 14) | | |
|---|---|---|---|---|
| Parameter | Visit Statistics | Baseline [1] | Observed | Change from Baseline |
| Physician Global Assessment of Gout | Baseline [2] | | | |
| | n | | 14 | |
| | Mean (SD) | | 6.0 (2.45) | |
| | Median | | 7.0 | |
| | Min, Max | | 0, 9 | |
| Physician Global Assessment of Gout | Week 14 | | | |
| | n | 14 | 14 | 14 |
| | Mean (SD) | 6.0 (2.45) | 1.9 (1.64) | −4.1 (2.40) |
| | Median | 7.0 | 2.0 | −4.5 |
| | Min, Max | 0, 9 | 0, 6 | −8, 0 |
| | 95% CI [3] | | | −5.5, −2.7 |
| | Week 24 | | | |
| | n | 11 | 11 | 11 |
| | Mean (SD) | 6.1 (2.70) | 0.8 (0.87) | −5.3 (2.41) |
| | Median | 7.0 | 1.0 | −6.0 |
| | Min, Max | 0, 9 | 0, 3 | −8, 0 |
| | 95% CI [3] | | | −6.9, −3.7 |
| | Week 36 | | | |
| | n | 9 | 9 | 9 |
| | Mean (SD) | 6.1 (2.98) | 0.7 (1.00) | −5.4 (2.46) |
| | Median | 7.0 | 0.0 | −7.0 |
| | Min, Max | 0, 9 | 0, 2 | −7, 0 |
| | 95% CI [3] | | | −7.3, −3.6 |
| | Week 52/ET | | | |
| | n | 3 | 3 | 3 |
| | Mean (SD) | 8.3 (1.15) | 1.0 (0.00) | −7.3 (1.15) |
| | Median | 9.0 | 1.0 | −8.0 |
| | Min, Max | 7, 9 | 1, 1 | −8, −6 |
| | 95% CI [3] | | | −10.2, −4.5 |
| Physician Global Assessment of Gout | End of Pegloticase Infusions Visit | | | |
| | n | 2 | 2 | 2 |
| | Mean (SD) | 7.0 (0.00) | 0.5 (0.71) | −6.5 (0.71) |
| | Median | 7.0 | 0.5 | −6.5 |
| | Min, Max | 7, 7 | 0, 1 | −7, −6 |
| | 95% CI [3] | | | −12.9, −0.1 |
| | Early Termination Visit | | | |
| | n | 3 | 3 | 3 |
| | Mean (SD) | 5.7 (1.53) | 3.7 (2.08) | −2.0 (1.00) |
| | Median | 6.0 | 3.0 | −2.0 |
| | Min, Max | 4, 7 | 2, 6 | −3, −1 |
| | 95% CI [3] | | | −4.5, 0.5 |

Joint Pain Assessment after Treatment with KXX and MTX

TABLE 18

Joint Pain Associated with Gout Assessment: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| Average Joint Pain | Baseline [2] | | | |
| | n | | 14 | |
| | Mean (SD) | | 4.9 (2.18) | |
| | Median | | 5.0 | |
| | Min, Max | | 0, 8 | |
| | Day 1 | | | |
| | n | 14 | 14 | 14 |
| | Mean (SD) | 4.9 (2.18) | 4.9 (1.94) | 0.1 (1.54) |

TABLE 18-continued

Joint Pain Associated with Gout Assessment: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| | Median | 5.0 | 5.5 | 0.0 |
| | Min, Max | 0, 8 | 2, 8 | −3, 3 |
| | 95% CI [3] | | | −0.8, 1.0 |
| | Week 14 | | | |
| | n | 14 | 14 | 14 |
| | Mean (SD) | 4.9 (2.18) | 3.2 (2.42) | −1.6 (3.00) |
| | Median | 5.0 | 2.5 | −1.5 |
| | Min, Max | 0, 8 | 0, 9 | −6, 6 |
| | 95% CI [3] | | | −3.4, 0.1 |
| Average Joint Pain | Week 24 | | | |
| | n | 11 | 11 | 11 |
| | Mean (SD) | 5.1 (2.39) | 2.3 (2.41) | −2.8 (3.28) |
| | Median | 6.0 | 2.0 | −3.0 |
| | Min, Max | 0, 8 | 0, 8 | −8, 3 |
| | 95% CI [3] | | | −5.0, −0.6 |
| | Week 36 | | | |
| | n | 9 | 9 | 9 |
| | Mean (SD) | 5.1 (2.62) | 2.1 (2.76) | −3.0 (2.78) |
| | Median | 6.0 | 1.0 | −2.0 |
| | Min, Max | 0, 8 | 0, 8 | −8, 1 |
| | 95% CI [3] | | | −5.1, −0.9 |
| | Week 52/ET | | | |
| | n | 3 | 3 | 3 |
| | Mean (SD) | 5.0 (2.00) | 2.0 (0.00) | −3.0 (2.00) |
| | Median | 5.0 | 2.0 | −3.0 |
| | Min, Max | 3, 7 | 2, 2 | −5, −1 |
| | 95% CI [3] | | | −8.0, 2.0 |
| Average Joint Pain | End of Pegloticase Infusions Visit | | | |
| | n | 2 | 2 | 2 |
| | Mean (SD) | 6.0 (1.41) | 4.0 (5.66) | −2.0 (7.07) |
| | Median | 6.0 | 4.0 | −2.0 |
| | Min, Max | 5, 7 | 0, 8 | −7, 3 |
| | 95% CI [3] | | | −65.5, 61.5 |
| | Early Termination Visit | | | |
| | n | 3 | 3 | 3 |
| | Mean (SD) | 4.0 (1.00) | 6.0 (3.00) | 2.0 (3.61) |
| | Median | 4.0 | 6.0 | 1.0 |
| | Min, Max | 3, 5 | 3, 9 | −1, 6 |
| | 95% CI [3] | | | −7.0, 11.0 |
| Least Joint Pain | Baseline [2] | | | |
| | n | | 14 | |
| | Mean (SD) | | 3.1 (2.03) | |
| | Median | | 3.5 | |
| | Min, Max | | 0, 6 | |
| Least Joint Pain | Day 1 | | | |
| | n | 14 | 14 | 14 |
| | Mean (SD) | 3.1 (2.03) | 3.4 (2.47) | 0.3 (1.73) |
| | Median | 3.5 | 3.0 | 0.5 |
| | Min, Max | 0, 6 | 0, 8 | −4, 3 |
| | 95% CI [3] | | | −0.7, 1.3 |
| | Week 14 | | | |
| | n | 14 | 14 | 14 |
| | Mean (SD) | 3.1 (2.03) | 1.7 (1.20) | −1.4 (2.14) |
| | Median | 3.5 | 2.0 | −1.5 |
| | Min, Max | 0, 6 | 0, 3 | −6, 3 |
| | 95% CI [3] | | | −2.7, −0.2 |
| | Week 24 | | | |
| | n | 11 | 11 | 11 |
| | Mean (SD) | 3.5 (2.02) | 1.1 (1.45) | −2.4 (1.86) |
| | Median | 4.0 | 0.0 | −2.0 |
| | Min, Max | 0, 6 | 0, 4 | −5, 0 |
| | 95% CI [3] | | | −3.6, −1.1 |

TABLE 18-continued

Joint Pain Associated with Gout Assessment: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| Least Joint Pain | Week 36 | | | |
| | n | 9 | 9 | 9 |
| | Mean (SD) | 3.2 (2.17) | 1.3 (2.69) | −1.9 (2.15) |
| | Median | 3.0 | 0.0 | −2.0 |
| | Min, Max | 0, 6 | 0, 8 | −5, 2 |
| | 95% CI [3] | | | −3.5, −0.2 |
| | Week 52/ET | | | |
| | n | 3 | 3 | 3 |
| | Mean (SD) | 3.7 (2.08) | 1.0 (1.00) | −2.7 (1.15) |
| | Median | 3.0 | 1.0 | −2.0 |
| | Min, Max | 2, 6 | 0, 2 | −4, −2 |
| | 95% CI [3] | | | −5.5, 0.2 |
| | End of Pegloticase Infusions Visit | | | |
| | n | 2 | 2 | 2 |
| | Mean (SD) | 4.0 (1.41) | 0.0 (0.00) | −4.0 (1.41) |
| | Median | 4.0 | 0.0 | −4.0 |
| | Min, Max | 3, 5 | 0, 0 | −5, −3 |
| | 95% CI [3] | | | −16.7, 8.7 |
| Least Joint Pain | Early Termination Visit | | | |
| | n | 3 | 3 | 3 |
| | Mean (SD) | 2.0 (2.00) | 3.0 (0.00) | 1.0 (2.00) |
| | Median | 2.0 | 3.0 | 1.0 |
| | Min, Max | 0, 4 | 3, 3 | −1, 3 |
| | 95% CI [3] | | | −4.0, 6.0 |
| Worst Joint Pain | Baseline [2] | | | |
| | n | | 14 | |
| | Mean (SD) | | 5.8 (2.49) | |
| | Median | | 6.0 | |
| | Min, Max | | 0, 9 | |
| | Day 1 | | | |
| | n | 14 | 14 | 14 |
| | Mean (SD) | 5.8 (2.49) | 6.3 (2.23) | 0.5 (2.28) |
| | Median | 6.0 | 7.0 | 0.5 |
| | Min, Max | 0, 9 | 2, 9 | −3, 4 |
| | 95% CI [3] | | | −0.8, 1.8 |

TABLE 18-continued

Joint Pain Associated with Gout Assessment: Observed Values and Change from Methotrexate Baseline Values (mITT Population)

| | | mITT Population (N = 14) | | |
|---|---|---|---|---|
| Parameter | Visit Statistics | Baseline [1] | Observed | Change from Baseline |
| Worst Joint Pain | Week 14 | | | |
| | n | 14 | 14 | 14 |
| | Mean (SD) | 5.8 (2.49) | 4.4 (2.76) | −1.4 (3.16) |
| | Median | 6.0 | 3.5 | −1.0 |
| | Min, Max | 0, 9 | 0, 9 | −6, 6 |
| | 95% CI [3] | | | −3.3, 0.4 |
| | Week 24 | | | |
| | n | 11 | 11 | 11 |
| | Mean (SD) | 5.9 (2.66) | 2.9 (2.66) | −3.0 (4.22) |
| | Median | 6.0 | 3.0 | −2.0 |
| | Min, Max | 0, 9 | 0, 8 | −9, 5 |
| | 95% CI [3] | | | −5.8, −0.2 |
| | Week 36 | | | |
| | n | 9 | 9 | 9 |
| | Mean (SD) | 5.7 (2.74) | 2.8 (3.15) | −2.9 (3.44) |
| | Median | 6.0 | 2.0 | −3.0 |
| | Min, Max | 0, 9 | 0, 8 | −9, 2 |
| | 95% CI [3] | | | −5.5, −0.2 |
| Worst Joint Pain | Week 52/ET | | | |
| | n | 3 | 3 | 3 |
| | Mean (SD) | 5.0 (2.00) | 2.0 (1.00) | −3.0 (1.73) |
| | Median | 5.0 | 2.0 | −2.0 |
| | Min, Max | 3, 7 | 1, 3 | −5, −2 |
| | 95% CI [3] | | | −7.3, 1.3 |
| | End of Pegloticase Infusions Visit | | | |
| | n | 2 | 2 | 2 |
| | Mean (SD) | 5.5 (3.54) | 4.0 (5.66) | −1.5 (9.19) |
| | Median | 5.5 | 4.0 | −1.5 |
| | Min, Max | 3, 8 | 0, 8 | −8, 5 |
| | 95% CI [3] | | | −84.1, 81.1 |
| | Early Termination Visit | | | |
| | n | 3 | 3 | 3 |
| | Mean (SD) | 5.3 (2.08) | 7.3 (1.53) | 2.0 (3.46) |
| | Median | 6.0 | 7.0 | 0.0 |
| | Min, Max | 3, 7 | 6, 9 | 0, 6 |
| | 95% CI [3] | | | −6.6, 10.6 |

Chronic Response to Treatment with KXX+MTX

TABLE 19

Gout Chronic Response - Relative to Methotrexate Baseline (mITT Population)

| Visit in Dual Therapy Period | Category | Parameter Statistics | mITT Population N = 14 |
|---|---|---|---|
| Day 1 | GCR20 | 20% Reduction in Tender Joint Count, n/m (%) | 6/13 (46.2) |
| | | 20% Reduction in Swollen Joint Count, n/m (%) | 4/13 (30.8) |
| | | 20% Reduction in HAQ-Health Score, n/m (%) | 5/12 (41.7) |
| | | 20% Reduction in HAQ-Pain, n/m (%) | 4/12 (33.3) |
| | | GCR20 Responders [1], n (%) | 2/13 (15.4) |
| | | 95% Confidence Interval [2] | 1.9, 45.4 |
| | GCR50 | 50% Reduction in Tender Joint Count, n/m (%) | 4/13 (30.8) |
| | | 50% Reduction in Swollen Joint Count, n/m (%) | 3/13 (23.1) |
| | | 50% Reduction in HAQ-Health Score, n/m (%) | 5/12 (41.7) |
| | | 50% Reduction in HAQ-Pain, n/m (%) | 1/12 (8.3) |
| | | GCR50 Responders [1], n (%) | 1/13 (7.7) |
| | | 95% Confidence Interval [2] | 0.2, 36.0 |
| | GCR70 | 70% Reduction in Tender Joint Count, n/m (%) | 3/13 (23.1) |
| | | 70% Reduction in Swollen Joint Count, n/m (%) | 3/13 (23.1) |
| | | 70% Reduction in HAQ-Health Score, n/m (%) | 4/12 (33.3) |
| | | 70% Reduction in HAQ-Pain, n/m (%) | 1/12 (8.3) |
| | | GCR70 Responders [1], n (%) | 1/13 (7.7) |
| | | 95% Confidence Interval [2] | 0.2, 36.0 |

TABLE 19-continued

| Gout Chronic Response - Relative to Methotrexate Baseline (mITT Population) | | | |
|---|---|---|---|
| Visit in Dual Therapy Period | Category | Parameter Statistics | mITT Population N = 14 |
| Week 14 | GCR20 | 20% Reduction in Tender Joint Count, n/m (%) | 9/13 (69.2) |
| | | 20% Reduction in Swollen Joint Count, n/m (%) | 12/13 (92.3) |
| | | 20% Reduction in HAQ-Health Score, n/m (%) | 7/13 (53.8) |
| | | 20% Reduction in HAQ-Pain, n/m (%) | 9/13 (69.2) |
| | | GCR20 Responders [1], n (%) | 8/13 (61.5) |
| | | 95% Confidence Interval [2] | 31.6, 86.1 |
| | GCR50 | 50% Reduction in Tender Joint Count, n/m (%) | 9/13 (69.2) |
| | | 50% Reduction in Swollen Joint Count, n/m (%) | 10/13 (76.9) |
| | | 50% Reduction in HAQ-Health Score, n/m (%) | 6/13 (46.2) |
| | | 50% Reduction in HAQ-Pain, n/m (%) | 7/13 (53.8) |
| | | GCR50 Responders [1], n (%) | 6/13 (46.2) |
| | | 95% Confidence Interval [2] | 19.2, 74.9 |
| | GCR70 | 70% Reduction in Tender Joint Count, n/m (%) | 7/13 (53.8) |
| | | 70% Reduction in Swollen Joint Count, n/m (%) | 10/13 (76.9) |
| | | 70% Reduction in HAQ-Health Score, n/m (%) | 5/13 (38.5) |
| | | 70% Reduction in HAQ-Pain, n/m (%) | 5/13 (38.5) |
| | | GCR70 Responders [1], n (%) | 5/13 (38.5) |
| | | 95% Confidence Interval [2] | 13.9, 68.4 |
| Week 24 | GCR20 | 20% Reduction in Tender Joint Count, n/m (%) | 10/10 (100) |
| | | 20% Reduction in Swollen Joint Count, n/m (%) | 10/10 (100) |
| | | 20% Reduction in HAQ-Health Score, n/m (%) | 7/10 (70.0) |
| | | 20% Reduction in HAQ-Pain, n/m (%) | 9/10 (90.0) |
| | | GCR20 Responders [1], n (%) | 10/10 (100) |
| | | 95% Confidence Interval [2] | 69.2, 100.0 |
| | GCR50 | 50% Reduction in Tender Joint Count, n/m (%) | 9/10 (90.0) |
| | | 50% Reduction in Swollen Joint Count, n/m (%) | 10/10 (100) |
| | | 50% Reduction in HAQ-Health Score, n/m (%) | 7/10 (70.0) |
| | | 50% Reduction in HAQ-Pain, n/m (%) | 5/10 (50.0) |
| | | GCR50 Responders [1], n (%) | 6/10 (60.0) |
| | | 95% Confidence Interval [2] | 26.2, 87.8 |
| | GCR70 | 70% Reduction in Tender Joint Count, n/m (%) | 8/10 (80.0) |
| | | 70% Reduction in Swollen Joint Count, n/m (%) | 10/10 (100) |
| | | 70% Reduction in HAQ-Health Score, n/m (%) | 6/10 (60.0) |
| | | 70% Reduction in HAQ-Pain, n/m (%) | 5/10 (50.0) |
| | | GCR70 Responders [1], n (%) | 6/10 (60.0) |
| | | 95% Confidence Interval [2] | 26.2, 87.8 |
| Week 36 | GCR20 | 20% Reduction in Tender Joint Count, n/m (%) | 9/9 (100) |
| | | 20% Reduction in Swollen Joint Count, n/m (%) | 9/9 (100) |
| | | 20% Reduction in HAQ-Health Score, n/m (%) | 6/9 (66.7) |
| | | 20% Reduction in HAQ-Pain, n/m (%) | 8/9 (88.9) |
| | | GCR20 Responders [1], n (%) | 8/9 (88.9) |
| | | 95% Confidence Interval [2] | 51.8, 99.7 |
| | GCR50 | 50% Reduction in Tender Joint Count, n/m (%) | 9/9 (100) |
| | | 50% Reduction in Swollen Joint Count, n/m (%) | 9/9 (100) |
| | | 50% Reduction in HAQ-Health Score, n/m (%) | 6/9 (66.7) |
| | | 50% Reduction in HAQ-Pain, n/m (%) | 6/9 (66.7) |
| | | GCR50 Responders [1], n (%) | 8/9 (88.9) |
| | | 95% Confidence Interval [2] | 51.8, 99.7 |
| | GCR70 | 70% Reduction in Tender Joint Count, n/m (%) | 9/9 (100) |
| | | 70% Reduction in Swollen Joint Count, n/m (%) | 9/9 (100) |
| | | 70% Reduction in HAQ-Health Score, n/m (%) | 4/9 (44.4) |
| | | 70% Reduction in HAQ-Pain, n/m (%) | 5/9 (55.6) |
| | | GCR70 Responders [1], n (%) | 6/9 (66.7) |
| | | 95% Confidence Interval [2] | 29.9, 92.5 |
| Week 52/ET | GCR20 | 20% Reduction in Tender Joint Count, n/m (%) | 3/3 (100) |
| | | 20% Reduction in Swollen Joint Count, n/m (%) | 3/3 (100) |
| | | 20% Reduction in HAQ-Health Score, n/m (%) | 1/3 (33.3) |
| | | 20% Reduction in HAQ-Pain, n/m (%) | 3/3 (100) |
| | | GCR20 Responders [1], n (%) | 3/3 (100) |
| | | 95% Confidence Interval [2] | 29.2, 100.0 |
| | GCR50 | 50% Reduction in Tender Joint Count, n/m (%) | 2/3 (66.7) |
| | | 50% Reduction in Swollen Joint Count, n/m (%) | 3/3 (100) |
| | | 50% Reduction in HAQ-Health Score, n/m (%) | 1/3 (33.3) |
| | | 50% Reduction in HAQ-Pain, n/m (%) | 3/3 (100) |
| | | GCR50 Responders [1], n (%) | 3/3 (100) |
| | | 95% Confidence Interval [2] | 29.2, 100.0 |
| | GCR70 | 70% Reduction in Tender Joint Count, n/m (%) | 2/3 (66.7) |
| | | 70% Reduction in Swollen Joint Count, n/m (%) | 3/3 (100) |
| | | 70% Reduction in HAQ-Health Score, n/m (%) | 1/3 (33.3) |
| | | 70% Reduction in HAQ-Pain, n/m (%) | 3/3 (100) |
| | | GCR70 Responders [1], n (%) | 3/3 (100) |
| | | 95% Confidence Interval [2] | 29.2, 100.0 |

TABLE 20

Gout Chronic Response - Relative to Pegloticase Baseline (mITT Population)

| Visit in Dual Therapy Period | Category | Parameter Statistics | mITT Population N = 14 |
|---|---|---|---|
| Week 14 | GCR20 | 20% Reduction in Tender Joint Count, n/m (%) | 11/13 (84.6) |
| | | 20% Reduction in Swollen Joint Count, n/m (%) | 11/13 (84.6) |
| | | 20% Reduction in HAQ-Health Score, n/m (%) | 6/13 (46.2) |
| | | 20% Reduction in HAQ-Pain, n/m (%) | 9/13 (69.2) |
| | | GCR20 Responders [1], n (%) | 8/13 (61.5) |
| | | 95% Confidence Interval [2] | 31.6, 86.1 |
| | GCR50 | 50% Reduction in Tender Joint Count, n/m (%) | 8/13 (61.5) |
| | | 50% Reduction in Swollen Joint Count, n/m (%) | 11/13 (84.6) |
| | | 50% Reduction in HAQ-Health Score, n/m (%) | 4/13 (30.8) |
| | | 50% Reduction in HAQ-Pain, n/m (%) | 7/13 (53.8) |
| | | GCR50 Responders [1], n (%) | 5/13 (38.5) |
| | | 95% Confidence Interval [2] | 13.9, 68.4 |
| | GCR70 | 70% Reduction in Tender Joint Count, n/m (%) | 7/13 (53.8) |
| | | 70% Reduction in Swollen Joint Count, n/m (%) | 11/13 (84.6) |
| | | 70% Reduction in HAQ-Health Score, n/m (%) | 3/13 (23.1) |
| | | 70% Reduction in HAQ-Pain, n/m (%) | 5/13 (38.5) |
| | | GCR70 Responders [1], n (%) | 4/13 (30.8) |
| | | 95% Confidence Interval [2] | 9.1, 61.4 |
| Week 24 | GCR20 | 20% Reduction in Tender Joint Count, n/m (%) | 9/10 (90.0) |
| | | 20% Reduction in Swollen Joint Count, n/m (%) | 10/10 (100) |
| | | 20% Reduction in HAQ-Health Score, n/m (%) | 6/10 (60.0) |
| | | 20% Reduction in HAQ-Pain, n/m (%) | 6/10 (60.0) |
| | | GCR20 Responders [1], n (%) | 6/10 (60.0) |
| | | 95% Confidence Interval [2] | 26.2, 87.8 |
| | GCR50 | 50% Reduction in Tender Joint Count, n/m (%) | 8/10 (80.0) |
| | | 50% Reduction in Swollen Joint Count, n/m (%) | 10/10 (100) |
| | | 50% Reduction in HAQ-Health Score, n/m (%) | 6/10 (60.0) |
| | | 50% Reduction in HAQ-Pain, n/m (%) | 5/10 (50.0) |
| | | GCR50 Responders [1], n (%) | 5/10 (50.0) |
| | | 95% Confidence Interval [2] | 18.7, 81.3 |
| | GCR70 | 70% Reduction in Tender Joint Count, n/m (%) | 7/10 (70.0) |
| | | 70% Reduction in Swollen Joint Count, n/m (%) | 10/10 (100) |
| | | 70% Reduction in HAQ-Health Score, n/m (%) | 6/10 (60.0) |
| | | 70% Reduction in HAQ-Pain, n/m (%) | 5/10 (50.0) |
| | | GCR70 Responders [1], n (%) | 5/10 (50.0) |
| | | 95% Confidence Interval [2] | 18.7, 81.3 |
| Week 36 | GCR20 | 20% Reduction in Tender Joint Count, n/m (%) | 9/9 (100) |
| | | 20% Reduction in Swollen Joint Count, n/m (%) | 9/9 (100) |
| | | 20% Reduction in HAQ-Health Score, n/m (%) | 5/9 (55.6) |
| | | 20% Reduction in HAQ-Pain, n/m (%) | 7/9 (77.8) |
| | | GCR20 Responders [1], n (%) | 7/9 (77.8) |
| | | 95% Confidence Interval [2] | 40.0, 97.2 |
| | GCR50 | 50% Reduction in Tender Joint Count, n/m (%) | 8/9 (88.9) |
| | | 50% Reduction in Swollen Joint Count, n/m (%) | 9/9 (100) |
| | | 50% Reduction in HAQ-Health Score, n/m (%) | 5/9 (55.6) |
| | | 50% Reduction in HAQ-Pain, n/m (%) | 5/9 (55.6) |
| | | GCR50 Responders [1], n (%) | 6/9 (66.7) |
| | | 95% Confidence Interval [2] | 29.9, 92.5 |
| | GCR70 | 70% Reduction in Tender Joint Count, n/m (%) | 7/9 (77.8) |
| | | 70% Reduction in Swollen Joint Count, n/m (%) | 9/9 (100) |
| | | 70% Reduction in HAQ-Health Score, n/m (%) | 5/9 (55.6) |
| | | 70% Reduction in HAQ-Pain, n/m (%) | 4/9 (44.4) |
| | | GCR70 Responders [1], n (%) | 4/9 (44.4) |
| | | 95% Confidence Interval [2] | 13.7, 78.8 |
| Week 52/ET | GCR20 | 20% Reduction in Tender Joint Count, n/m (%) | 2/3 (66.7) |
| | | 20% Reduction in Swollen Joint Count, n/m (%) | 3/3 (100) |
| | | 20% Reduction in HAQ-Health Score, n/m (%) | 1/3 (33.3) |
| | | 20% Reduction in HAQ-Pain, n/m (%) | 3/3 (100) |
| | | GCR20 Responders [1], n (%) | 2/3 (66.7) |
| | | 95% Confidence Interval [2] | 9.4, 99.2 |
| | GCR50 | 50% Reduction in Tender Joint Count, n/m (%) | 2/3 (66.7) |
| | | 50% Reduction in Swollen Joint Count, n/m (%) | 3/3 (100) |
| | | 50% Reduction in HAQ-Health Score, n/m (%) | 1/3 (33.3) |
| | | 50% Reduction in HAQ-Pain, n/m (%) | 3/3 (100) |
| | | GCR50 Responders [1], n (%) | 2/3 (66.7) |
| | | 95% Confidence Interval [2] | 9.4, 99.2 |
| | GCR70 | 70% Reduction in Tender Joint Count, n/m (%) | 1/3 (33.3) |
| | | 70% Reduction in Swollen Joint Count, n/m (%) | 3/3 (100) |
| | | 70% Reduction in HAQ-Health Score, n/m (%) | 1/3 (33.3) |
| | | 70% Reduction in HAQ-Pain, n/m (%) | 3/3 (100) |
| | | GCR70 Responders [1], n (%) | 2/3 (66.7) |
| | | 95% Confidence Interval [2] | 9.4, 99.2 |

Assessment of Safety of KXX+MTX Treatment (ADD 195-200 HERE (SAFETY))

TABLE 21

Treatment-Emergent Adverse Events by System Organ Class and Preferred Term during the Methotrexate Run-in Period (ITT Population and mITT Population)

| System Organ Class Preferred Term | ITT Population (N = 15)/ Total PY of MTX = 1.1 n (%) | Total Events/ Incidence Rate (Events/PY of MTX) | mITT Population (N = 14)/ Total PY of MTX = 1.0 n (%) | Total Events/ Incidence Rate (Events/PY of MTX) |
|---|---|---|---|---|
| Any TEAEs | 10 (66.7) | 20/18.2 | 10 (71.4) | 20/20.0 |
| Blood And Lymphatic System Disorders | 1 (6.7) | 2/1.8 | 1 (7.1) | 2/2.0 |
| Leukopenia | 1 (6.7) | 1/0.9 | 1 (7.1) | 1/1.0 |
| Neutropenia | 1 (6.7) | 1/0.9 | 1 (7.1) | 1/1.0 |
| Eye Disorders | 1 (6.7) | 1/0.9 | 1 (7.1) | 1/1.0 |
| Dry Eye | 1 (6.7) | 1/0.9 | 1 (7.1) | 1/1.0 |
| Gastrointestinal Disorders | 5 (33.3) | 6/5.5 | 5 (35.7) | 6/6.0 |
| Abdominal Discomfort | 2 (13.3) | 2/1.8 | 2 (14.3) | 2/2.0 |
| Dental Caries | 1 (6.7) | 1/0.9 | 1 (7.1) | 1/1.0 |
| Diarrhoea | 1 (6.7) | 1/0.9 | 1 (7.1) | 1/1.0 |
| Nausea | 2 (13.3) | 2/1.8 | 2 (14.3) | 2/2.0 |
| Infections And Infestations | 2 (13.3) | 2/1.8 | 2 (14.3) | 2/2.0 |
| Chronic Sinusitis | 1 (6.7) | 1/0.9 | 1 (7.1) | 1/1.0 |
| Nasopharyngitis | 1 (6.7) | 1/0.9 | 1 (7.1) | 1/1.0 |
| Metabolism And Nutrition Disorders | 5 (33.3) | 6/5.5 | 5 (35.7) | 6/6.0 |
| Gout | 5 (33.3) | 6/5.5 | 5 (35.7) | 6/6.0 |
| Nervous System Disorders | 1 (6.7) | 1/0.9 | 1 (7.1) | 1/1.0 |
| Headache | 1 (6.7) | 1/0.9 | 1 (7.1) | 1/1.0 |
| Respiratory, Thoracic And Mediastinal Disorders | 1 (6.7) | 1/0.9 | 1 (7.1) | 1/1.0 |
| Cough | 1 (6.7) | 1/0.9 | 1 (7.1) | 1/1.0 |
| Skin And Subcutaneous Tissue Disorders | 1 (6.7) | 1/0.9 | 1 (7.1) | 1/1.0 |
| Pruritus | 1 (6.7) | 1/0.9 | 1 (7.1) | 1/1.0 |

TABLE 22

Treatment-Emergent Adverse Events by System Organ Class and Preferred Term during the Pegloticase + Immunomodulator Period Through Week 24 (mITT Population)

| System Organ Class Preferred Term | mITT Population (N = 14)/ Total PY of MTX = 5.2/ Total PY of Pegloticase = 5.4 n (%) | Total Events/ Incidence Rate (Events/PY of MTX) | Total Events/ Incidence Rate (Events/PY of Pegloticase) |
|---|---|---|---|
| Any TEAEs | 14 (100) | 110/21.2 | 110/20.4 |
| Eye Disorders | 1 (7.1) | 1/0.2 | 1/0.2 |
| Eye Irritation | 1 (7.1) | 1/0.2 | 1/0.2 |
| Gastrointestinal Disorders | 4 (28.6) | 7/1.3 | 7/1.3 |
| Abdominal Pain | 1 (7.1) | 1/0.2 | 1/0.2 |
| Constipation | 1 (7.1) | 1/0.2 | 1/0.2 |
| Diarrhoea | 3 (21.4) | 3/0.6 | 3/0.6 |
| Gastrooesophageal Reflux Disease | 1 (7.1) | 1/0.2 | 1/0.2 |
| Tooth Impacted | 1 (7.1) | 1/0.2 | 1/0.2 |
| General Disorders And Administration Site Conditions | 1 (7.1) | 1/0.2 | 1/0.2 |
| Non-Cardiac Chest Pain | 1 (7.1) | 1/0.2 | 1/0.2 |
| Hepatobiliary Disorders | 1 (7.1) | 1/0.2 | 1/0.2 |
| Cholecystitis Acute | 1 (7.1) | 1/0.2 | 1/0.2 |
| Infections And Infestations | 7 (50.0) | 10/1.9 | 10/1.9 |

TABLE 22-continued

Treatment-Emergent Adverse Events by System Organ Class and Preferred Term during the Pegloticase + Immunomodulator Period Through Week 24 (mITT Population)

| System Organ Class Preferred Term | mITT Population (N = 14)/ Total PY of MTX = 5.2/ Total PY of Pegloticase = 5.4 n (%) | Total Events/ Incidence Rate (Events/PY of MTX) | Total Events/ Incidence Rate (Events/PY of Pegloticase) |
|---|---|---|---|
| Bacterial Sepsis | 1 (7.1) | 1/0.2 | 1/0.2 |
| Chronic Sinusitis | 1 (7.1) | 1/0.2 | 1/0.2 |
| Gastroenteritis Viral | 1 (7.1) | 1/0.2 | 1/0.2 |
| Influenza | 1 (7.1) | 1/0.2 | 1/0.2 |
| Nasopharyngitis | 1 (7.1) | 1/0.2 | 1/0.2 |
| Sinusitis | 2 (14.3) | 2/0.4 | 2/0.4 |
| Upper Respiratory Tract Infection | 3 (21.4) | 3/0.6 | 3/0.6 |
| Injury, Poisoning And Procedural Complications | 3 (21.4) | 4/0.8 | 4/0.7 |
| Infusion Related Reaction | 1 (7.1) | 1/0.2 | 1/0.2 |
| Limb Injury | 1 (7.1) | 1/0.2 | 1/0.2 |
| Muscle Strain | 2 (14.3) | 2/0.4 | 2/0.4 |
| Investigations | 2 (14.3) | 2/0.4 | 2/0.4 |
| Alanine Aminotransferase Increased | 1 (7.1) | 1/0.2 | 1/0.2 |
| Liver Function Test Increased | 1 (7.1) | 1/0.2 | 1/0.2 |

TABLE 22-continued

Treatment-Emergent Adverse Events by System Organ Class and Preferred Term during the Pegloticase + Immunomodulator Period Through Week 24 (mITT Population)

| System Organ Class Preferred Term | mITT Population (N = 14)/ Total PY of MTX = 5.2/ Total PY of Pegloticase = 5.4 n (%) | Total Events/ Incidence Rate (Events/PY of MTX) | Total Events/ Incidence Rate (Events/PY of Pegloticase) |
|---|---|---|---|
| Metabolism And Nutrition Disorders | 12 (85.7) | 68/13.1 | 68/12.6 |
| Gout | 12 (85.7) | 67/12.9 | 67/12.4 |
| Hypercholesterolaemia | 1 (7.1) | 1/0.2 | 1/0.2 |
| Musculoskeletal And Connective Tissue Disorders | 3 (21.4) | 3/0.6 | 3/0.6 |
| Arthralgia | 1 (7.1) | 1/0.2 | 1/0.2 |
| Plantar Fasciitis | 1 (7.1) | 1/0.2 | 1/0.2 |
| Tendonitis | 1 (7.1) | 1/0.2 | 1/0.2 |
| Nervous System Disorders | 3 (21.4) | 4/0.8 | 4/0.7 |
| Carpal Tunnel Syndrome | 1 (7.1) | 1/0.2 | 1/0.2 |
| Dysgeusia | 1 (7.1) | 1/0.2 | 1/0.2 |
| Headache | 1 (7.1) | 1/0.2 | 1/0.2 |
| Parosmia | 1 (7.1) | 1/0.2 | 1/0.2 |
| Renal And Urinary Disorders | 1 (7.1) | 1/0.2 | 1/0.2 |
| Dysuria | 1 (7.1) | 1/0.2 | 1/0.2 |
| Respiratory, Thoracic And Mediastinal Disorders | 1 (7.1) | 1/0.2 | 1/0.2 |
| Cough | 1 (7.1) | 1/0.2 | 1/0.2 |
| Skin And Subcutaneous Tissue Disorders | 3 (21.4) | 4/0.8 | 4/0.7 |
| Pruritus | 1 (7.1) | 2/0.4 | 2/0.4 |
| Rash Papular | 1 (7.1) | 1/0.2 | 1/0.2 |
| Skin Lesion | 1 (7.1) | 1/0.2 | 1/0.2 |
| Vascular Disorders | 2 (14.3) | 2/0.4 | 2/0.4 |
| Hypertension | 2 (14.3) | 2/0.4 | 2/0.4 |
| Uncoded | 1 (7.1) | 1/0.2 | 1/0.2 |
| Uncoded | 1 (7.1) | 1/0.2 | 1/0.2 |

Assessment of Adverse Events for Treatment with KXX+ MTX (ADD 230-248 HERE (GOUT FLARE))

TABLE 23

Treatment-Emergent Adverse Events of Special Interest during the Methotrexate Run-in Period: Gout Flares (ITT Population and mITT Population)

| Preferred Term | ITT Population N = 15 | mITT Population N = 14 |
|---|---|---|
| Gout Flares, n (%) | 5 (33.3) | 5 (35.7) |
| Number of Gout Flares per Subject, n (%) | | |
| 1 | 4 (26.7) | 4 (28.6) |
| 2 | 1 (6.7) | 1 (7.1) |

TABLE 23-continued

Treatment-Emergent Adverse Events of Special Interest during the Methotrexate Run-in Period: Gout Flares (ITT Population and mITT Population)

| Preferred Term | ITT Population N = 15 | mITT Population N = 14 |
|---|---|---|
| Among subjects with at least one gout flare | | |
| Mean (SD) | 1.2 (0.45) | 1.2 (0.45) |
| Median | 1.0 | 1.0 |
| Min, Max | 1, 2 | 1, 2 |

TABLE 24

Treatment-Emergent Adverse Events of Special Interest during the Pegloticase + Immunomodulator Period Through Week 24: Gout Flares (mITT Population)

| Preferred Term Time Period | mITT Population N = 14 n/m (%) |
|---|---|
| Gout Flares | |
| Full Pegloticase + Immunomodulator Period | 12/14 (85.7) |
| Number of Gout Flares per Subject | |
| 1 | 1/14 (7.1) |
| 2 | 2/14 (14.3) |
| 3 | 1/14 (7.1) |
| 4 | 1/14 (7.1) |
| 5 | 3/14 (21.4) |
| 6 | 1/14 (7.1) |
| 9 | 1/14 (7.1) |
| 10 | 1/14 (7.1) |
| 15 | 1/14 (7.1) |
| Among subjects with at least one gout flare | |
| Mean (SD) | 5.6 (4.01) |
| Median | 5.0 |
| Min, Max | 1, 15 |
| Day 1-Week 12 of the Pegloticase + Immunomodulator Period | 12/14 (85.7) |
| Number of Gout Flares per Subject | |
| 1 | 1/14 (7.1) |
| 2 | 2/14 (14.3) |
| 3 | 1/14 (7.1) |
| 4 | 3/14 (21.4) |
| 5 | 1/14 (7.1) |
| 6 | 2/14 (14.3) |
| 7 | 1/14 (7.1) |
| 8 | 1/14 (7.1) |
| Among subjects with at least one gout flare | |
| Mean (SD) | 4.3 (2.15) |
| Median | 4.0 |
| Min, Max | 1, 8 |
| >Week 12-Week 24 of the Pegloticase + Immunomodulator Period | 5/11 (45.5) |
| Number of Gout Flares per Subject | |
| 1 | 2/11 (18.2) |
| 2 | 1/11 (9.1) |
| 4 | 1/11 (9.1) |
| 7 | 1/11 (9.1) |
| Among subjects with at least one gout flare | |
| Mean (SD) | 3.0 (2.55) |
| Median | 2.0 |
| Min, Max | 1, 7 |

TABLE 25

Assessment of Gout Flares during the Methotrexate Run-in Period and Pegloticase + Immunomodulator Period (ITT Population and mITT Population)

| Time Point | | ITT Population N = 15 | mITT Population N = 14 |
|---|---|---|---|
| Week −4 | Number Assessed | 14 | 13 |
| | Any Gout Flares Since the Last Visit, n (%) | 8 (57.1) | 7 (53.8) |
| | If Yes, the following are assessed | | |
| | Pain different than normal, n (%) | 6 (42.9) | 5 (38.5) |
| | Pain at rest >3 out of 10, n (%) | 7 (50.0) | 6 (46.2) |
| | Swelling in Joints, n (%) | 7 (50.0) | 6 (46.2) |
| | Maximum Reported Intensity of Flare (0-10 scale) [1] | | |
| | n | 6 | 5 |
| | Mean (SD) | 8.5 (1.22) | 8.2 (1.10) |
| | Median | 8.0 | 8.0 |
| | Min, Max | 7, 10 | 7, 10 |
| Day 1 | Number Assessed | 14 | 14 |
| | Any Gout Flares Since the Last Visit, n (%) | 8 (57.1) | 8 (57.1) |
| | If Yes, the following are assessed | | |
| | Pain different than normal, n (%) | 7 (50.0) | 7 (50.0) |
| | Pain at rest >3 out of 10, n (%) | 8 (57.1) | 8 (57.1) |
| | Swelling in Joints, n (%) | 6 (42.9) | 6 (42.9) |
| | Maximum Reported Intensity of Flare (0-10 scale) [1] | | |
| | n | 8 | 8 |
| | Mean (SD) | 5.8 (1.28) | 5.8 (1.28) |
| | Median | 5.5 | 5.5 |
| | Min, Max | 4, 8 | 4, 8 |
| Week 2 | Number Assessed | NA | 14 |
| | Any Gout Flares Since the Last Visit, n (%) | | 12 (85.7) |
| | If Yes, the following are assessed | | |
| | Pain different than normal, n (%) | | 11 (78.6) |
| | Pain at rest >3 out of 10, n (%) | | 12 (85.7) |
| | Swelling in Joints, n (%) | | 10 (71.4) |
| | Maximum Reported Intensity of Flare (0-10 scale) [1] | | |
| | n | | 12 |
| | Mean (SD) | | 6.5 (1.17) |
| | Median | | 7.0 |
| | Min, Max | | 4, 8 |
| Week 4 | Number Assessed | NA | 14 |
| | Any Gout Flares Since the Last Visit, n (%) | | 11 (78.6) |
| | If Yes, the following are assessed | | |
| | Pain different than normal, n (%) | | 9 (64.3) |
| | Pain at rest >3 out of 10, n (%) | | 9 (64.3) |
| | Swelling in Joints, n (%) | | 9 (64.3) |
| | Maximum Reported Intensity of Flare (0-10 scale) [1] | | |
| | n | | 11 |
| | Mean (SD) | | 6.5 (2.62) |
| | Median | | 7.0 |
| | Min, Max | | 2, 10 |
| Week 6 | Number Assessed | NA | 13 |
| | Any Gout Flares Since the Last Visit, n (%) | | 9 (69.2) |
| | If Yes, the following are assessed | | |
| | Pain different than normal, n (%) | | 8 (61.5) |
| | Pain at rest >3 out of 10, n (%) | | 7 (53.8) |
| | Swelling in Joints, n (%) | | 8 (61.5) |
| | Maximum Reported Intensity of Flare (0-10 scale) [1] | | |
| | n | | 9 |
| | Mean (SD) | | 6.0 (2.18) |
| | Median | | 6.0 |
| | Min, Max | | 3, 9 |

TABLE 25-continued

Assessment of Gout Flares during the Methotrexate Run-in Period and Pegloticase + Immunomodulator Period (ITT Population and mITT Population)

| Time Point | | ITT Population N = 15 | mITT Population N = 14 |
|---|---|---|---|
| Week 8 | Number Assessed | NA | 12 |
| | Any Gout Flares Since the Last Visit, n (%) | | 7 (58.3) |
| | If Yes, the following are assessed | | |
| | Pain different than normal, n (%) | | 5 (41.7) |
| | Pain at rest >3 out of 10, n (%) | | 6 (50.0) |
| | Swelling in Joints, n (%) | | 5 (41.7) |
| | Maximum Reported Intensity of Flare (0-10 scale) [1] | | |
| | n | | 6 |
| | Mean (SD) | | 5.8 (2.23) |
| | Median | | 6.0 |
| | Min, Max | | 2, 8 |
| Week 10 | Number Assessed | NA | 12 |
| | Any Gout Flares Since the Last Visit, n (%) | | 6 (50.0) |
| | If Yes, the following are assessed | | |
| | Pain different than normal, n (%) | | 4 (33.3) |
| | Pain at rest >3 out of 10, n (%) | | 4 (33.3) |
| | Swelling in Joints, n (%) | | 4 (33.3) |
| | Maximum Reported Intensity of Flare (0-10 scale) [1] | | |
| | n | | 5 |
| | Mean (SD) | | 6.2 (2.86) |
| | Median | | 6.0 |
| | Min, Max | | 3, 10 |
| Week 12 | Number Assessed | NA | 11 |
| | Any Gout Flares Since the Last Visit, n (%) | | 7 (63.6) |
| | If Yes, the following are assessed | | |
| | Pain different than normal, n (%) | | 5 (45.5) |
| | Pain at rest >3 out of 10, n (%) | | 5 (45.5) |
| | Swelling in Joints, n (%) | | 4 (36.4) |
| | Maximum Reported Intensity of Flare (0-10 scale) [1] | | |
| | n | | 6 |
| | Mean (SD) | | 4.3 (0.82) |
| | Median | | 4.5 |
| | Min, Max | | 3, 5 |
| Week 14 | Number Assessed | NA | 11 |
| | Any Gout Flares Since the Last Visit, n (%) | | 5 (45.5) |
| | If Yes, the following are assessed | | |
| | Pain different than normal, n (%) | | 4 (36.4) |
| | Pain at rest >3 out of 10, n (%) | | 3 (27.3) |
| | Swelling in Joints, n (%) | | 3 (27.3) |
| | Maximum Reported Intensity of Flare (0-10 scale) [1] | | |
| | n | | 4 |
| | Mean (SD) | | 5.0 (2.45) |
| | Median | | 4.5 |
| | Min, Max | | 3, 8 |
| Week 16 | Number Assessed | NA | 11 |
| | Any Gout Flares Since the Last Visit, n (%) | | 4 (36.4) |
| | If Yes, the following are assessed | | |
| | Pain different than normal, n (%) | | 3 (27.3) |
| | Pain at rest >3 out of 10, n (%) | | 3 (27.3) |
| | Swelling in Joints, n (%) | | 2 (18.2) |
| | Maximum Reported Intensity of Flare (0-10 scale) [1] | | |
| | n | | 3 |
| | Mean (SD) | | 5.0 (1.73) |
| | Median | | 6.0 |
| | Min, Max | | 3, 6 |

TABLE 25-continued

Assessment of Gout Flares during the Methotrexate Run-in Period and Pegloticase + Immunomodulator Period (ITT Population and mITT Population)

| Time Point | | ITT Population N = 15 | mITT Population N = 14 |
|---|---|---|---|
| Week 18 | Number Assessed | NA | 11 |
| | Any Gout Flares Since the Last Visit, n (%) | | 5 (45.5) |
| | If Yes, the following are assessed | | |
| | Pain different than normal, n (%) | | 3 (27.3) |
| | Pain at rest >3 out of 10, n (%) | | 3 (27.3) |
| | Swelling in Joints, n (%) | | 3 (27.3) |
| | Maximum Reported Intensity of Flare (0-10 scale) [1] | | |
| | n | | 3 |
| | Mean (SD) | | 6.3 (1.53) |
| | Median | | 6.0 |
| | Min, Max | | 5, 8 |
| Week 20 | Number Assessed | NA | 11 |
| | Any Gout Flares Since the Last Visit, n (%) | | 4 (36.4) |
| | If Yes, the following are assessed | | |
| | Pain different than normal, n (%) | | 2 (18.2) |
| | Pain at rest >3 out of 10, n (%) | | 3 (27.3) |
| | Swelling in Joints, n (%) | | 3 (27.3) |
| | Maximum Reported Intensity of Flare (0-10 scale) [1] | | |
| | n | | 3 |
| | Mean (SD) | | 6.7 (0.58) |
| | Median | | 7.0 |
| | Min, Max | | 6, 7 |
| Week 22 | Number Assessed | NA | 11 |
| | Any Gout Flares Since the Last Visit, n (%) | | 3 (27.3) |
| | If Yes, the following are assessed | | |
| | Pain different than normal, n (%) | | 2 (18.2) |
| | Pain at rest >3 out of 10, n (%) | | 3 (27.3) |
| | Swelling in Joints, n (%) | | 2 (18.2) |
| | Maximum Reported Intensity of Flare (0-10 scale) [1] | | |
| | n | | 2 |
| | Mean (SD) | | 9.0 (0.00) |
| | Median | | 9.0 |
| | Min, Max | | 9, 9 |
| Week 24 | Number Assessed | NA | 11 |
| | Any Gout Flares Since the Last Visit, n (%) | | 2 (18.2) |
| | If Yes, the following are assessed | | |
| | Pain different than normal, n (%) | | 1 (9.1) |
| | Pain at rest >3 out of 10, n (%) | | 1 (9.1) |
| | Swelling in Joints, n (%) | | 1 (9.1) |
| | Maximum Reported Intensity of Flare (0-10 scale) [1] | | |
| | n | | 1 |
| | Mean (SD) | | 8.0 (NE) |
| | Median | | 8.0 |
| | Min, Max | | 8, 8 |
| Week 26 | Number Assessed | NA | 10 |
| | Any Gout Flares Since the Last Visit, n (%) | | 3 (30.0) |
| | If Yes, the following are assessed | | |
| | Pain different than normal, n (%) | | 2 (20.0) |
| | Pain at rest >3 out of 10, n (%) | | 3 (30.0) |
| | Swelling in Joints, n (%) | | 2 (20.0) |
| | Maximum Reported Intensity of Flare (0-10 scale) [1] | | |
| | n | | 2 |
| | Mean (SD) | | 7.5 (0.71) |
| | Median | | 7.5 |
| | Min, Max | | 7, 8 |

TABLE 25-continued

Assessment of Gout Flares during the Methotrexate Run-in Period and Pegloticase + Immunomodulator Period (ITT Population and mITT Population)

| Time Point | | ITT Population N = 15 | mITT Population N = 14 |
|---|---|---|---|
| Week 28 | Number Assessed | NA | 10 |
| | Any Gout Flares Since the Last Visit, n (%) | | 2 (20.0) |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 1 |
| | Mean (SD) | | 3.0 (NE) |
| | Median | | 3.0 |
| | Min, Max | | 3, 3 |
| Week 30 | Number Assessed | NA | 10 |
| | Any Gout Flares Since the Last Visit, n (%) | | 1 (10.0) |
| | If Yes, the following are assessed | | |
| | Pain different than normal, n (%) | | 1 (10.0) |
| | Pain at rest >3 out of 10, n (%) | | 1 (10.0) |
| | Swelling in Joints, n (%) | | 0 |
| | Maximum Reported Intensity of Flare (0-10 scale) [1] | | |
| | n | | 1 |
| | Mean (SD) | | 5.0 (NE) |
| | Median | | 5.0 |
| | Min, Max | | 5, 5 |
| Week 32 | Number Assessed | NA | 10 |
| | Any Gout Flares Since the Last Visit, n (%) | | 1 (10.0) |
| | If Yes, the following are assessed | | |
| | Pain different than normal, n (%) | | 1 (10.0) |
| | Pain at rest >3 out of 10, n (%) | | 1 (10.0) |
| | Swelling in Joints, n (%) | | 0 |
| | Maximum Reported Intensity of Flare (0-10 scale) [1] | | |
| | n | | 1 |
| | Mean (SD) | | 7.0 (NE) |
| | Median | | 7.0 |
| | Min, Max | | 7, 7 |
| Week 34 | Number Assessed | NA | 10 |
| | Any Gout Flares Since the Last Visit, n (%) | | 2 (20.0) |
| | If Yes, the following are assessed | | |
| | Pain different than normal, n (%) | | 2 (20.0) |
| | Pain at rest >3 out of 10, n (%) | | 2 (20.0) |
| | Swelling in Joints, n (%) | | 1 (10.0) |
| | Maximum Reported Intensity of Flare (0-10 scale) [1] | | |
| | n | | 2 |
| | Mean (SD) | | 7.0 (4.24) |
| | Median | | 7.0 |
| | Min, Max | | 4, 10 |
| Week 36 | Number Assessed | NA | 8 |
| | Any Gout Flares Since the Last Visit, n (%) | | 2 (25.0) |
| | If Yes, the following are assessed | | |
| | Pain different than normal, n (%) | | 2 (25.0) |
| | Pain at rest >3 out of 10, n (%) | | 1 (12.5) |
| | Swelling in Joints, n (%) | | 1 (12.5) |
| | Maximum Reported Intensity of Flare (0-10 scale) [1] | | |
| | n | | 1 |
| | Mean (SD) | | 8.0 (NE) |
| | Median | | 8.0 |
| | Min, Max | | 8, 8 |

TABLE 25-continued

Assessment of Gout Flares during the Methotrexate Run-in Period and Pegloticase + Immunomodulator Period (ITT Population and mITT Population)

| Time Point | | ITT Population N = 15 | mITT Population N = 14 |
|---|---|---|---|
| Week 38 | Number Assessed | NA | 6 |
| | Any Gout Flares Since the Last Visit, n (%) | | 2 (33.3) |
| | If Yes, the following are assessed | | |
| | Pain different than normal, n (%) | | 2 (33.3) |
| | Pain at rest >3 out of 10, n (%) | | 1 (16.7) |
| | Swelling in Joints, n (%) | | 1 (16.7) |
| | Maximum Reported Intensity of Flare (0-10 scale) [1] | | |
| | n | | 2 |
| | Mean (SD) | | 4.0 (2.83) |
| | Median | | 4.0 |
| | Min, Max | | 2, 6 |
| Week 40 | Number Assessed | NA | 4 |
| | Any Gout Flares Since the Last Visit, n (%) | | 0 |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 0 |
| | Mean (SD) | | |
| | Median | | |
| | Min, Max | | |
| Week 42 | Number Assessed | NA | 4 |
| | Any Gout Flares Since the Last Visit, n (%) | | 1 (25.0) |
| | If Yes, the following are assessed | | |
| | Pain different than normal, n (%) | | 0 |
| | Pain at rest >3 out of 10, n (%) | | 1 (25.0) |
| | Swelling in Joints, n (%) | | 1 (25.0) |
| | Maximum Reported Intensity of Flare (0-10 scale) [1] | | |
| | n | | 1 |
| | Mean (SD) | | 8.0 (NE) |
| | Median | | 8.0 |
| | Min, Max | | 8, 8 |
| Week 44 | Number Assessed | NA | 4 |
| | Any Gout Flares Since the Last Visit, n (%) | | 0 |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 0 |
| | Mean (SD) | | |
| | Median | | |
| | Min, Max | | |
| Week 46 | Number Assessed | NA | 3 |
| | Any Gout Flares Since the Last Visit, n (%) | | 0 |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 0 |
| | Mean (SD) | | |
| | Median | | |
| | Min, Max | | |

TABLE 25-continued

Assessment of Gout Flares during the Methotrexate Run-in Period and Pegloticase + Immunomodulator Period (ITT Population and mITT Population)

| Time Point | | ITT Population N = 15 | mITT Population N = 14 |
|---|---|---|---|
| Week 48 | Number Assessed | NA | 3 |
| | Any Gout Flares Since the Last Visit, n (%) | | 0 |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 0 |
| | Mean (SD) | | |
| | Median | | |
| | Min, Max | | |
| Week 50 | Number Assessed | NA | 3 |
| | Any Gout Flares Since the Last Visit, n (%) | | 0 |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 0 |
| | Mean (SD) | | |
| | Median | | |
| | Min, Max | | |
| Week 52/ET | Number Assessed | NA | 3 |
| | Any Gout Flares Since the Last Visit, n (%) | | 0 |
| | If Yes, the following are assessed | | |
| | Pain different than normal, n (%) | | 0 |
| | Pain at rest >3 out of 10, n (%) | | 0 |
| | Swelling in Joints, n (%) | | 0 |
| | Maximum Reported Intensity of Flare (0-10 scale) [1] | | |
| | n | | 0 |
| | Mean (SD) | | |
| | Median | | |
| | Min, Max | | |
| End of Pegloticase Infusions Visit | Number Assessed | NA | 2 |
| | Any Gout Flares Since the Last Visit, n (%) | | 1 (50.0) |
| | If Yes, the following are assessed | | |
| | Pain different than normal, n (%) | | 1 (50.0) |
| | Pain at rest >3 out of 10, n (%) | | 1 (50.0) |
| | Swelling in Joints, n (%) | | 1 (50.0) |
| | Maximum Reported Intensity of Flare (0-10 scale) [1] | | |
| | n | | 1 |
| | Mean (SD) | | 8.0 (NE) |
| | Median | | 8.0 |
| | Min, Max | | 8, 8 |

Extent of Methotrexate Exposure (ADD 670-676 HERE)

TABLE 26

| Extent of Methotrexate Exposure | | |
|---|---|---|
| Period<br>Variable<br>Statistic | ITT Population<br>N = 15 | mITT Population<br>N = 14 |
| MTX Run-in Period | | |
| Duration of MTX Treatment (days) [1] | | |
| n | 15 | 14 |
| Mean (SD) | 23.0 (4.90) | 24.1 (2.70) |
| Median | 22.0 | 22.0 |
| Min, Max | 8, 28 | 21, 28 |
| Total Dosage (mg) [2] | | |
| n | 15 | 14 |
| Mean (SD) | 64.0 (11.98) | 66.4 (7.70) |
| Median | 60.0 | 60.0 |
| Min, Max | 30, 75 | 60, 75 |
| Any Reductions in dosage from planned 15 mg/week, n (%) [3] | 0 | 0 |
| Pegloticase + Immunomodulator Period Through Week 24 | | |
| Duration of MTX Treatment (days) [1] | | |
| n | 14 | 14 |
| Mean (SD) | 132.2 (50.95) | 132.2 (50.95) |
| Median | 161.5 | 161.5 |
| Min, Max | 22, 164 | 22, 164 |
| Total Dosage (mg) [2] | | |
| n | 14 | 14 |
| Mean (SD) | 288.9 (112.08) | 288.9 (112.08) |
| Median | 357.5 | 357.5 |
| Min, Max | 60, 375 | 60, 375 |
| Any Reductions in dosage from planned 15 mg/week, n (%) [3] | 3 (20.0) | 3 (21.4) |
| Overall | | |
| Duration of MTX Treatment (days) [4] | | |
| n | 15 | 14 |
| Mean (SD) | 152.7 (63.41) | 163.1 (51.02) |
| Median | 190.0 | 190.0 |
| Min, Max | 8, 198 | 57, 198 |
| Total Dosage (mg) [5] | | |
| n | 15 | 14 |
| Mean (SD) | 333.7 (137.78) | 355.4 (113.33) |
| Median | 415.0 | 417.5 |
| Min, Max | 30, 450 | 135, 450 |
| Any Reductions in dosage from planned 15 mg/week, n (%) [3] | 3 (20.0) | 3 (21.4) |

TABLE 27

| Extent of Pegloticase Exposure in the Pegloticase + Immunomodulator Period Through Week 24 (mITT Population) | |
|---|---|
| | mITT Population<br>N = 14 |
| Pegloticase + Immunomodulator Treatment Period | |
| Number of Infusions Received Overall, n (%) [1] | |
| 2 | 1 (7.1) |
| 3 | 1 (7.1) |
| 5 | 1 (7.1) |
| 12 | 3 (21.4) |
| 13 | 8 (57.1) |
| Mean (SD) | 10.7 (4.07) |
| Median | 13.0 |
| Min, Max | 2, 13 |
| Duration of Exposure (days) [2] | |
| n | 14 |
| Mean (SD) | 137.3 (56.89) |
| Median | 168.5 |
| Min, Max | 16, 172 |

TABLE 27-continued

| Extent of Pegloticase Exposure in the Pegloticase + Immunomodulator Period Through Week 24 (mITT Population) | |
|---|---|
| | mITT Population<br>N = 14 |
| Number of Incomplete Infusions Received, n (%) [1] [3] | |
| 0 Incomplete Infusions | 14 (100) |
| At Least 1 Incomplete Infusion | 0 (0.0) |
| Mean (SD) | |
| Median | |
| Min, Max | |
| Number of Infusions Received with Interruption, n (%) [1] | |
| 0 Infusions with Interruptions | 13 (92.9) |
| At Least 1 Infusion with Interruption | 1 (7.1) |
| 2 | 1 (7.1) |
| Mean (SD) | 2.0 (NE) |
| Median | 2.0 |
| Min, Max | 2, 2 |

TABLE 27-continued

Extent of Pegloticase Exposure in the Pegloticase + Immunomodulator Period Through Week 24 (mITT Population)

| | mITT Population N = 14 |
|---|---|
| Day 1 Infusion | |
| Number of Subjects Infused | 14 |
| Complete Infusion, n (%) [3] [4] | 14 (100) |
| Completed Infusion without Interruption, n (%) [4] | 14 (100) |
| Interrupted Infusion, n (%) [4] | 0 |
| Week 2 Infusion | |
| Number of Subjects Infused | 14 |
| Complete Infusion, n (%) [3] [4] | 14 (100) |
| Completed Infusion without Interruption, n (%) [4] | 14 (100) |
| Interrupted Infusion, n (%) [4] | 0 |
| Week 4 Infusion | |
| Number of Subjects Infused | 13 |
| Complete Infusion, n (%) [3] [4] | 13 (100) |
| Completed Infusion without Interruption, n (%) [4] | 13 (100) |
| Interrupted Infusion, n (%) [4] | 0 |
| Week 6 Infusion | |
| Number of Subjects Infused | 12 |
| Complete Infusion, n (%) [3] [4] | 12 (100) |
| Completed Infusion without Interruption, n (%) [4] | 12 (100) |
| Interrupted Infusion, n (%) [4] | 0 |
| Week 8 Infusion | |
| Number of Subjects Infused | 12 |
| Complete Infusion, n (%) [3] [4] | 12 (100) |
| Completed Infusion without Interruption, n (%) [4] | 11 (91.7) |
| Interrupted Infusion, n (%) [4] | 1 (8.3) |
| Week 10 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 12 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 14 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 16 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 18 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 20 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 22 Infusion | |
| Number of Subjects Infused | 11 |
| Complete Infusion, n (%) [3] [4] | 11 (100) |
| Completed Infusion without Interruption, n (%) [4] | 11 (100) |
| Interrupted Infusion, n (%) [4] | 0 |
| Week 24 Infusion | |
| Number of Subjects Infused | 8 |
| Complete Infusion, n (%) [3] [4] | 8 (100) |
| Completed Infusion without Interruption, n (%) [4] | 8 (100) |
| Interrupted Infusion, n (%) [4] | 0 |

Example 4—Phase 4, Open-Label Study to Assess Efficacy, Safety, PK, and PD Parameters of IV KXX Q4 Weeks Co-Administered with Weekly Doses of MTX in Patients with Uncontrolled Gout (FORWARD OL)

This trial is to assess efficacy, safety, blood levels and bodily effects of up to 2 dose levels of intravenous (IV) KXX infusions at every 4 week intervals (Q4 Weeks) for up to 6 months (Day 1 to 24 weeks with an optional 24-48 weeks treatment duration) when given in combination with weekly oral doses of methotrexate (MTX). The goal is to identify an appropriate dose to be administered every 4 weeks to be used for patients with chronic gout that does not adequately respond to conventional therapy.

The primary objective is to assess the effect of pegloticase at 16 mg dose with a possibility of potential additional dose (e.g., 24 or 32 mg) administered via IV every 4 weeks, co-administered with weekly doses of oral MTX, as measured by the sustained normalization of serum uric acid (sUA) to <6 mg/dL for at least 80% of the time during Month 6 and the duration of sUA to <6 mg/dL over 24 week treatment period in adult participants with chronic gout refractory to conventional therapy.

Secondary objectives include the assessment of up to 2 dose levels of pegloticase (16 mg IV and a possible second dose of 24 mg IV or 32 mg IV) every 4 weeks co-administered with weekly doses of oral MTX in adult subjects with chronic gout refractory to conventional therapy. The following measures may be made: pharmacokinetics; pharmacodynamics, including the proportion of subjects with pre-infusion sUA levels <6 mg/dL, area under the sUA concentration vs. time curve from day 1 to week 24 and from day 1 to week 48, and proportion of time subjects sustain sUA<6 mg/dL from day 1 to week 24 to day 1 to week 48; and profile of anti-uricase antibodies and anti-poly (ethylene glycol) antibodies.

Exploratory objectives may include the assessment of the following of up to 2 dose levels of pegloticase (16 mg IV and a possible second dose of 24 mg IV or 32 mg IVQ4W co-administered with weekly doses of oral MTX in adult subjects with chronic gout refractory to conventional therapy:

- Profile of MTX polyglutamates (MTX-PG 1 through 5)
- Proportion of subjects with complete resolution of ≥1 tophi (using digital photography) at Weeks 24 and 36 and 48 in subjects with tophi at baseline
- Proportion of subjects who experienced any infusion reaction or anaphylaxis following multiple doses of pegloticase
- Change from baseline to each scheduled visit in physician global assessment of gout
- Change from baseline in tophus size (long axis measured using digital photography) to Weeks 14, 24, 36 and 48 in subjects with tophus present at baseline

- Proportion of overall responders, defined as subjects achieving and maintaining sUA<6 mg/dL for at least 80% of the time at each time interval: Month 3 (Weeks 10, 11, 12, 13 and 14), Month 6 (Weeks 20, 21, 22, 23 and 24), Month 9 (Weeks 32, 34, 36) and Month 12 (Weeks 44, 46 and 48)
- Change from baseline in sUA at Weeks 14, 24, 36 and 48
- Time to first sUA≥6 mg/dL after first achieving sUA<6 mg/dL
- Time to two consecutive sUA≥6 mg/dL
- Percentage of time sUA is <6 mg/dL during Month 3 (Weeks 10, 11, 12, 13 and 14), Month 6 (Weeks 20, 21, 22, 23 and 24), Month 9 (Weeks 32, 34, 36) and Month 12 (Weeks 44, 46 and 48)
- Change from baseline in Health Assessment Questionnaire (HAQ) Pain score at Weeks 14, 24, 36 and 48
- Change from baseline in HAQ Health score at Weeks 14, 24, 36 and 48
- Change from baseline in Health Assessment Questionnaire—Disability Index (HAQ-DI) score at Weeks 14, 24, 36 and 48
- Change from baseline in physician global assessment of gout at Weeks 14, 24, 36 and 48
- Change from baseline in Systolic Blood Pressure (SBP) and Diastolic Blood Pressure (DBP) to each scheduled visit The trial design will include 5 to 6 distinct components: 1) a Screening Period (screening should be completed within 35 days prior to Week −4); 2) a 4-week Run-In MTX Tolerability Assessment Period; 3) a 20-week Q4 Wks pegloticase+MTX Treatment Period which includes a Week 24/End of Trial/Early Termination (ET) Visit; 4) an optional extension Q4 Wks pegloticase+MTX Treatment Period from Week 24 to Week 44 if a subject might benefit from additional pegloticase treatment; 5) an End of Pegloticase Infusions Visit (if applicable) within 2 weeks following the final infusion if the infusion is prior to Week 48; and 6) an End of Trial/Week 48/ET Visit. All subjects who meet eligibility criteria at Screening will begin 15 mg MTX orally weekly at the Week −4 visit. Subjects will also take folic acid 1 mg daily dose orally, which may be increased to 2 mg daily dose if MTX tolerability is inadequate at 1 mg. The folic acid daily dose will begin at the MTX Tolerability Assessment Period (Week −4) and continuing until prior to the Week 21 Visit, with an optional extension for an additional 24 (total of 45) weeks. All subjects who complete the Run-In Period will receive the first pegloticase infusion on Day 1.

It is required that before a subject begins the pegloticase+MTX Period, he or she has been taking at least one protocol standard gout flare prophylaxis regimen (i.e. colchicine and/or non-steroidal anti-inflammatory drugs and/or low-dose prednisone ≤10 mg/day) for ≥1 week before the first dose of pegloticase and continues flare prophylaxis per American College of Rheumatology guidelines. For infusion reaction (IR) prophylaxis, fexofenadine (180 mg orally) will be taken the day before each infusion; fexofenadine (180 mg orally) and acetaminophen (1000 mg orally) will be taken the morning of each infusion; and methylprednisolone (125 mg IV) given over an infusion duration between 10-30 minutes, immediately prior to each infusion.

For the first cohort, during the Pegloticase+MTX Period, pegloticase 16 mg will be administered intravenously (IV) every 4 weeks from Day 1 through the Week 20 Visit with an End of Trial Visit at Week 24 for a total of 6 infusions. An optional extension will be available for continued infusions through the Week 44 Visit with an End of Trial Visit at Week 48 for a total of up to 12 infusions. Pegloticase will be administered after all pre-dose trial visit assessments have been completed at Day 1 and each Q4 Wk visit.

Serum uric acid stopping criteria will be applied: subjects with sUA level ≥6 mg/dL at 2 consecutive weekly visits beginning with the Week 1 Visit, with observations 1 and 2 weeks after each infusion prioritized over sUA values 3 and 4 weeks after each infusion, may discontinue treatment (complete the End of Pegloticase Infusion Visit procedures within 2 weeks and continue the subject visits according to the protocol (without treatment). sUA levels will be collected prior to and post infusion on the day of all infusions as well as weekly at each non-infusion visit until Week 24 then bi-weekly during the optional duration of the trial (Week 24 though Week 48). Given that the sUA may rise towards the end of the Q4 interval simply due to the pharmacokinetics of pegloticase rather than necessarily indicating a loss of efficacy due to formation of Anti-Drug Antibodies (ADA), the 1- and 2-week post infusion values will be prioritized for the purpose of the stopping criteria.

During the Pegloticase+MTX Period, subjects will be instructed to take MTX weekly on the same day each week, within 1 to 3 days prior to each pegloticase infusion and one additional weekly dose after the last infusion for subjects who have not stopped pegloticase due to sUA stopping criteria; however, if a subject does not do so, MTX must be taken ≥60 minutes prior to each pegloticase infusion.

After Day 1, if a subject becomes unable to tolerate MTX, the MTX dose may be reduced and/or discontinued based on pre-defined criteria, and the subject may remain in the trial.

Eligible subjects must meet/provide all of the following criteria:

- Uncontrolled gout, defined as meeting the following criteria
  - Hyperuricemia during the screening period defined as sUA 26 mg/dL, and;
  - Failure to maintain normalization of sUA with xanthine oxidase inhibitors at the maximum medically appropriate dose, or with contraindication to xanthine oxidase inhibitor therapy, and;
  - Symptoms of gout including at least 1 of the folio
    - Presence of at least one tophus
    - Recurrent flares defined as 2 or more flares in the past 12 months prior to screening
    - Presence of chronic gouty arthritis as evidenced by either clinical signs consistent with chronic synovitis on clinical examination or the presence of typical gouty erosion(s) on hand and/or foot X-rays
  - Willing to discontinue any oral urate lowering therapy for at least 7 days prior to MTX dosing at Week −4 and remain off while receiving pegloticase treatments.
  - Able to tolerate MTX 15 mg orally for 4 weeks (Week −4 through Day 1) prior to enrollment.

Subjects will be ineligible for trial participation if they meet any of the following criteria:

- Weight >160 kg (352 pounds) at Screening.
- Any serious acute bacterial infection, unless treated and completely resolved with antibiotics at least 2 weeks prior to the Day 1 Visit.
- Severe chronic or recurrent bacterial infections, such as recurrent pneumonia or chronic bronchiectasis.
- Current or chronic treatment with systemic immunosuppressive agents such as MTX, azathioprine, or mycophenolate mofetil prednisone 210 mg/day or equivalent dose of other corticosteroid on a chronic basis (3 months or longer) would also meet exclusion criteria.

History of any transplant surgery requiring maintenance immunosuppressive therapy.

Known history of hepatitis B virus surface antigen positivity or hepatitis B DNA positivity.

Known history of hepatitis C virus RNA positivity, unless treated and viral load is negative.

Known history of Human Immunodeficiency Virus (HIV) positivity.

Glucose-6-phosphate dehydrogenase deficiency (tested at the Screening Visit centrally or locally).

Chronic renal impairment defined as estimated glomerular filtration rate (eGFR) <40 mL/min/1.73 mA2 or currently on dialysis.

Non-compensated congestive heart failure or hospitalization for congestive heart failure within 3 months of the Screening Visit, uncontrolled arrhythmia, treatment for acute coronary syndrome (myocardial infarction or unstable angina), or uncontrolled blood pressure (>160/100 mmHg) prior to enrollment at Day 1.

Prior treatment with pegloticase, another recombinant uricase (rasburicase), or concomitant therapy with a polyethylene glycol-conjugated drug.

Known allergy to pegylated products or history of anaphylactic reaction to a recombinant protein or porcine product.

Contraindication to MTX treatment orMTX treatment considered inappropriate.

Known intolerance to MTX.

Receipt of an investigational drug within 4 weeks or 5 half-lives, whichever is longer, prior to MTX administration at Week −4 or plans to take an investigational drug during the trial.

Liver transaminase levels (AST or ALT)>1.2.5×upper limit of normal (ULN) or albumin <the lower limit of normal (LLN) at the Screening Visit.

Chronic liver disease.

White blood cell count <4000/μl, hematocrit <32 percent, or platelet count <75,000/μl.

Currently receiving systemic or radiologic treatment for ongoing cancer, excluding non-melanoma skin cancer.

History of malignancy within 5 years other than non-melanoma skin cancer or in situ carcinoma of cervix.

Diagnosis of osteomyelitis.

Known history of hypoxanthine-guanine phosphoribosyltransferase deficiency, such as Lesch-Nyhan and Kelley-Seegmiller syndrome.

A known intolerance to all protocol standard gout flare prophylaxis regimens (i.e., subject must be able to tolerate at least one: colchicine and/or non-steroidal anti-inflammatory drugs and/or low dose prednisone s10 mg/day).

Current pulmonary fibrosis, bronchiectasis or interstitial pneumonitis.

In some embodiments, KXX is administered intravenously to a patient at a dosage of 16 mg every 4 weeks, along with 15 mg oral doses of MTX weekly. The duration of the study is for up to 6 months (Day 1 to 24 weeks with an optional 24-48 weeks treatment duration) when both drugs are given in combination. The Screening period is up to 35 days, followed by a 4-week methotrexate (MTX) tolerability run-in. Treatment will comprise 16 mg KXX given IV every 4 weeks for a total of 6 infusions (over a period of 24 Weeks) with co-administered weekly doses of oral MTX. An optional extension treatment (24-48 weeks) will be available for 6 more infusions (total of 12 infusions). Auer completing 2 infusions, the data from the first ~10 participants will be analyzed to determine if: (1) 5 more participants in the first cohort should be enrolled, (2)>5 participants should be enrolled in the first cohort, (3) enrollment in the first cohort should discontinue, and/or 4) enrollment for a second cohort should begin.

Parameters to be collected include sUA, AUC, Cmax, Ctrough, proportion of participants with sUA<6 mg/di, at each scheduled visit, area under the sUA concentration vs time curve from Day 1 to Week 24 (including extended treatment period), area under the sUA concentration vs time curve from Day 1 to Week 48 (including extended treatment period), proportion of participants with anti-PEG antibodies and its titer at each scheduled visit, and proportion of participants with anti-KXX antibodies and its titer at each scheduled visit.

In some embodiments, KXX is administered intravenously to a patient at a dosage of 24 mg every 4 weeks, along with 15 mg oral doses of MTX weekly. The duration of the study is for up to 6 months (Day 1 to 24 weeks with an optional 24-48 weeks treatment duration) when both drugs are given in combination. The Screening period is up to 35 day, followed by a 4-week methotrexate (MTX) tolerability run-in. Treatment will consist of 24 mg KXX given IV every 4 weeks for a total of 6 infusions (over a period of 24 Weeks) with co-administered weekly doses of oral MTX. An optional extension treatment (24-48 weeks) will be available for 6 more infusions (total of 12 infusions). After completing 2 infusions, the data from the first ~10 participants will be analyzed to determine if: (1) 5 more participants in the first cohort should be enrolled, (2)>5 participants should be enrolled in the first cohort. (3) enrollment in the first cohort should discontinue, and/or 4) enrollment for a second cohort should begin.

Parameters to be collected include sUA, AUC, Cmax, Ctrough, proportion of participants with sUA<6 mg/dL, at each scheduled visit, area under the sUA concentration vs time curve from Day 1 to Week 24 (including extended treatment period), area under the sUA concentration vs time curve from Day 1 to Week 48 (including extended treatment period), proportion of participants with anti-PEG antibodies and its titer at each scheduled visit, and proportion of participants with anti-KXX antibodies and its titer at each scheduled visit.

In some embodiments, KXX is administered intravenously to a patient at a dosage of 32 mg every 4 weeks, along with 15 mg oral doses of MTX weekly. The duration of the study is for up to 6 months (Pay 1 to 24 weeks with an optional 24-48 weeks treatment duration) when both drugs are given in combination. The Screening period is up to 35 days, followed by a 4-week methotrexate (MTX) tolerability run-in. Treatment consist of 32 mg KXX given IV every 4 weeks for a total of 6 infusions (over a period of 24 Weeks) with co-administered weekly doses of oral MTX. An optional extension treatment (24-48 weeks) will be available for 6 more infusions (total of 12 infusions). After completing 2 infusions, the data from the first ~10 participants will be analyzed to determine if: (1) 5 more participants in the first cohort should be enrolled, (2)>5 participants should be enrolled in the first cohort. (3) enrollment in the first cohort should discontinue, and/or 4) enrollment for a second cohort should begin.

Parameters to be collected include sUA, AUC, Cmax, Ctrough, proportion of participants with sUA<6 mg/dL at each scheduled visit, area under the sUA concentration vs time curve from Day 1 to Week 24 (including extended treatment period), area under the sUA concentration vs time curve from Day 1 to Week 48 (including extended treatment period), proportion of participants with anti-PEG antibodies and its titer at each scheduled visit, and proportion of participants with anti-KXX antibodies and its titer at each scheduled visit.

What is claimed is:

1. A method of treating gout in a patient having a serum uric acid (SUA) level of ≥6 mg/dL comprising:

first administering methotrexate (MTX) to said patient at a dose of 15 mg per week for a period of 2 to 4 weeks prior to a first administration of a PEGylated uricase; and then co-administering the PEGylated uricase and MTX to said patient using a dosage regimen comprising a dose of 8 mg of pegloticase intravenously every 2 weeks, and a dose of 15 mg of MTX per week;

wherein the pegloticase is administered over an infusion period of 60 minutes; and wherein the pegloticase infusion volume is 50 mL.

2. The method of claim 1, wherein the patient experiences an adverse event profile similar in nature and severity to patients receiving pegloticase over a 120-minute infusion period and an infusion volume of 250 mL.

3. The method of claim 1, further comprising administering folic acid to said patient at a dosage of 1 mg per day from the start of methotrexate administration.

4. The method of claim 1, further comprising administering colchicine for a period of at least 2 weeks prior to the first administration of pegloticase.

5. The method of claim 1, wherein the SUA levels of the patient are determined prior to each dose of pegloticase.

6. The method of claim 1, further comprising measuring one or more of trough pegloticase levels, anti-pegloticase antibody levels, and anti-PEG antibody levels, prior to each dose of pegloticase after the first dose.

7. The method of claim 1, wherein said co-administration of pegloticase and MTX results in normalization of the SUA level in the patient relative to a patient not receiving co-administration of pegloticase and MTX immunosuppressive therapy.

8. The method of claim 1, wherein the SUA level is reduced to less than 6 mg/dL as a result of co-administration of pegloticase and MTX immunosuppressive therapy.

9. The method of claim 1, wherein the SUA level is reduced to less than 5 mg/dL as a result of co-administration of pegloticase and MTX immunosuppressive therapy.

10. The method of claim 1, wherein the SUA level is reduced to less than 2 mg/dL as a result of co-administration of pegloticase and MTX immunosuppressive therapy.

11. The method of claim 1, wherein the incidence of infusion reaction, gout flare, or anaphylaxis is reduced as a result of co-administration of pegloticase and MTX immunosuppressive therapy.

12. The method of claim 1, wherein the serum uric acid level is normalized by week 12 after co-administration of pegloticase and MTX treatment begins.

13. The method of claim 1, wherein MTX is administered orally.

14. The method of claim 1, wherein the gout is chronic refractory gout.

* * * * *